United States Patent
Artman, III et al.

(10) Patent No.: US 11,370,777 B2
(45) Date of Patent: Jun. 28, 2022

(54) SOLID FORMS COMPRISING (S)-4-(4-(4-(((2-(2,6-DIOXOPIPERIDIN-3-YL)-1-OXOISOINDOLIN-4-YL)OXY) METHYL)BENZYL)PIPERAZIN-1-YL)-3-FLUOROBENZONITRILE AND SALTS THEREOF, AND COMPOSITIONS COMPRISING AND METHODS OF USING THE SAME

(71) Applicant: Celgene Corporation, Summit, NJ (US)

(72) Inventors: Gerald D. Artman, III, Asbury, NJ (US); Antonio C. Ferretti, Summit, NJ (US); Lianfeng Huang, Basking Ridge, NJ (US); Udaykumar Jain, Plainsboro, NJ (US); Hon-Wah Man, Princeton, NJ (US); Paula A. Tavares-Greco, Parsippany, NJ (US); Wenju Wu, Warren, NJ (US); Nancy Nienhua Tsou, Edison, NJ (US); Zhiwei Yin, Harrison, NJ (US)

(73) Assignee: Celgene Corporation, Summit, NJ (US)

( * ) Notice: Subject to any disclaimer, the term of this patent is extended or adjusted under 35 U.S.C. 154(b) by 1 day.

(21) Appl. No.: 16/737,739

(22) Filed: Jan. 8, 2020

(65) Prior Publication Data

US 2020/0216418 A1   Jul. 9, 2020

Related U.S. Application Data

(60) Provisional application No. 62/790,342, filed on Jan. 9, 2019.

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC .................................................. C07D 401/14
See application file for complete search history.

(56) References Cited

U.S. PATENT DOCUMENTS 10,357,489 B2 *   7/2019   Alexander .............. A61P 35/00

FOREIGN PATENT DOCUMENTS

| WO | WO 2011/100380 A1 | 8/2011 |
| WO | WO 2019/014100 A1 | 1/2019 |
| WO | WO 2019/226761 A1 | 11/2019 |
| WO | WO 2019/226770 A1 | 11/2019 |

* cited by examiner

*Primary Examiner* — Brian E McDowell
(74) *Attorney, Agent, or Firm* — Jones Day

(57) ABSTRACT

Provided herein are formulations, processes, solid forms and methods of use relating to salts of and solid forms comprising free base or salts of (S)-4-(4-(4-(((2-(2,6-dioxopiperidin-3-yl)-1-oxoisoindolin-4-yl)oxy)methyl)benzyl)piperazin-1-yl)-3-fluorobenzonitrile.

28 Claims, 80 Drawing Sheets

Figure 1:
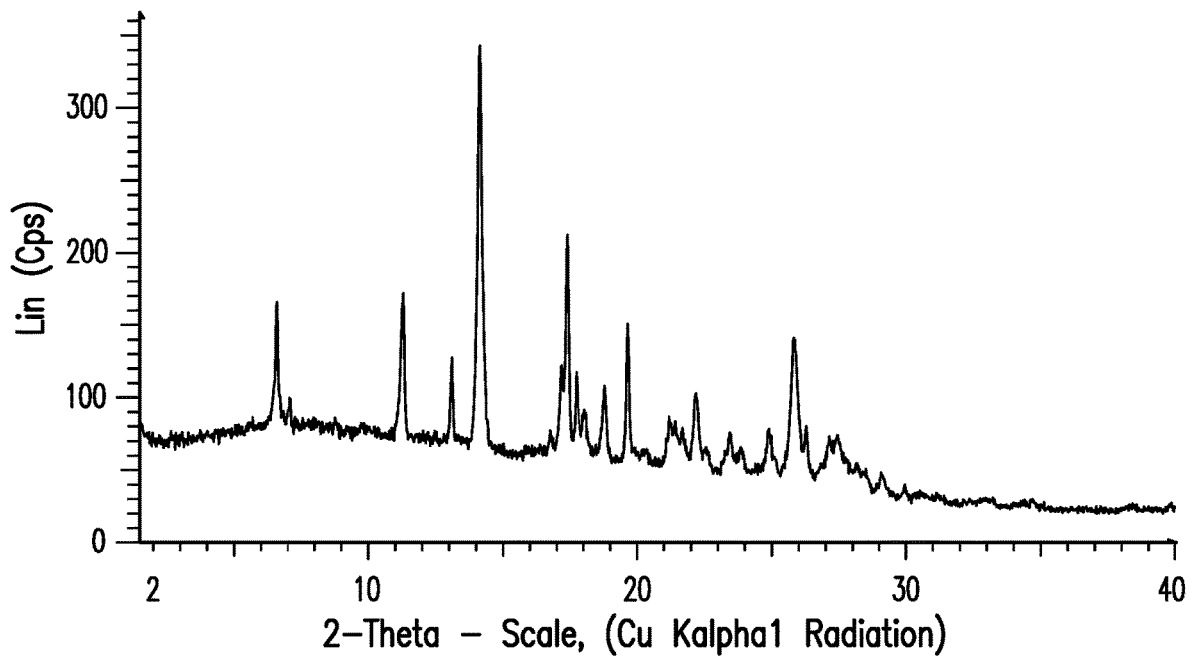

Form Conversion Scheme for Form L, Form M, and Form N of a Hydrochloride Salt of Compound 1

SOLID FORMS COMPRISING (S)-4-(4-(4-(((2-(2,6-DIOXOPIPERIDIN-3-YL)-1-OXOISOINDOLIN-4-YL)OXY)METHYL)BENZYL)PIPERAZIN-1-YL)-3-FLUOROBENZONITRILE AND SALTS THEREOF, AND COMPOSITIONS COMPRISING AND METHODS OF USING THE SAME

This application claims priority to U.S. Provisional Application No. 62/790,342, filed on Jan. 9, 2019, the entirety of which is incorporated herein by reference.

1. FIELD

Provided herein are salts of and solid forms comprising free base or salts of (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Pharmaceutical compositions comprising such salts and solid forms and methods of use of such salts and solid forms for treating, preventing, and managing various disorders are also provided herein.

2. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgery, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer multiple myeloma cells as a proportion of total bone marrow mononuclear cells is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and 10' by high-throughput sequencing. (Rawstron et al., *Blood* 2015; 125(12):1932-1935). Methods for measuring MRD include DNA sequencing of VDJ, polymerase chain reaction (PCR) (including allele specific PCR, ASO PCR) and multiparameter flow cytometry (MPF). Assays for MRD, e.g., based on clonotype profile measurement are also described in U.S. Pat. No. 8,628,927, to Faham et al., which is incorporated herein by reference.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

Alternative solid forms of pharmaceutical compounds have emerged as a possible approach to modulate or enhance the physical and chemical properties of drug products. The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solid forms include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The type of salt form of a particular active pharmaceutical ingredient may affect certain properties of the active pharmaceutical ingredient. These properties include solubility, stability, and bioavailability.

The variety of possible solid forms, including both free base forms and salt forms, creates potential diversity in physical and chemical properties for a given pharmaceutical compound. The discovery and selection of solid forms are of great importance in the development of an effective, stable and marketable pharmaceutical product.

3. SUMMARY

Provided herein are solid forms (e.g., crystalline forms, amorphous forms, polymorphs or mixtures thereof) comprising Compound 1:

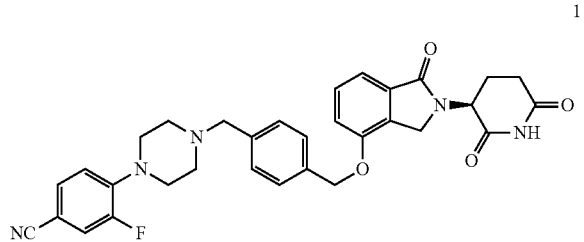 [SMILES: N#Cc1ccc(N2CCN(Cc3ccc(COc4cccc5c4CN([C@H]4CCC(=O)NC4=O)C5=O)cc3)CC2)c(F)c1]

1 having the chemical name (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Also provided herein are methods of preparing, isolating, and characterizing the solid forms.

In one embodiment, the solid form comprises a free base of Compound 1. In one embodiment, the solid form is Form A, Form B, Form C, Form D, Form E, Form F, Form G, Form H, Form I, Form J, Form K, Form K', Form L, Form M, Form N, Form O, Form P, Form Q, Form R, or Form S of a free base of Compound 1, as provided herein.

In one embodiment, the solid form comprises a salt of Compound 1.

In one embodiment, the solid form comprises a hydrochloride salt of Compound 1. In one embodiment, the solid form is Form A, Form B, Form C, Form D, Form E, Form F, Form G, Form H, Form I, Form J, Form K, Form L, Form M, Form N, Form O, Form P, Form Q, Form R, Form S, Form T, Form U, Form V, Form W, Form X, Form Y, Form Z, Form AA, Form AB, or Form AC of a hydrochloride salt of Compound 1, as provided herein.

In one embodiment, the solid form comprises a mesylate salt of Compound 1. In one embodiment, the solid form is Form A or Form B of a mesylate salt of Compound 1, as provided herein.

In one embodiment, the solid form comprises a hydrobromide salt of Compound 1. In one embodiment, the solid form is Form A, Form B, Form C, Form D, Form E, Form F, Form G, Form H, Form I, or Form J of a hydrobromide salt of Compound 1, as provided herein.

In one embodiment, the solid form comprises a besylate salt of Compound 1. In one embodiment, the solid form is Form A or Form B of a besylate salt of Compound 1, as provided herein.

In one embodiment, the solid form comprises a glycolate salt of Compound 1. In one embodiment, the solid form is Form A of a glycolate salt of Compound 1, as provided herein.

In one embodiment, the solid form comprises an L-malate salt of Compound 1. In one embodiment, the solid form is Form A of an L-malate salt of Compound 1, as provided herein.

Also provided herein are salts of Compound 1. In one embodiment, the salt is a hydrochloride salt, a mesylate salt, a hydrobromide salt, a besylate salt, a glycolate salt, an L-malate salt, a napadisylate salt, a sulfate salt, a tosylate salt, an oxalate salt, an isethionate salt, a maleate salt, a phosphate salt, a malonate salt, a gentisate salt, an L-tartrate salt, a fumarate salt, a citrate salt, an R-mandelate salt, an L-ascorbate salt, a succinate salt, a nitrate salt, a salicylate salt, an edisylate salt, a cyclamate salt, an esylate salt, a D-glucuronate salt, a 4-aminosalicylate salt, a caproate salt, a cinnamate salt, a caprylate salt, a camphorate salt, a D-aspartate salt, or a D-glutamate salt.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising Compound 1 and a pharmaceutically acceptable diluent, excipient or carrier.

Also provided are pharmaceutical compositions formulated for administration by an appropriate route and means containing effective concentrations of a solid form comprising Compound 1 provided herein, and optionally comprising at least one pharmaceutical carrier.

In one embodiment, the pharmaceutical compositions deliver amounts effective for the treatment of multiple myeloma. In one embodiment, the pharmaceutical compositions deliver amounts effective for the prevention of multiple myeloma. In one embodiment, the pharmaceutical compositions deliver amounts effective for the amelioration of multiple myeloma.

In one embodiment, provided herein are methods of treating multiple myeloma comprising administering the solid forms, salts, or pharmaceutical compositions provided herein. Also provided herein are combination therapies using the solid forms, salts, or pharmaceutical compositions provided herein, in combination with a therapy, e.g., another pharmaceutical agent with activity against multiple myeloma or its symptoms. Examples of therapies within the scope of the methods include, but are not limited to, surgery, chemotherapy, radiation therapy, biological therapy, stem cell transplantation, cell therapy, and combinations thereof.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

4. BRIEF DESCRIPTION OF THE DRAWINGS

FIG. 1 provides a representative X-ray powder diffraction (XRPD) pattern of Form A of a free base of Compound 1.

Figure 2:
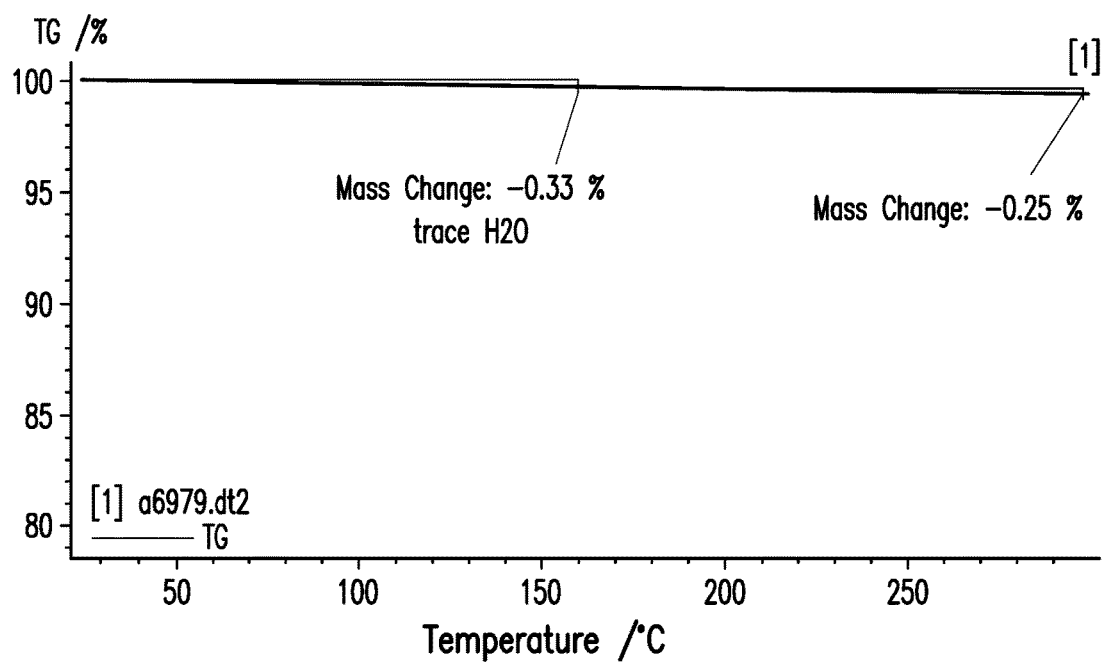

FIG. 2 provides a representative thermal gravimetric analysis (TGA) thermogram of Form A of a free base of Compound 1.

Figure 3:
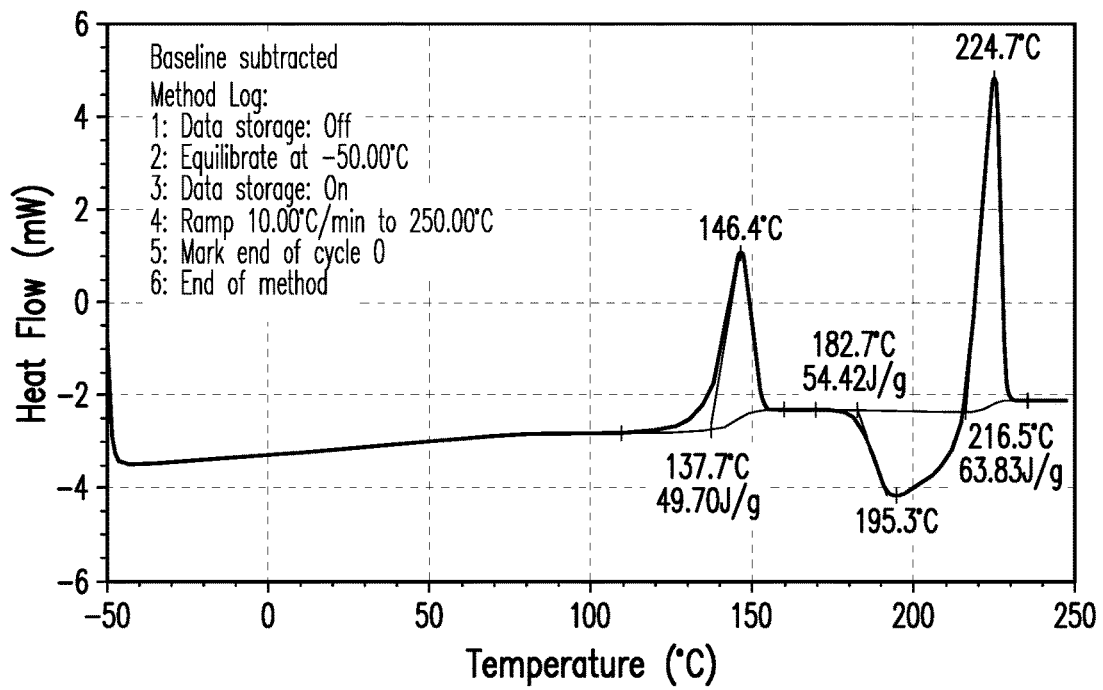

FIG. 3 provides a representative differential scanning calorimetry (DSC) thermogram of Form A of a free base of Compound 1.

Figure 4:
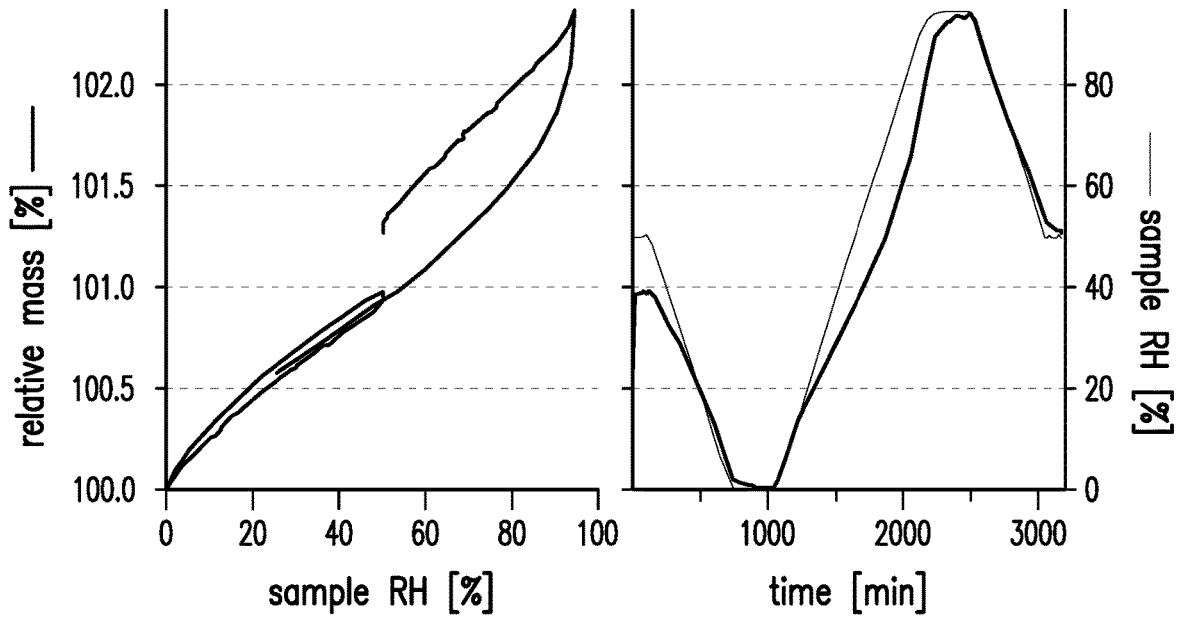

FIG. 4 provides a representative dynamic vapor sorption (DVS) isotherm plot of Form A of a free base of Compound 1.

Figure 5:
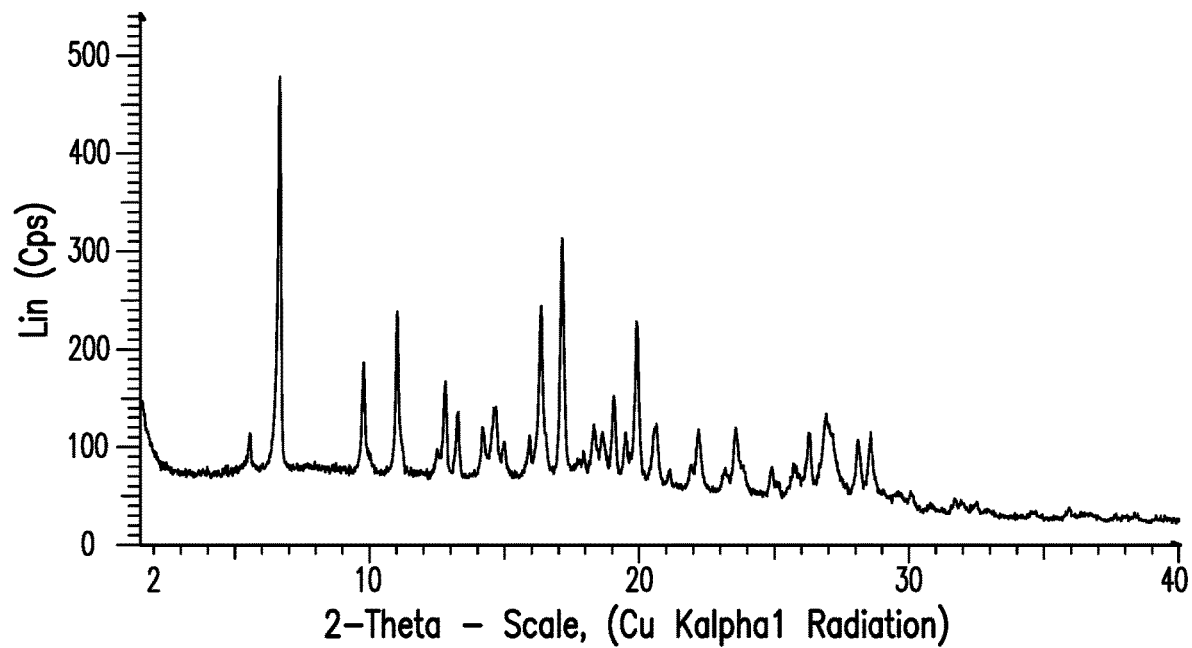

FIG. 5 provides a representative XRPD pattern of Form B of a free base of Compound 1.

Figure 6:
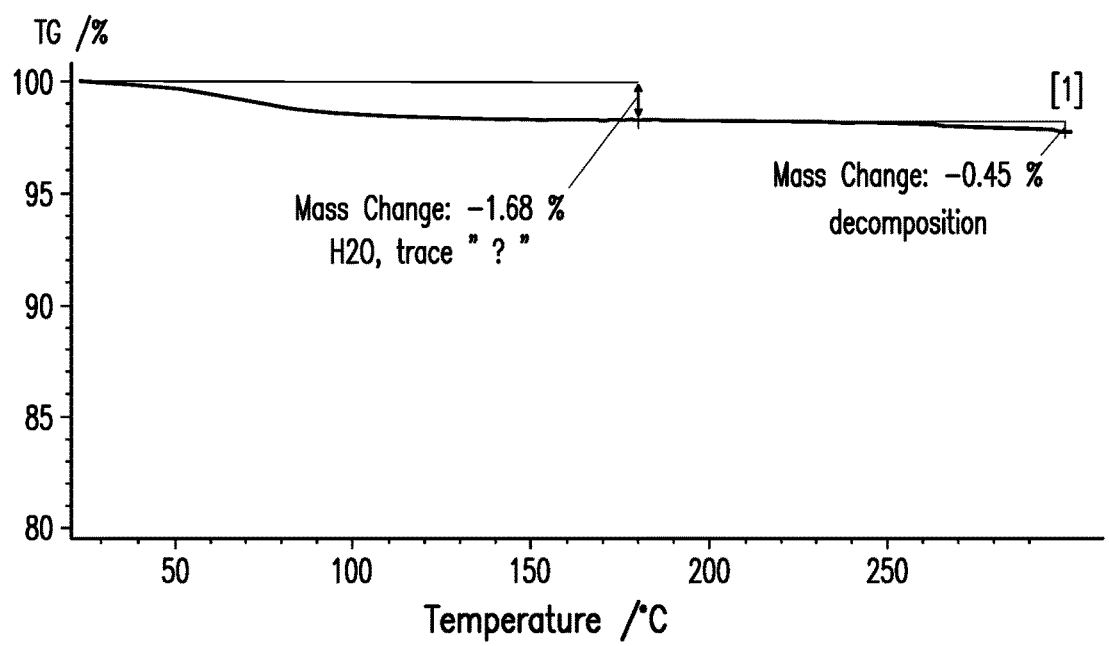

FIG. 6 provides a representative TGA thermogram of Form B of a free base of Compound 1.

Figure 7:
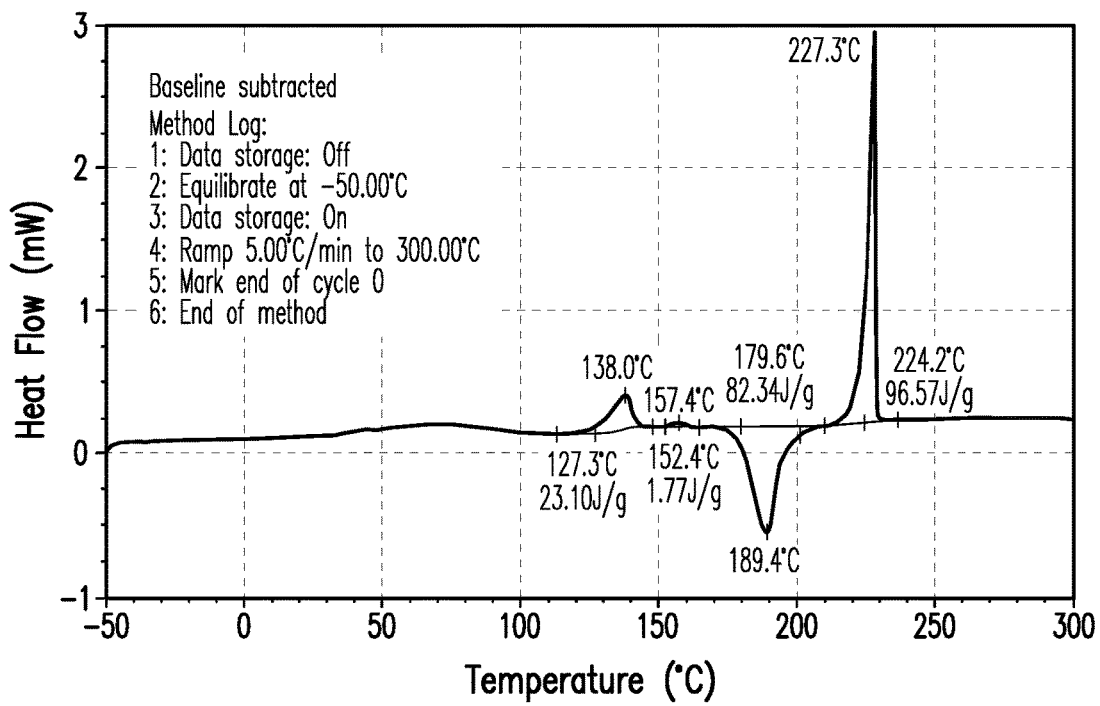

FIG. 7 provides a representative DSC thermogram of Form B of a free base of Compound 1.

Figure 8:
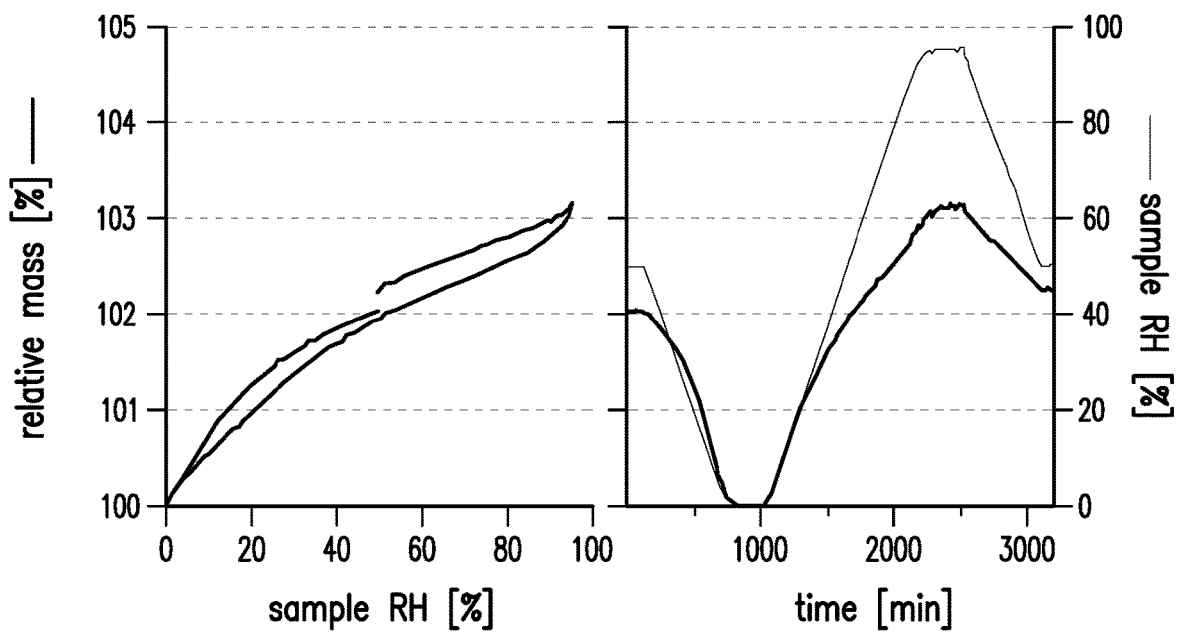

FIG. 8 provides a representative DVS isotherm plot of Form B of a free base of Compound 1.

Figure 9:
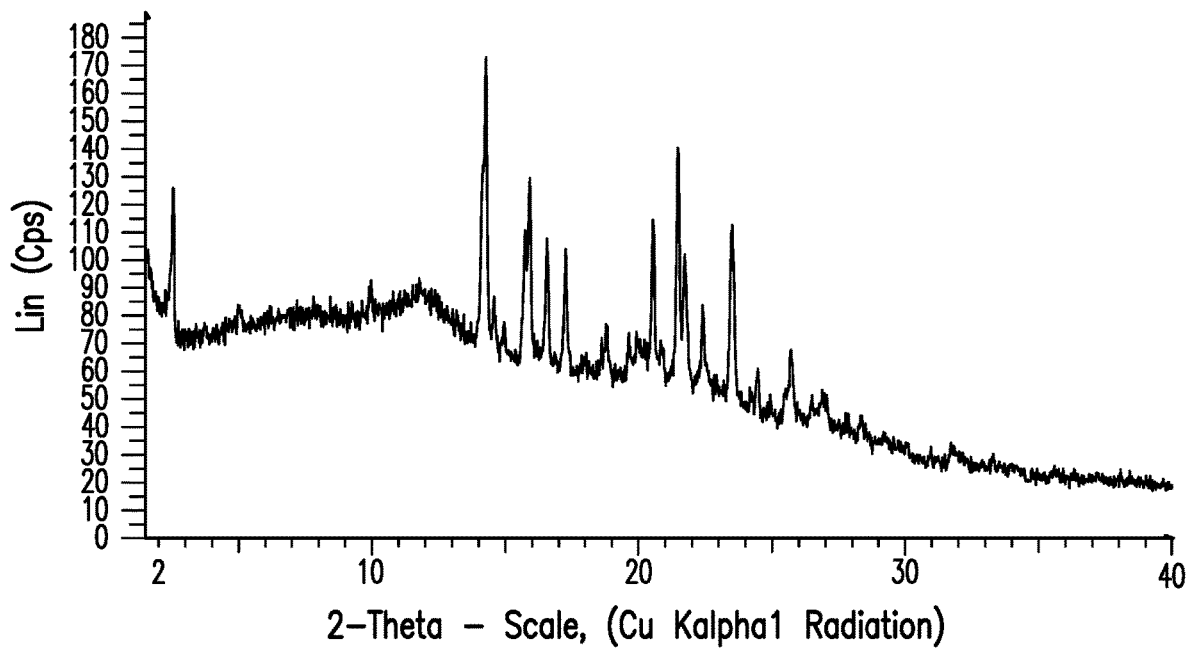

FIG. 9 provides a representative XRPD pattern of Form C of a free base of Compound 1.

Figure 10:
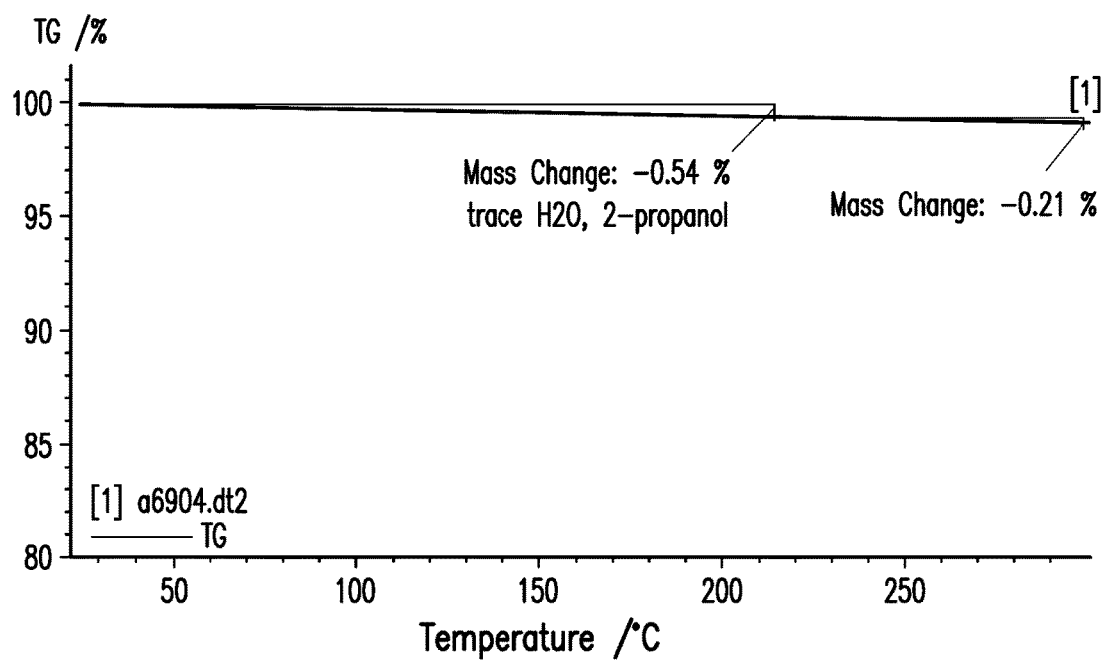

FIG. 10 provides a representative TGA thermogram of Form C of a free base of Compound 1.

Figure 11:
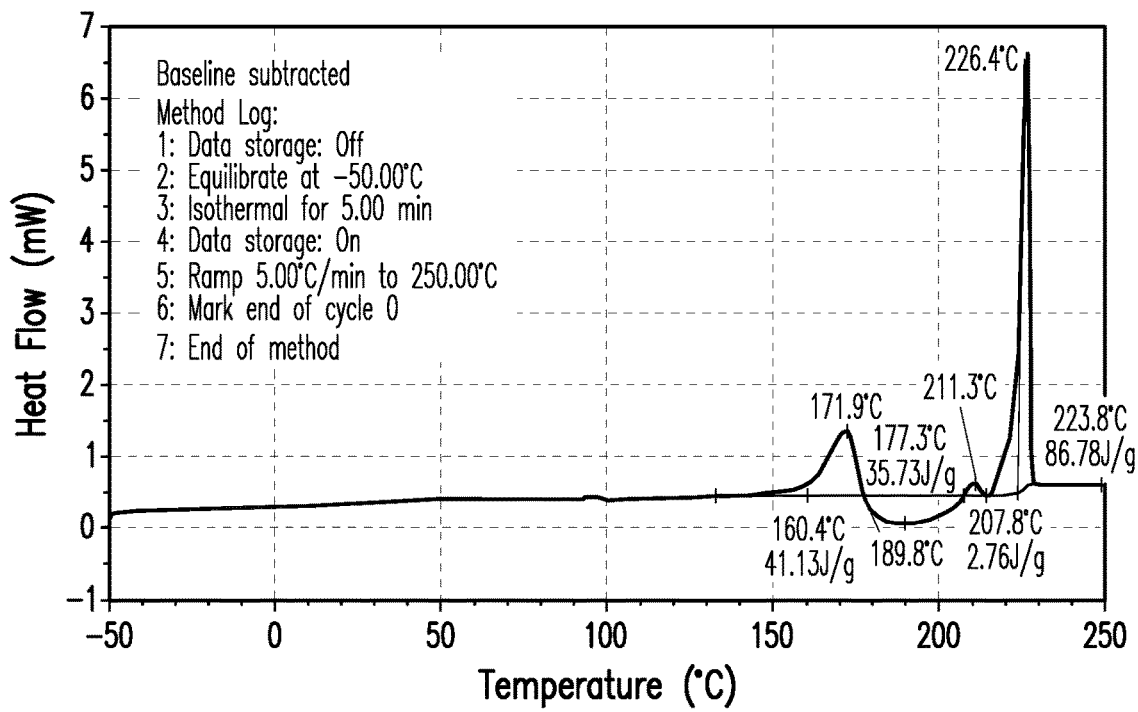

FIG. 11 provides a representative DSC thermogram of Form C of a free base of Compound 1.

Figure 12:
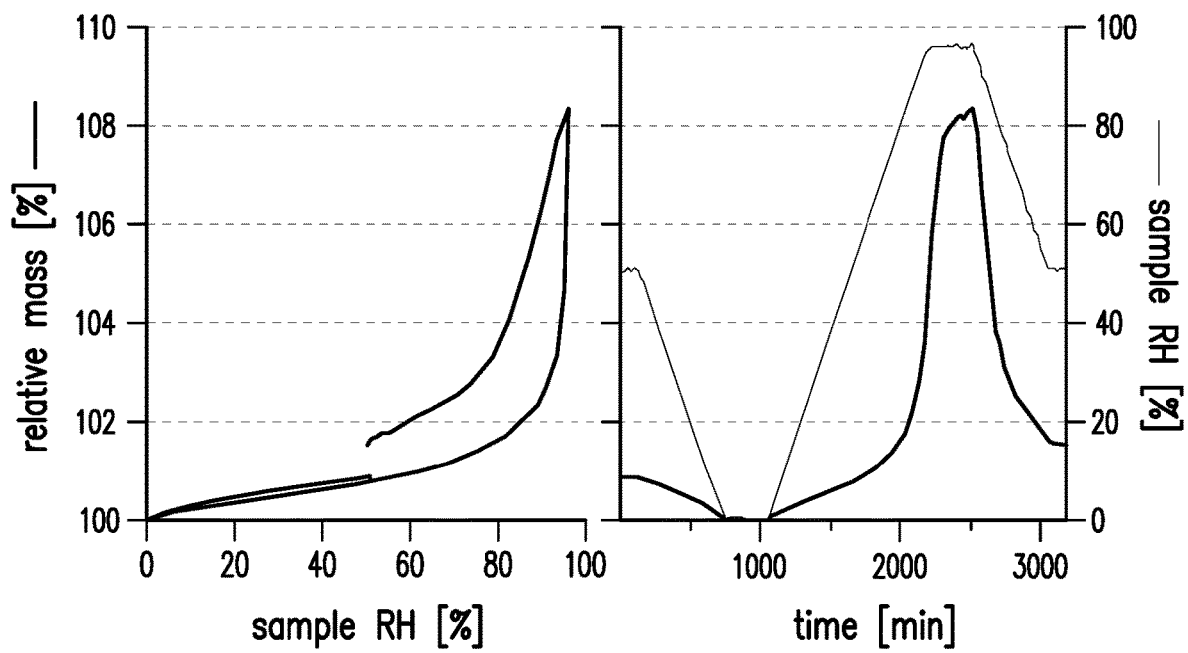

FIG. 12 provides a representative DVS isotherm plot of Form C of a free base of Compound 1.

Figure 13:
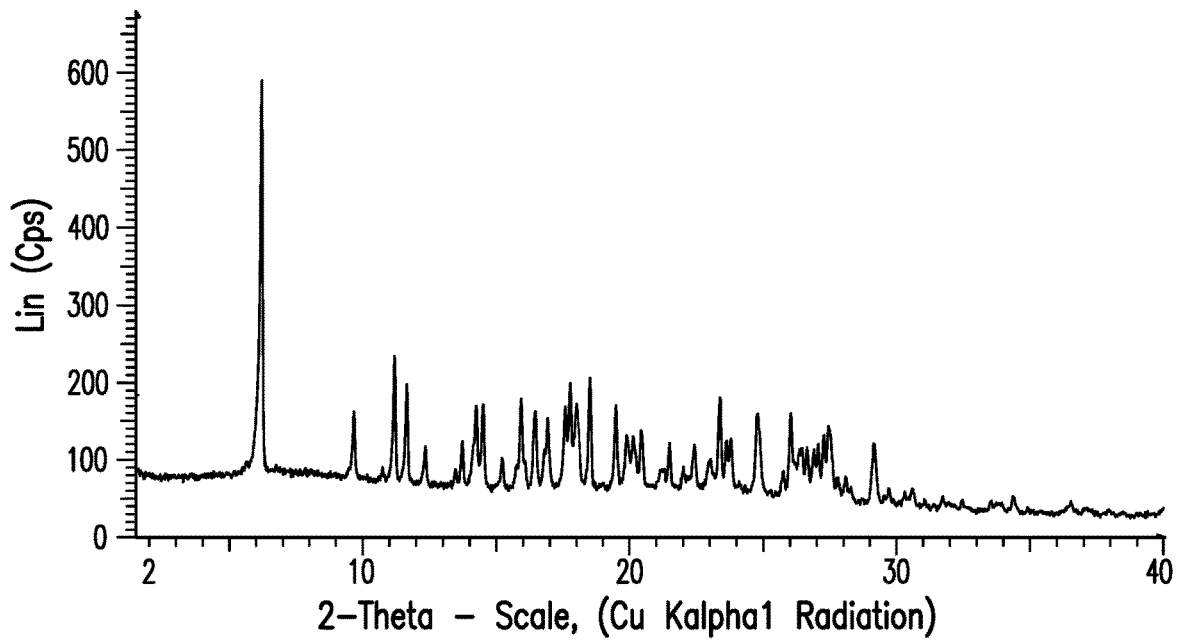

FIG. 13 provides a representative XRPD pattern of Form D of a free base of Compound 1.

Figure 14:
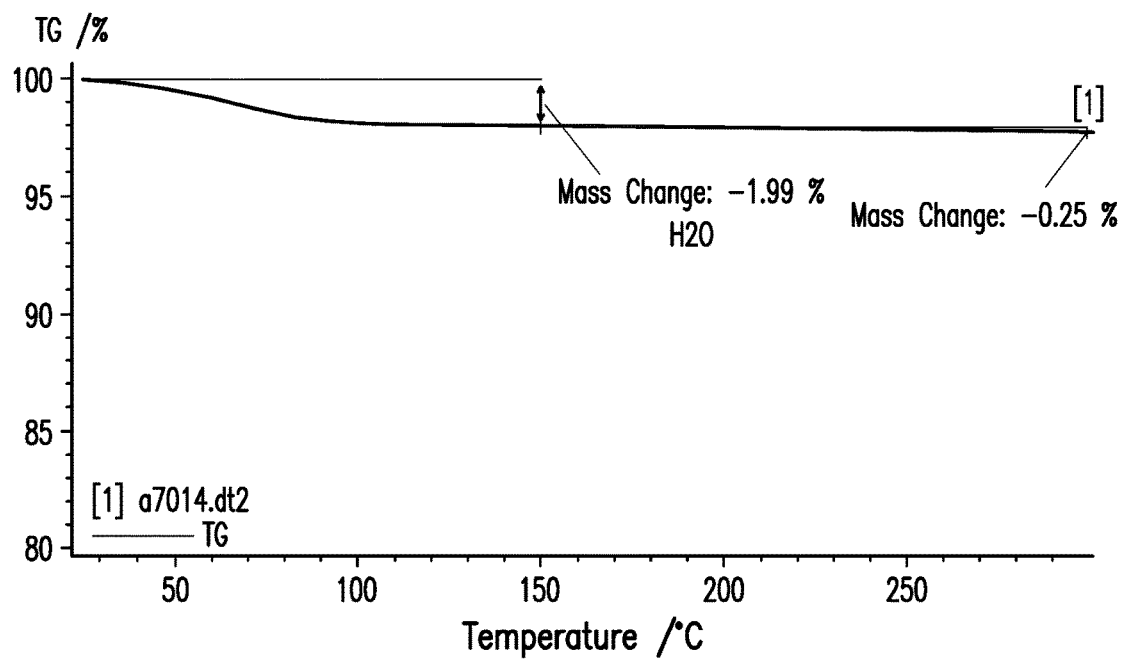

FIG. 14 provides a representative TGA thermogram of Form D of a free base of Compound 1.

Figure 15:
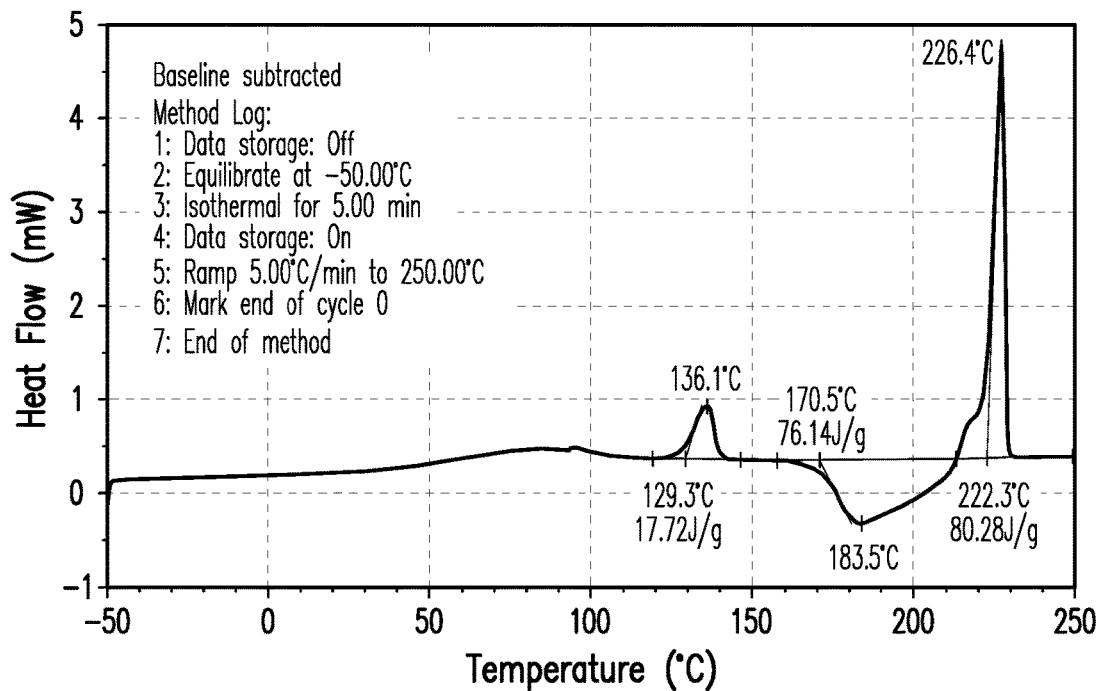

FIG. 15 provides a representative DSC thermogram of Form D of a free base of Compound 1.

Figure 16:
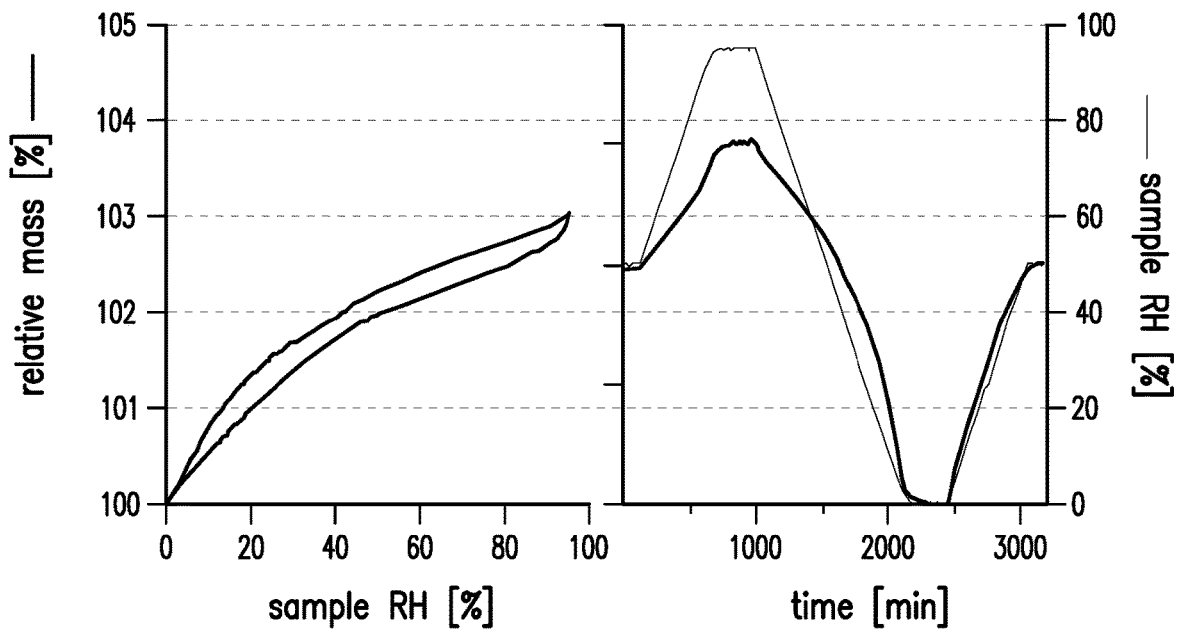

FIG. 16 provides a representative DVS isotherm plot of Form D of a free base of Compound 1.

Figure 17:
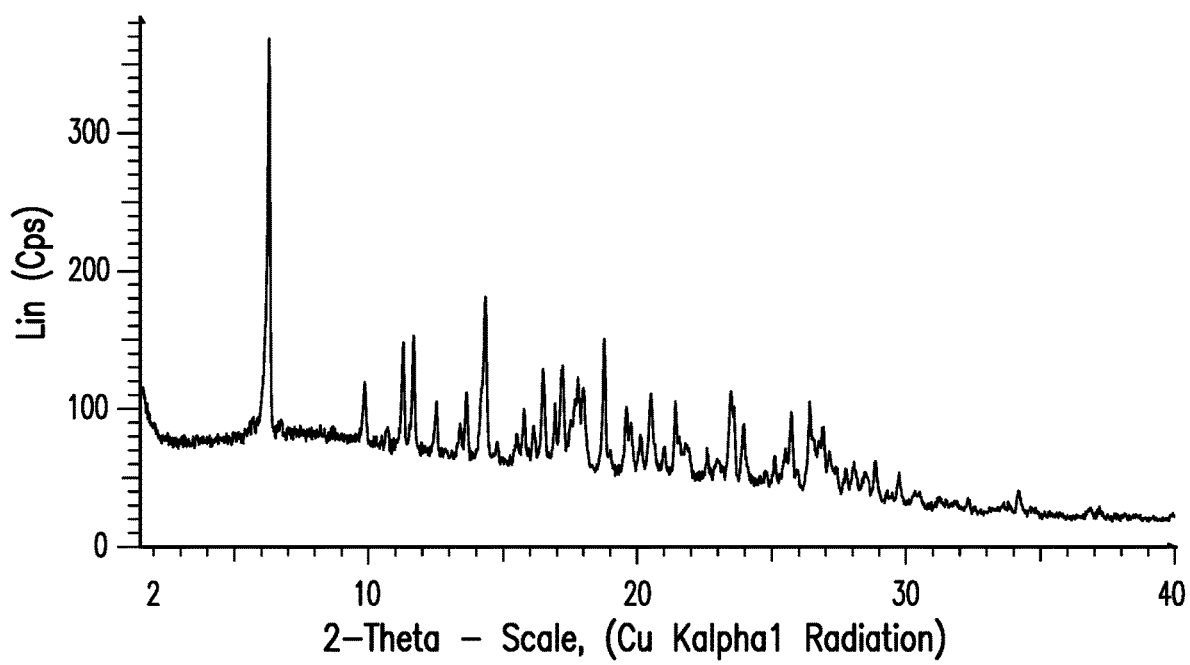

FIG. 17 provides a representative XRPD pattern of Form E of a free base of Compound 1.

Figure 18:
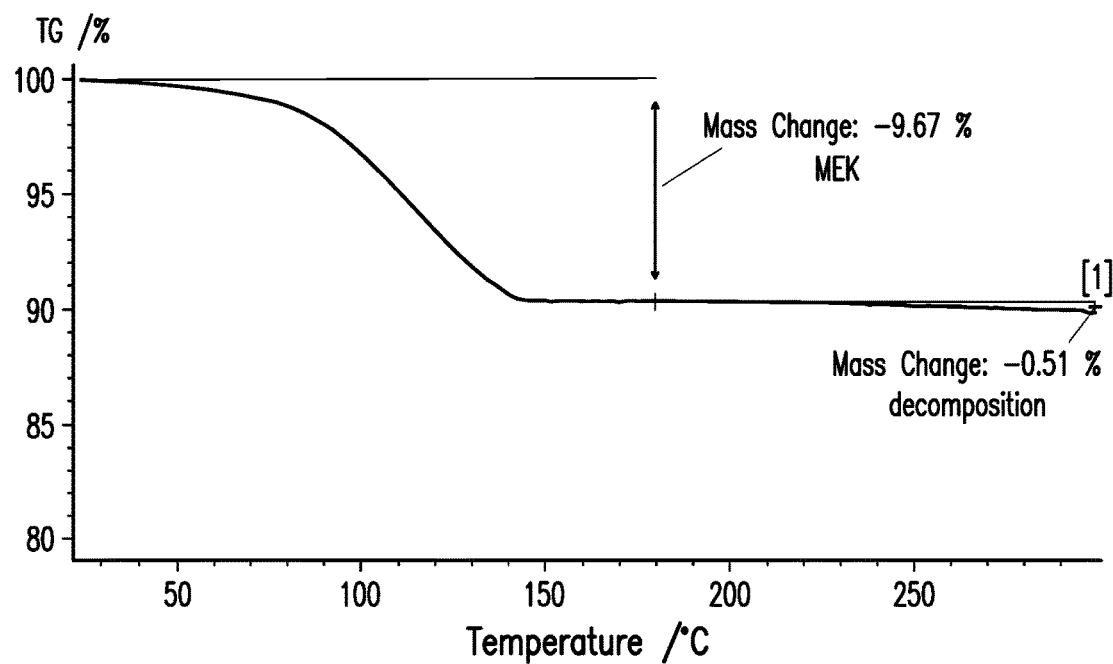

FIG. 18 provides a representative TGA thermogram of Form E of a free base of Compound 1.

Figure 19:
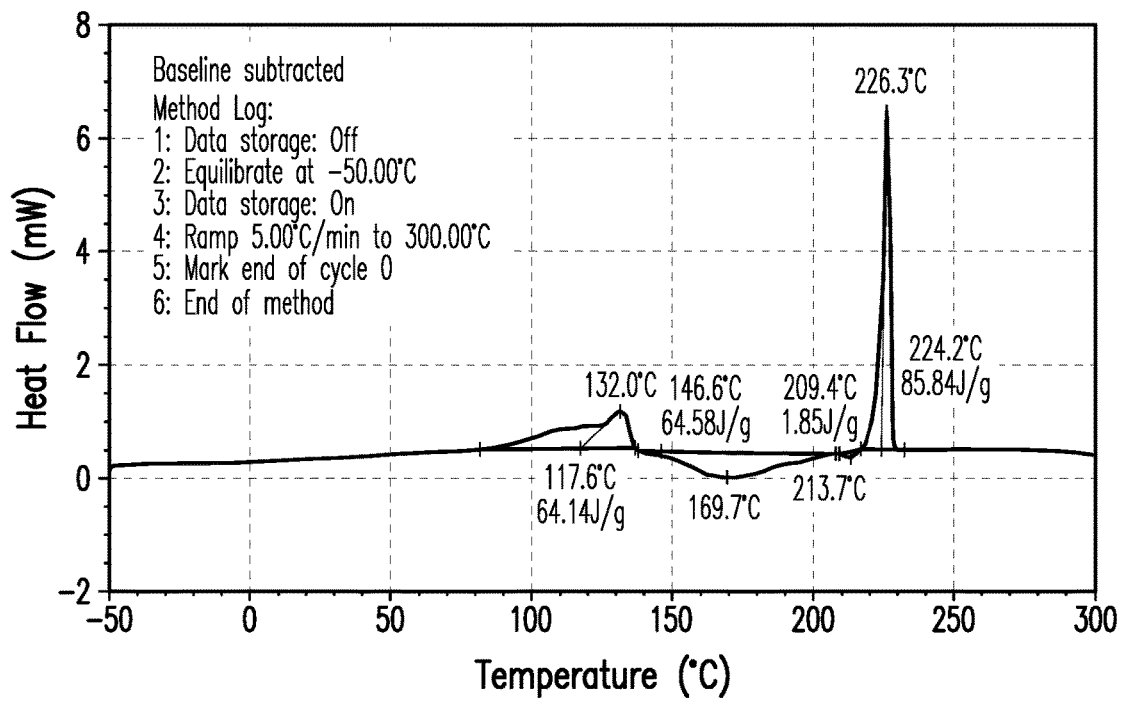

FIG. 19 provides a representative DSC thermogram of Form E of a free base of Compound 1.

Figure 20:
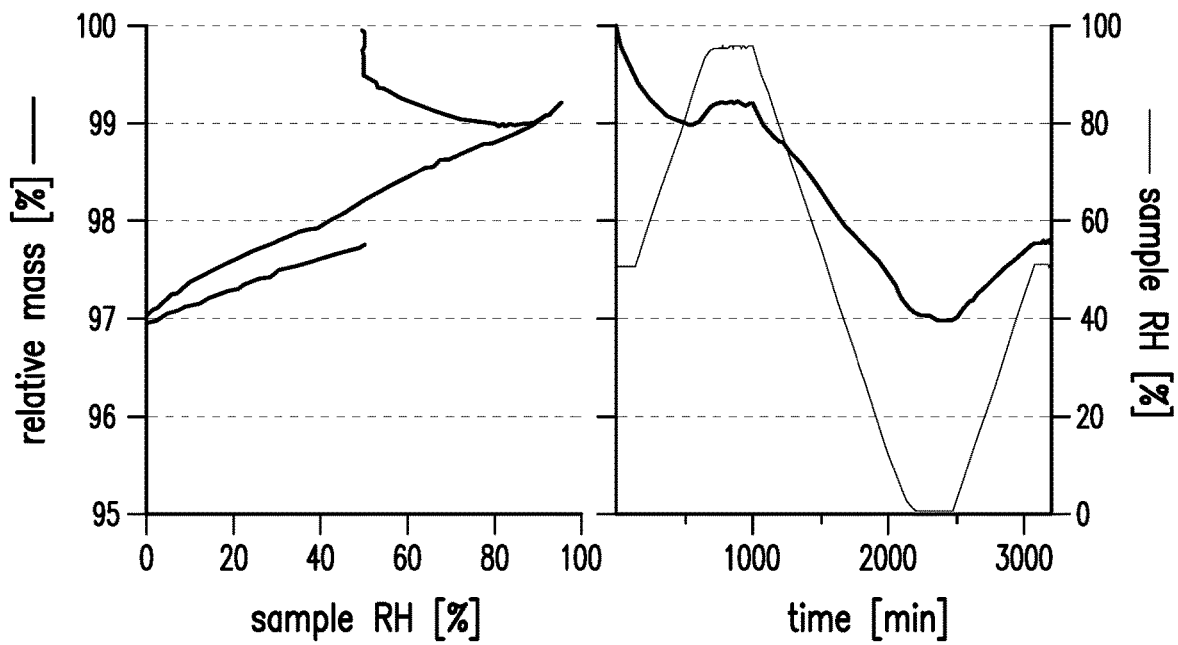

FIG. 20 provides a representative DVS isotherm plot of Form E of a free base of Compound 1.

Figure 21:
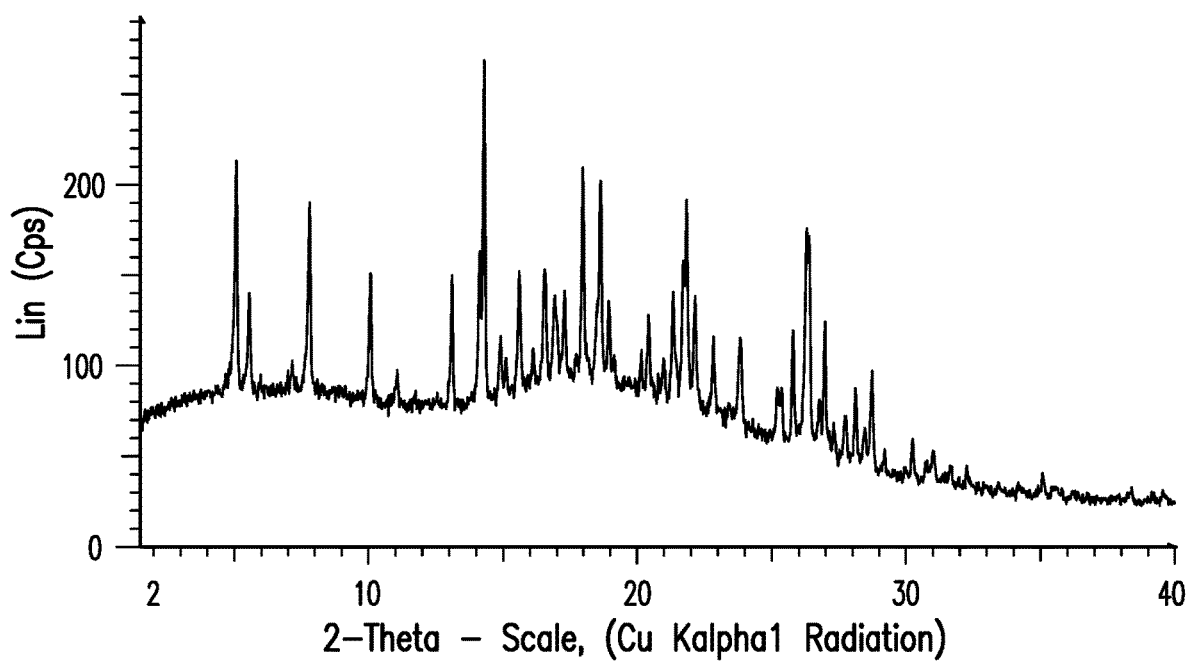

FIG. 21 provides a representative XRPD pattern of Form F of a free base of Compound 1.

Figure 22:
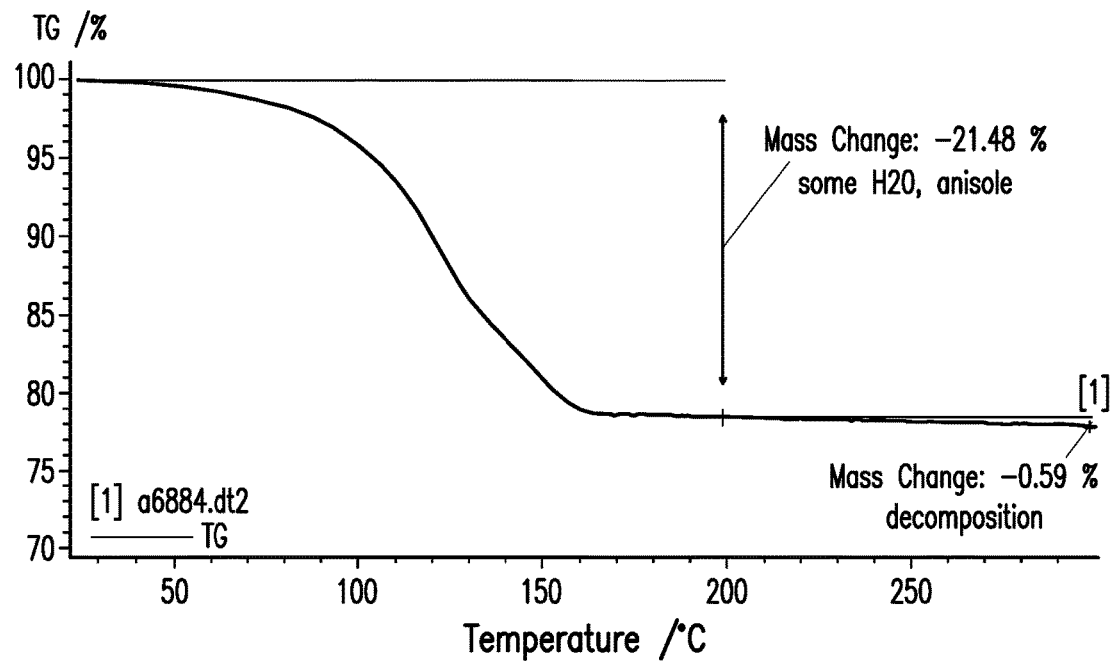

FIG. 22 provides a representative TGA thermogram of Form F of a free base of Compound 1.

Figure 23:
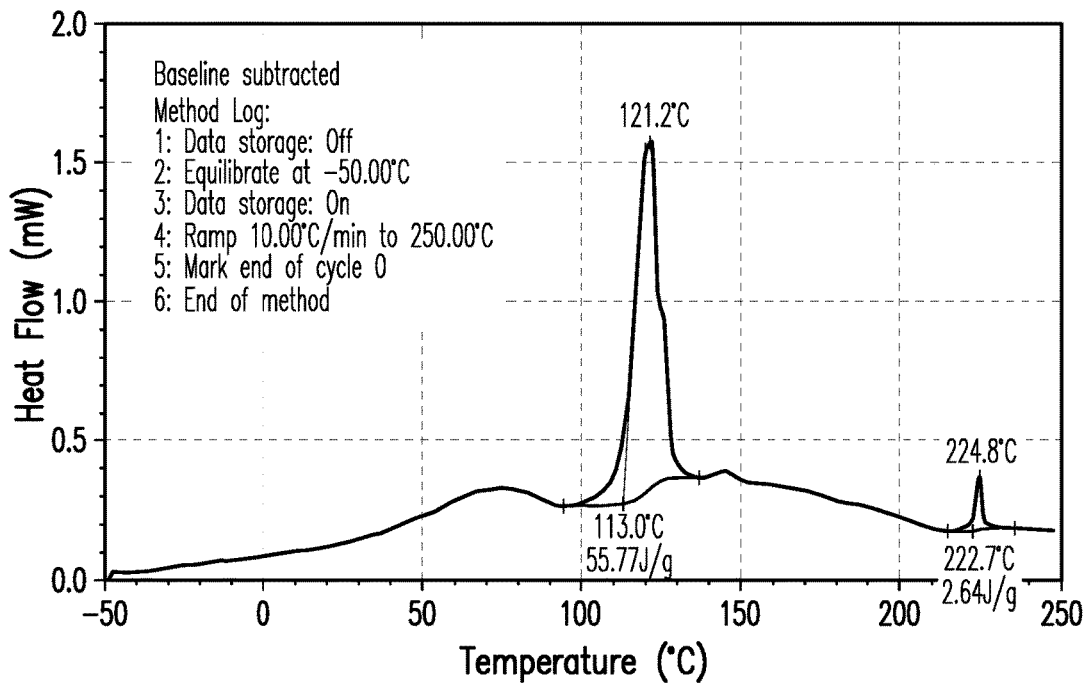

FIG. 23 provides a representative DSC thermogram of Form F of a free base of Compound 1.

Figure 24:
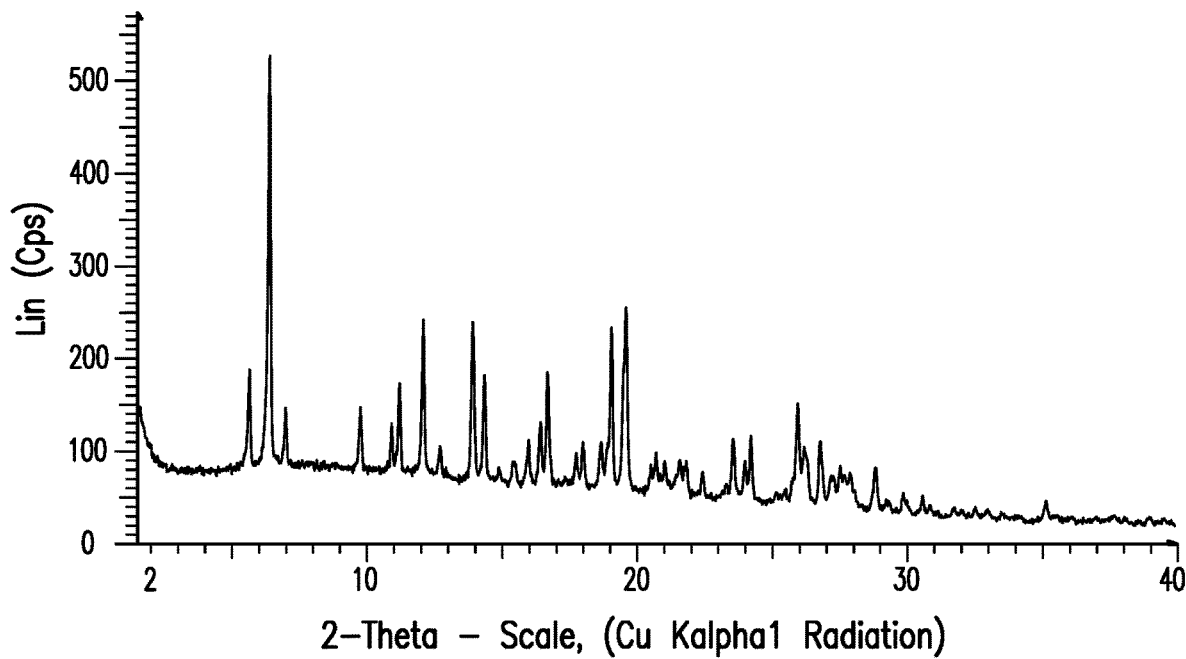

FIG. 24 provides a representative XRPD pattern of Form G of a free base of Compound 1.

Figure 25:
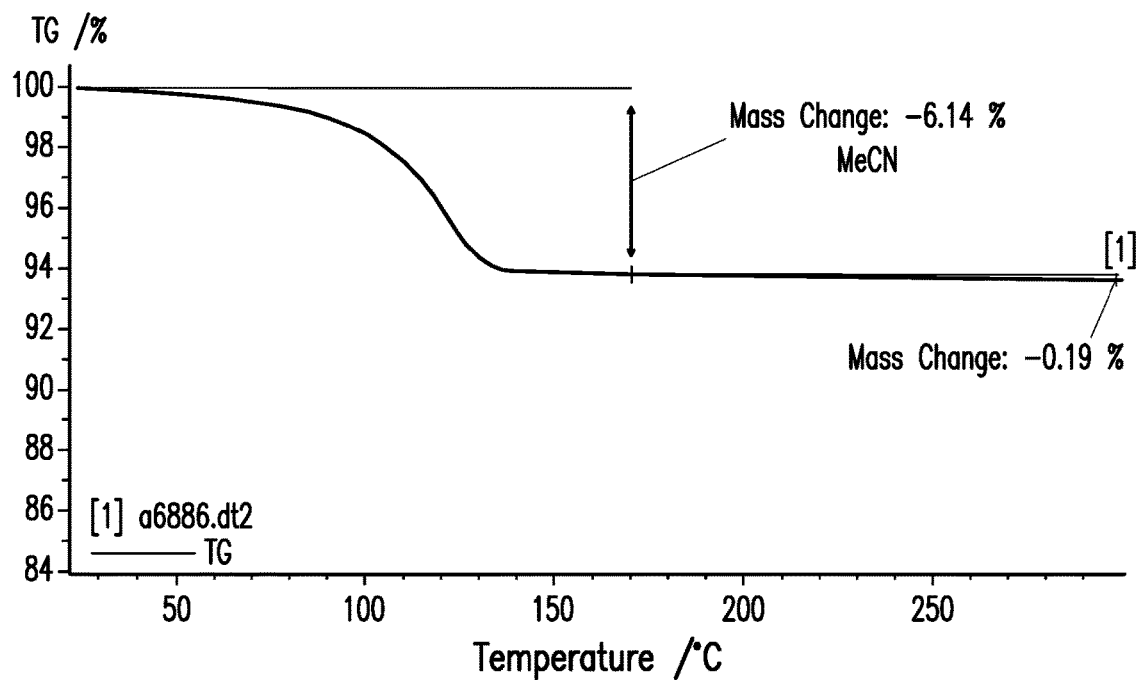

FIG. 25 provides a representative TGA thermogram of Form G of a free base of Compound 1.

Figure 26:
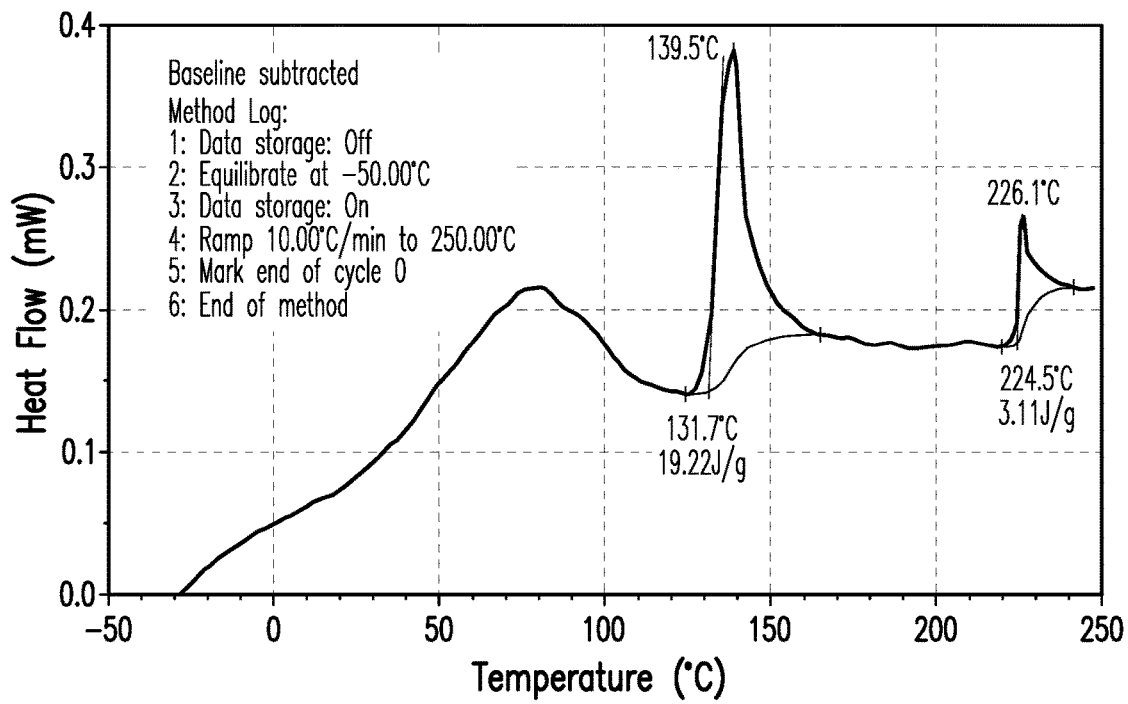

FIG. 26 provides a representative DSC thermogram of Form G of a free base of Compound 1.

Figure 27:
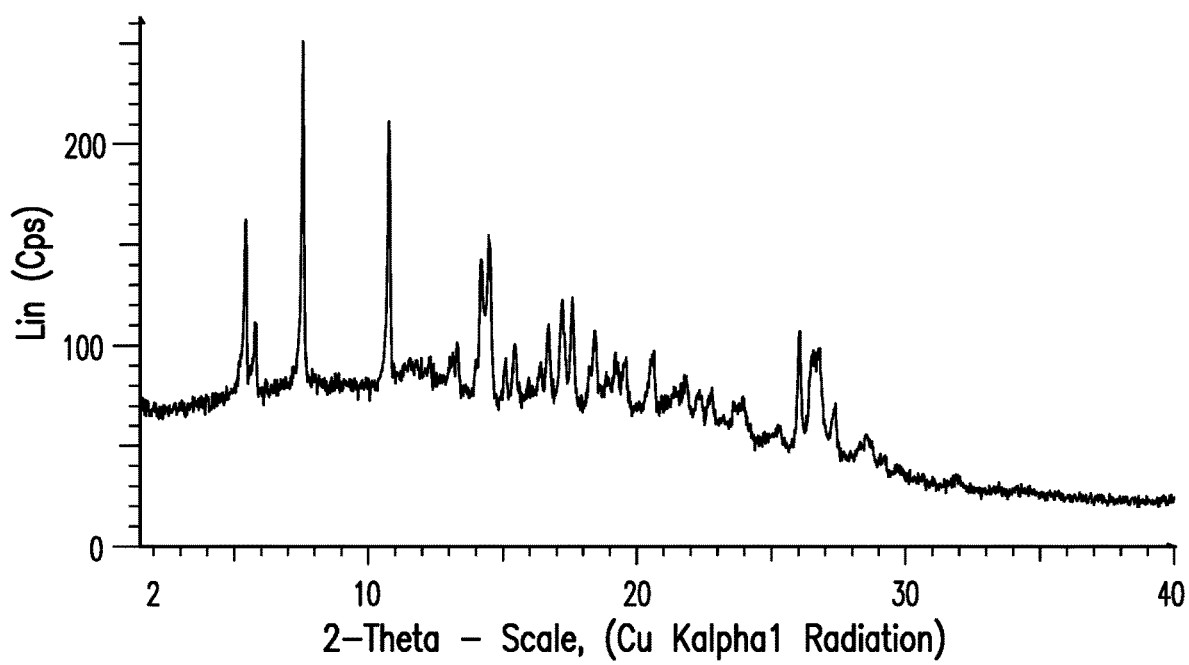

FIG. 27 provides a representative XRPD pattern of Form H of a free base of Compound 1.

Figure 28:
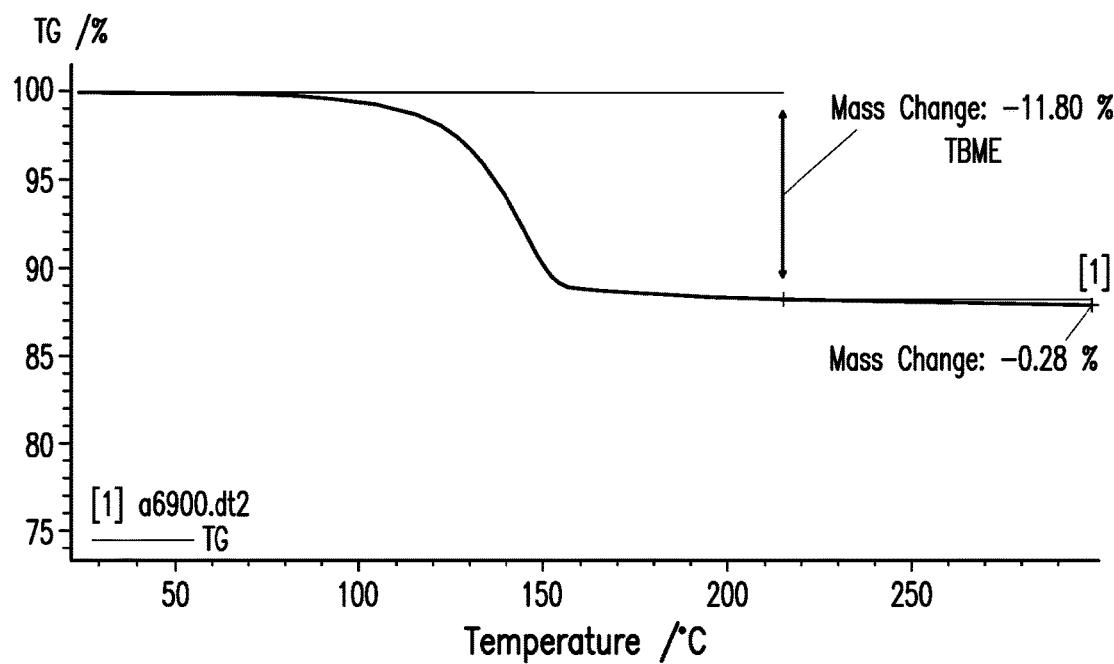

FIG. 28 provides a representative TGA thermogram of Form H of a free base of Compound 1.

Figure 29:
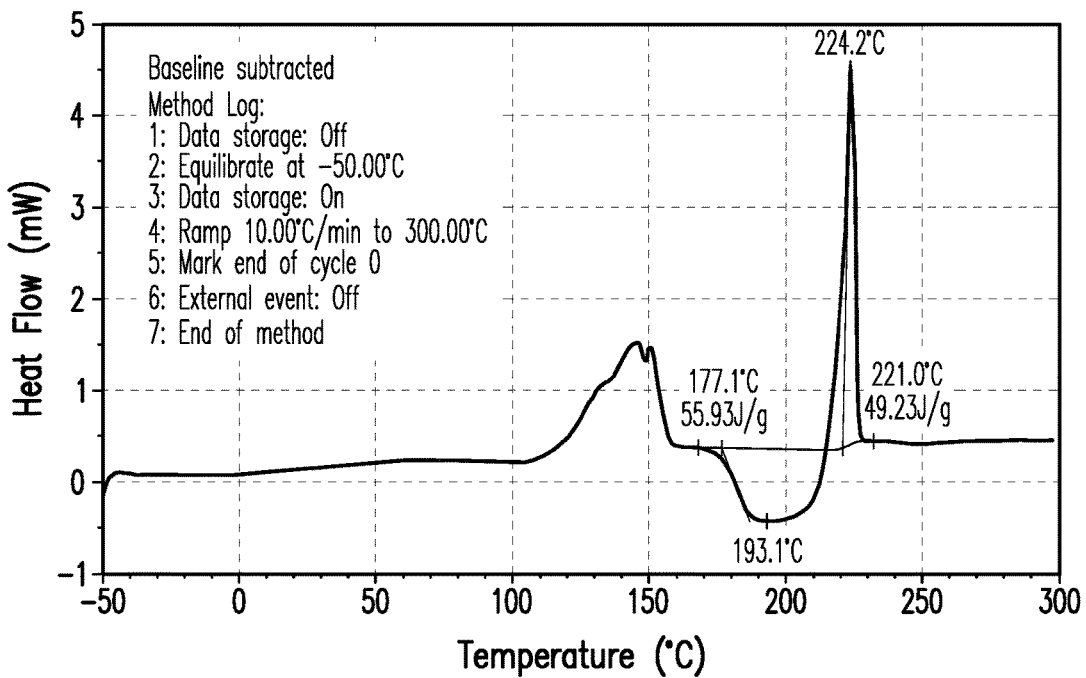

FIG. 29 provides a representative DSC thermogram of Form H of a free base of Compound 1.

Figure 30:
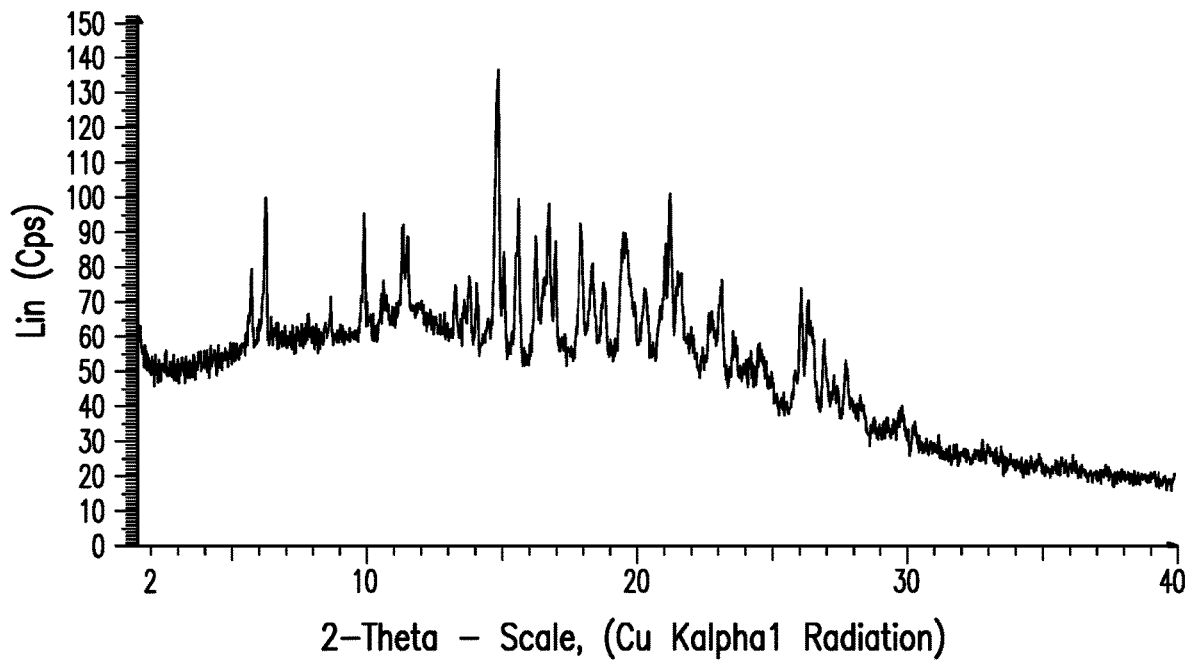

FIG. 30 provides a representative XRPD pattern of Form I of a free base of Compound 1.

Figure 31:
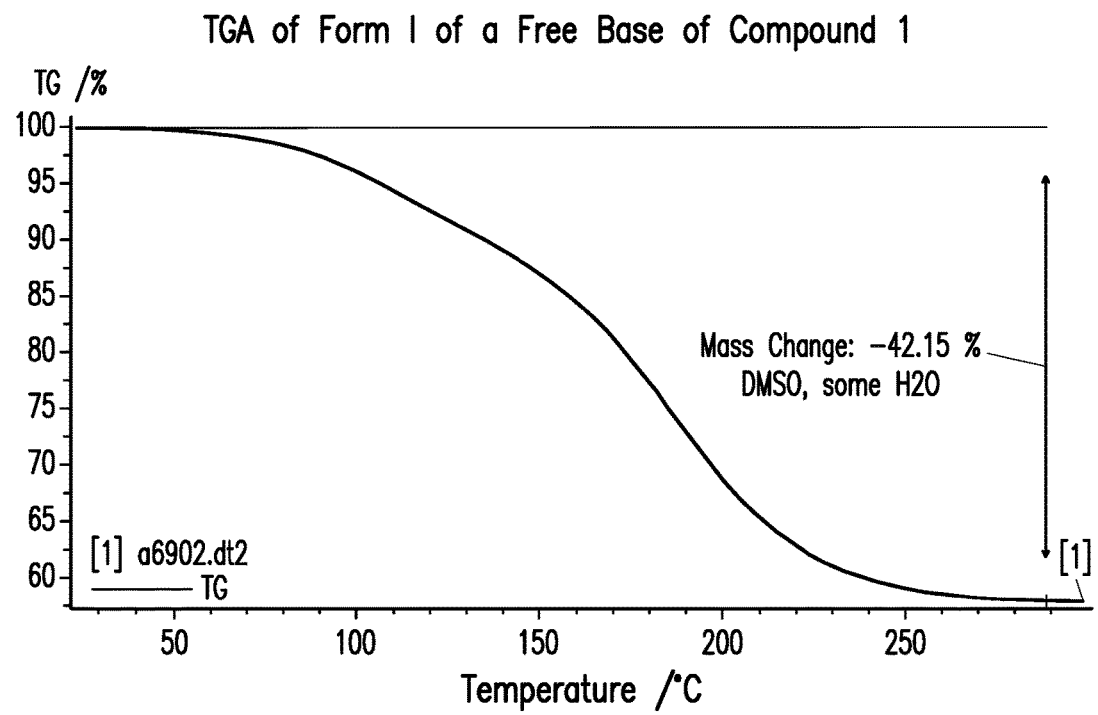

FIG. 31 provides a representative TGA thermogram of Form I of a free base of Compound 1.

Figure 32:
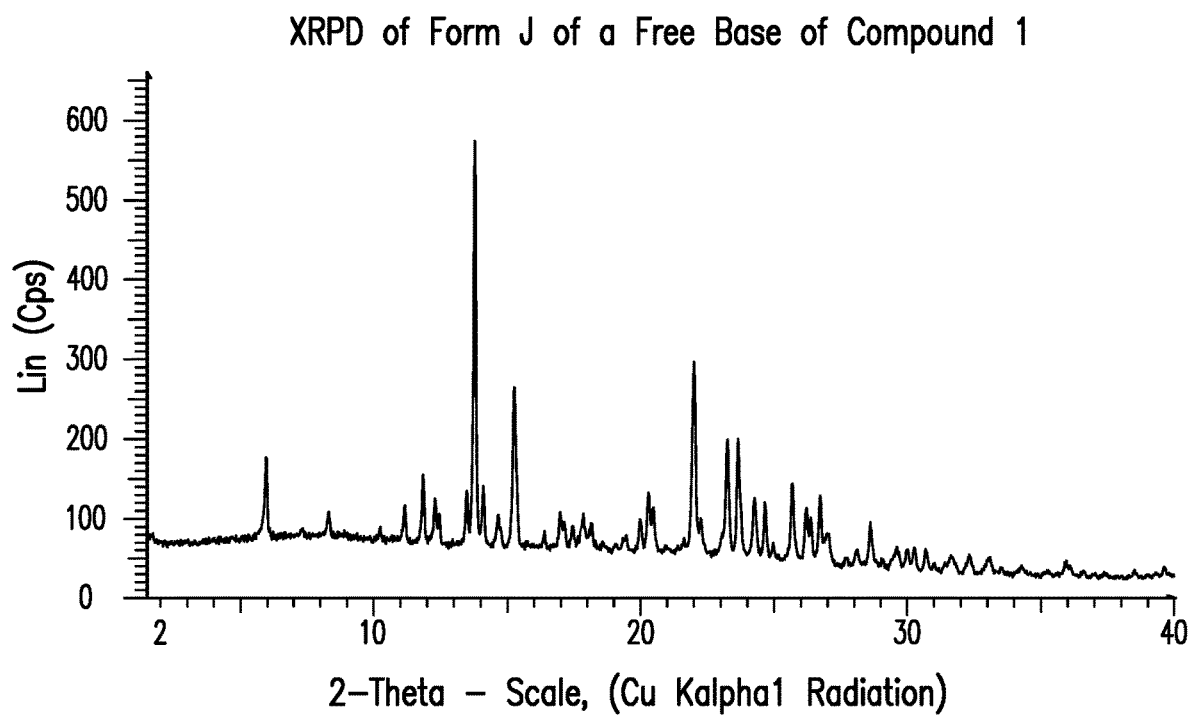

FIG. 32 provides a representative XRPD pattern of Form J of a free base of Compound 1.

Figure 33:
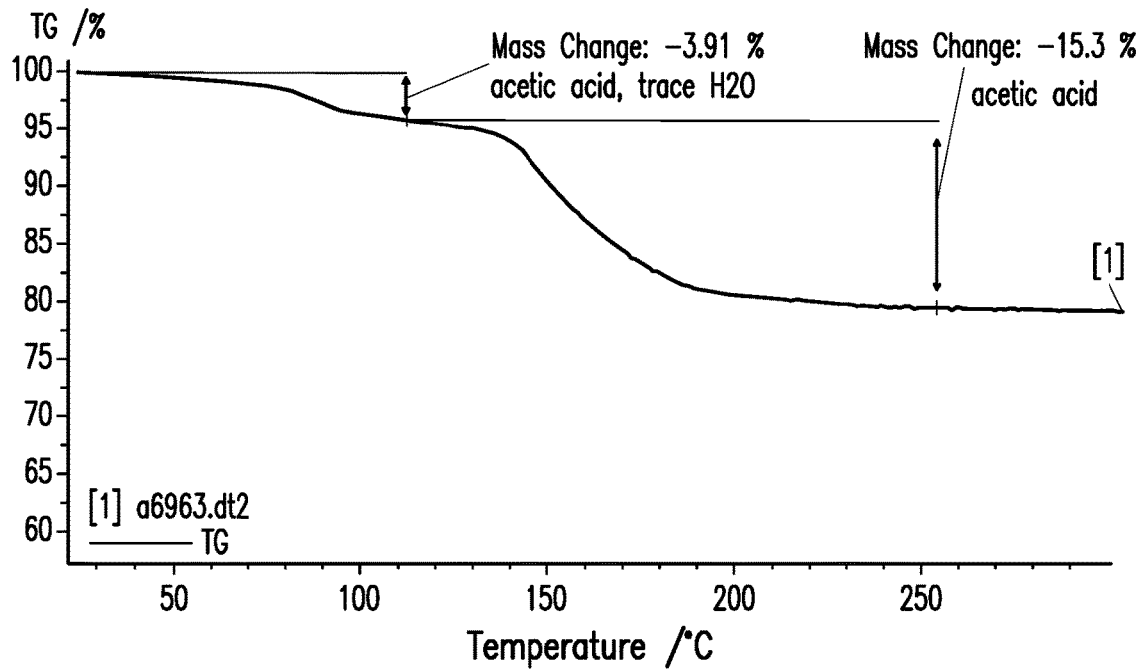

FIG. 33 provides a representative TGA thermogram of Form J of a free base of Compound 1.

Figure 34:
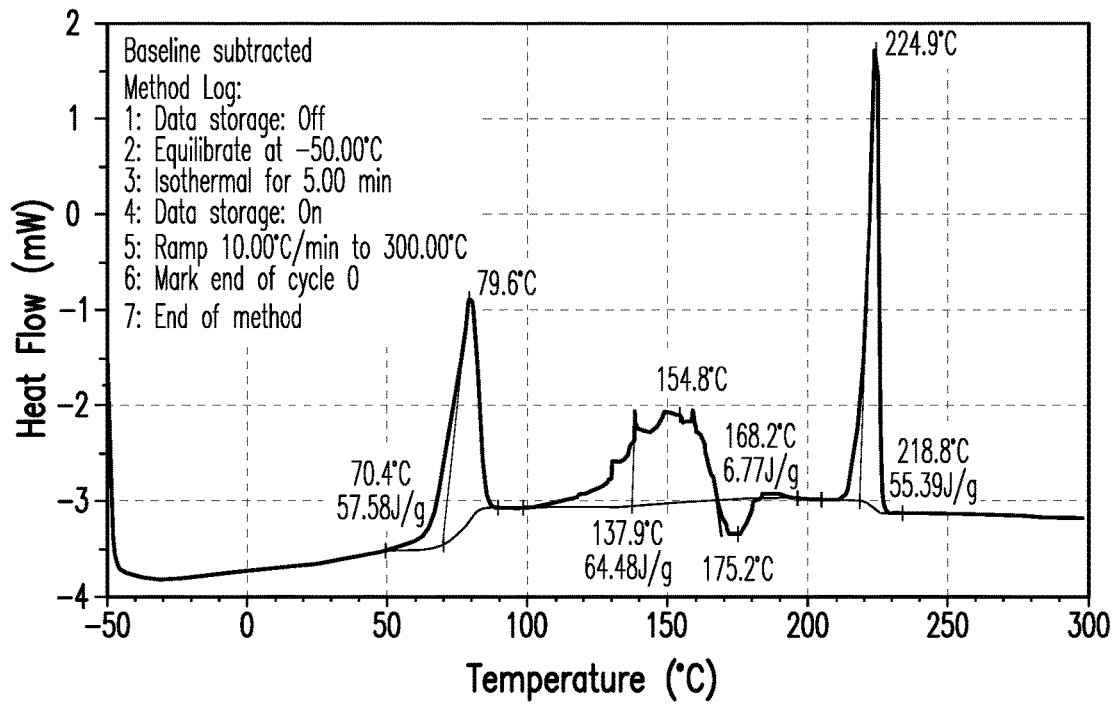

FIG. 34 provides a representative DSC thermogram of Form J of a free base of Compound 1.

Figure 35:
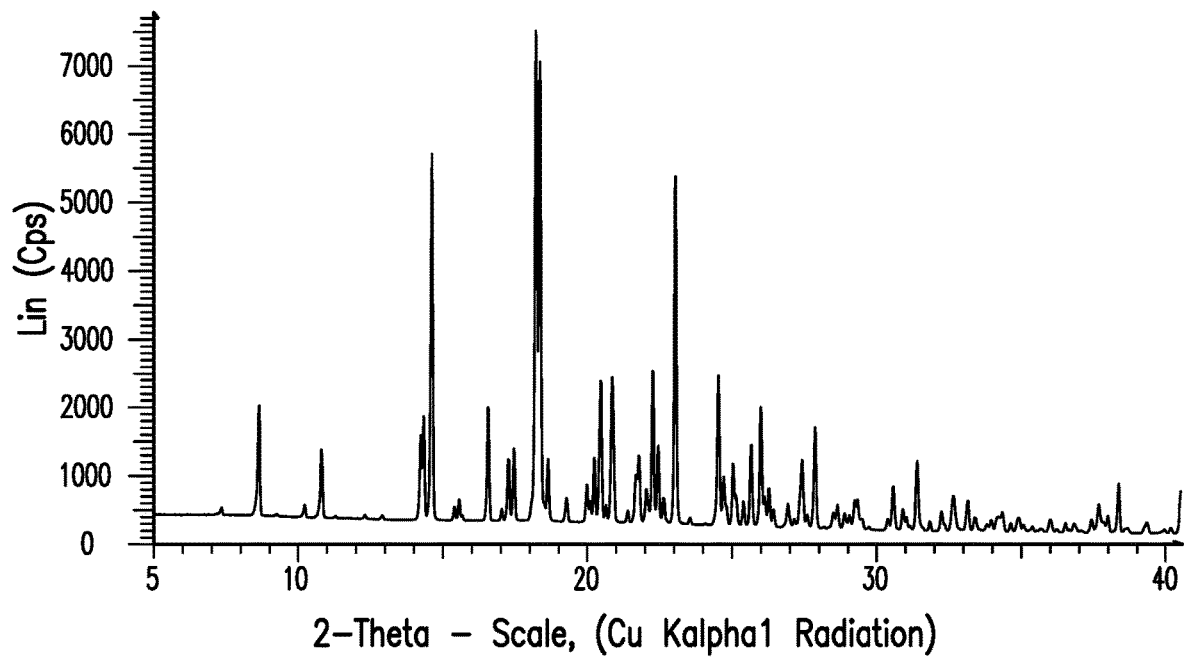

FIG. 35 provides a representative XRPD pattern of Form K of a free base of Compound 1.

Figure 36:
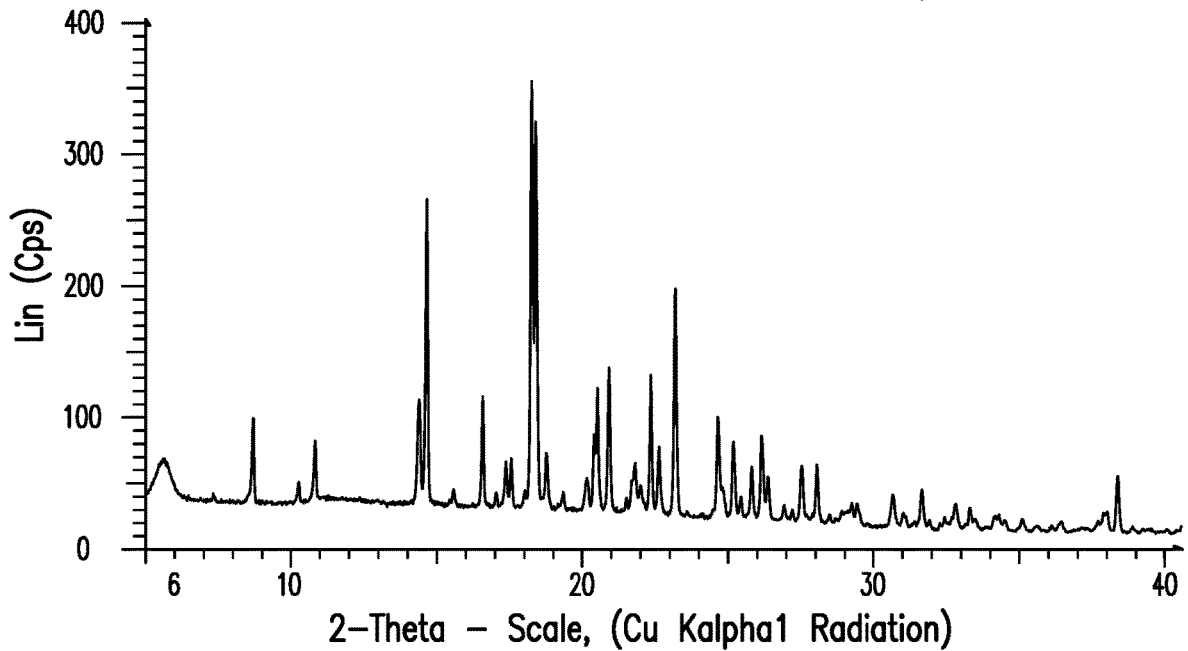

FIG. 36 provides a representative XRPD pattern of Form K' of a free base of Compound 1.

Figure 37:
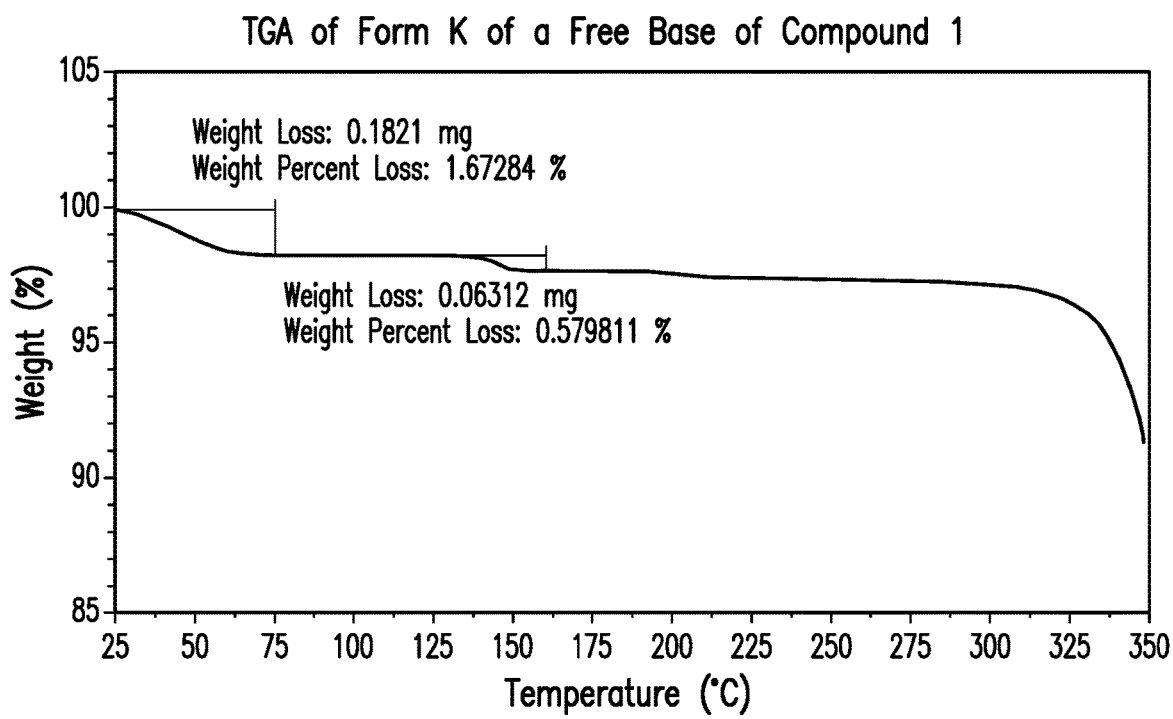

FIG. 37 provides a representative TGA thermogram of Form K of a free base of Compound 1.

Figure 38:
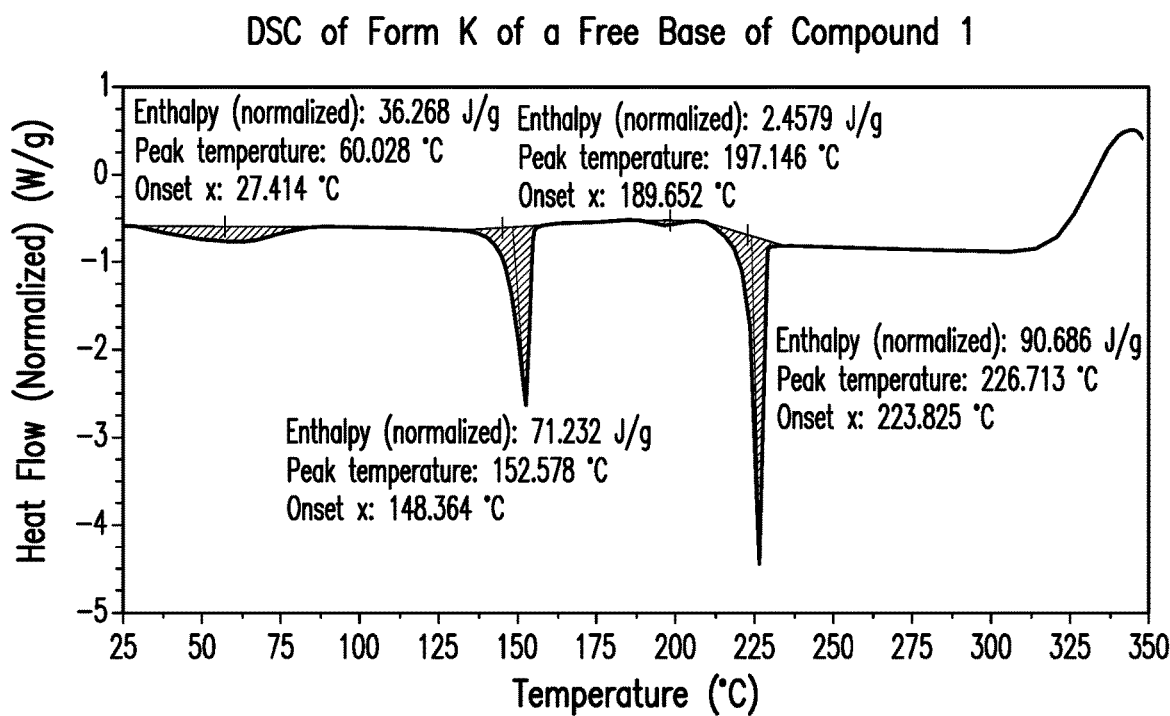

FIG. 38 provides a representative DSC thermogram of Form K of a free base of Compound 1.

Figure 39:
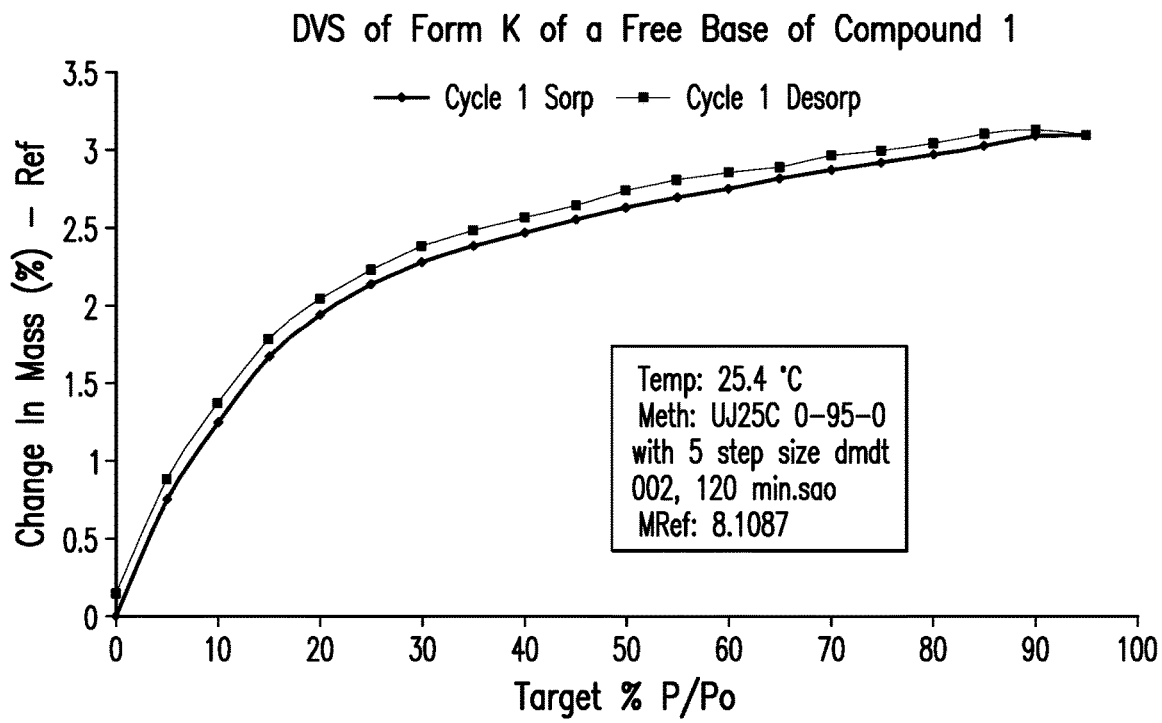

FIG. 39 provides a representative DVS isotherm plot of Form K of a free base of Compound 1.

Figure 40:
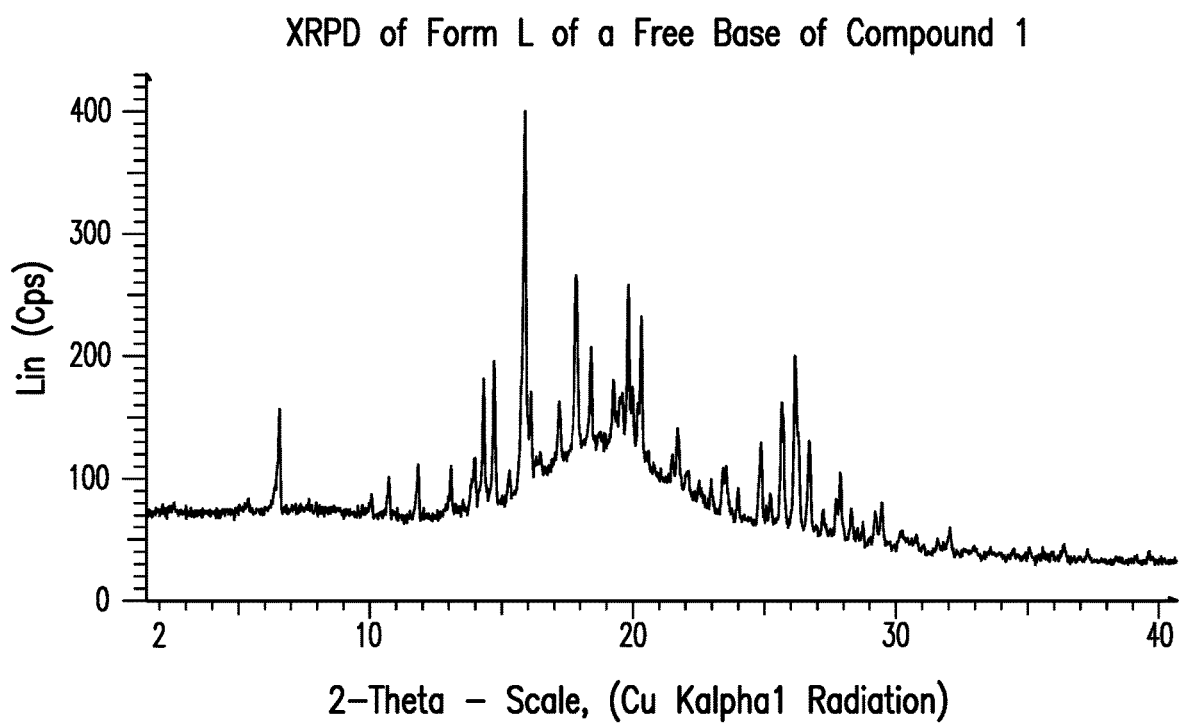

FIG. 40 provides a representative XRPD pattern of Form L of a free base of Compound 1.

Figure 41:
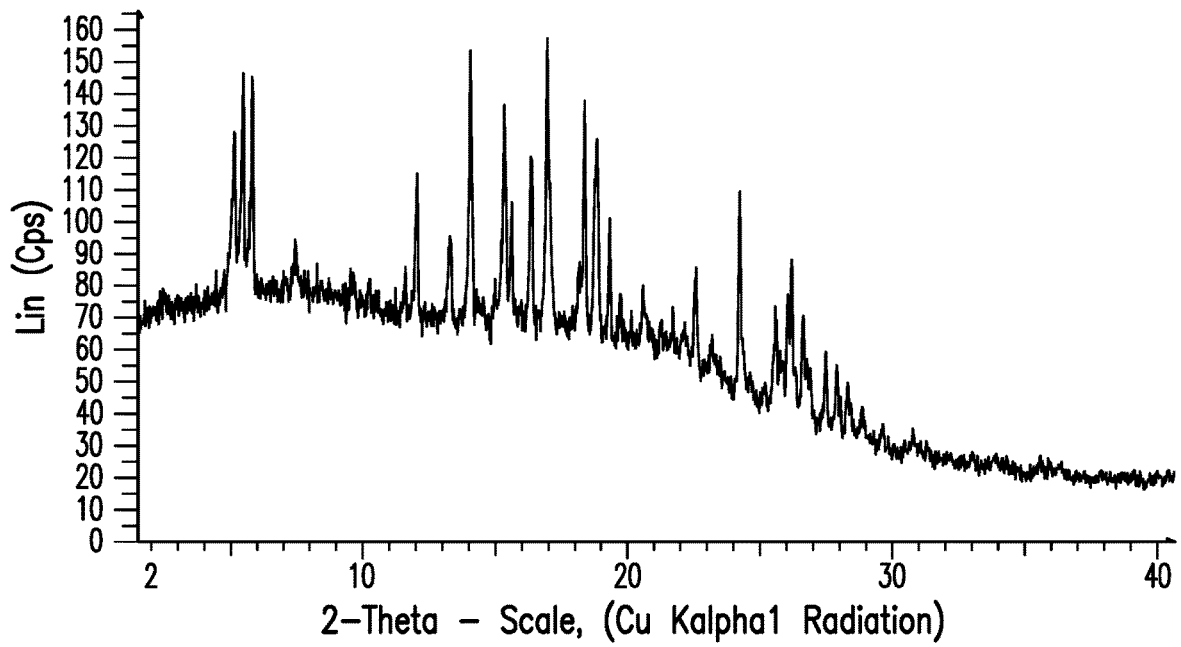

FIG. 41 provides a representative XRPD pattern of Form M of a free base of Compound 1.

Figure 42:
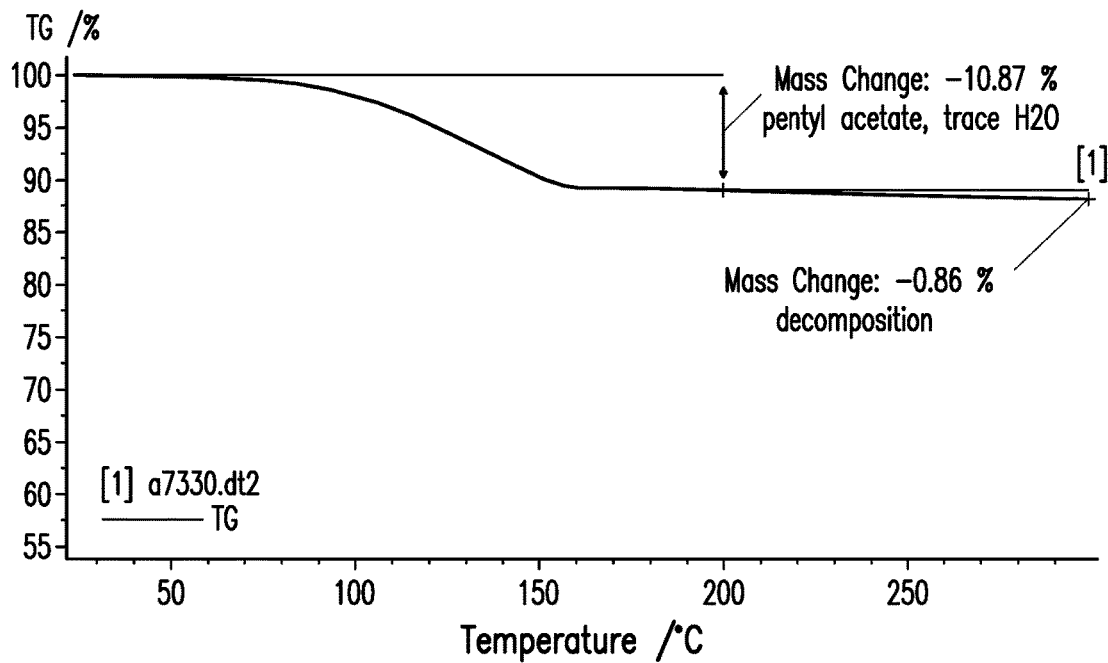

FIG. 42 provides a representative TGA thermogram of Form M of a free base of Compound 1.

Figure 43:
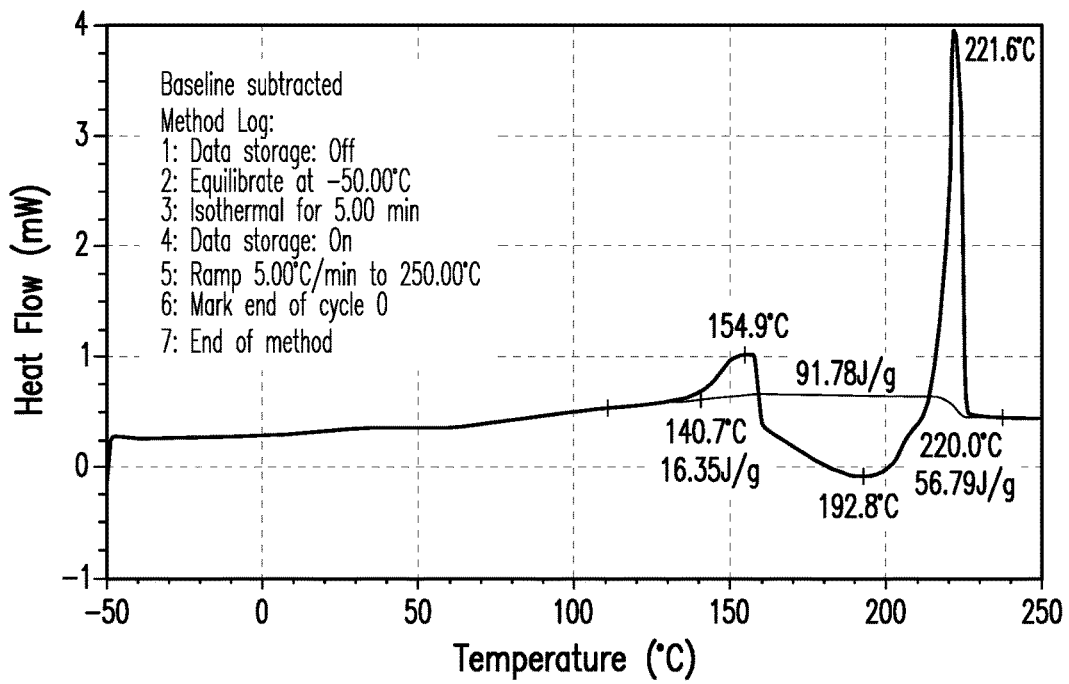

FIG. 43 provides a representative DSC thermogram of Form M of a free base of Compound 1.

Figure 44:
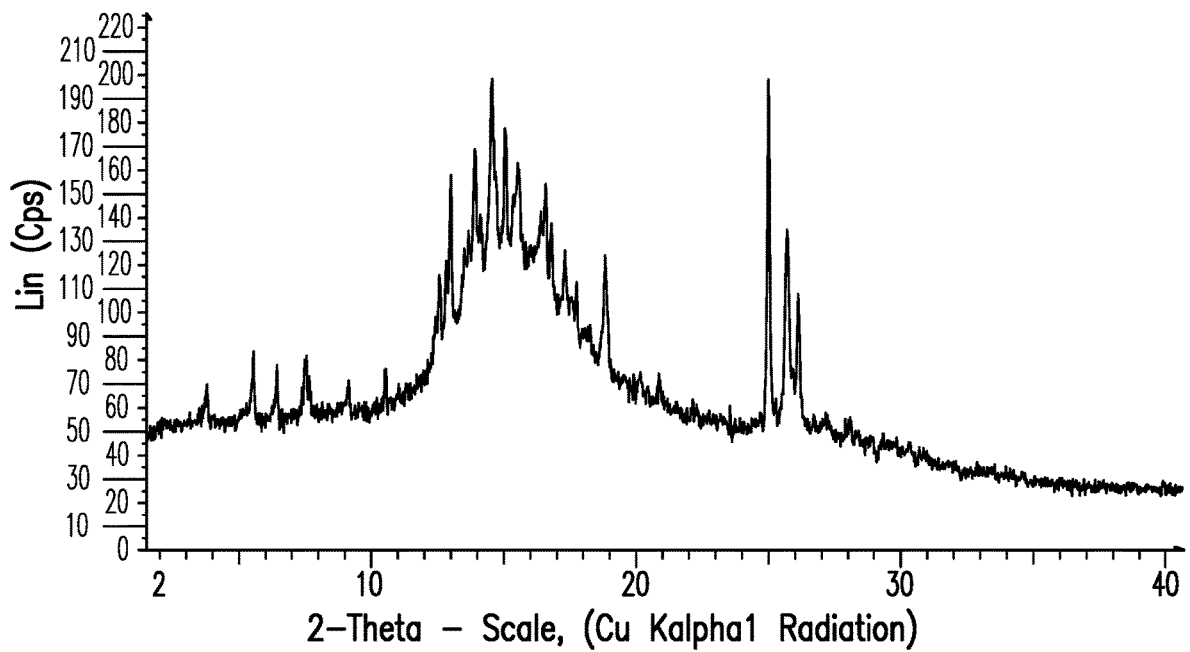

FIG. 44 provides a representative XRPD pattern of Form N of a free base of Compound 1.

Figure 45:
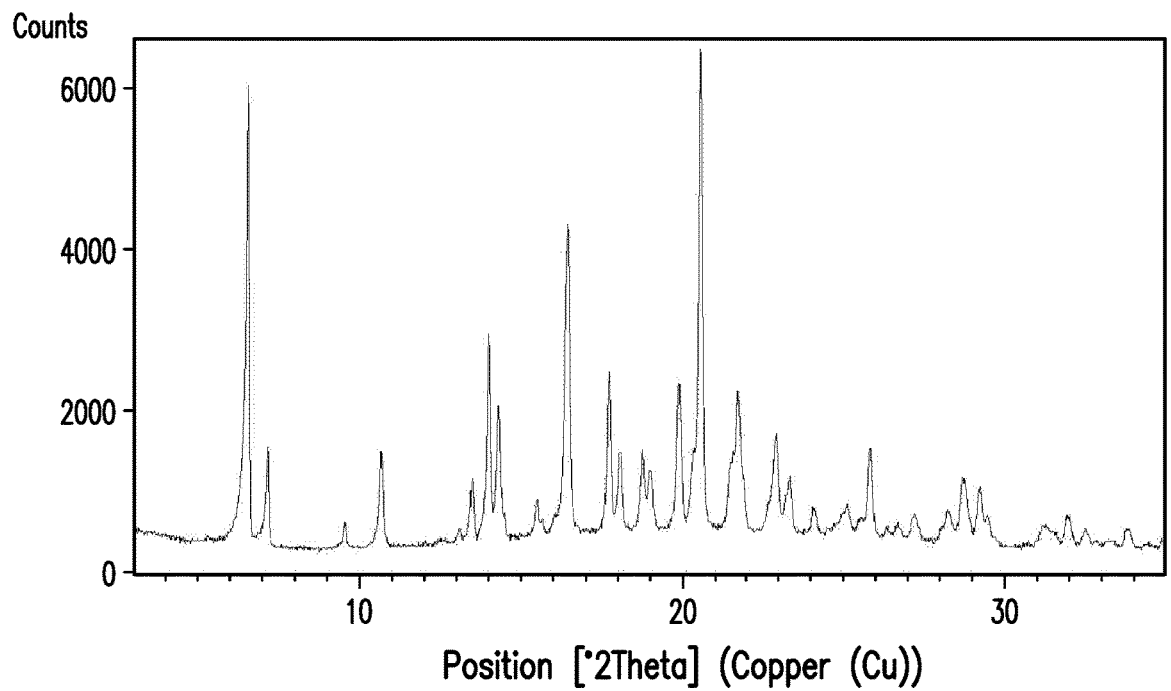

FIG. 45 provides a representative XRPD pattern of Form O of a free base of Compound 1.

Figure 46:
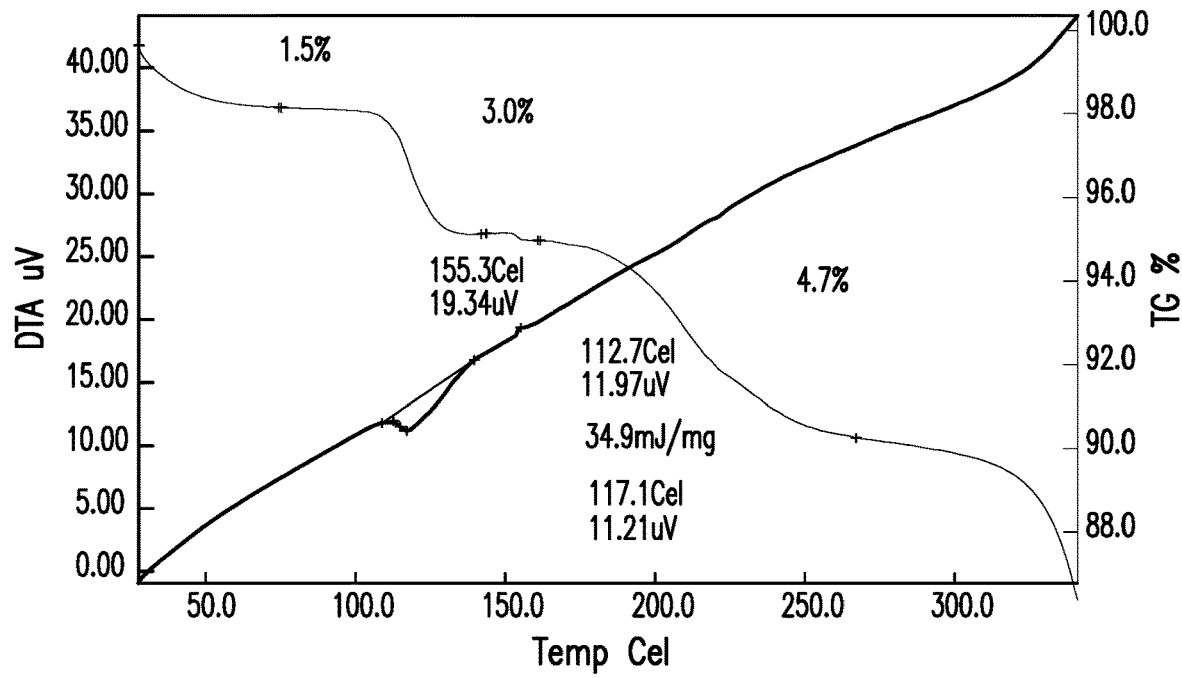

FIG. 46 provides representative TG/DTA thermograms of Form O of a free base of Compound 1.

Figure 47:
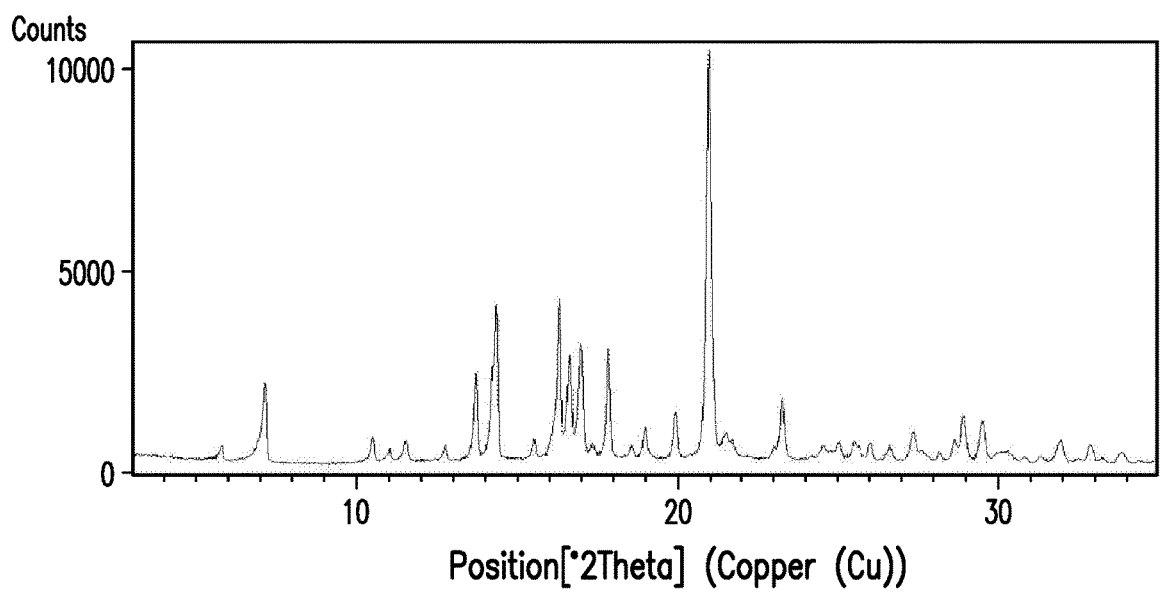

FIG. 47 provides a representative XRPD pattern of Form P of a free base of Compound 1.

Figure 48:
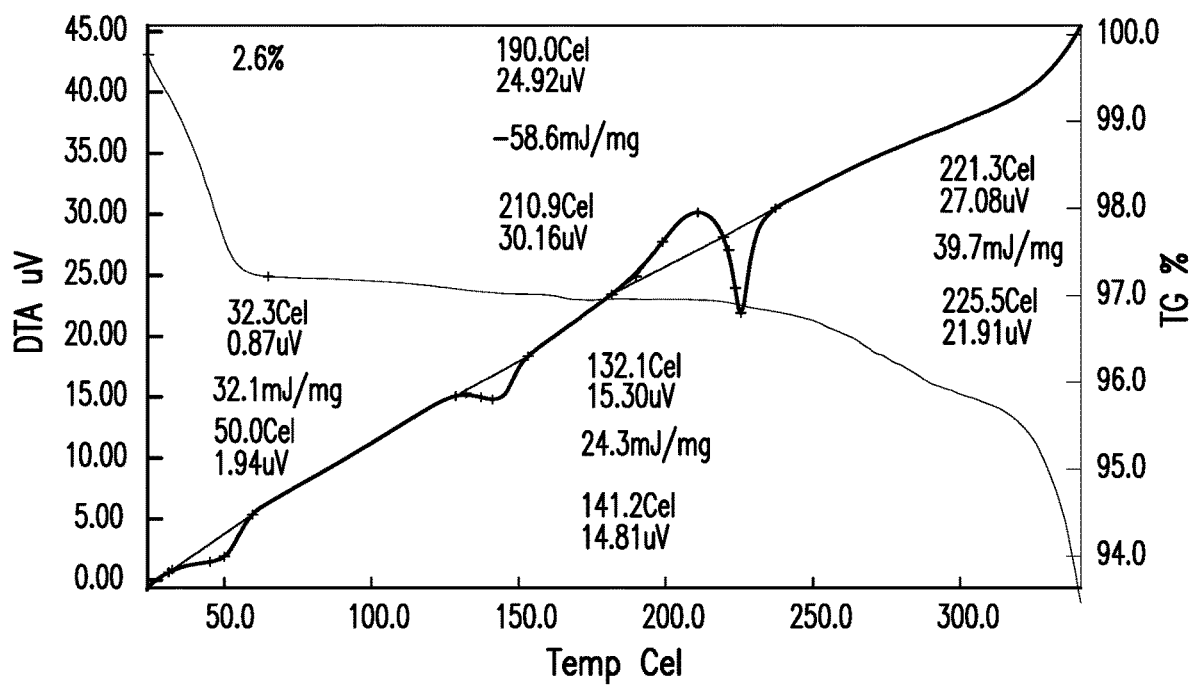

FIG. 48 provides representative TG/DTA thermograms of Form P of a free base of Compound 1.

Figure 49:
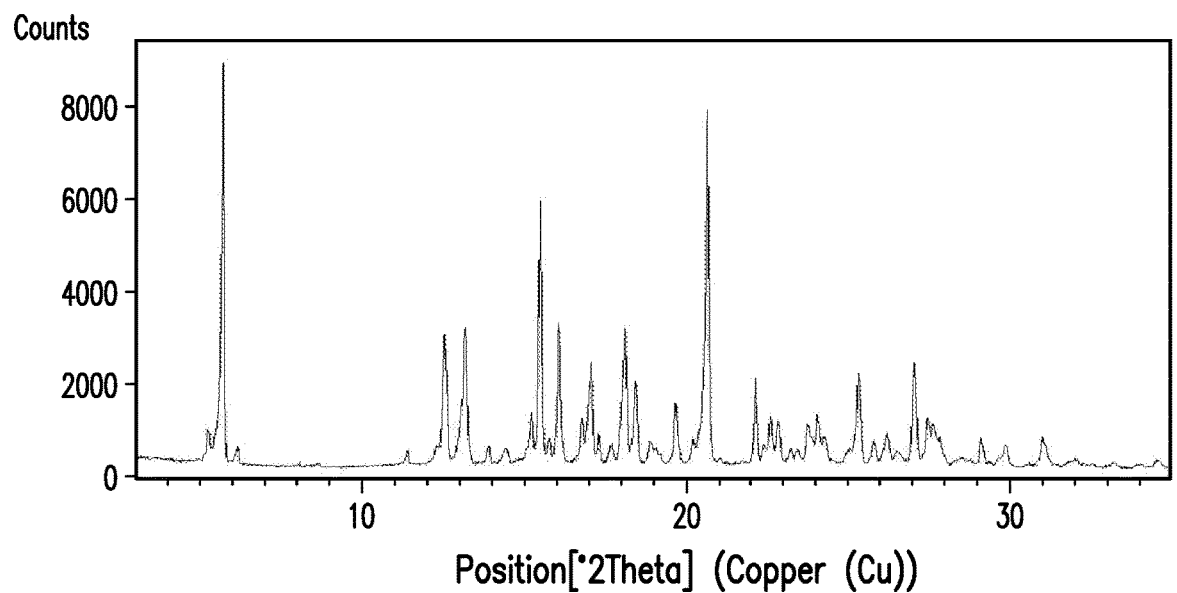

FIG. 49 provides a representative XRPD pattern of Form Q of a free base of Compound 1.

Figure 50:
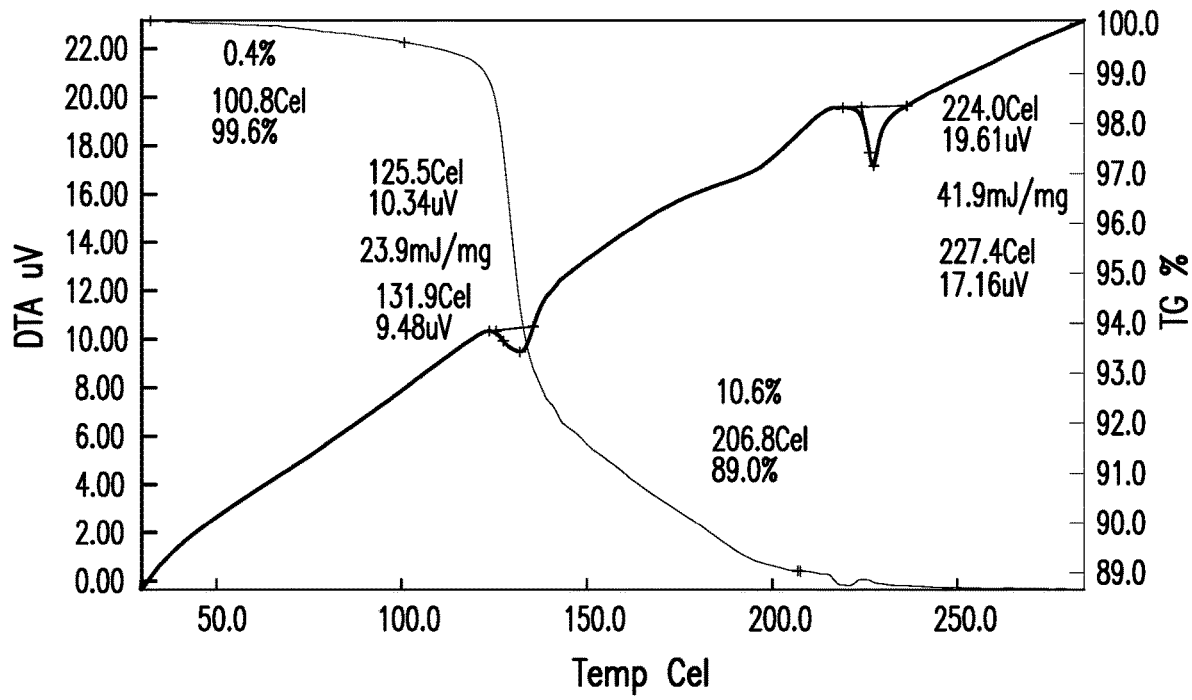

FIG. 50 provides representative TG/DTA thermograms of Form Q of a free base of Compound 1.

Figure 51:
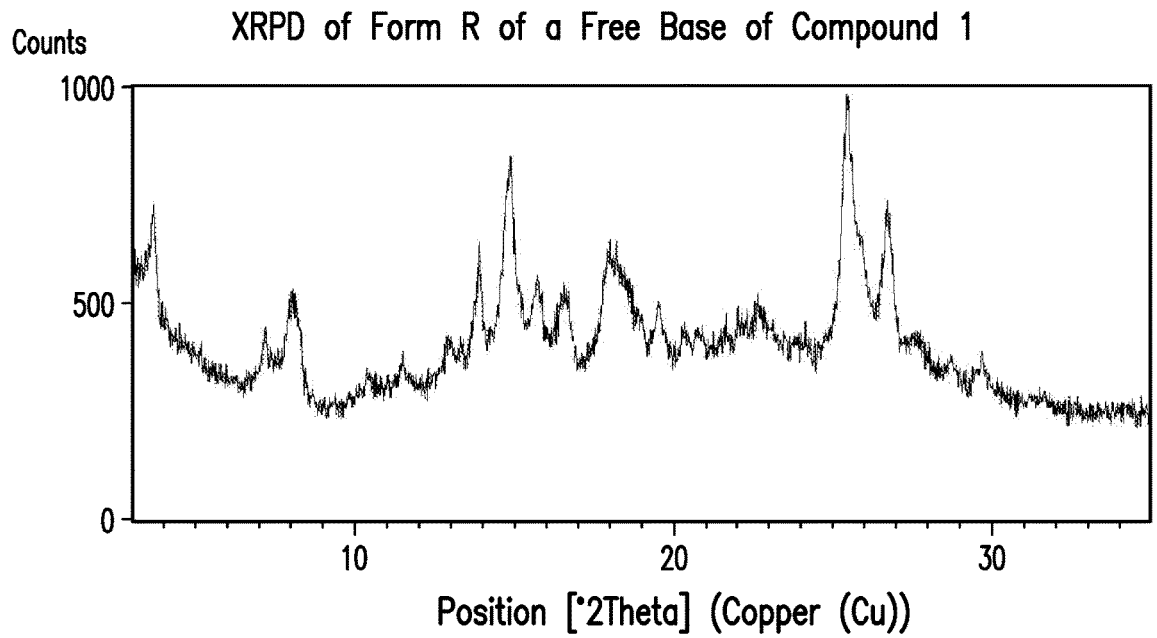

FIG. 51 provides a representative XRPD pattern of Form R of a free base of Compound 1.

Figure 52:
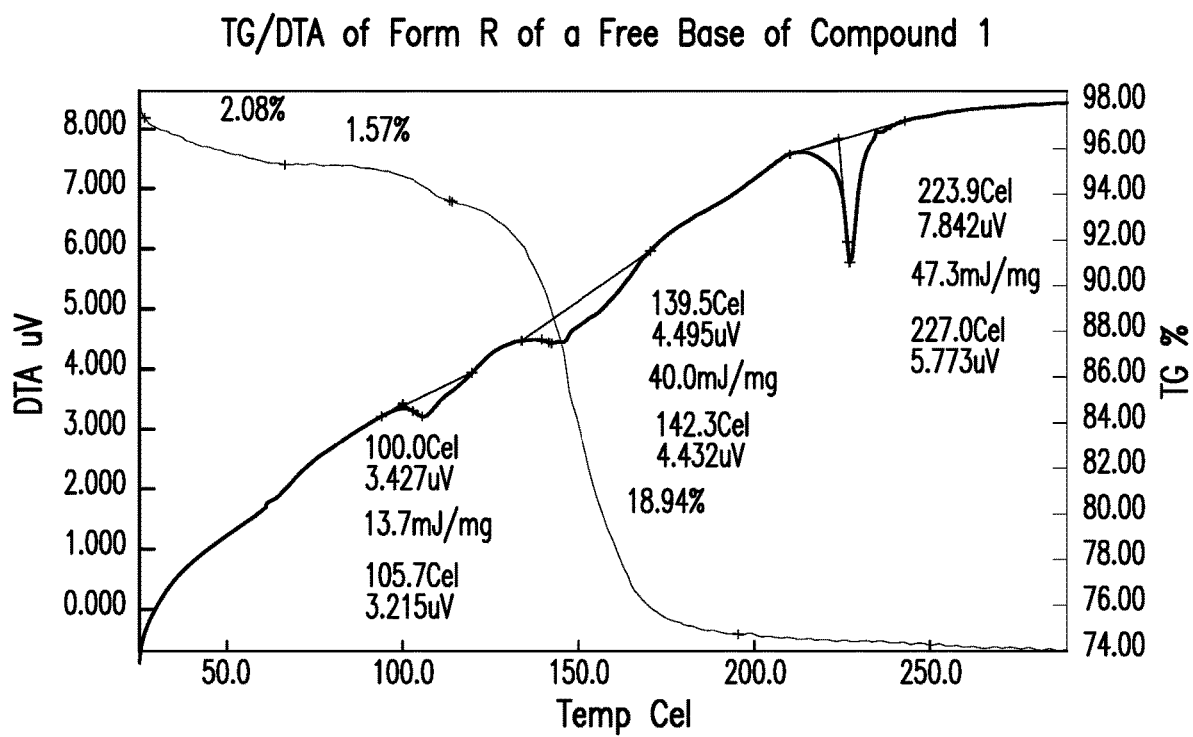

FIG. 52 provides representative TG/DTA thermograms of Form R of a free base of Compound 1.

Figure 53:
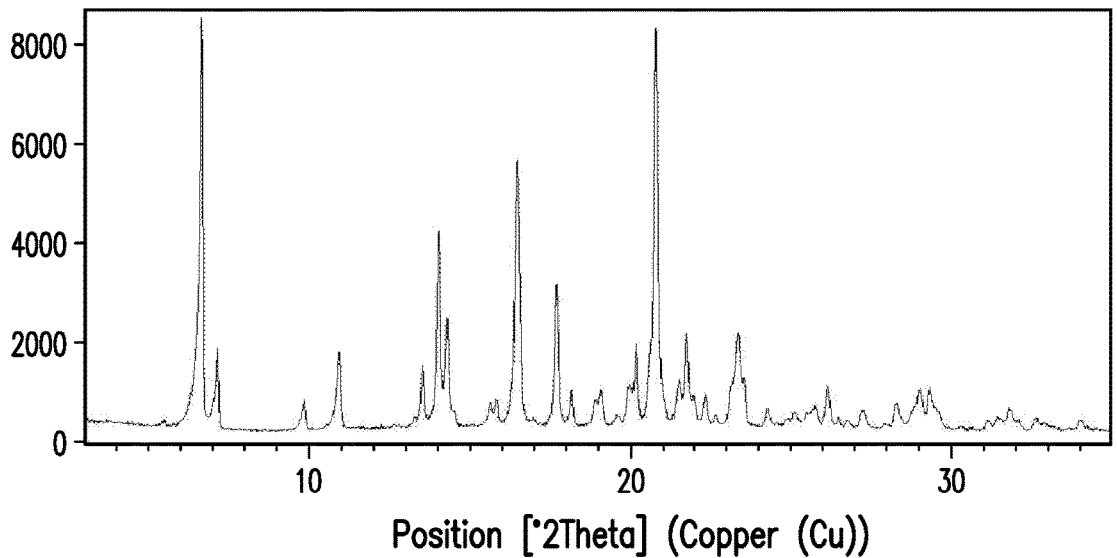

FIG. 53 provides a representative XRPD pattern of Form S of a free base of Compound 1.

Figure 54:
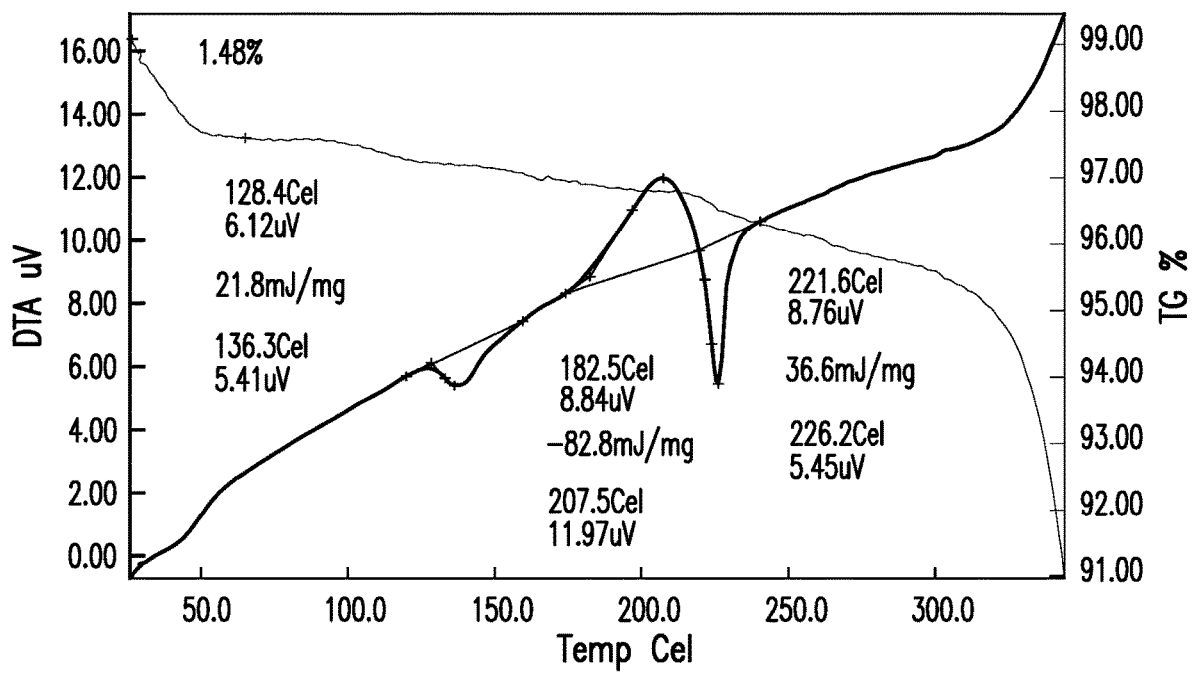

FIG. 54 provides representative TG/DTA thermograms of Form S of a free base of Compound 1.

Figure 55:
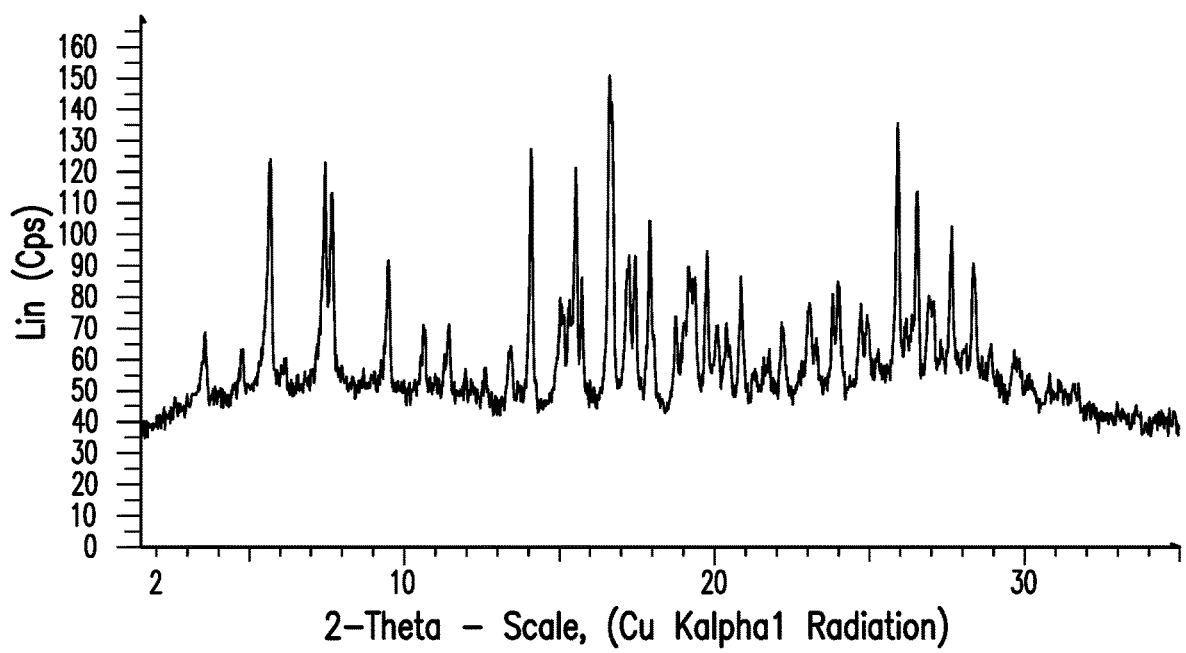

FIG. 55 provides a representative XRPD pattern of Form A of a hydrochloride salt of Compound 1.

Figure 56:
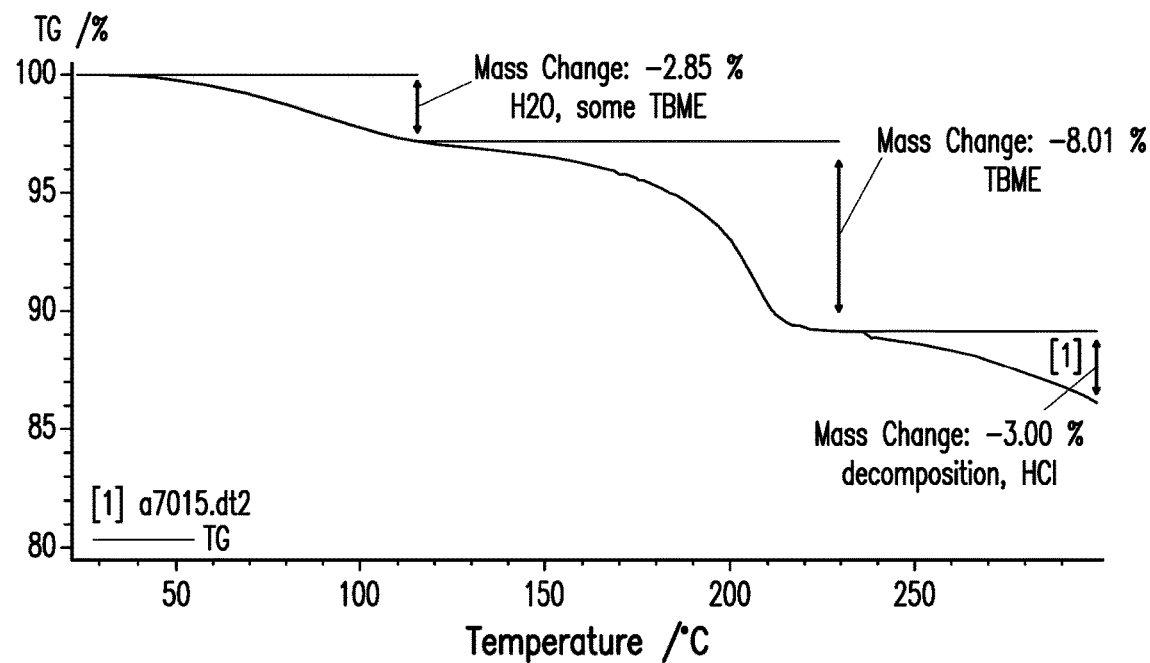

FIG. 56 provides a representative TGA thermogram of Form A of a hydrochloride salt of Compound 1.

Figure 57:
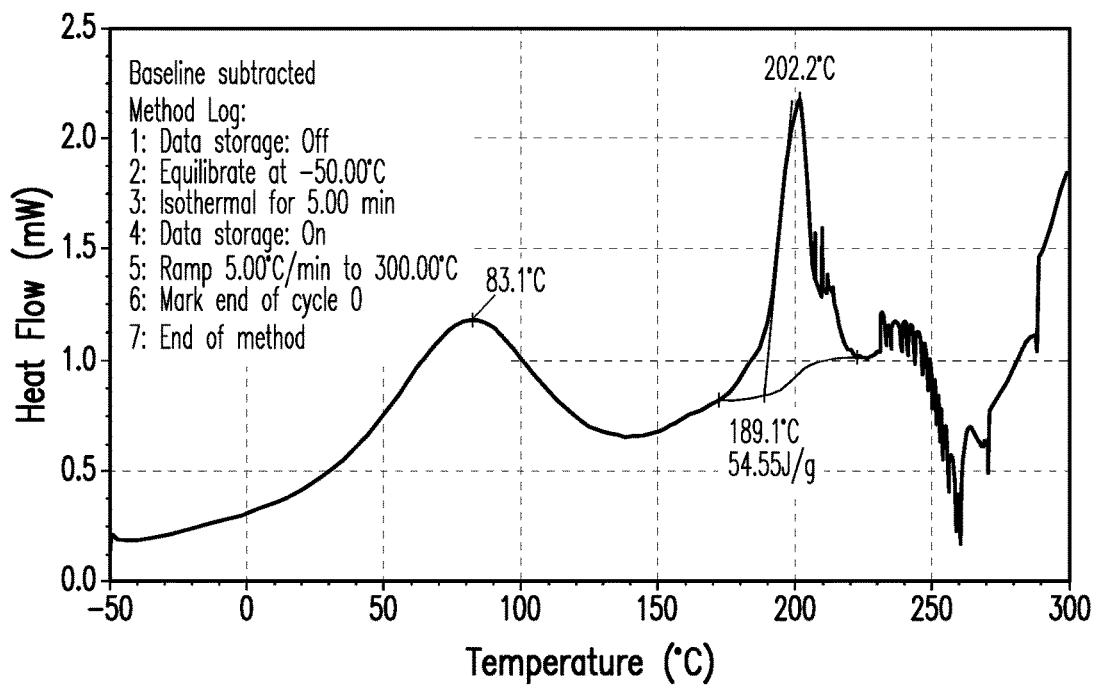

FIG. 57 provides a representative DSC thermogram of Form A of a hydrochloride salt of Compound 1.

Figure 58:
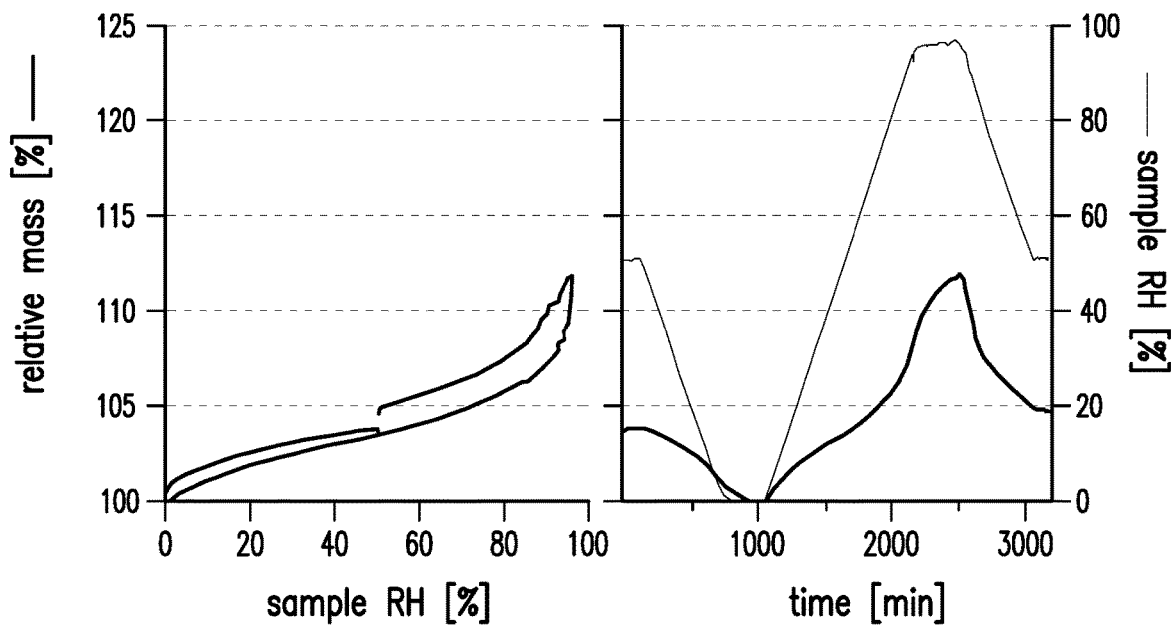

FIG. 58 provides a representative DVS isotherm plot of Form A of a hydrochloride salt of Compound 1.

Figure 59:
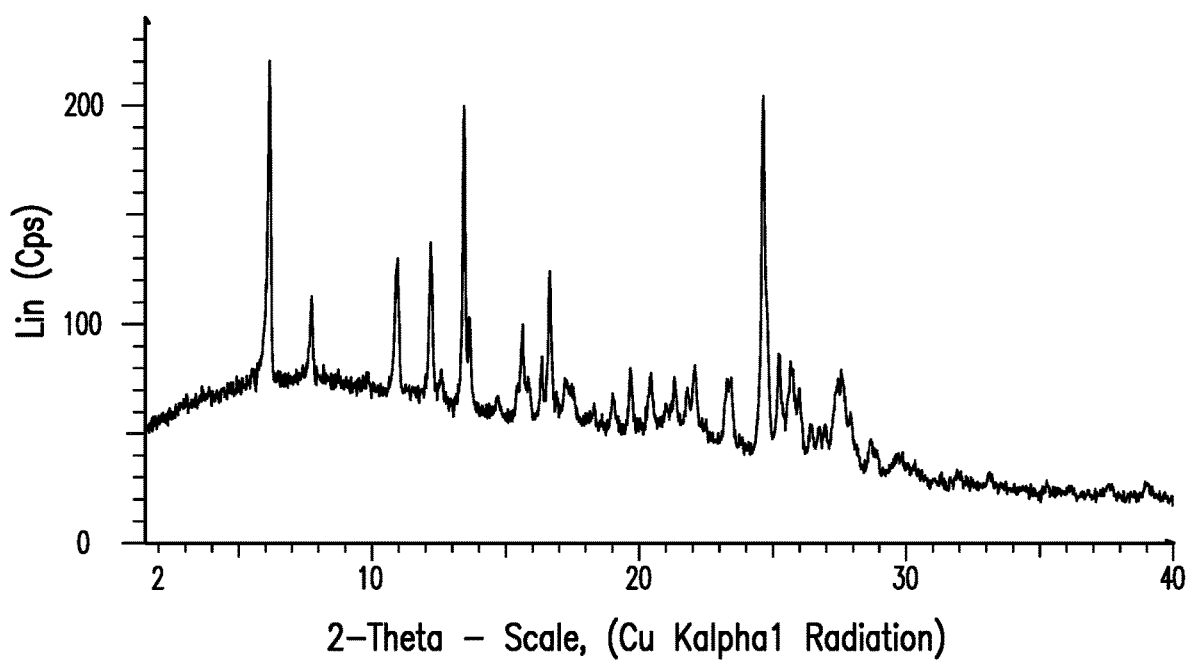

FIG. 59 provides a representative XRPD pattern of Form B of a hydrochloride salt of Compound 1.

Figure 60:
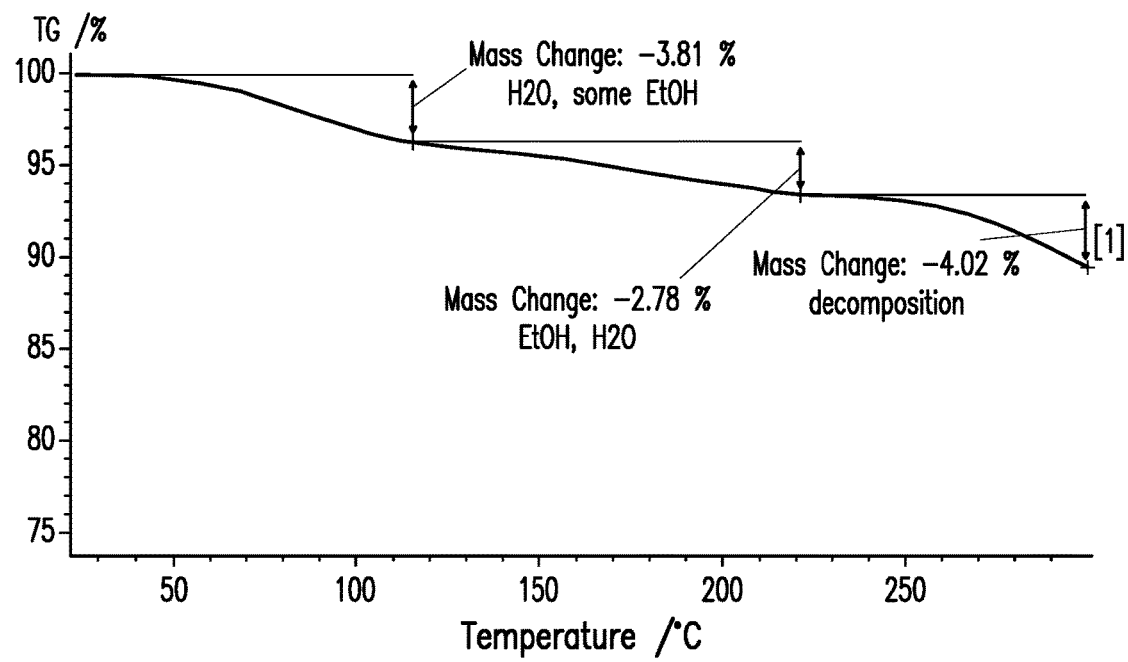

FIG. 60 provides a representative TGA thermogram of Form B of a hydrochloride salt of Compound 1.

Figure 61:
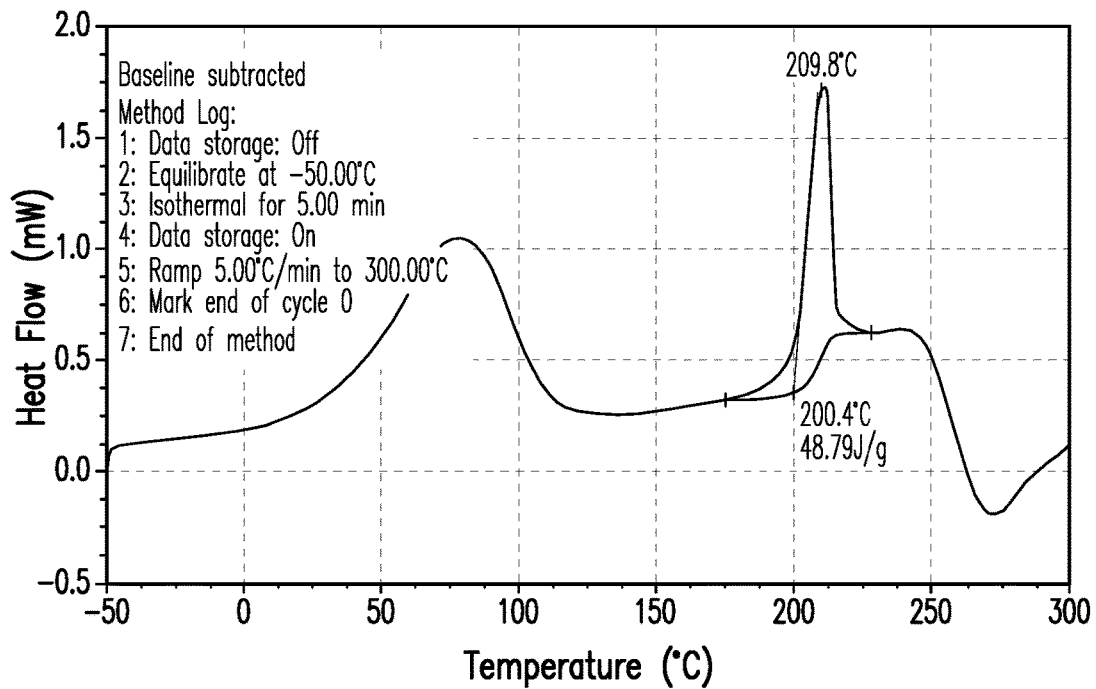

FIG. 61 provides a representative DSC thermogram of Form B of a hydrochloride salt of Compound 1.

Figure 62:
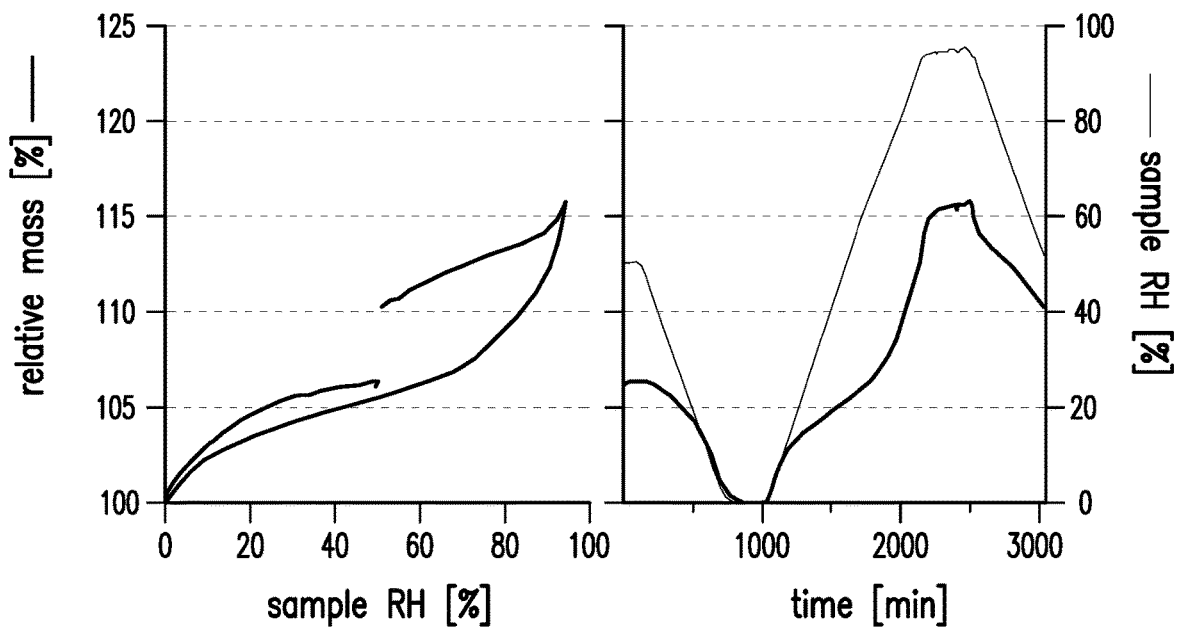

FIG. 62 provides a representative DVS isotherm plot of Form B of a hydrochloride salt of Compound 1.

Figure 63:
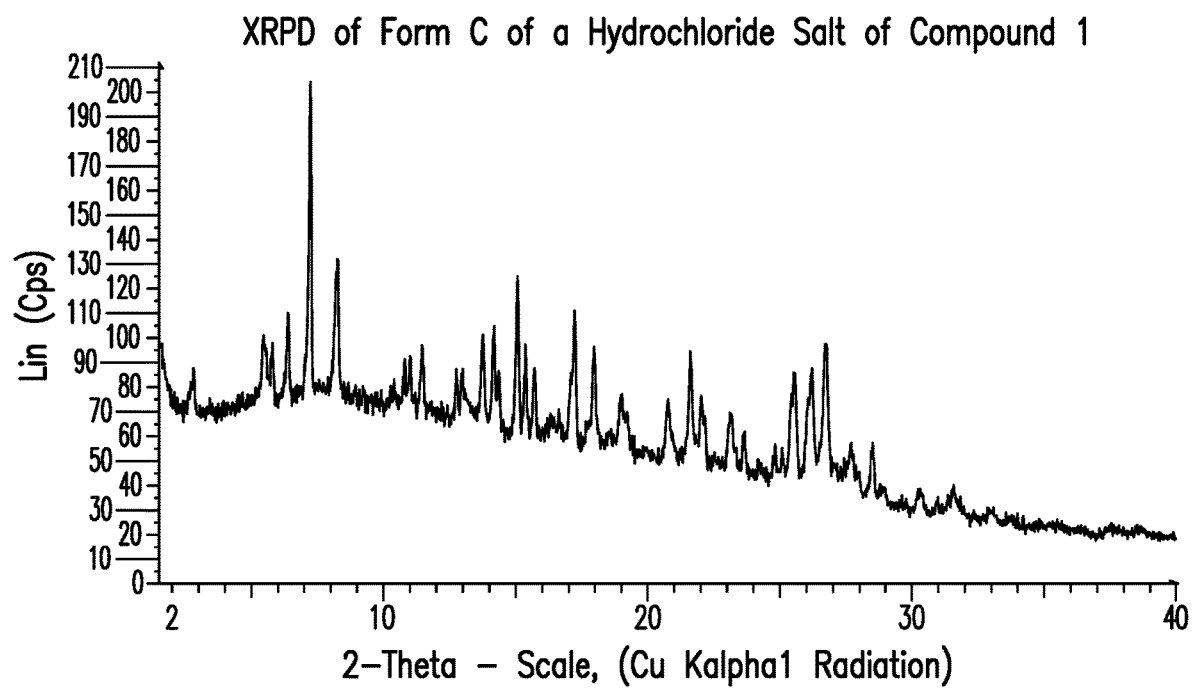

FIG. 63 provides a representative XRPD pattern of Form C of a hydrochloride salt of Compound 1.

Figure 64:
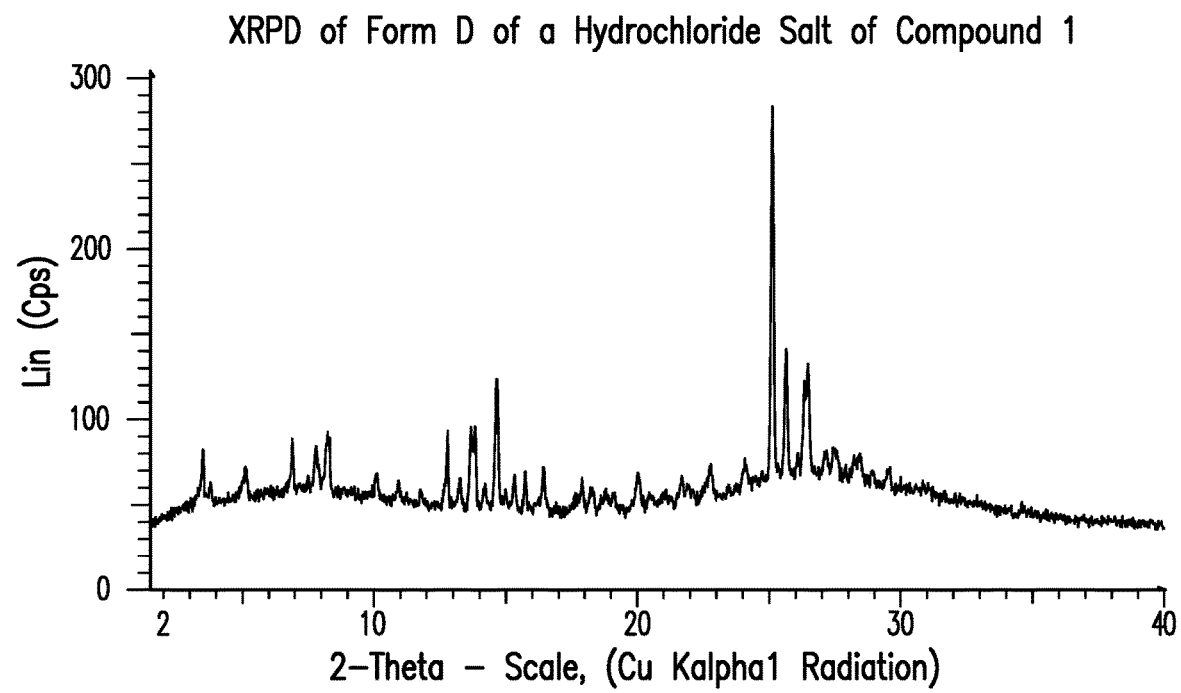

FIG. 64 provides a representative XRPD pattern of Form D of a hydrochloride salt of Compound 1.

Figure 65:
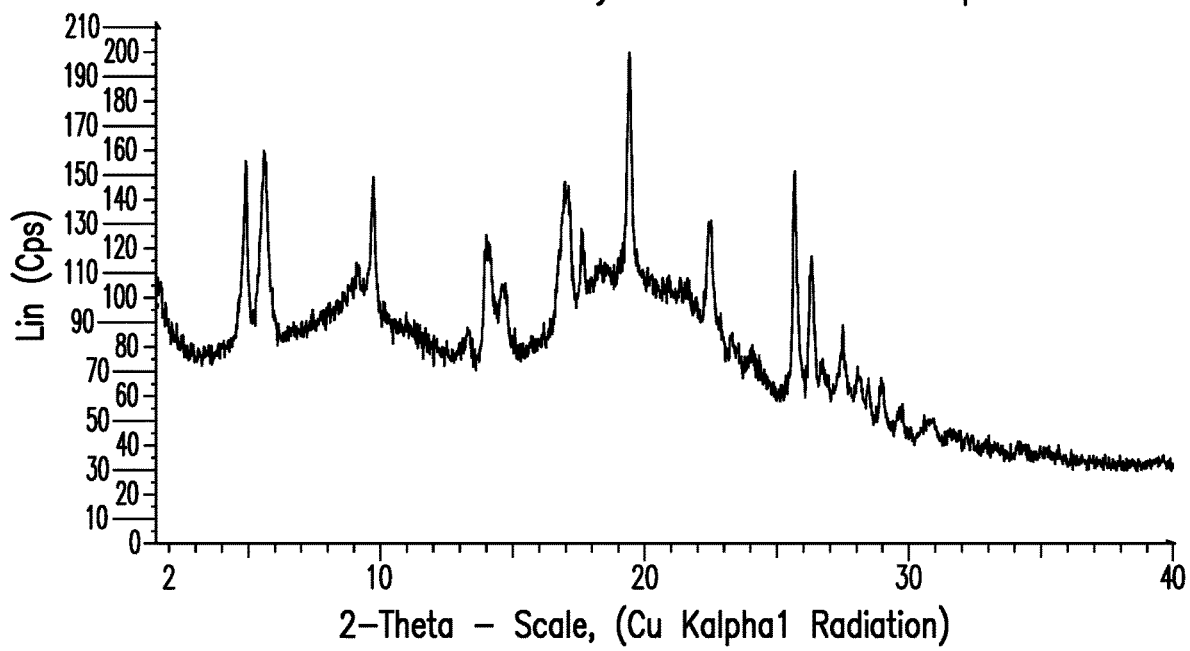

FIG. 65 provides a representative XRPD pattern of Form E of a hydrochloride salt of Compound 1.

Figure 66:
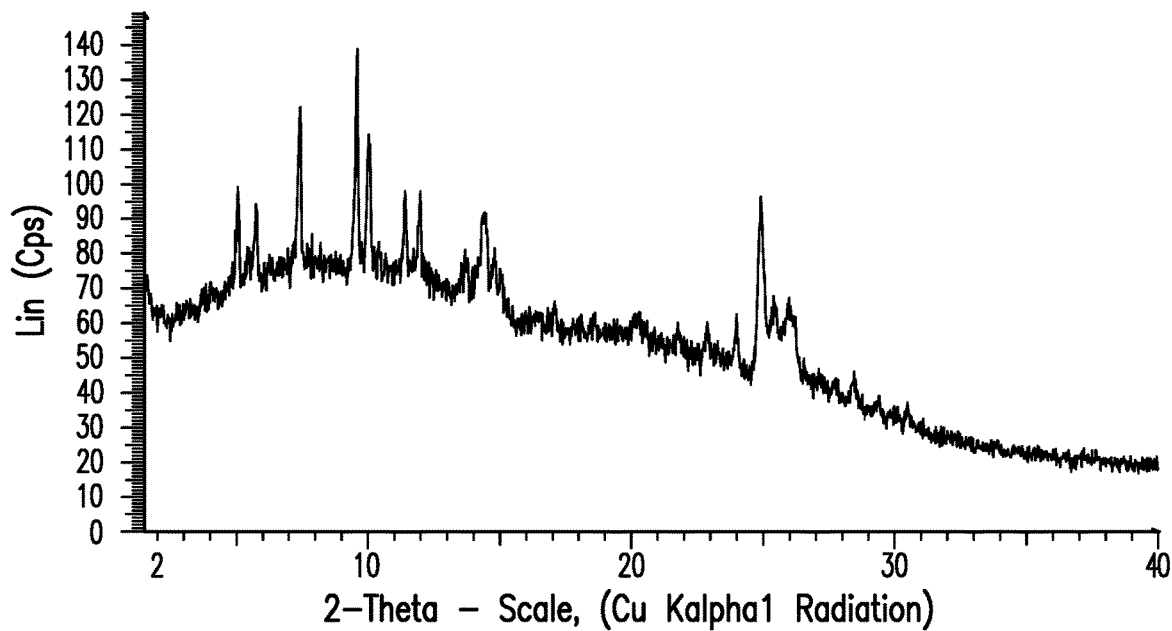

FIG. 66 provides a representative XRPD pattern of Form F of a hydrochloride salt of Compound 1.

Figure 67:
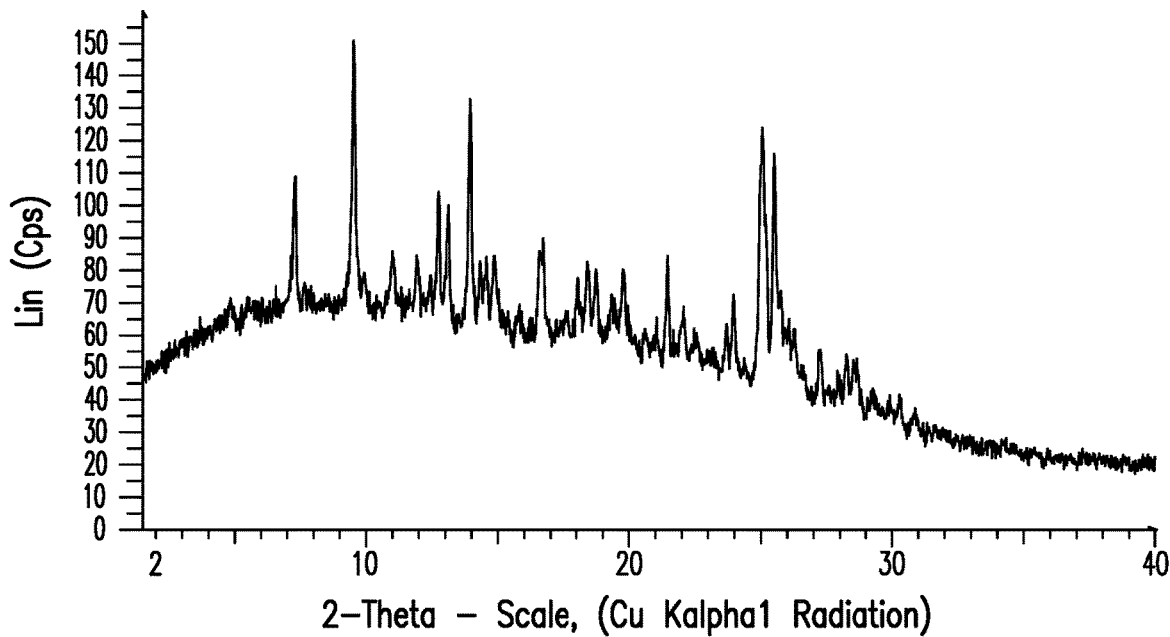

FIG. 67 provides a representative XRPD pattern of Form G of a hydrochloride salt of Compound 1.

Figure 68:
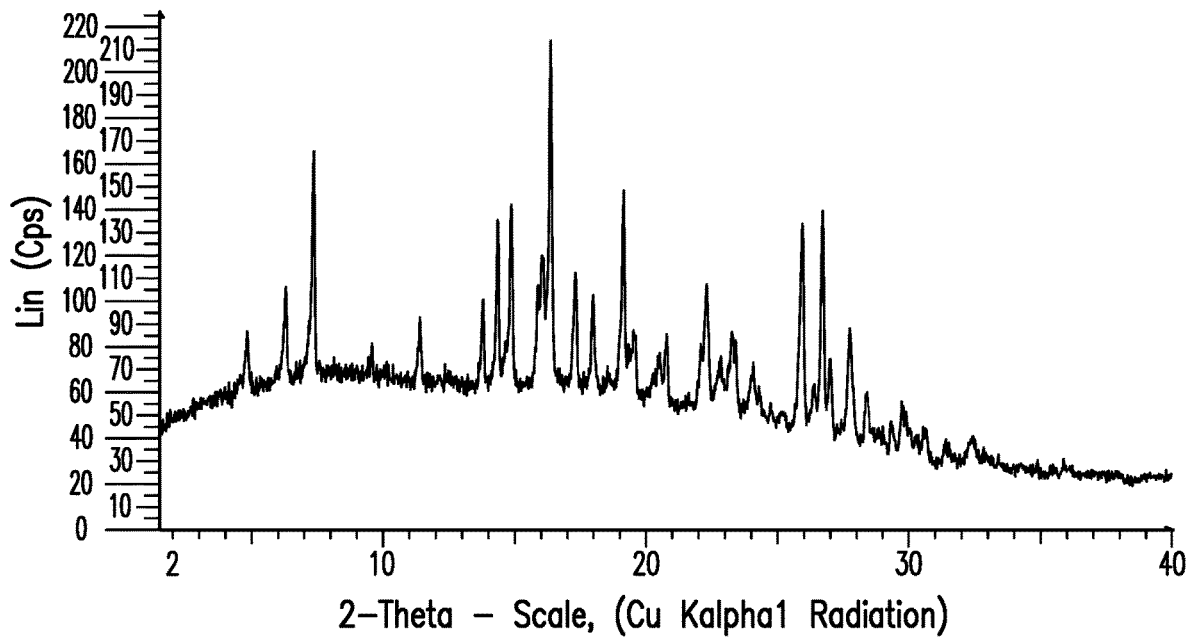

FIG. 68 provides a representative XRPD pattern of Form H of a hydrochloride salt of Compound 1.

Figure 69:
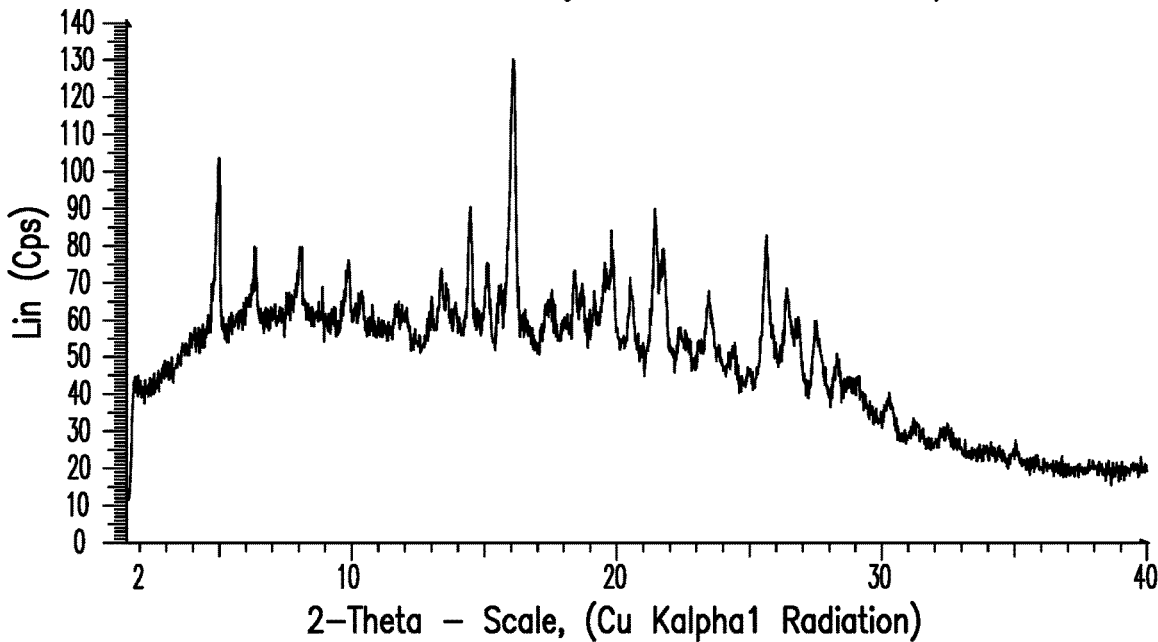

FIG. 69 provides a representative XRPD pattern of Form I of a hydrochloride salt of Compound 1.

Figure 70:
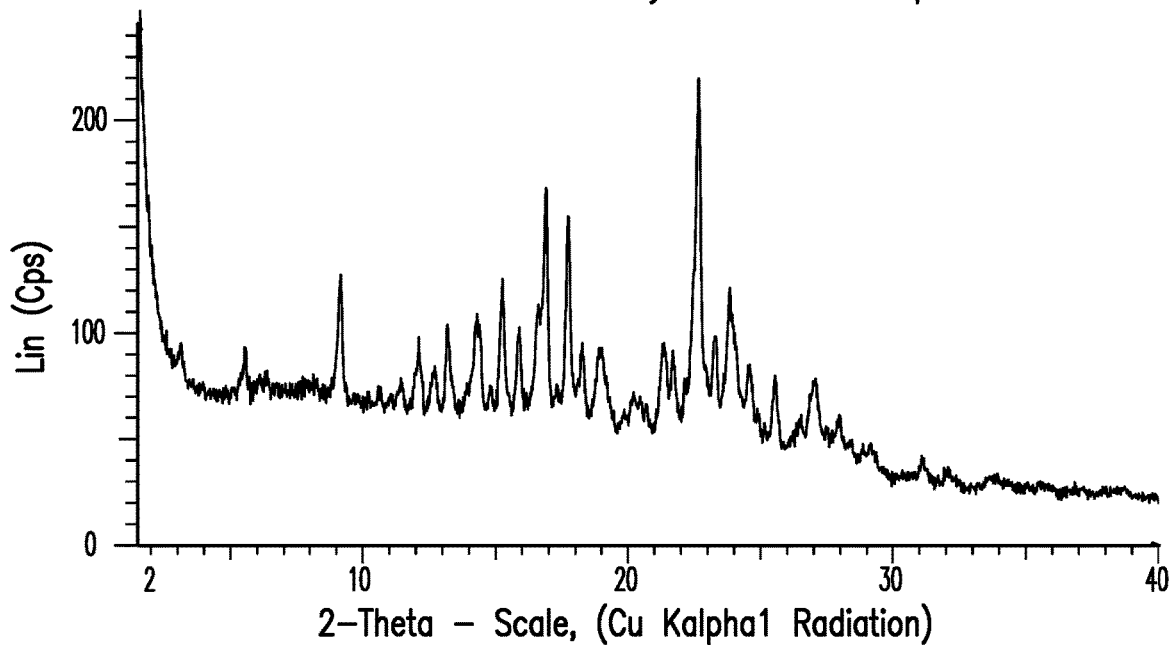

FIG. 70 provides a representative XRPD pattern of Form A of a mesylate salt of Compound 1.

Figure 71:
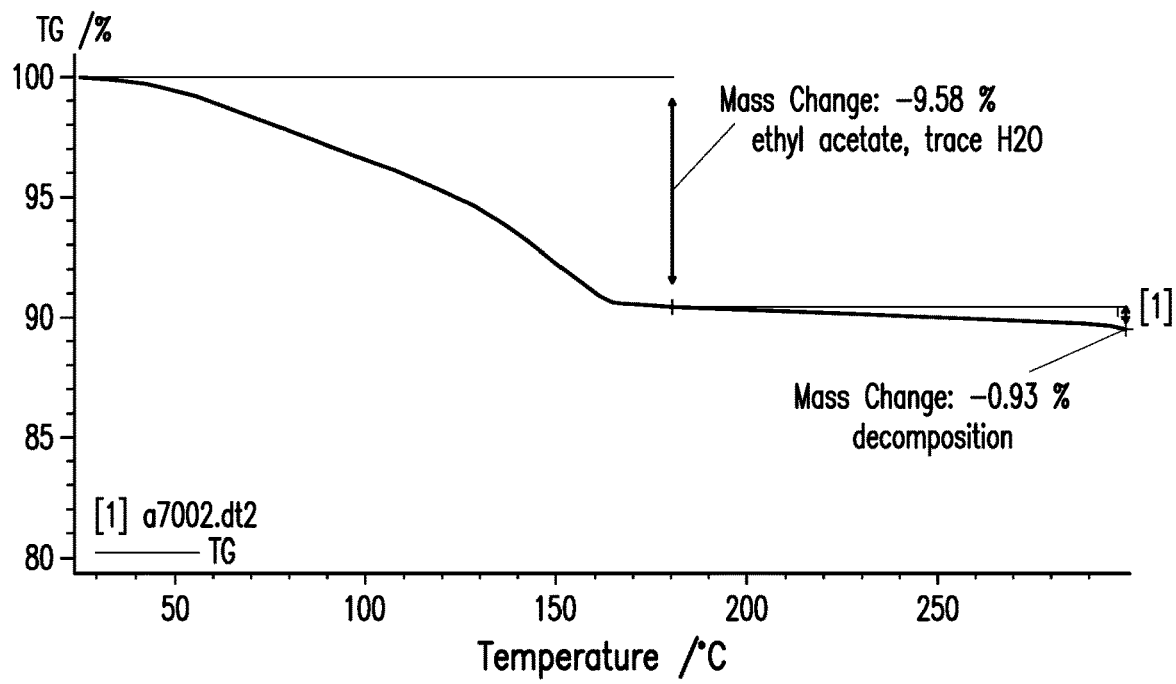

FIG. 71 provides a representative TGA thermogram of Form A of a mesylate salt of Compound 1.

Figure 72:
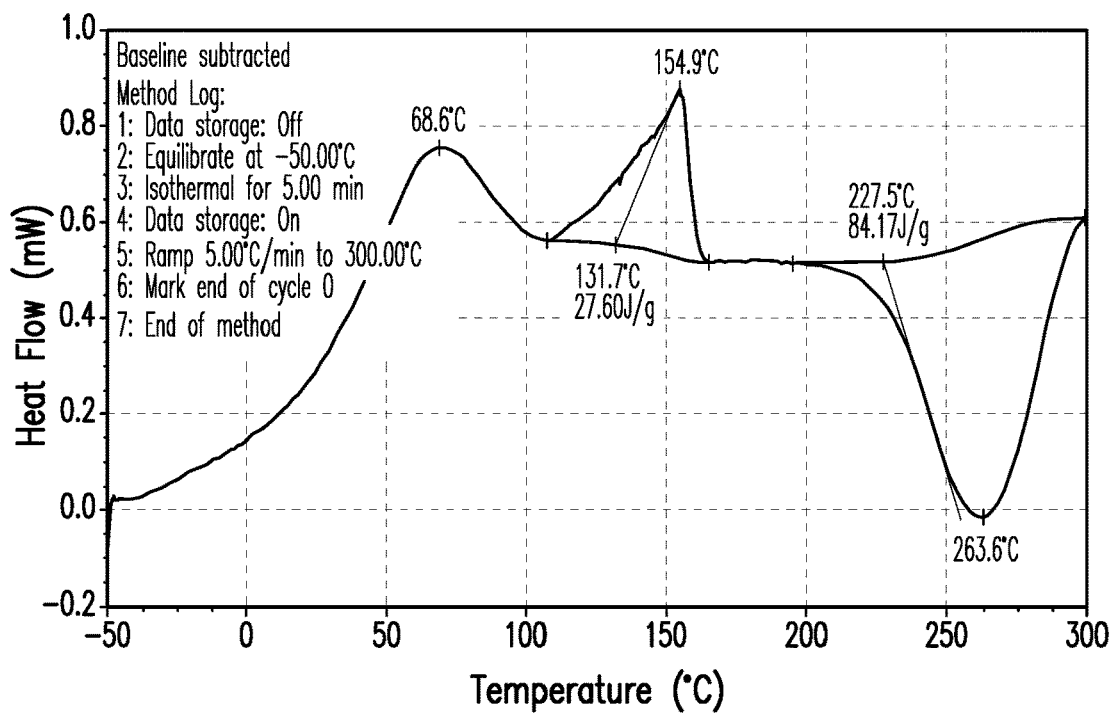

FIG. 72 provides a representative DSC thermogram of Form A of a mesylate salt of Compound 1.

Figure 73:
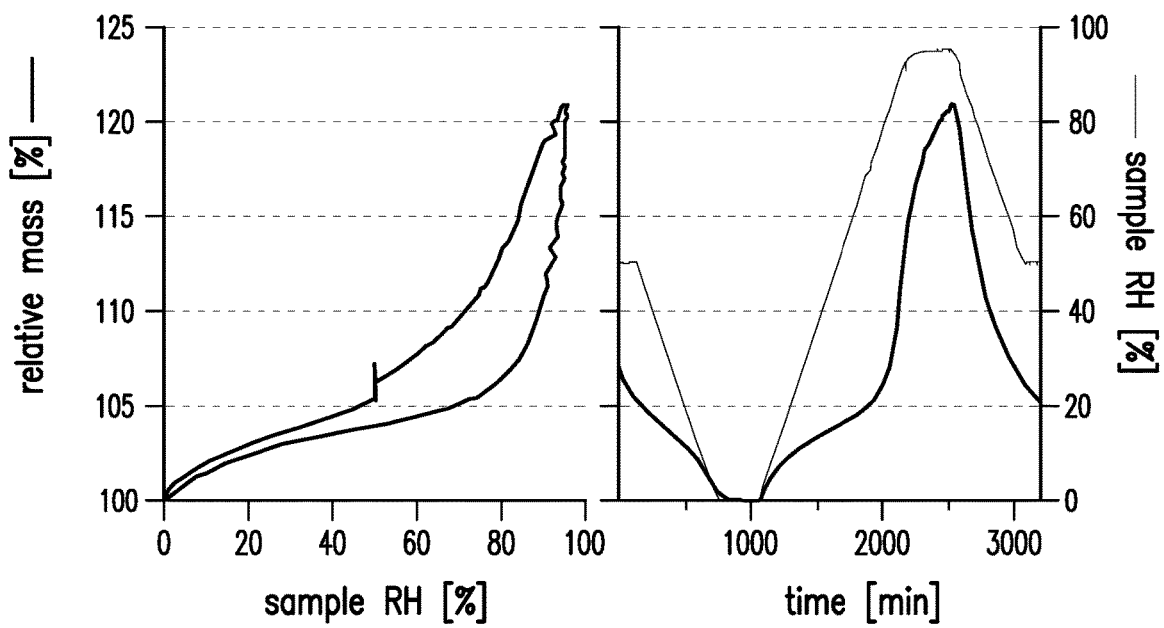

FIG. 73 provides a representative DVS isotherm plot of Form A of a mesylate salt of Compound 1.

Figure 74:
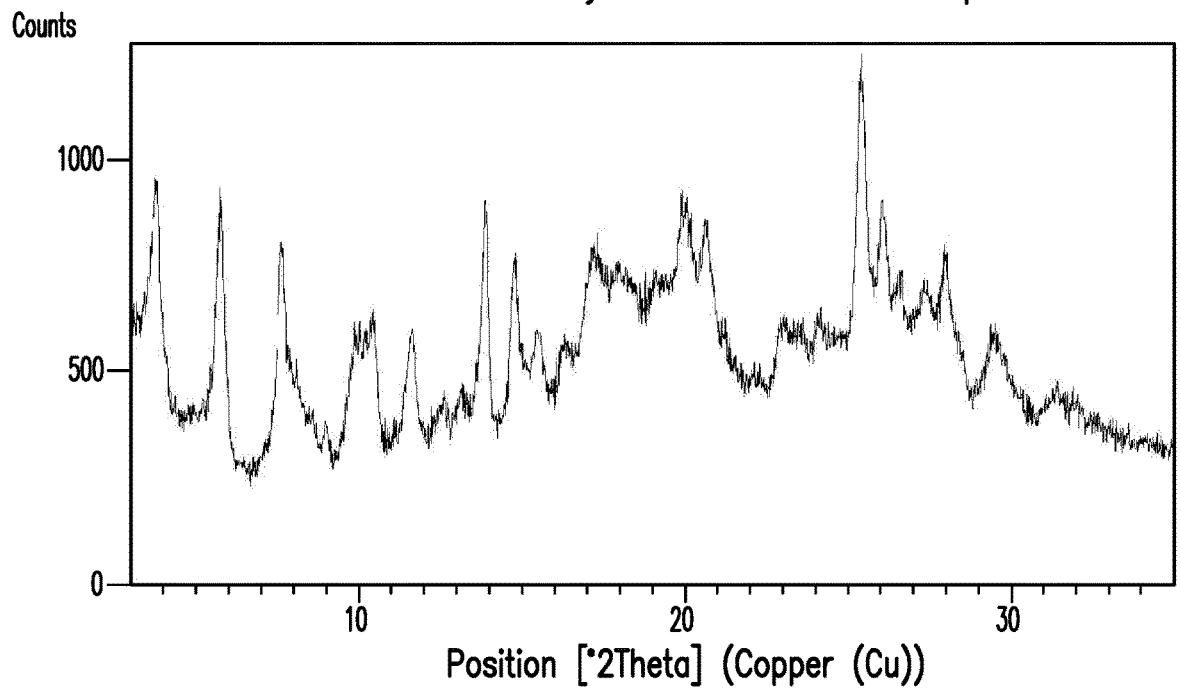

FIG. 74 provides a representative XRPD pattern of Form B of a hydrobromide salt of Compound 1.

Figure 75:
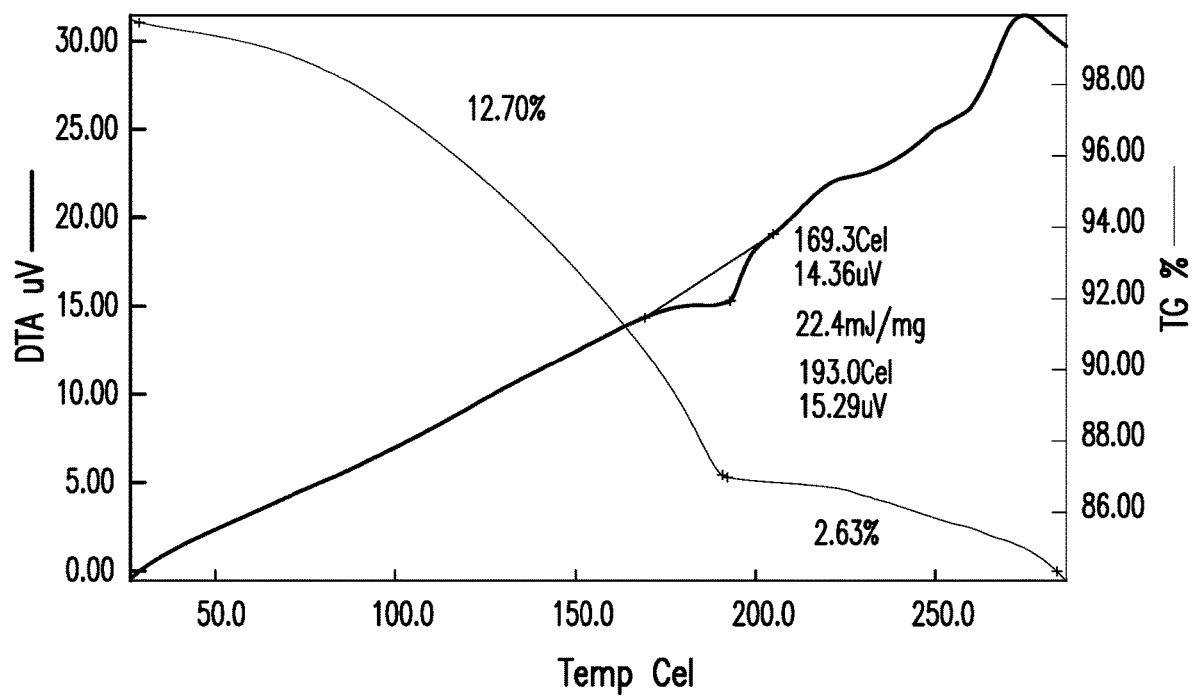

FIG. 75 provides representative TG/DTA thermograms of Form B of a hydrobromide salt of Compound 1.

Figure 76:
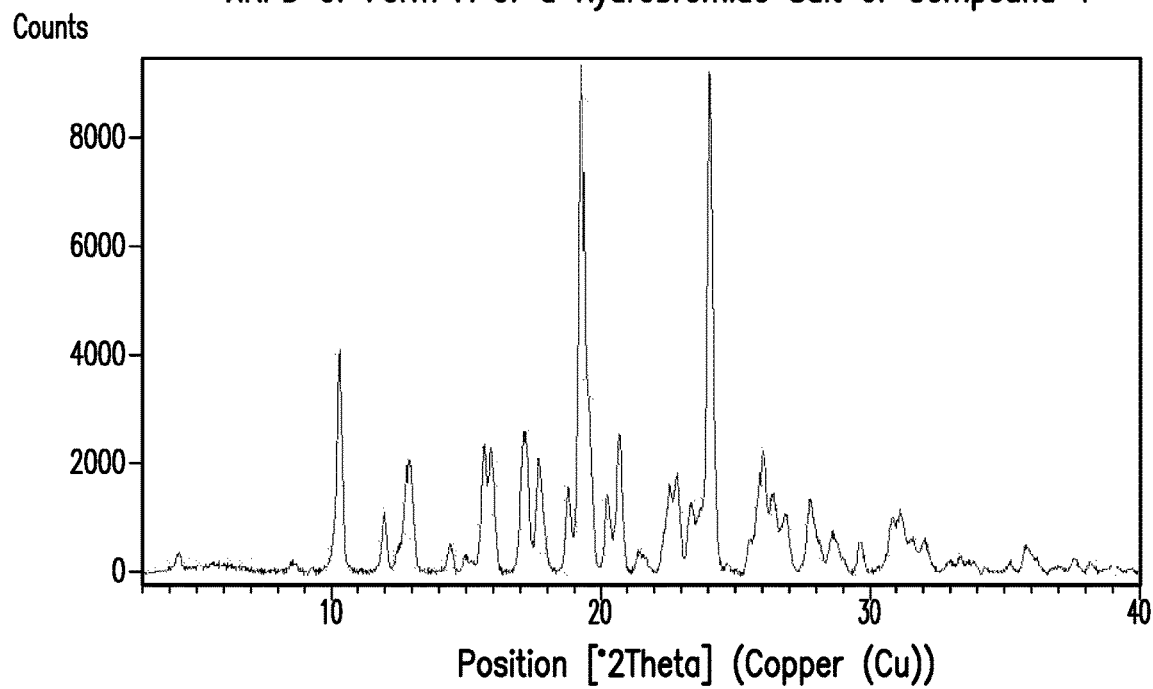

FIG. 76 provides a representative XRPD pattern of Form A of a hydrobromide salt of Compound 1.

Figure 77:
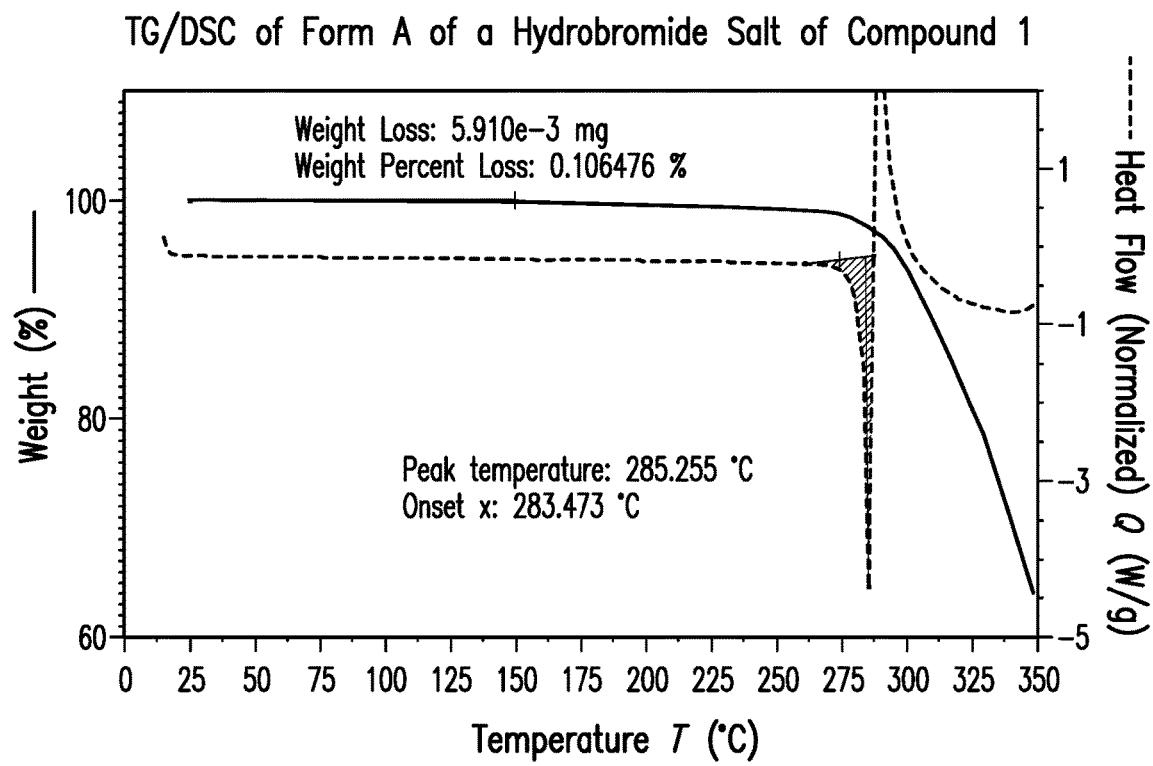

FIG. 77 provides representative TG/DSC thermograms of Form A of a hydrobromide salt of Compound 1.

Figure 78:
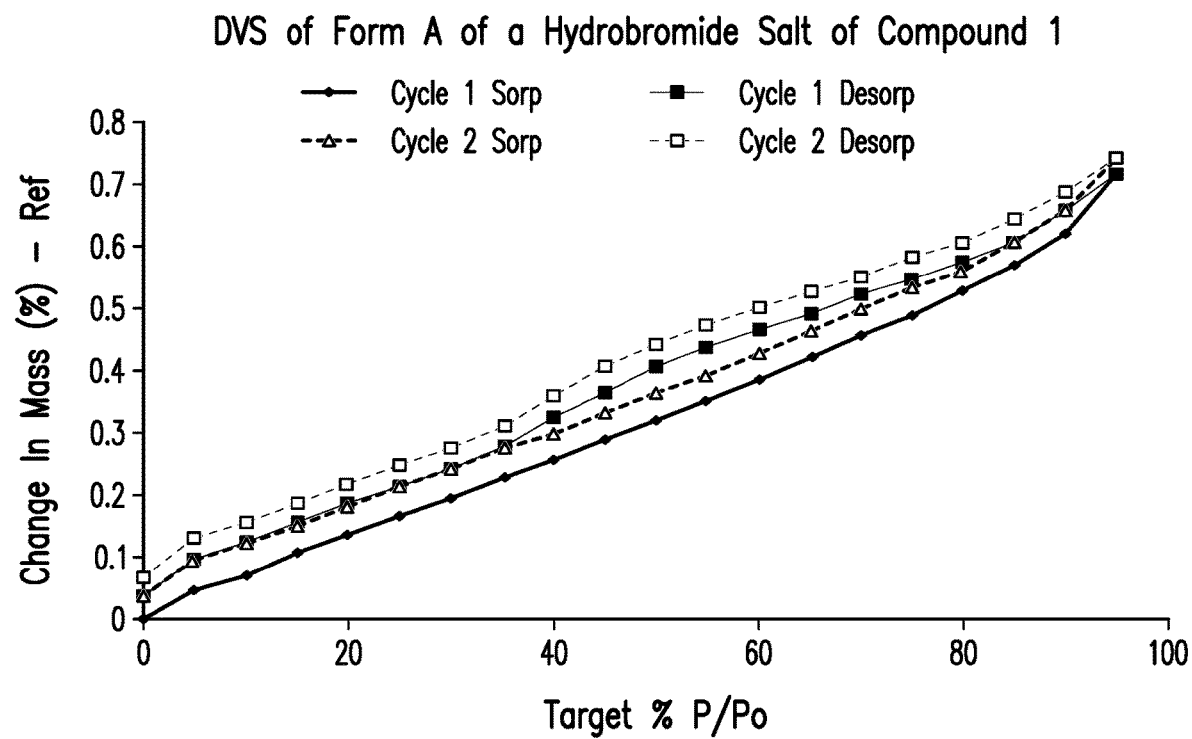

FIG. 78 provides a representative DVS isotherm plot of Form A of a hydrobromide salt of Compound 1.

Figure 79:
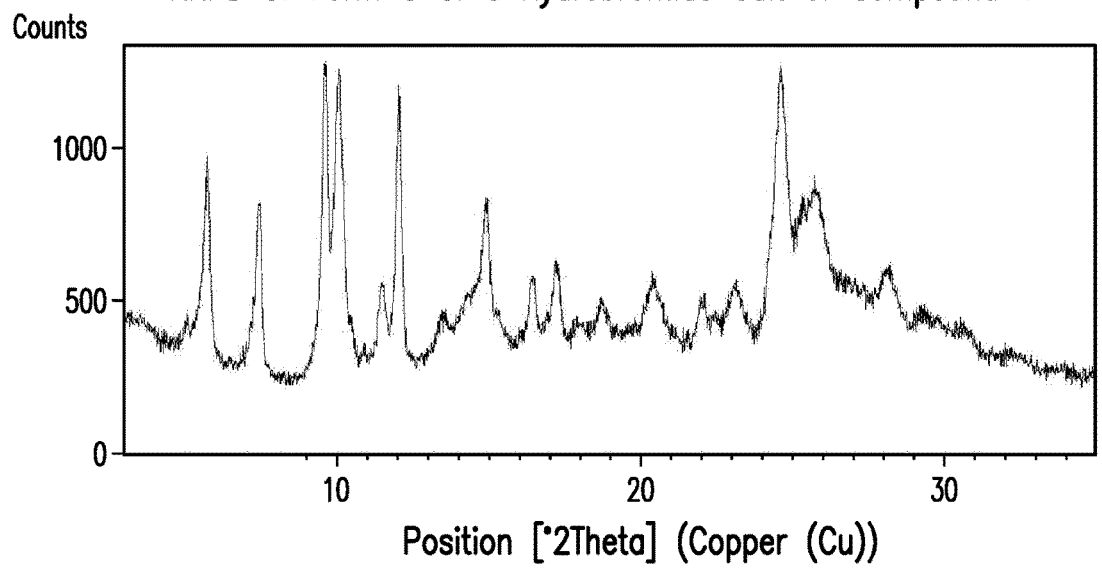

FIG. 79 provides a representative XRPD pattern of Form C of a hydrobromide salt of Compound 1.

Figure 80:
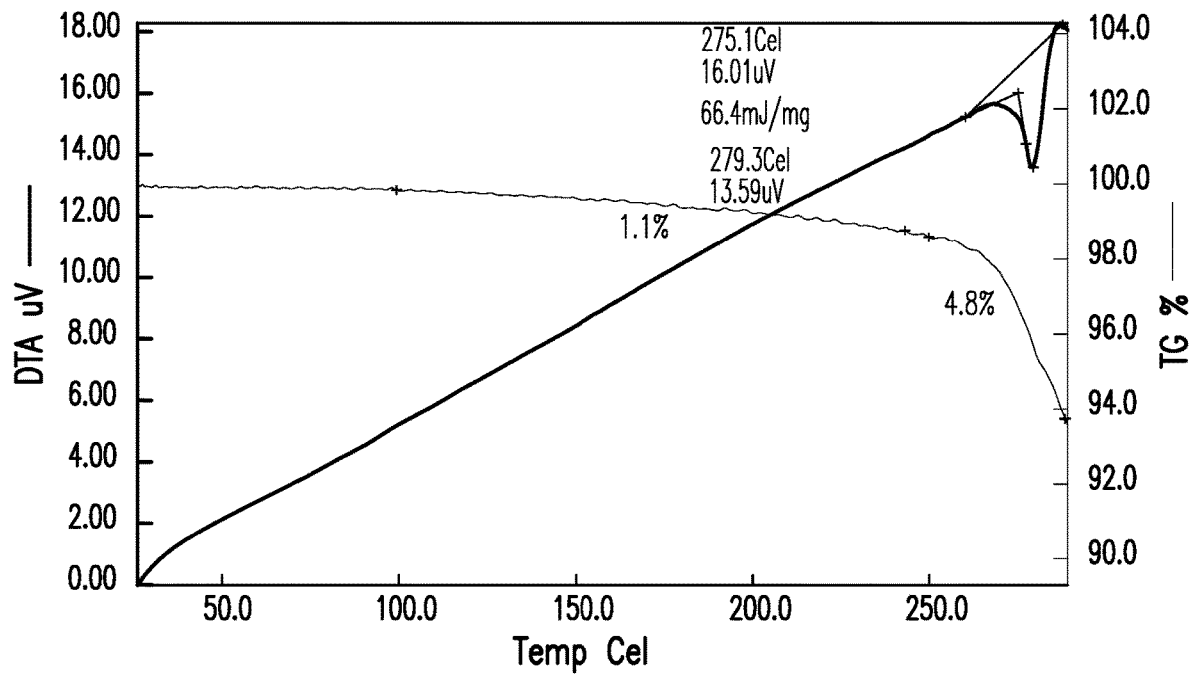

FIG. 80 provides representative TG/DTA thermograms of Form C of a hydrobromide salt of Compound 1.

Figure 81:
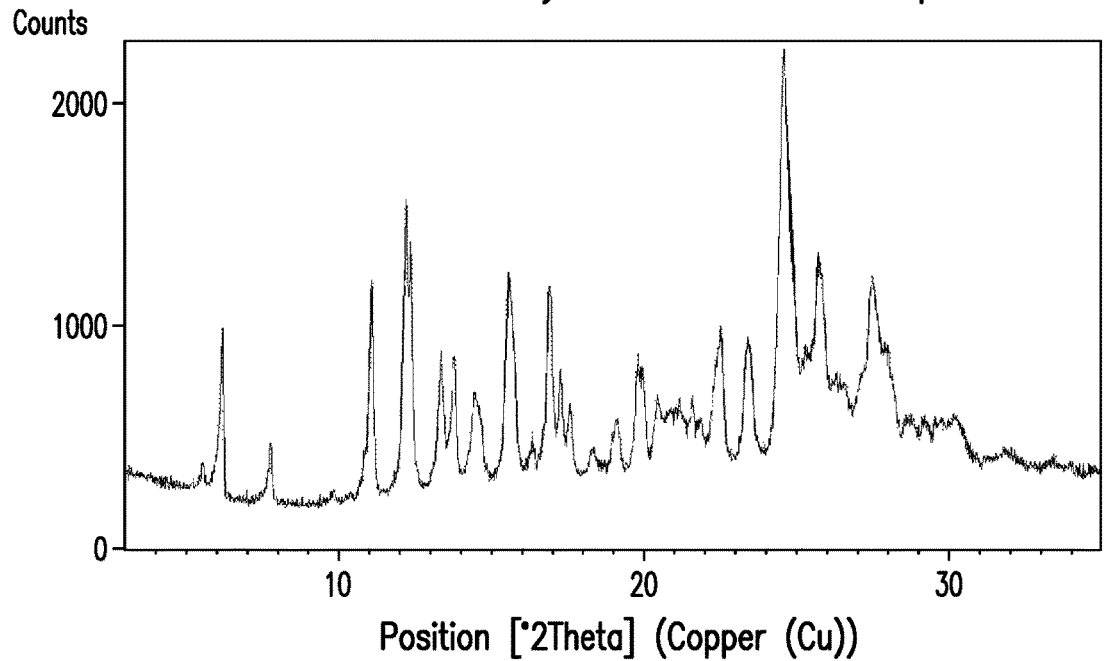

FIG. 81 provides a representative XRPD pattern of Form D of a hydrobromide salt of Compound 1.

Figure 82:
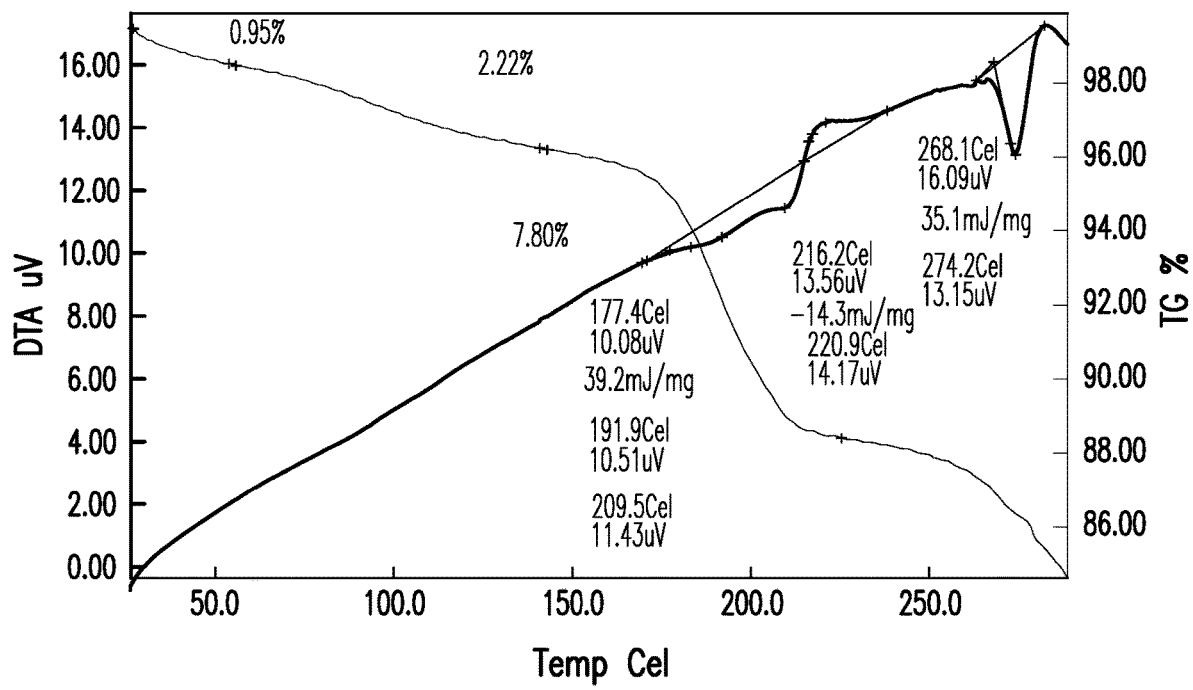

FIG. 82 provides representative TG/DTA thermograms of Form D of a hydrobromide salt of Compound 1.

Figure 83:
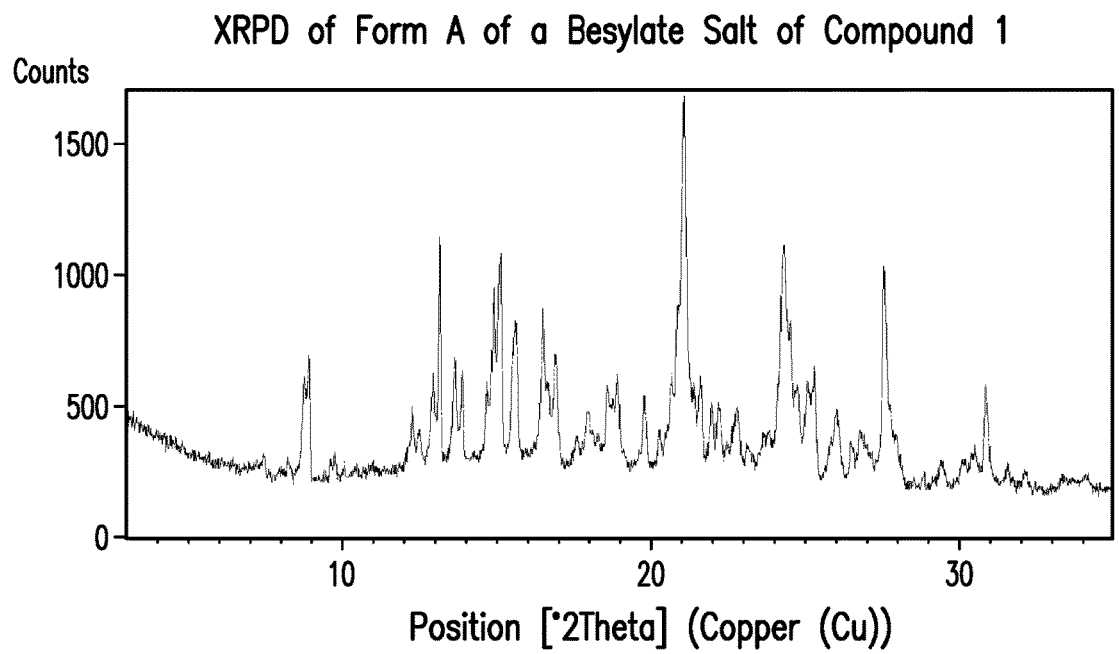

FIG. 83 provides a representative XRPD pattern of Form A of a besylate salt of Compound 1.

Figure 84:
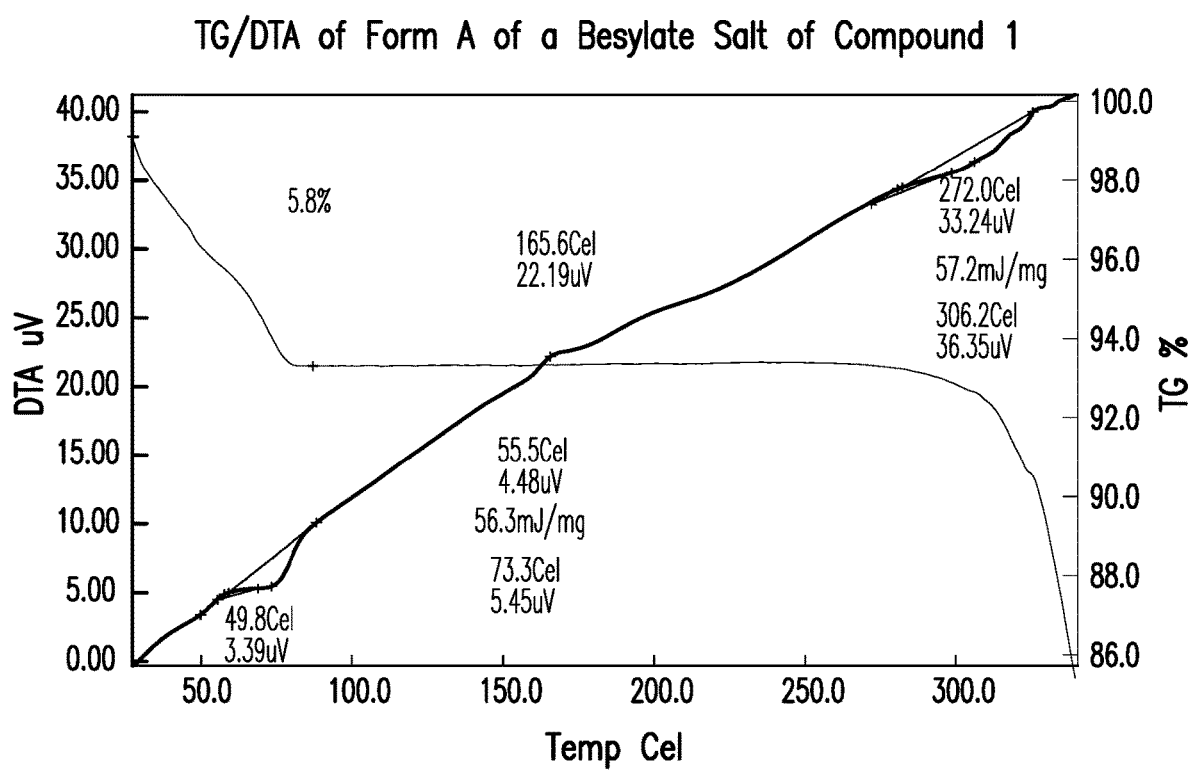

FIG. 84 provides representative TG/DTA thermograms of Form A of a besylate salt of Compound 1.

Figure 85:
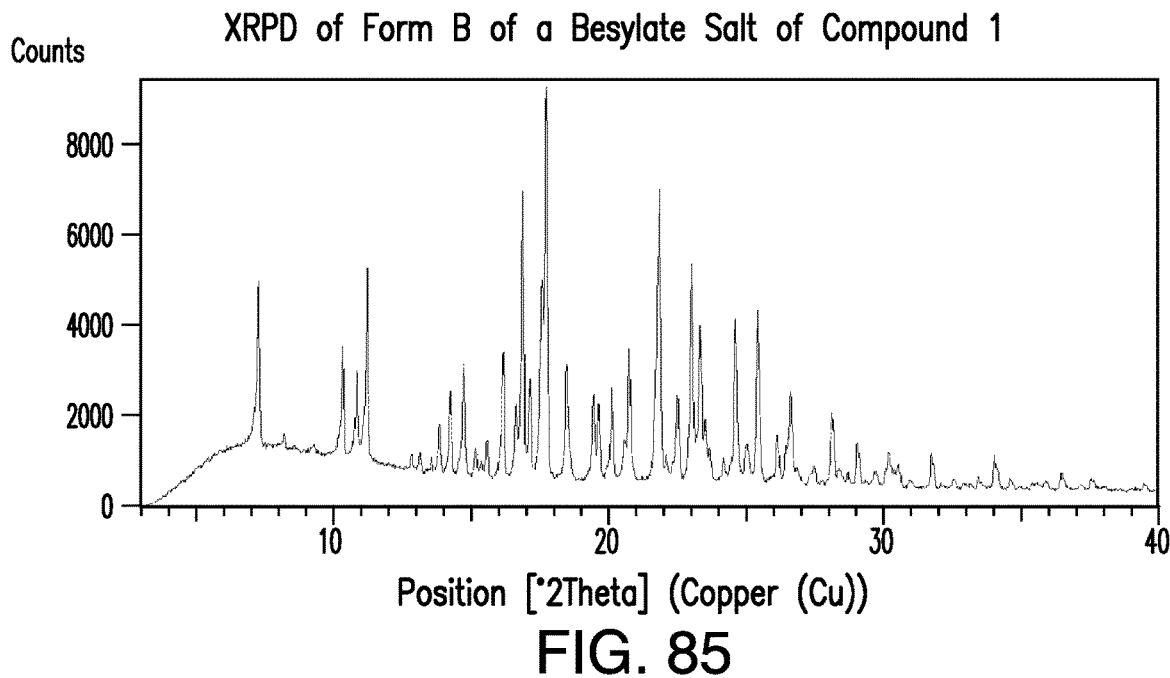

FIG. 85 provides a representative XRPD pattern of Form B of a besylate salt of Compound 1.

Figure 86A:
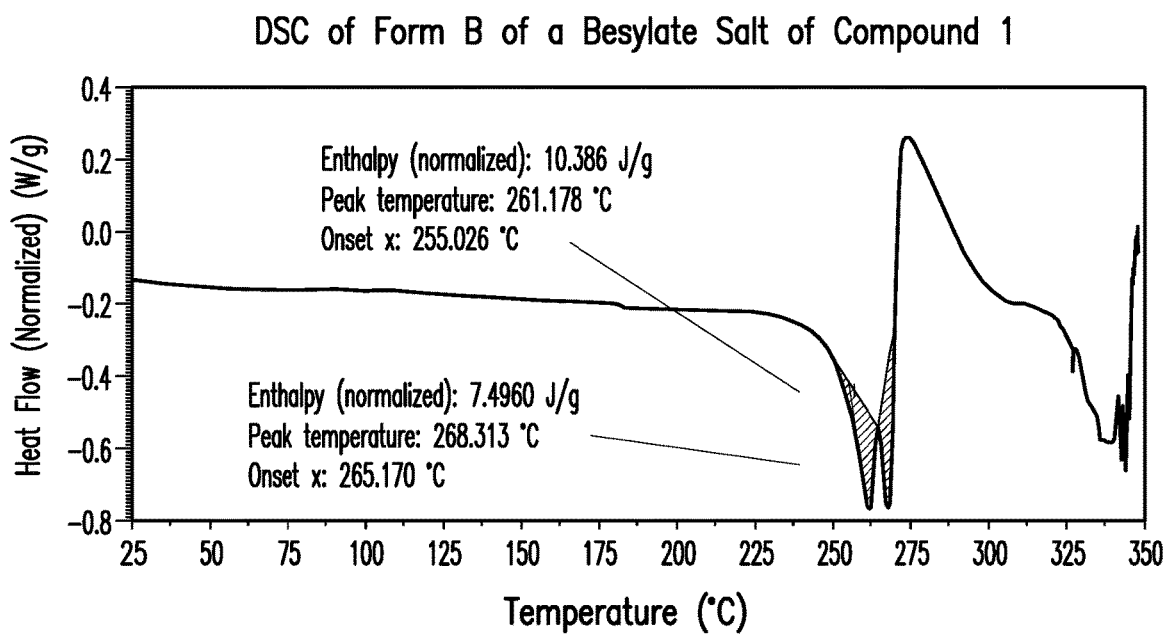

FIG. 86A provides a representative DSC thermogram of Form B of a besylate salt of Compound 1.

Figure 86B:
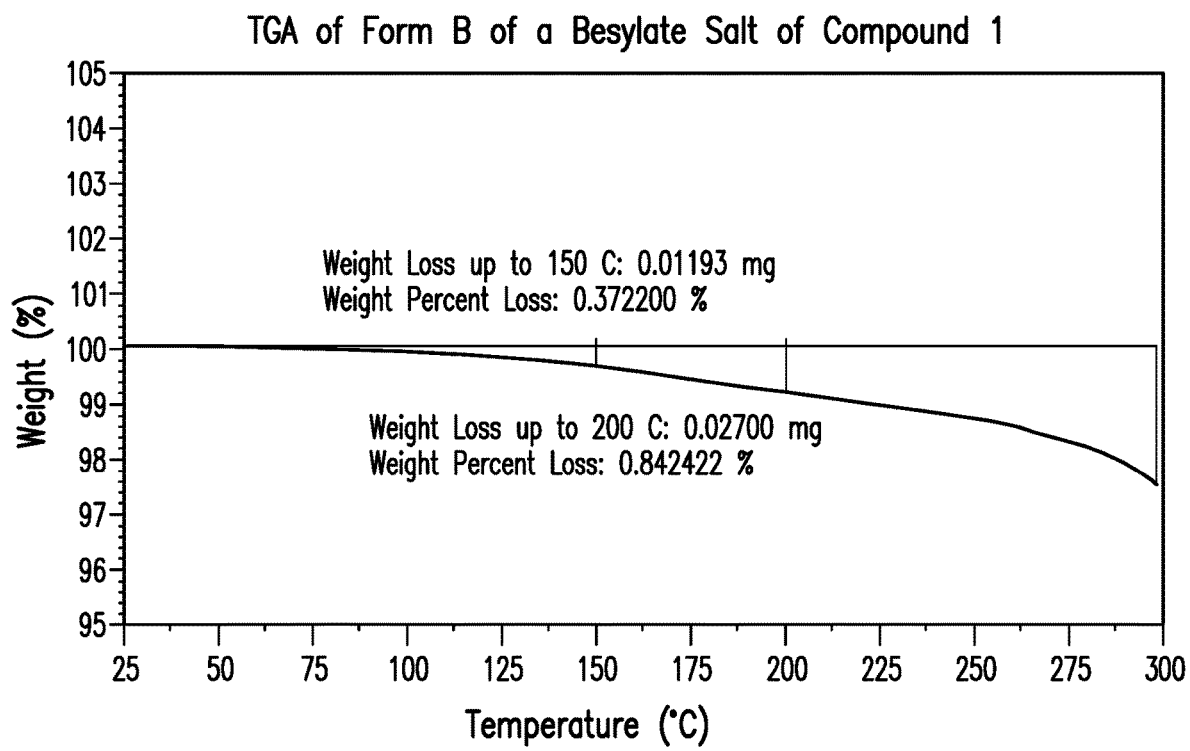

FIG. 86B provides a representative TGA thermogram of Form B of a besylate salt of Compound 1.

Figure 87:
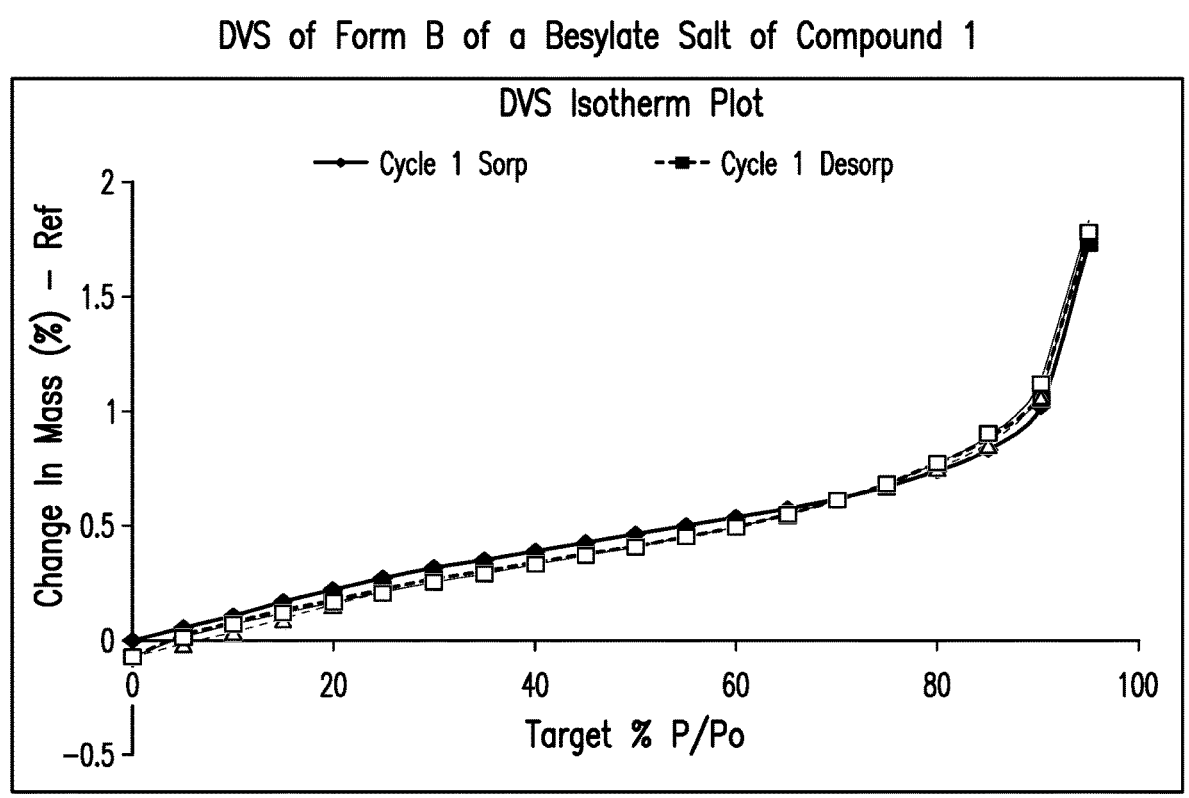

FIG. 87 provides a representative DVS isotherm plot of Form B of a besylate salt of Compound 1.

Figure 88:
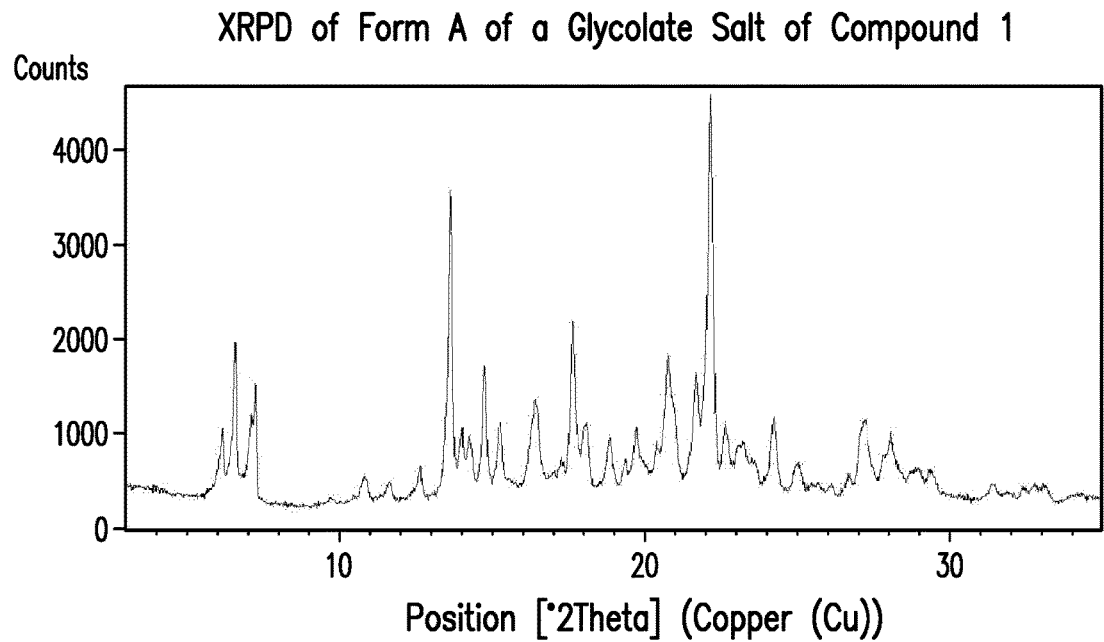

FIG. 88 provides a representative XRPD pattern of Form A of a glycolate salt of Compound 1.

Figure 89:
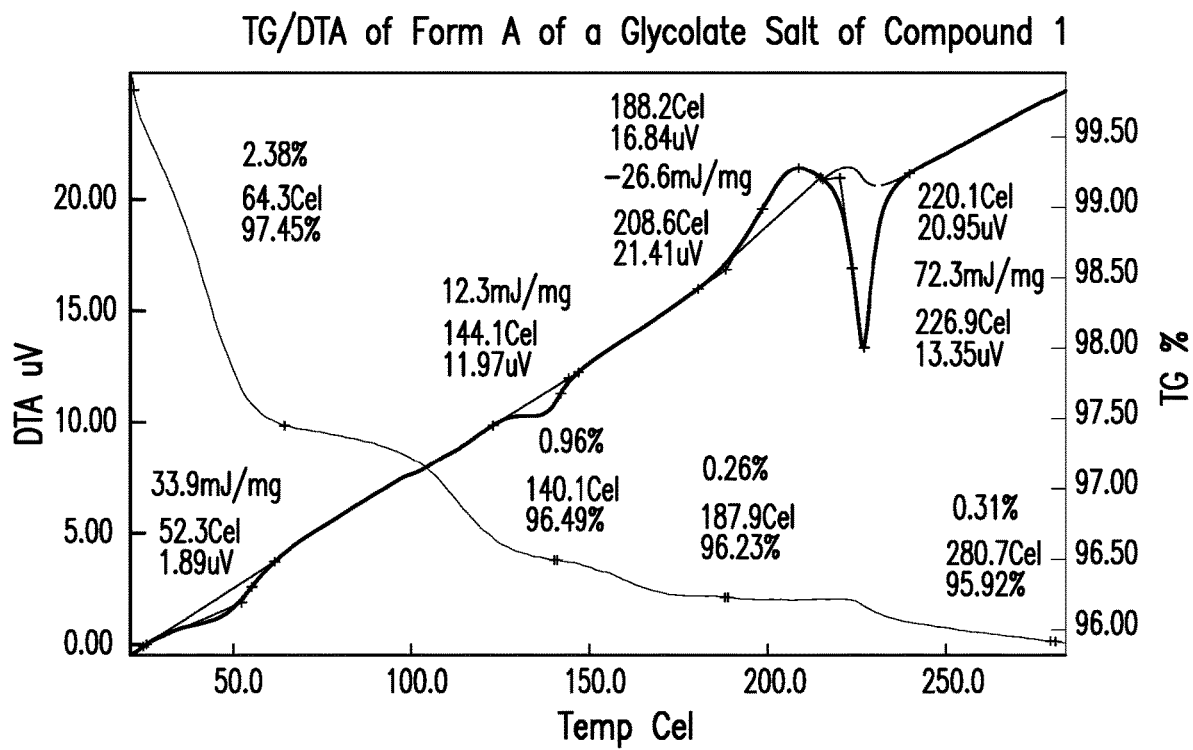

FIG. 89 provides representative TG/DTA thermograms of Form A of a glycolate salt of Compound 1.

Figure 90:
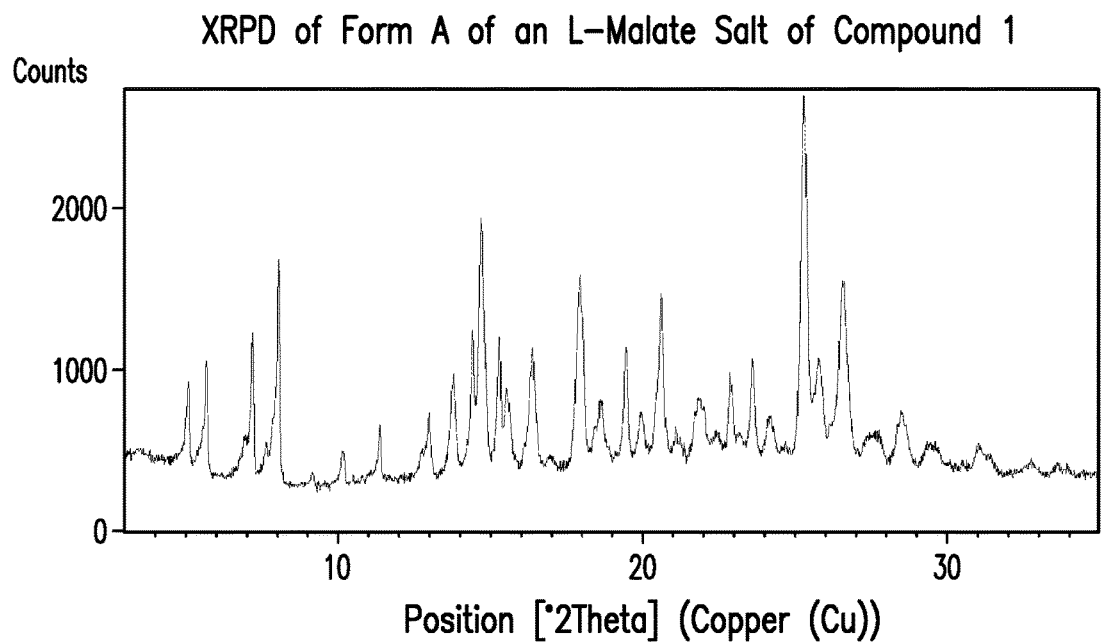

FIG. 90 provides a representative XRPD pattern of Form A of an L-malate salt of Compound 1.

Figure 91:
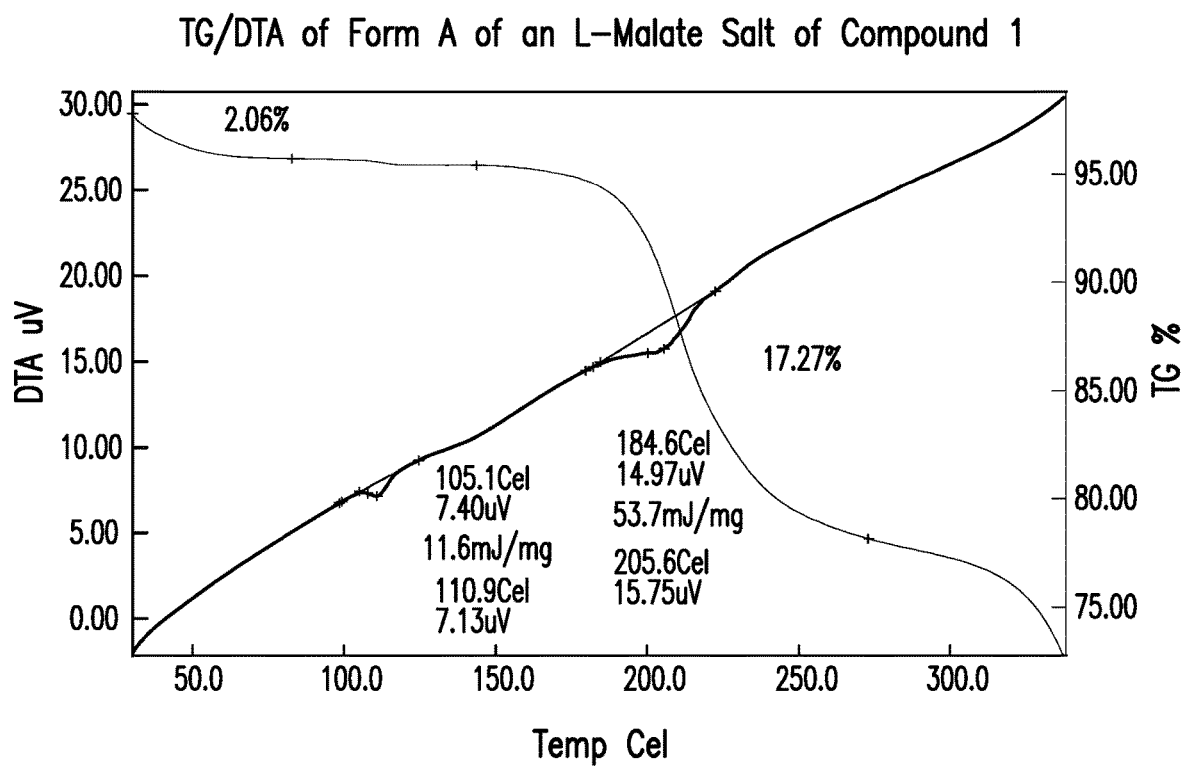

FIG. 91 provides representative TG/DTA thermograms of Form A of an L-malate salt of Compound 1.

Figure 92:
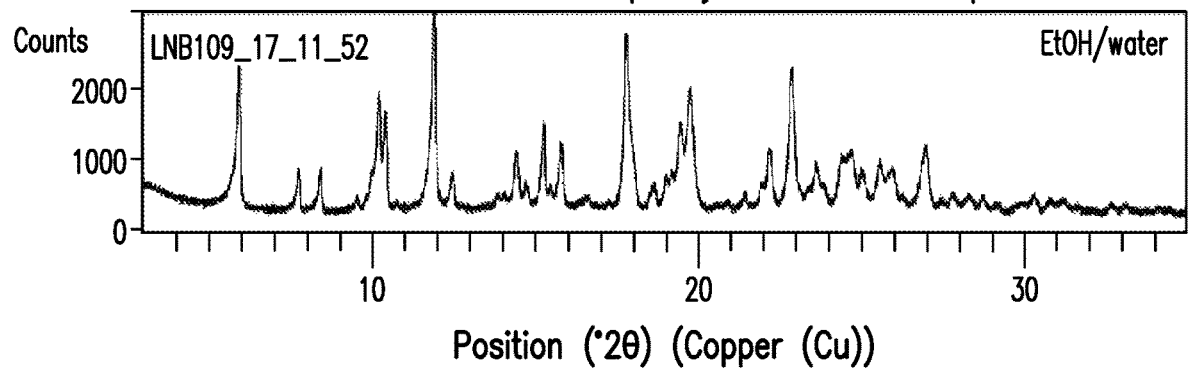

FIG. 92 provides a representative XRPD pattern of Form A of a napadisylate salt of Compound 1.

Figure 93:
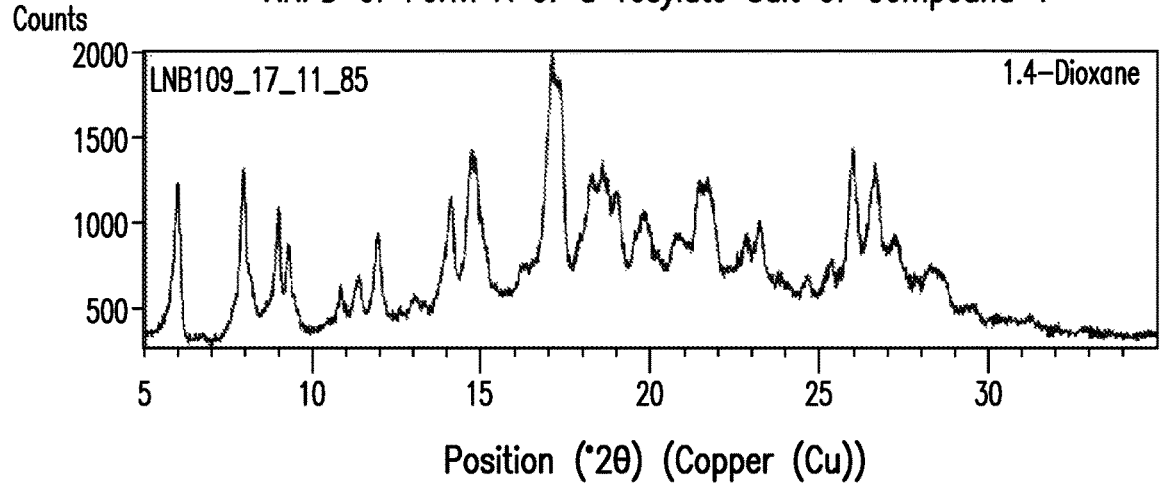

FIG. 93 provides a representative XRPD pattern of Form A of a tosylate salt of Compound 1.

Figure 94:
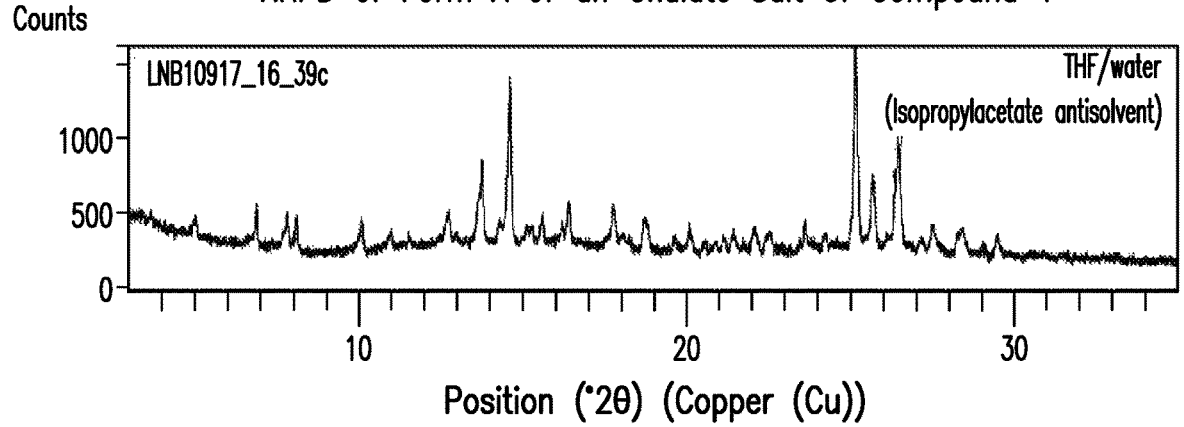

FIG. 94 provides a representative XRPD pattern of Form A of an oxalate salt of Compound 1.

Figure 95:
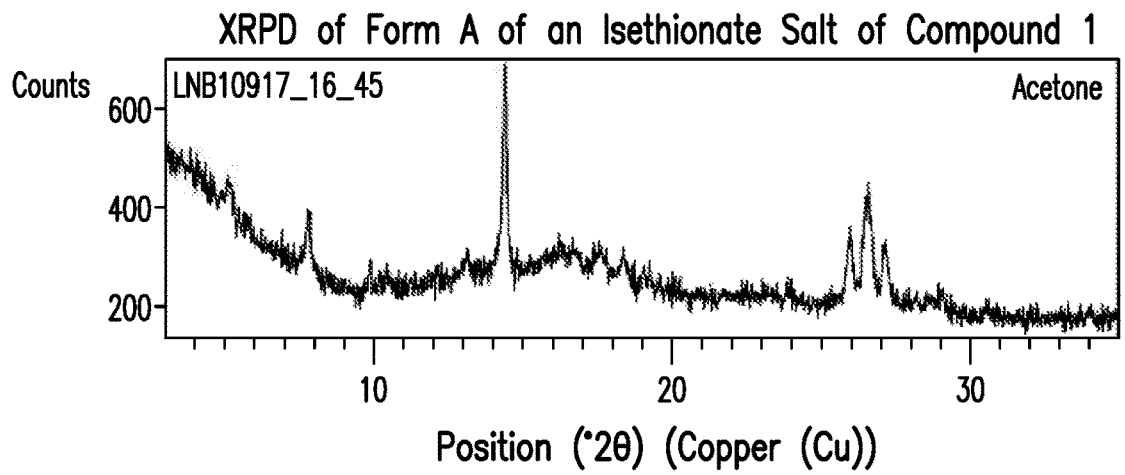

FIG. 95 provides a representative XRPD pattern of Form A of an isethionate salt of Compound 1.

Figure 96:
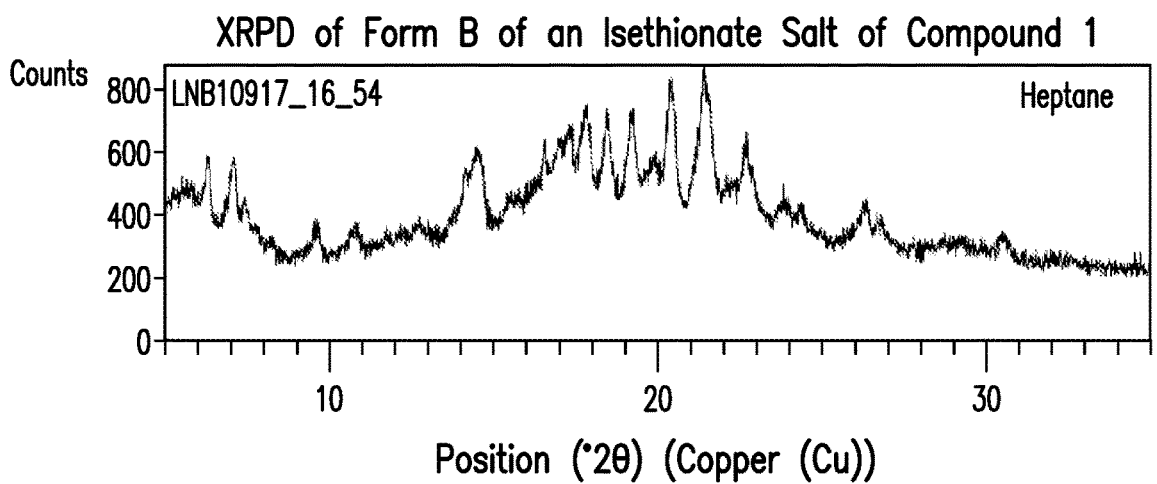

FIG. 96 provides a representative XRPD pattern of Form B of an isethionate salt of Compound 1.

Figure 97:
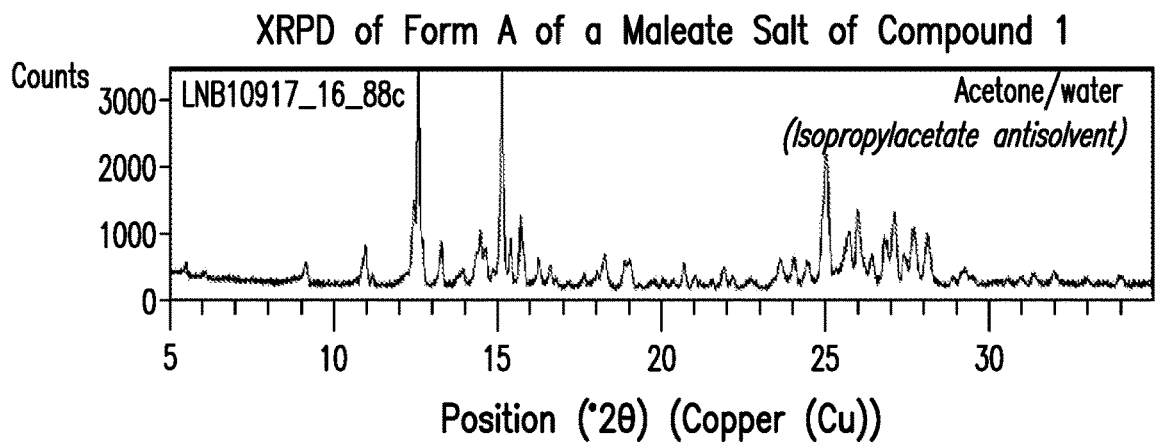

FIG. 97 provides a representative XRPD pattern of Form A of a maleate salt of Compound 1.

Figure 98:
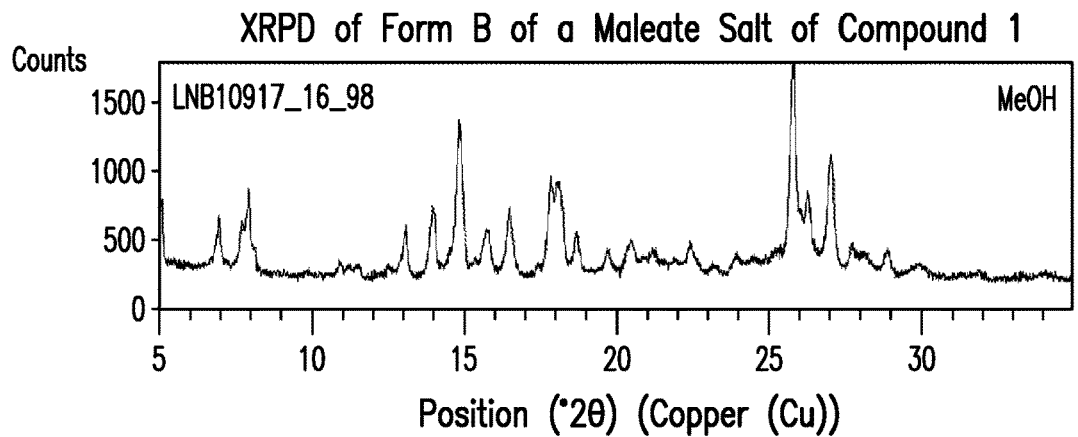

FIG. 98 provides a representative XRPD pattern of Form B of a maleate salt of Compound 1.

Figure 99:
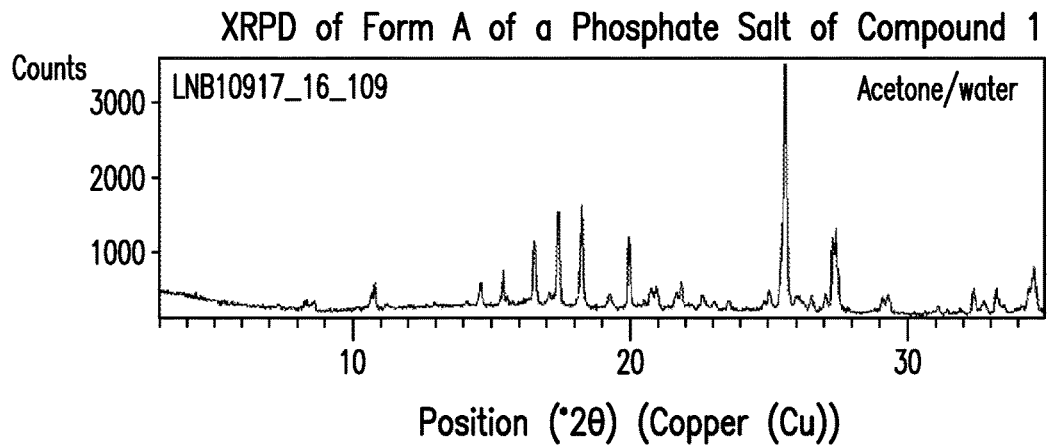

FIG. 99 provides a representative XRPD pattern of Form A of a phosphate salt of Compound 1.

Figure 100:
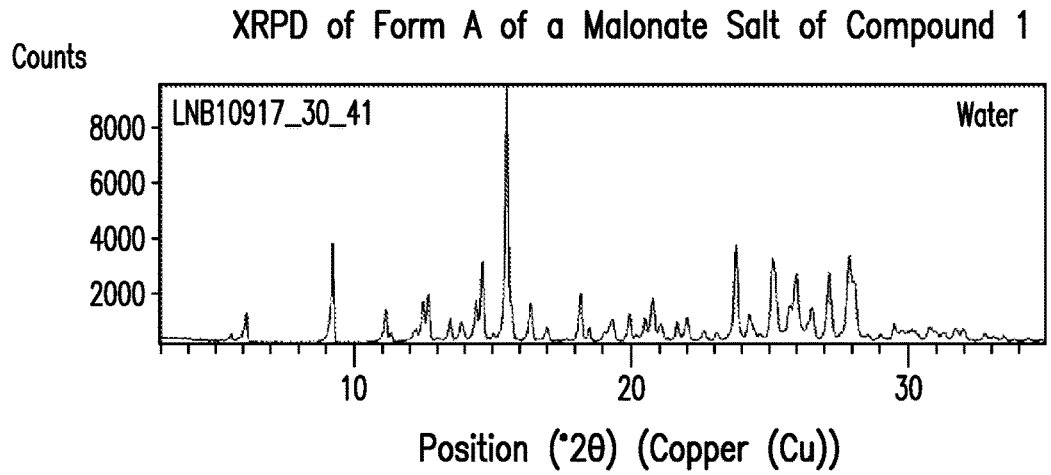

FIG. 100 provides a representative XRPD pattern of Form A of a malonate salt of Compound 1.

Figure 101:
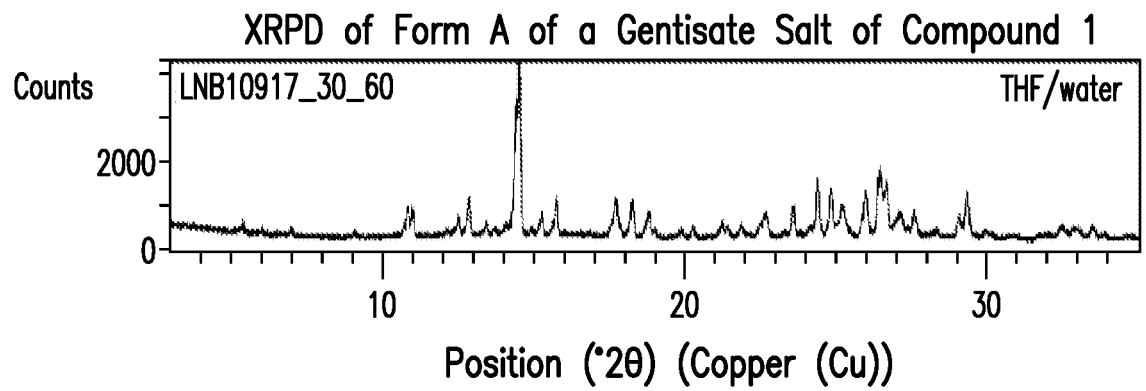

FIG. 101 provides a representative XRPD pattern of Form A of a gentisate salt of Compound 1.

Figure 102:
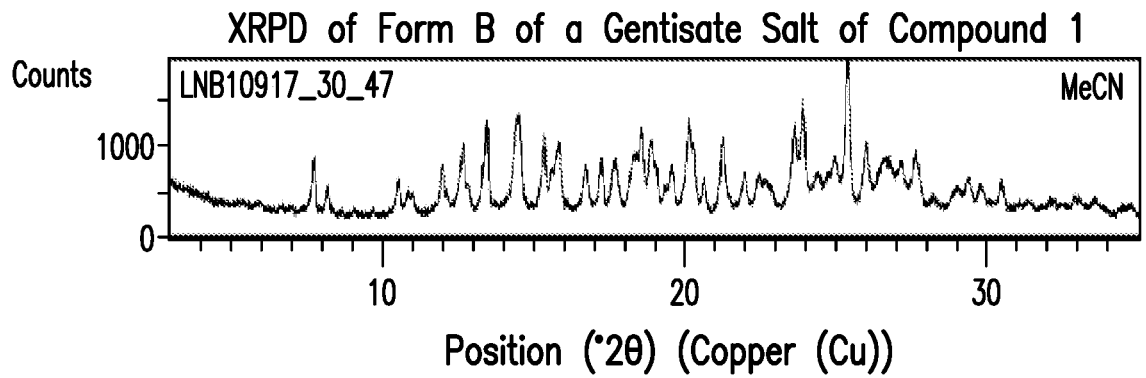

FIG. 102 provides a representative XRPD pattern of Form B of a gentisate salt of Compound 1.

Figure 103:
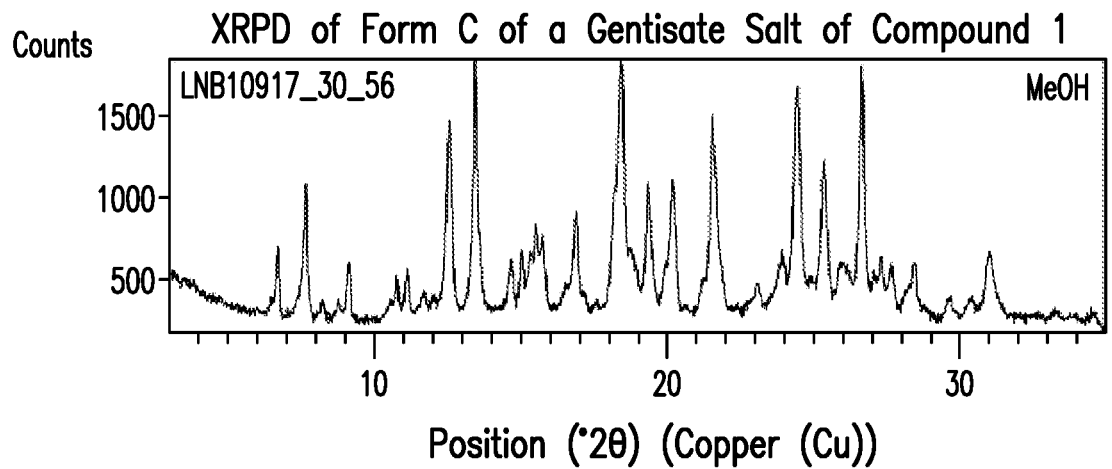

FIG. 103 provides a representative XRPD pattern of Form C of a gentisate salt of Compound 1.

Figure 104:
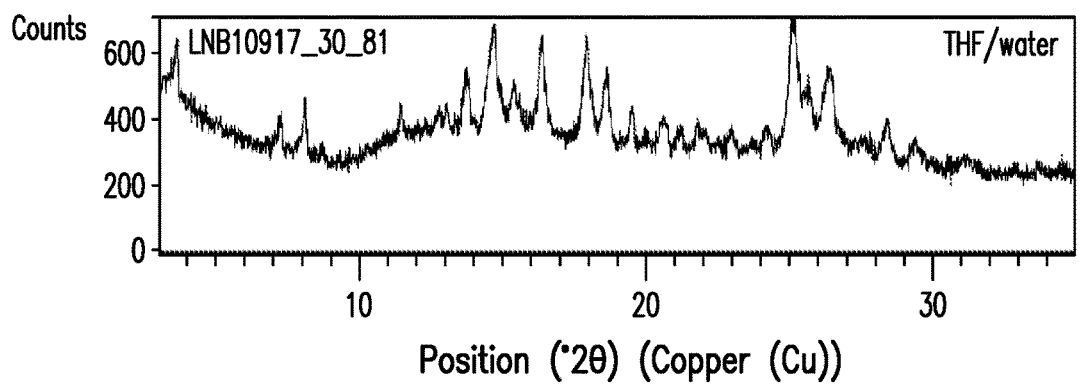

FIG. 104 provides a representative XRPD pattern of Form A of an L-tartrate salt of Compound 1.

Figure 105:
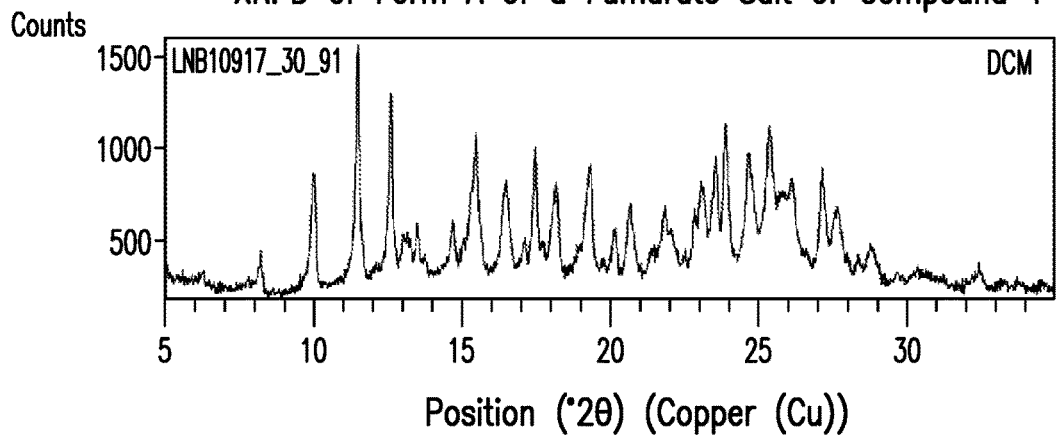

FIG. 105 provides a representative XRPD pattern of Form A of a fumarate salt of Compound 1.

Figure 106:
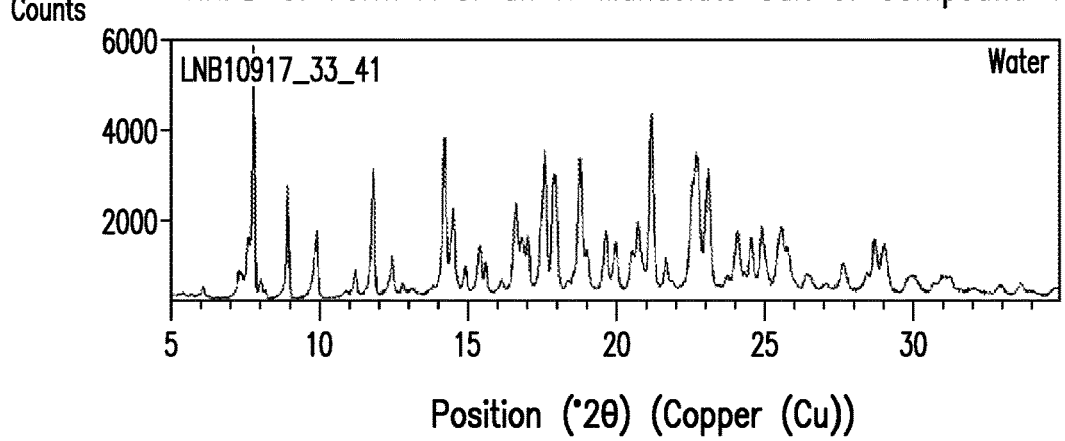

FIG. 106 provides a representative XRPD pattern of Form A of an R-mandelate salt of Compound 1.

Figure 107:
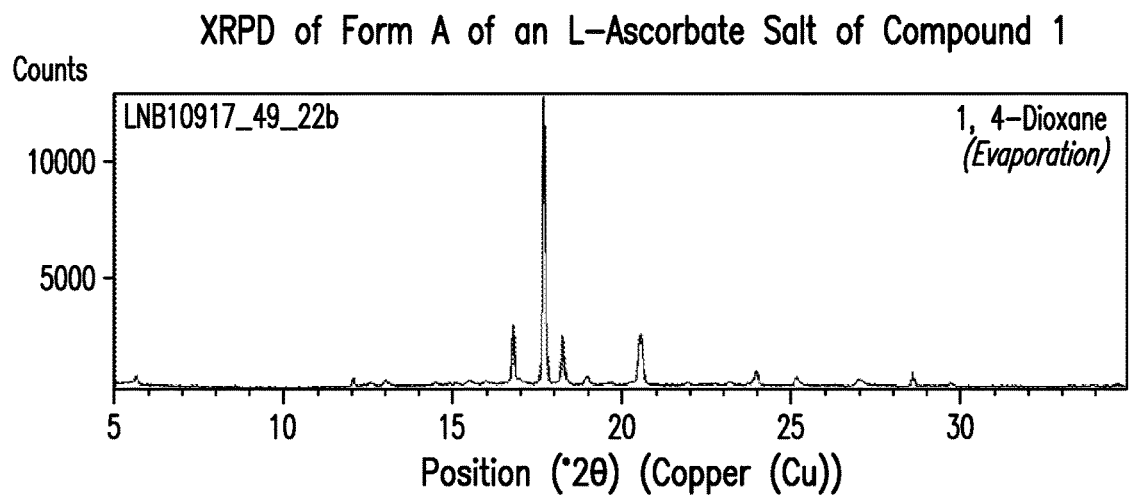

FIG. 107 provides a representative XRPD pattern of Form A of an L-ascorbate salt of Compound 1.

Figure 108:
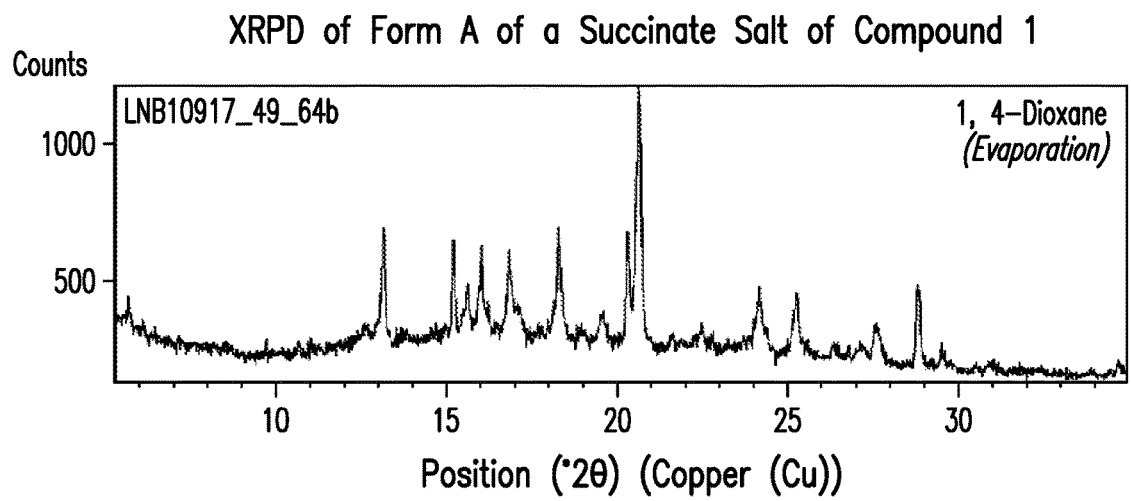

FIG. 108 provides a representative XRPD pattern of Form A of a succinate salt of Compound 1.

Figure 109:
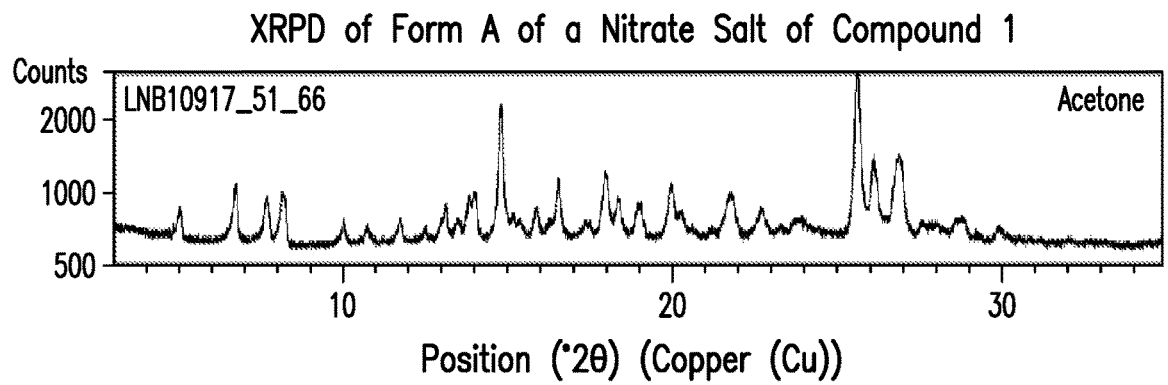

FIG. 109 provides a representative XRPD pattern of Form A of a nitrate salt of Compound 1.

Figure 110:
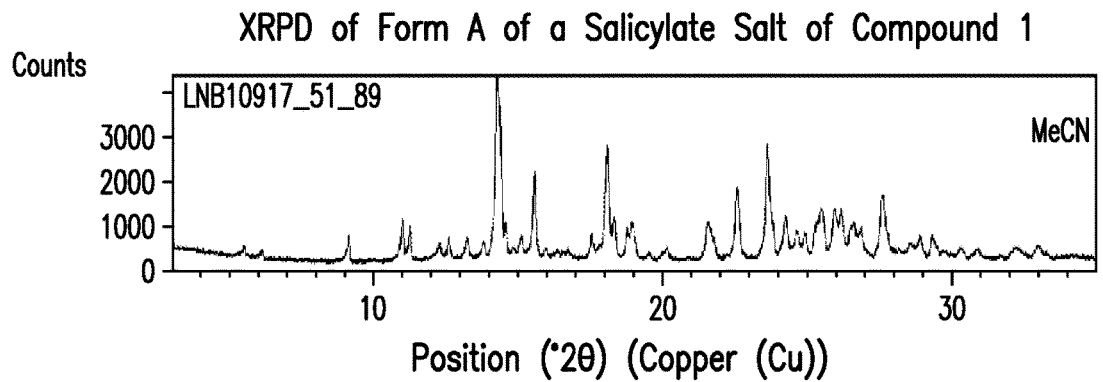

FIG. 110 provides a representative XRPD pattern of Form A of a salicylate salt of Compound 1.

Figure 111:
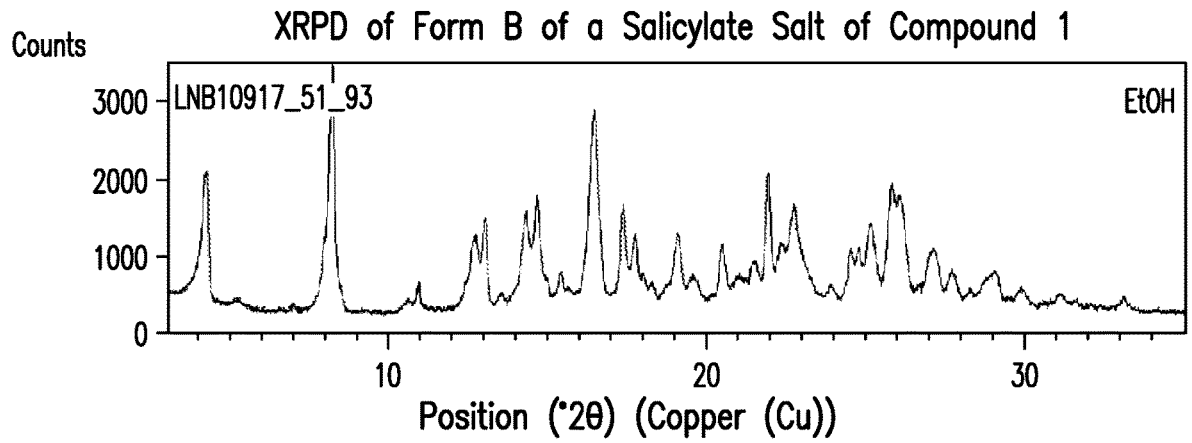

FIG. 111 provides a representative XRPD pattern of Form B of a salicylate salt of Compound 1.

Figure 112:
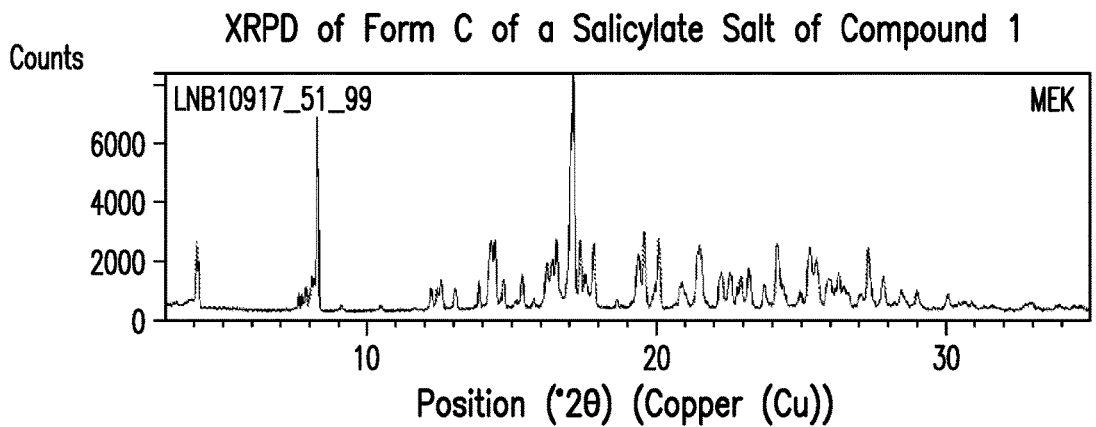

FIG. 112 provides a representative XRPD pattern of Form C of a salicylate salt of Compound 1.

Figure 113:
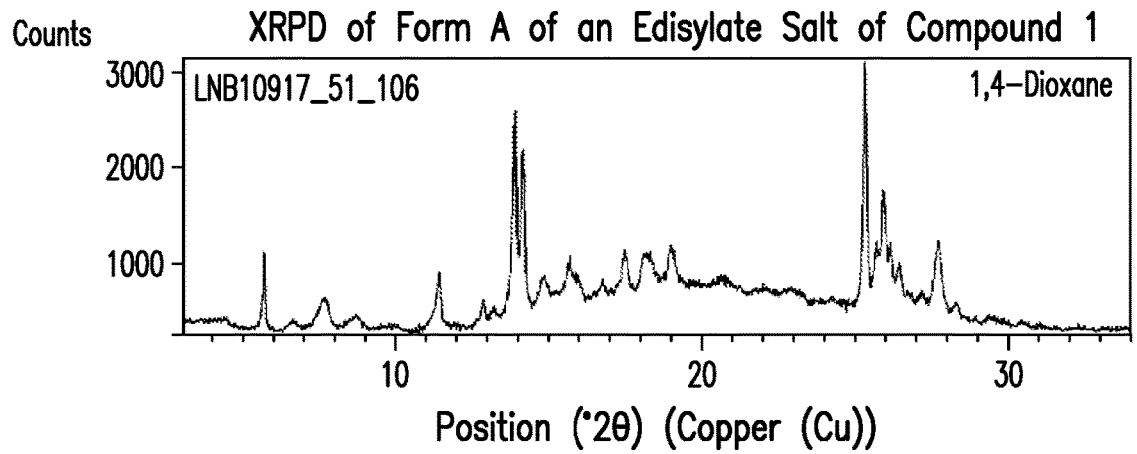

FIG. 113 provides a representative XRPD pattern of Form A of an edisylate salt of Compound 1.

Figure 114:
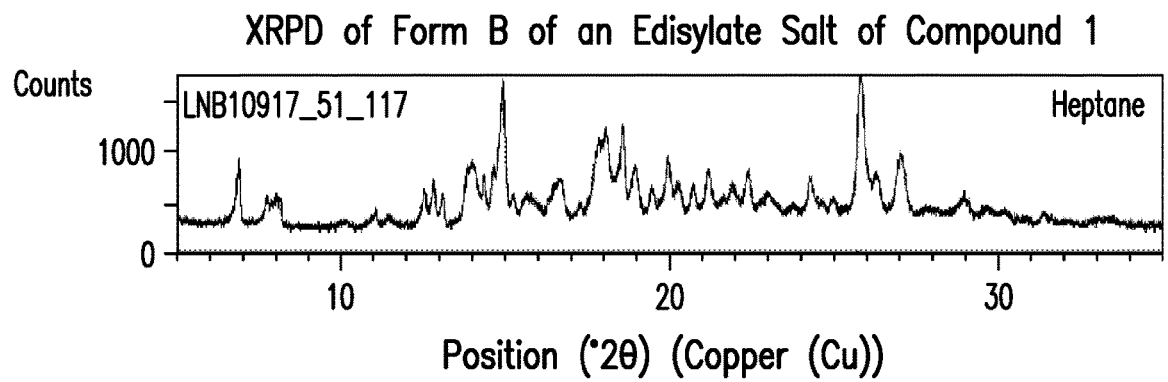

FIG. 114 provides a representative XRPD pattern of Form B of an edisylate salt of Compound 1.

Figure 115:
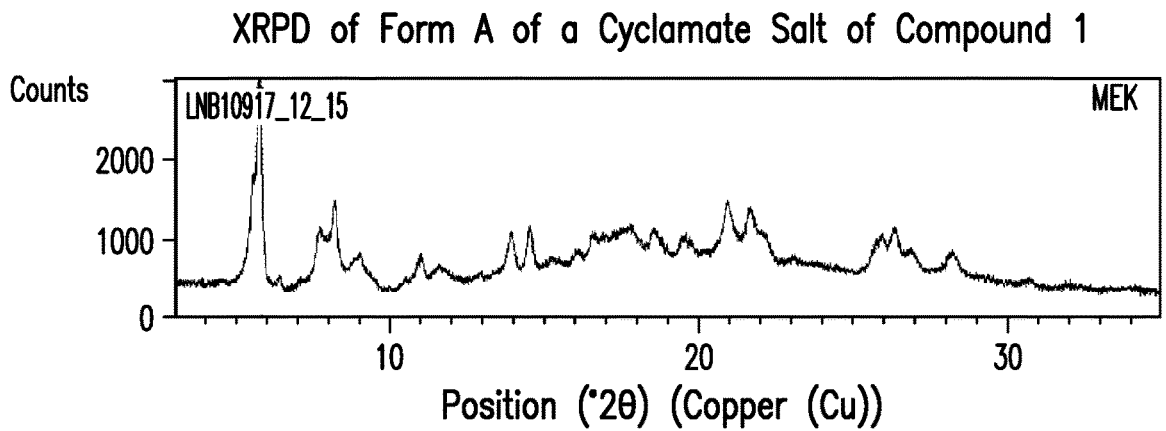

FIG. 115 provides a representative XRPD pattern of Form A of a cyclamate salt of Compound 1.

Figure 116:
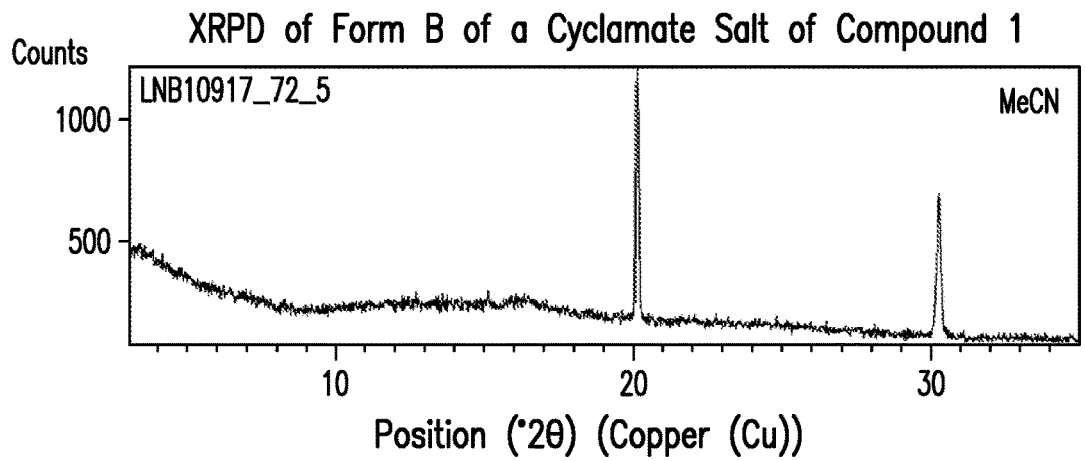

FIG. 116 provides a representative XRPD pattern of Form B of a cyclamate salt of Compound 1.

Figure 117:
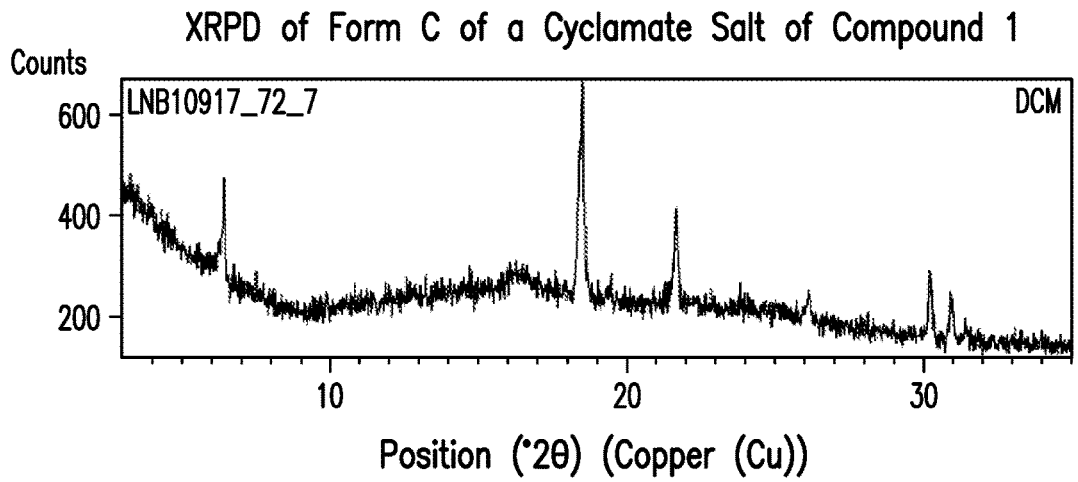

FIG. 117 provides a representative XRPD pattern of Form C of a cyclamate salt of Compound 1.

Figure 118:
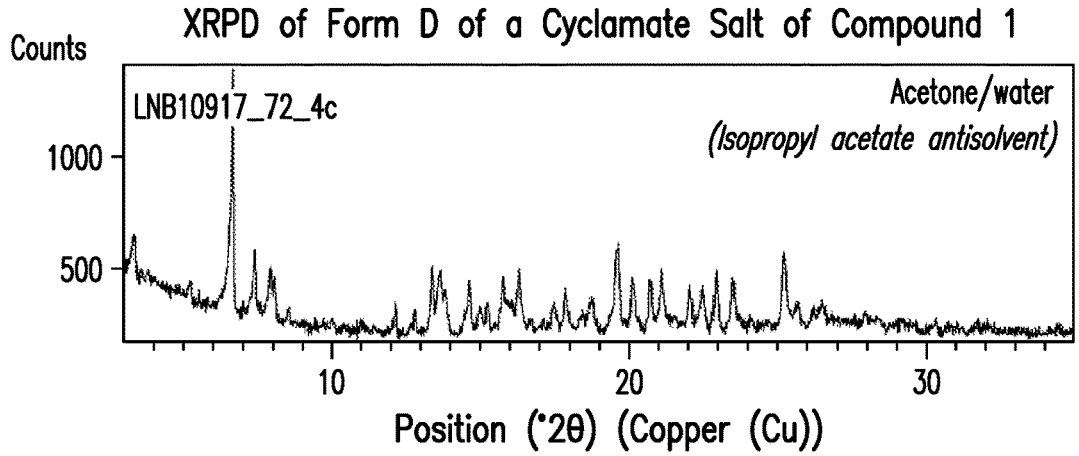

FIG. 118 provides a representative XRPD pattern of Form D of a cyclamate salt of Compound 1.

Figure 119:
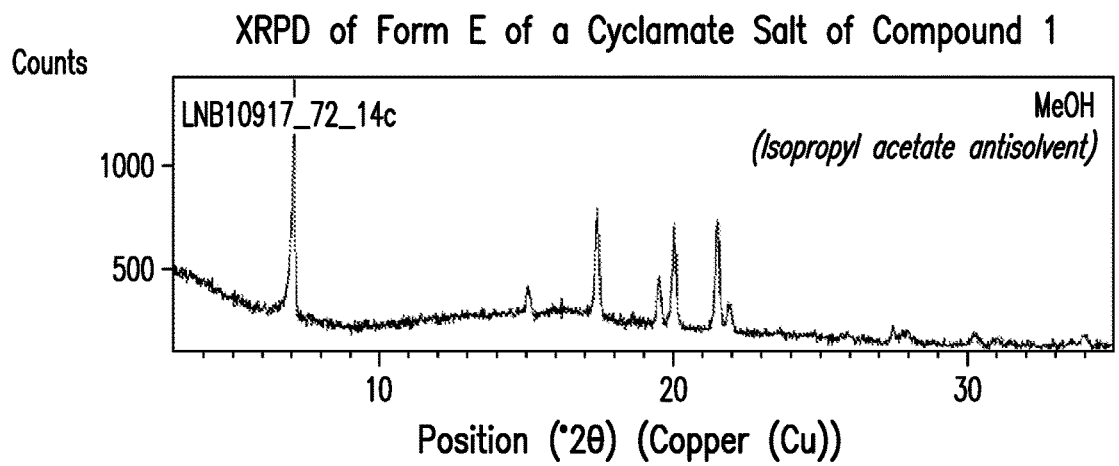

FIG. 119 provides a representative XRPD pattern of Form E of a cyclamate salt of Compound 1.

Figure 120:
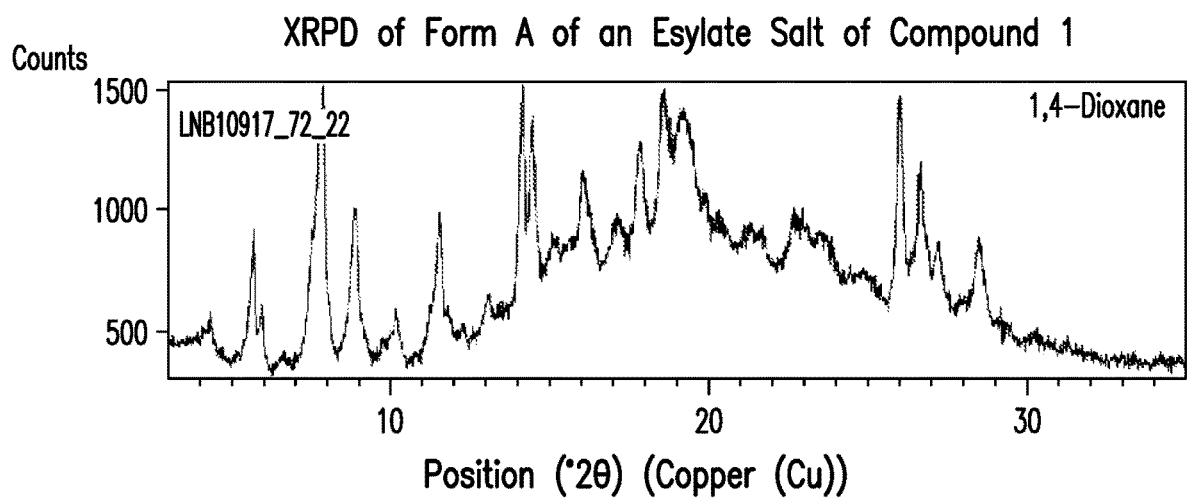

FIG. 120 provides a representative XRPD pattern of Form A of an esylate salt of Compound 1.

Figure 121:
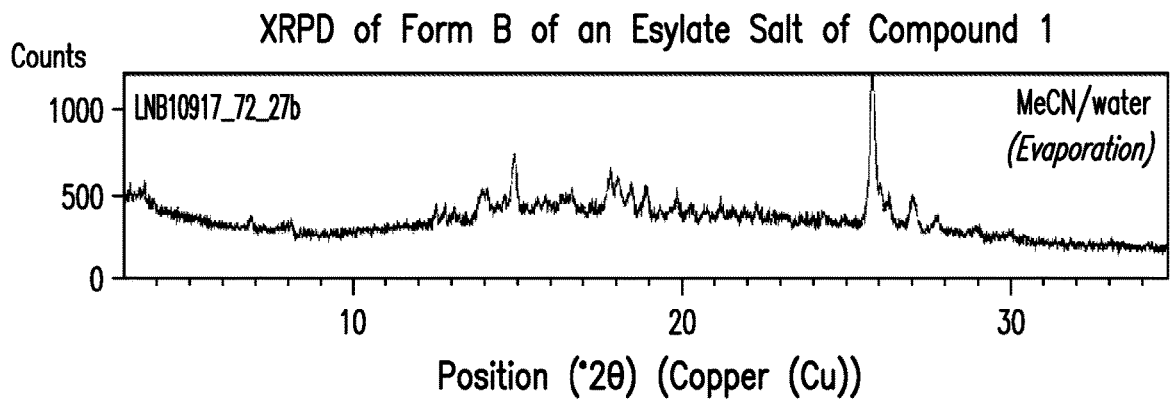

FIG. 121 provides a representative XRPD pattern of Form B of an esylate salt of Compound 1.

Figure 122:
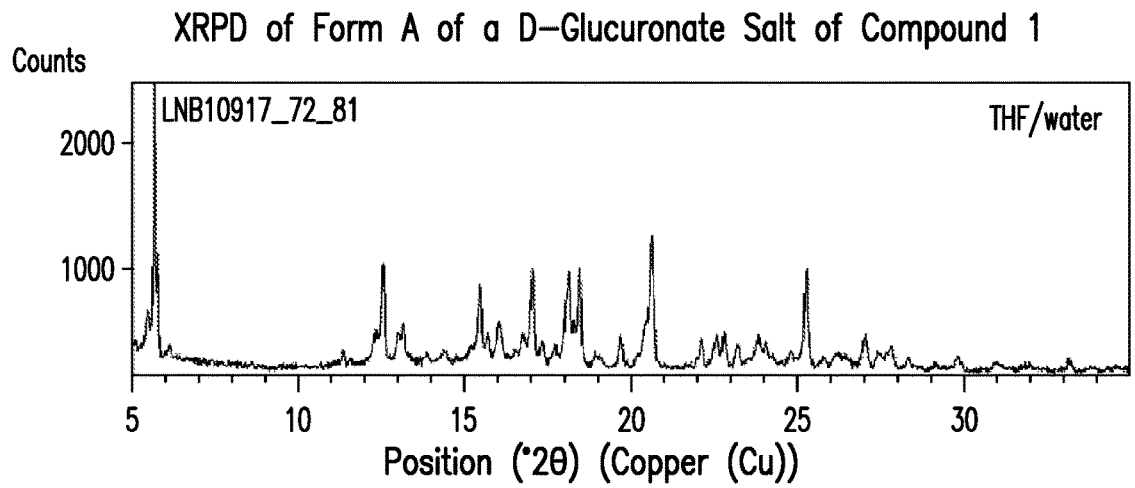

FIG. 122 provides a representative XRPD pattern of Form A of a D-glucuronate salt of Compound 1.

Figure 123:
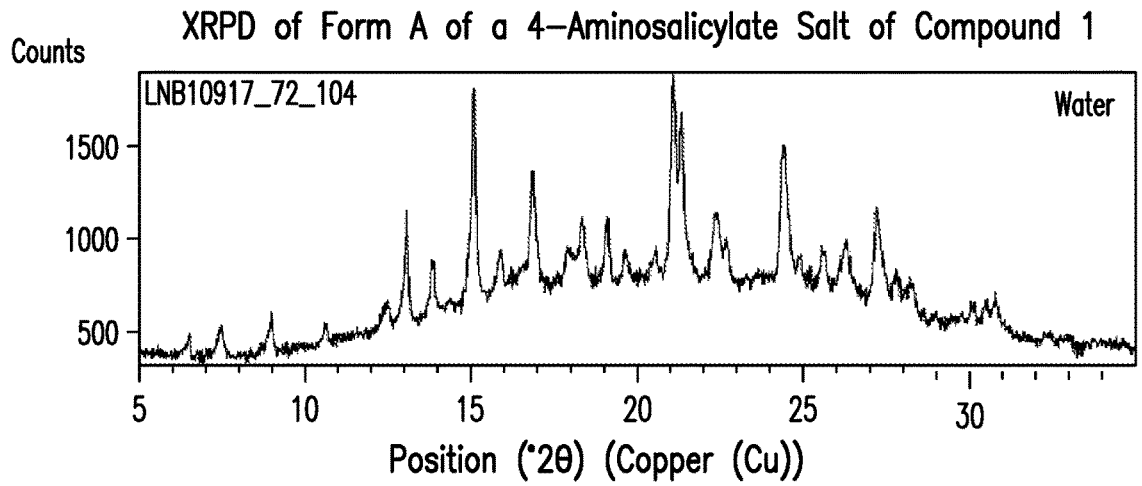

FIG. 123 provides a representative XRPD pattern of Form A of a 4-aminosalicylate salt of Compound 1.

Figure 124:
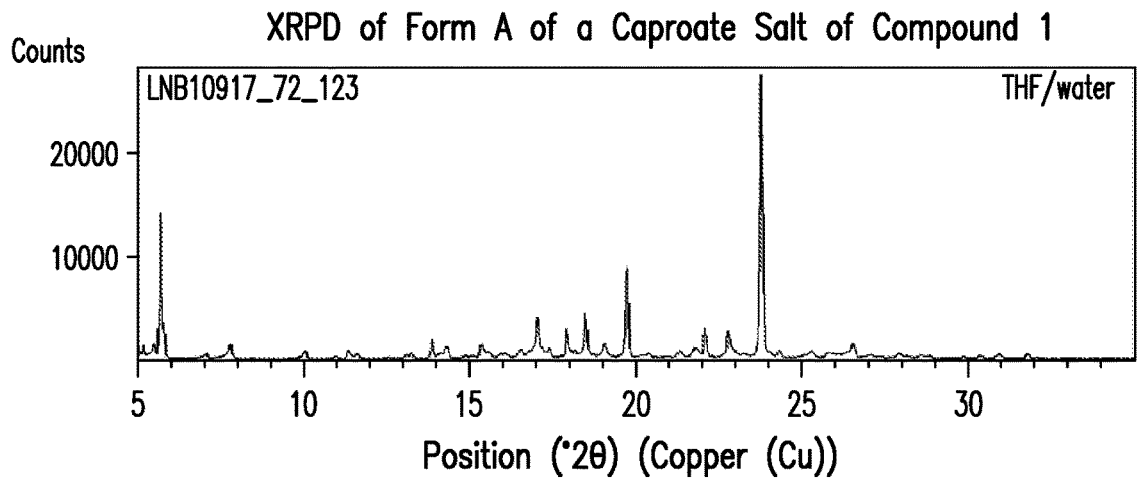

FIG. 124 provides a representative XRPD pattern of Form A of a caproate salt of Compound 1.

Figure 125:
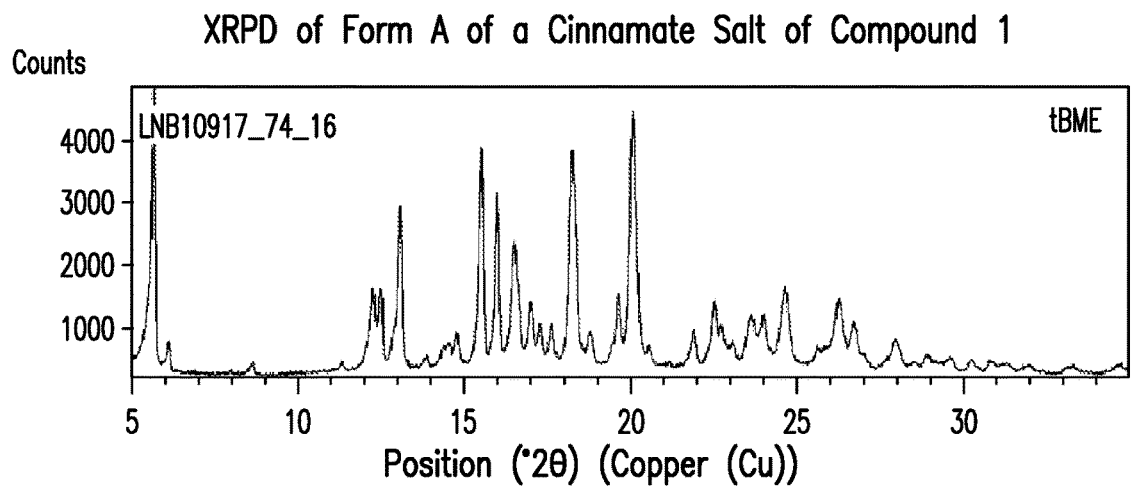

FIG. 125 provides a representative XRPD pattern of Form A of a cinnamate salt of Compound 1.

Figure 126:
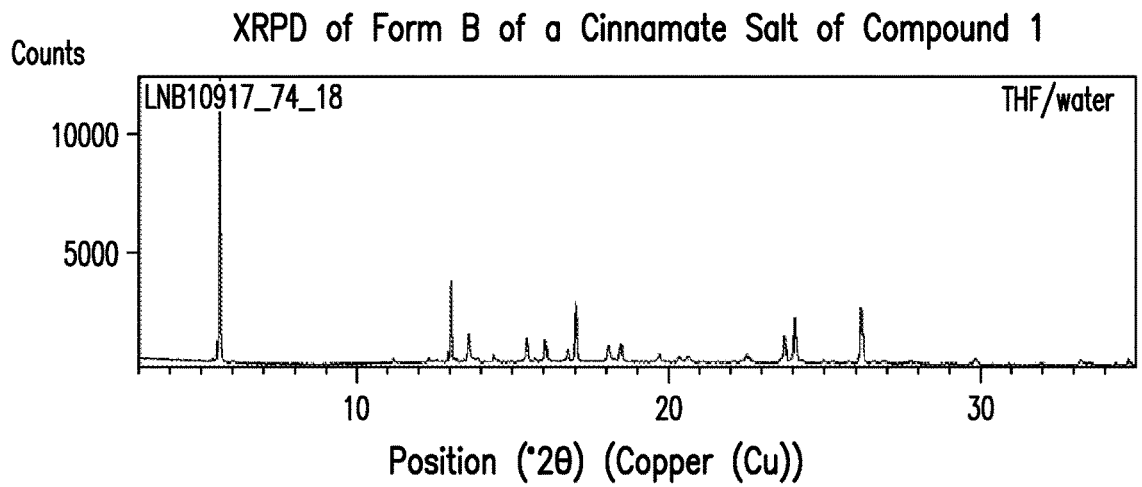

FIG. 126 provides a representative XRPD pattern of Form B of a cinnamate salt of Compound 1.

Figure 127:
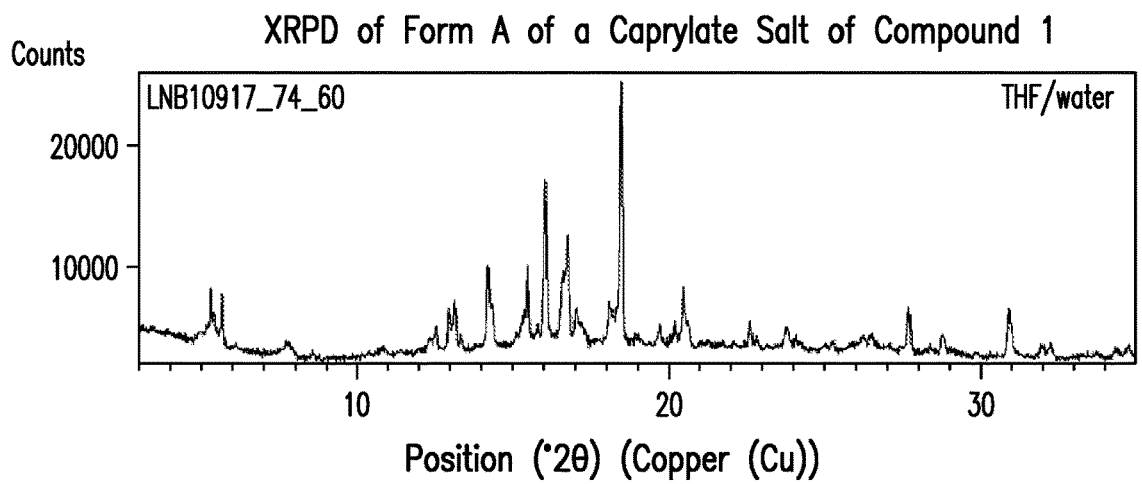

FIG. 127 provides a representative XRPD pattern of Form A of a caprylate salt of Compound 1.

Figure 128:
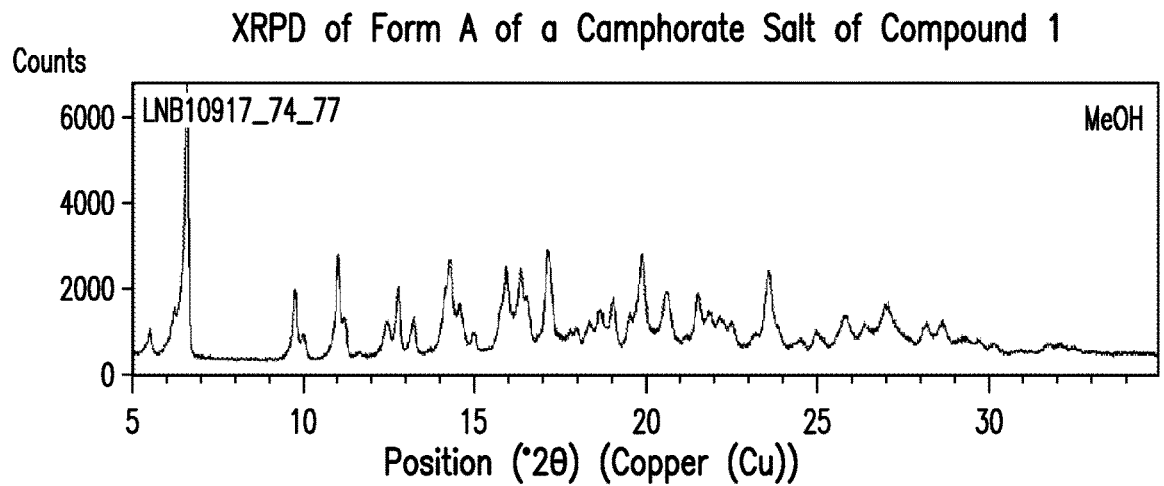

FIG. 128 provides a representative XRPD pattern of Form A of a camphorate salt of Compound 1.

Figure 129:
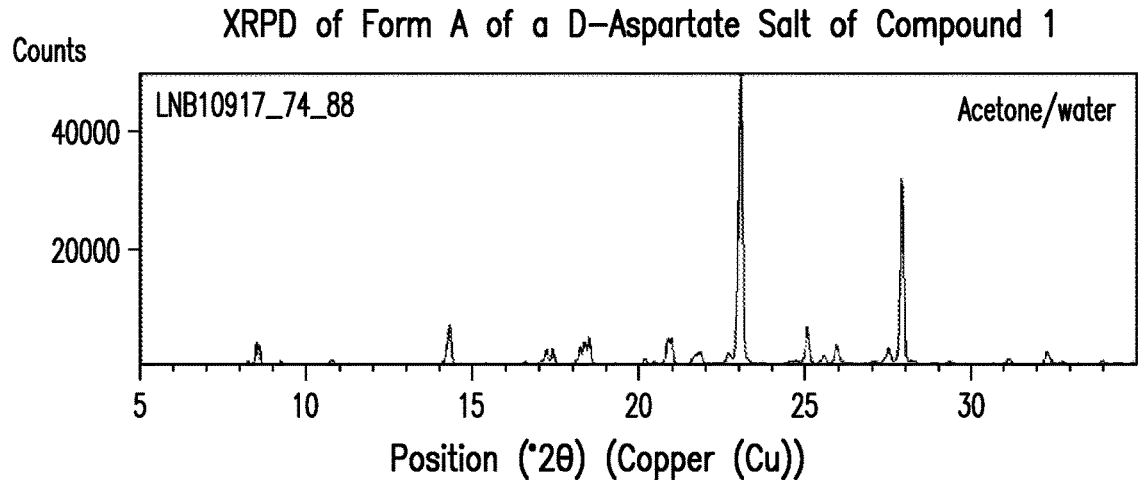

FIG. 129 provides a representative XRPD pattern of Form A of a D-aspartate salt of Compound 1.

Figure 130:
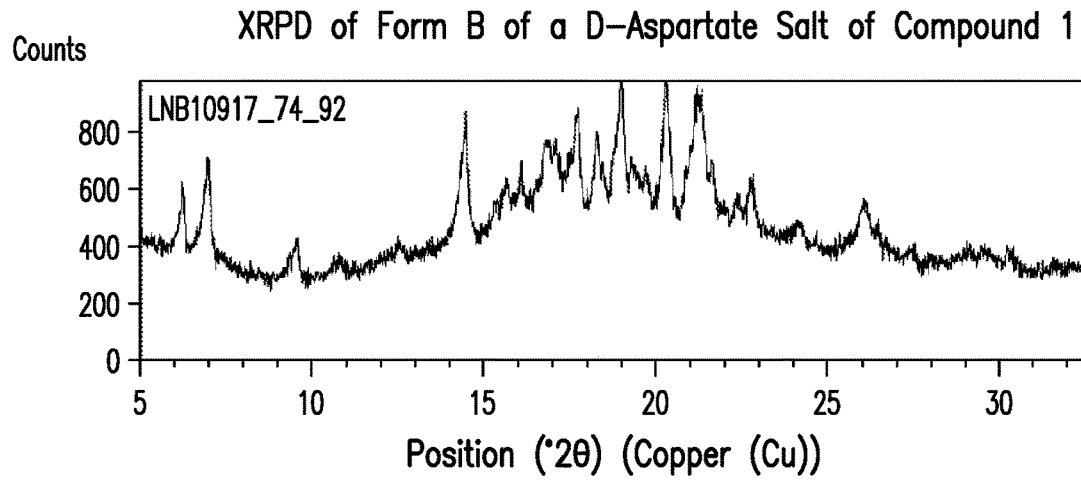

FIG. 130 provides a representative XRPD pattern of Form B of a D-aspartate salt of Compound 1.

Figure 131:
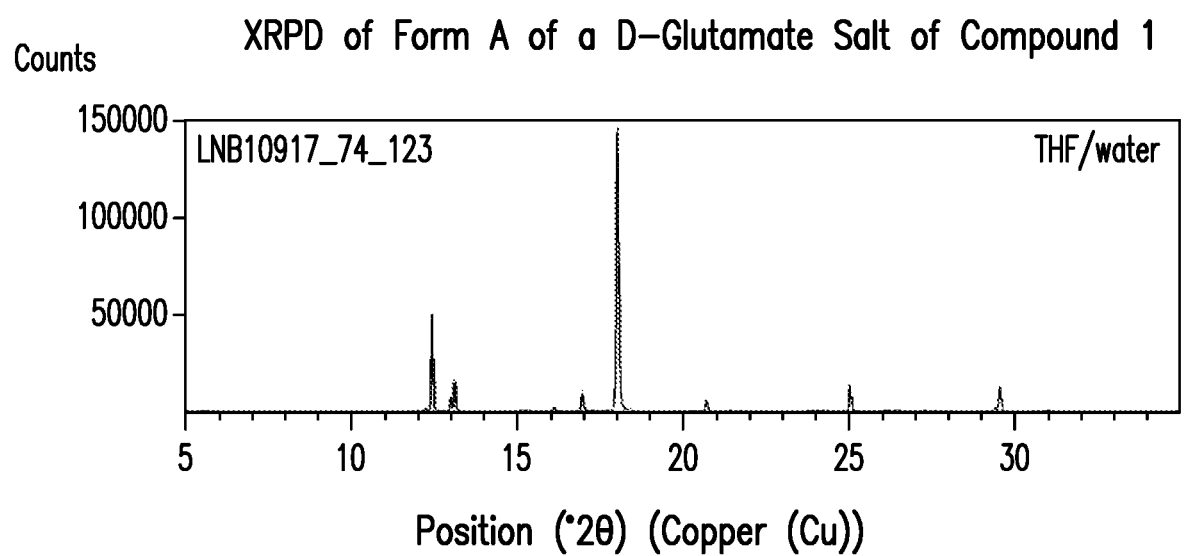

FIG. 131 provides a representative XRPD pattern of Form A of a D-glutamate salt of Compound 1.

Figure 132:
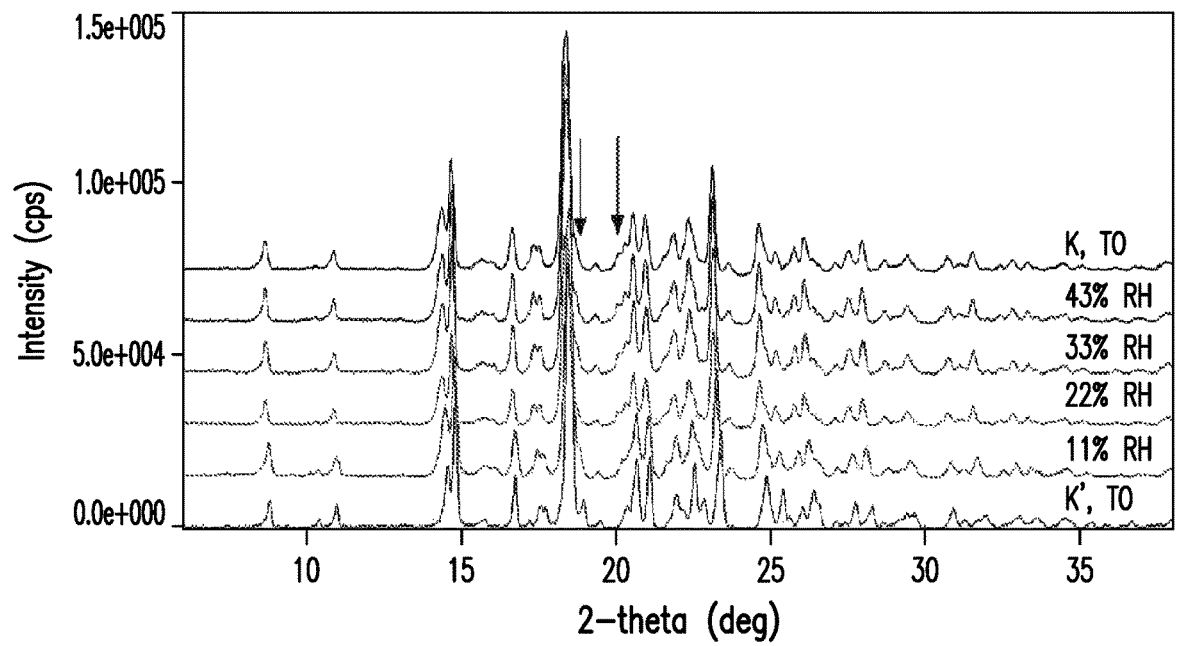

FIG. 132 provides an overlay of XRPD patterns of Form K of a free base of Compound 1 under different RH at ambient temperature for 2 days.

Figure 133:
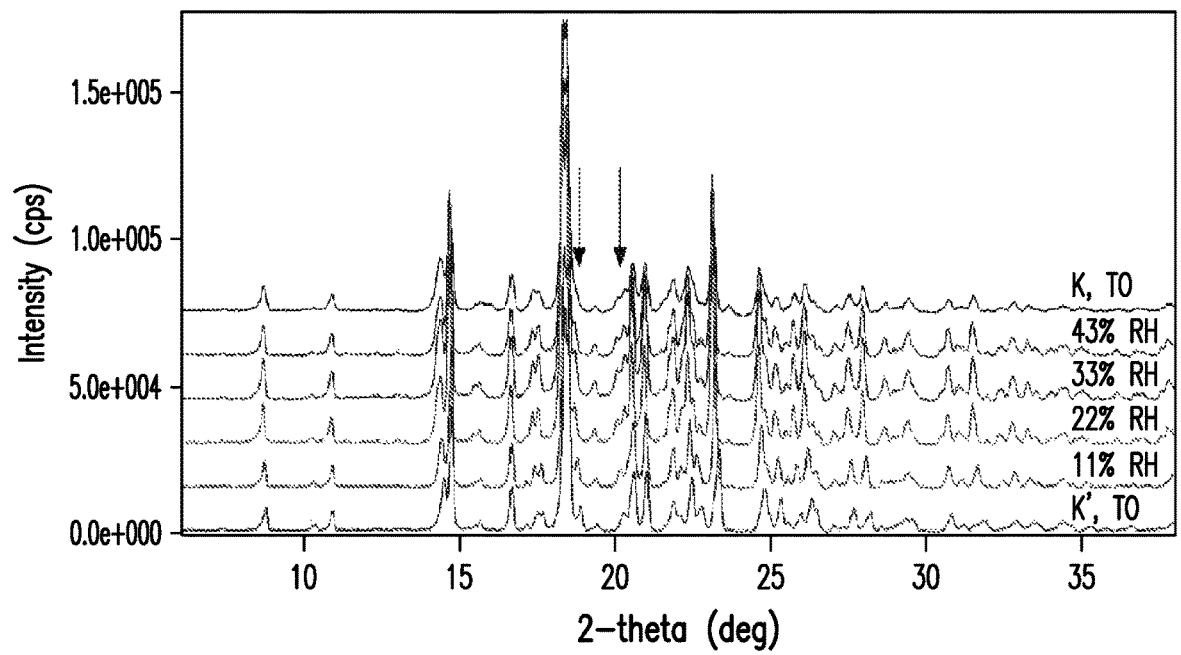

FIG. 133 provides an overlay of XRPD patterns of Form K' of a free base of Compound 1 under different RH at ambient temperature for 2 days.

Figure 134:
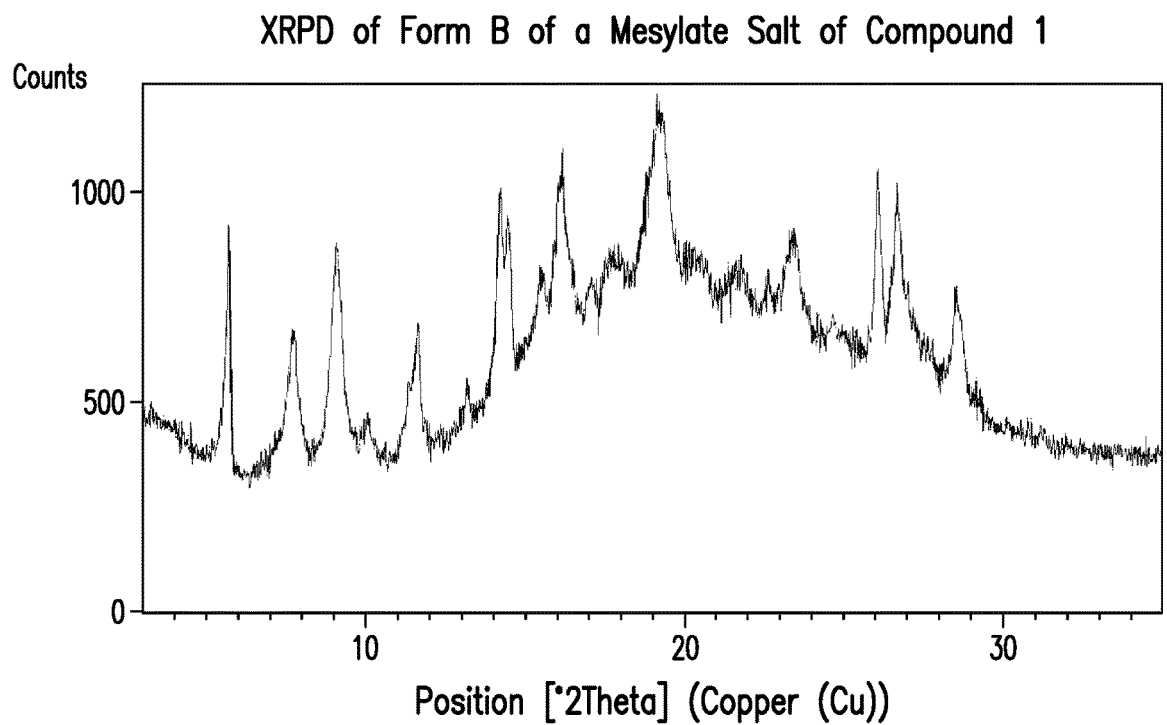

FIG. 134 provides a representative XRPD pattern of Form B of a mesylate salt of Compound 1.

Figure 135:
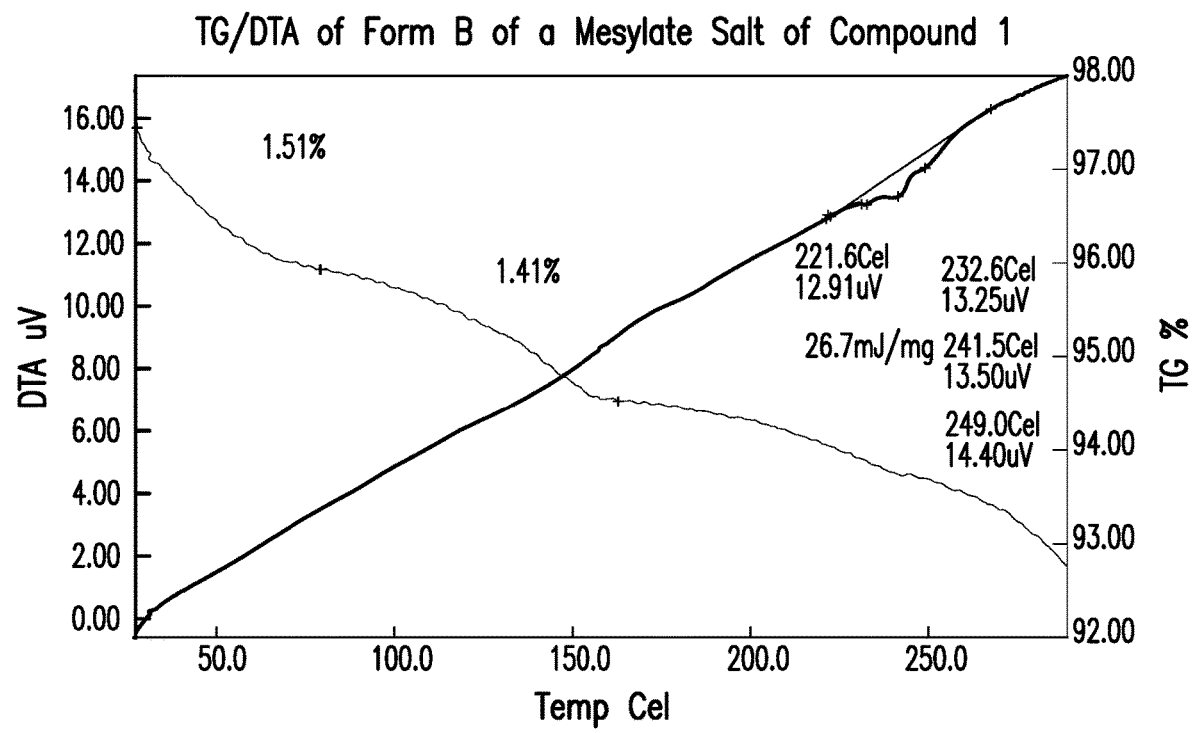

FIG. 135 provides representative TG/DTA thermograms of Form B of a mesylate salt of Compound 1.

Figure 136:
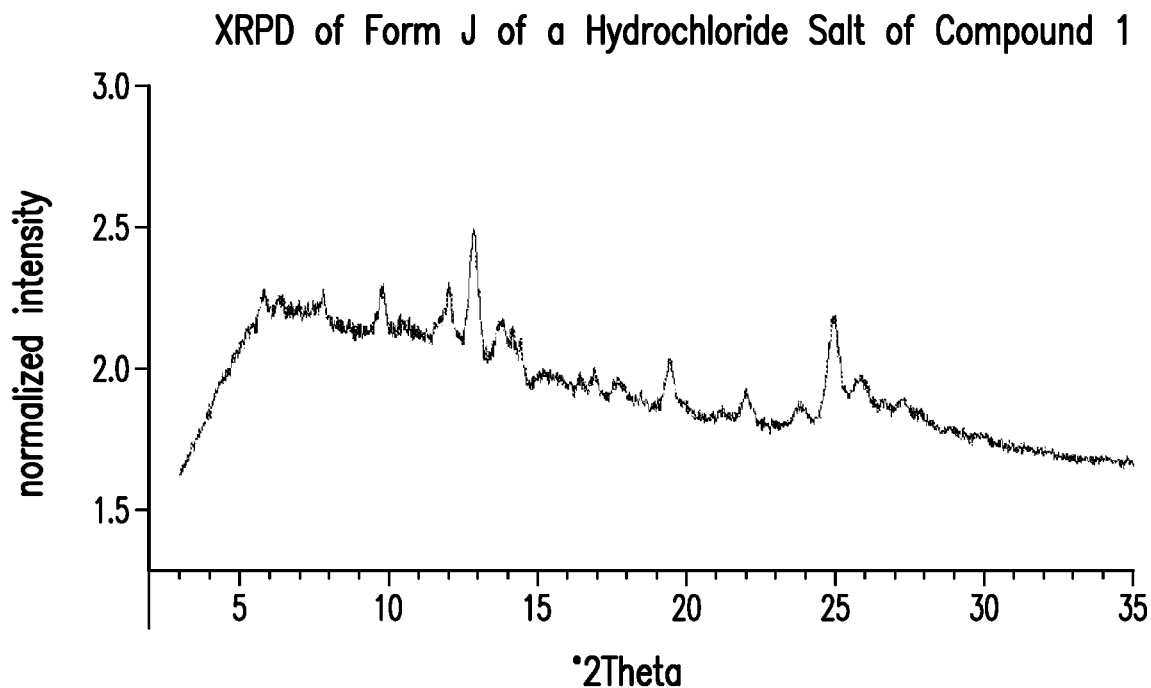

FIG. 136 provides a representative XRPD pattern of Form J of a hydrochloride salt of Compound 1.

Figure 137:
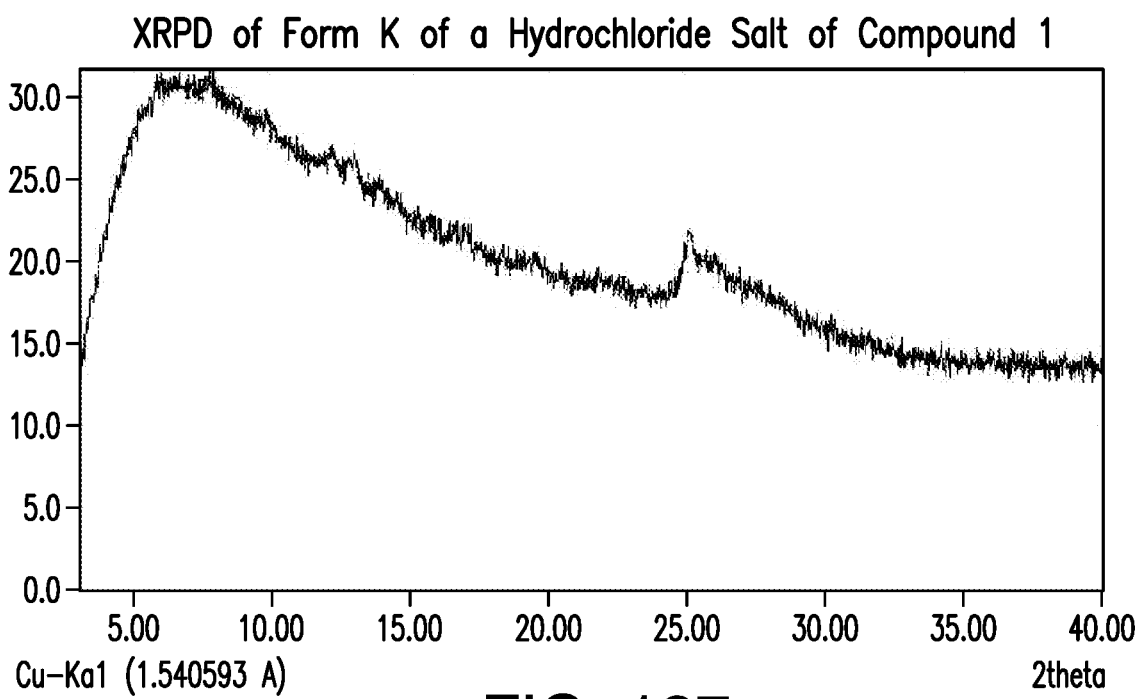

FIG. 137 provides a representative XRPD pattern of Form K of a hydrochloride salt of Compound 1.

Figure 138:
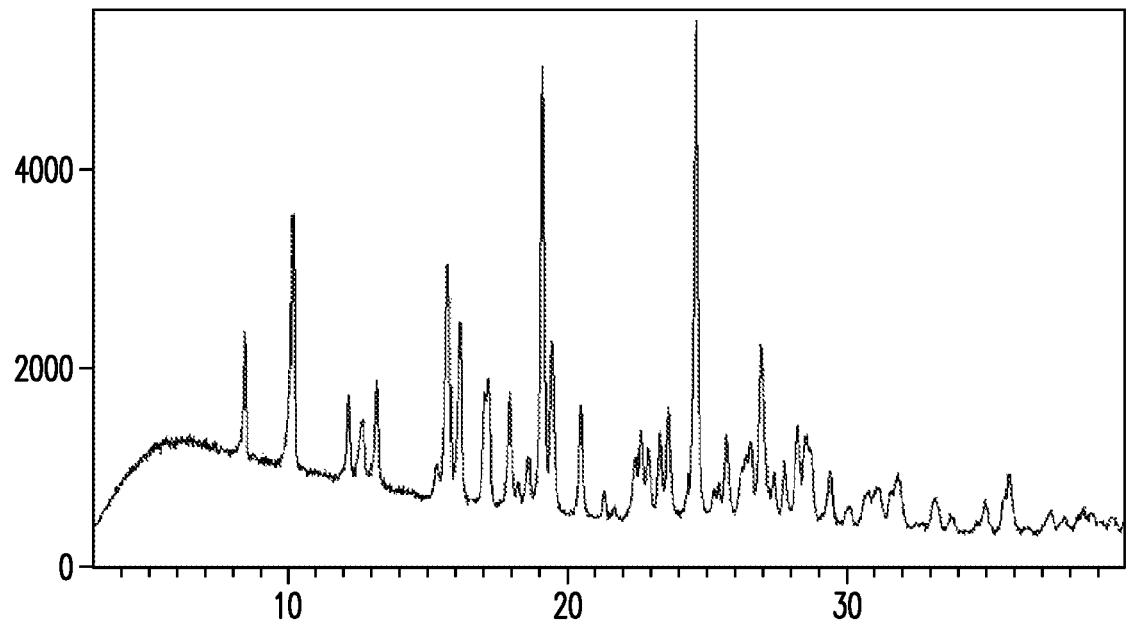

FIG. 138 provides a representative XRPD pattern of Form L of a hydrochloride salt of Compound 1.

Figure 139:
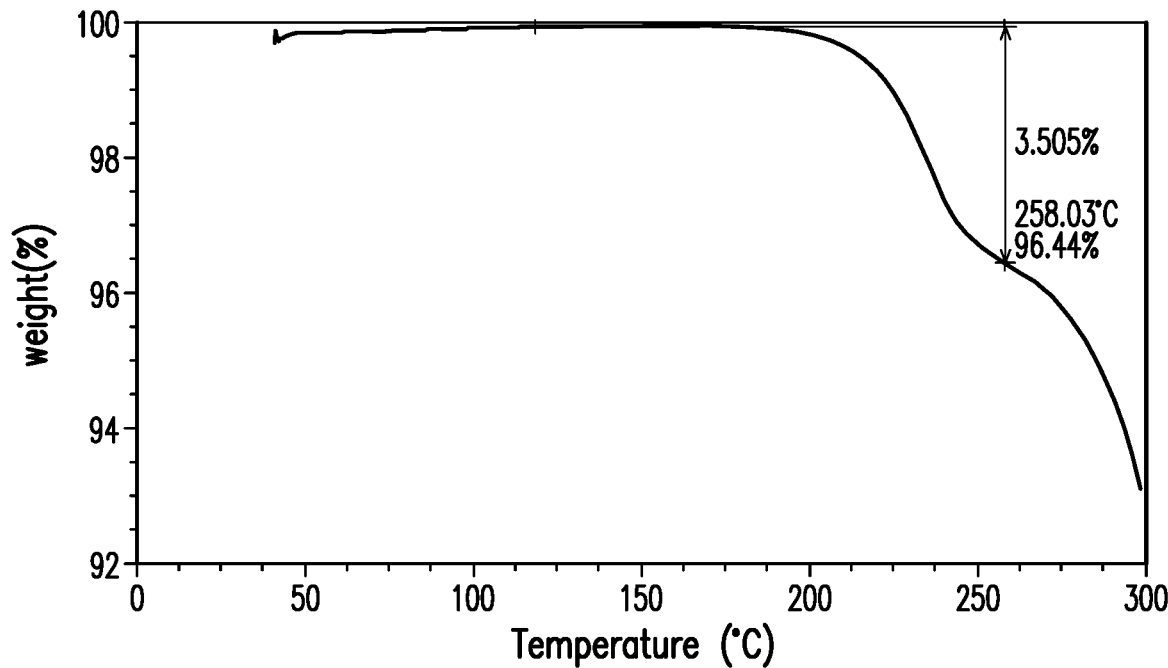

FIG. 139 provides a representative TGA thermogram of Form L of a hydrochloride salt of Compound 1.

Figure 140:
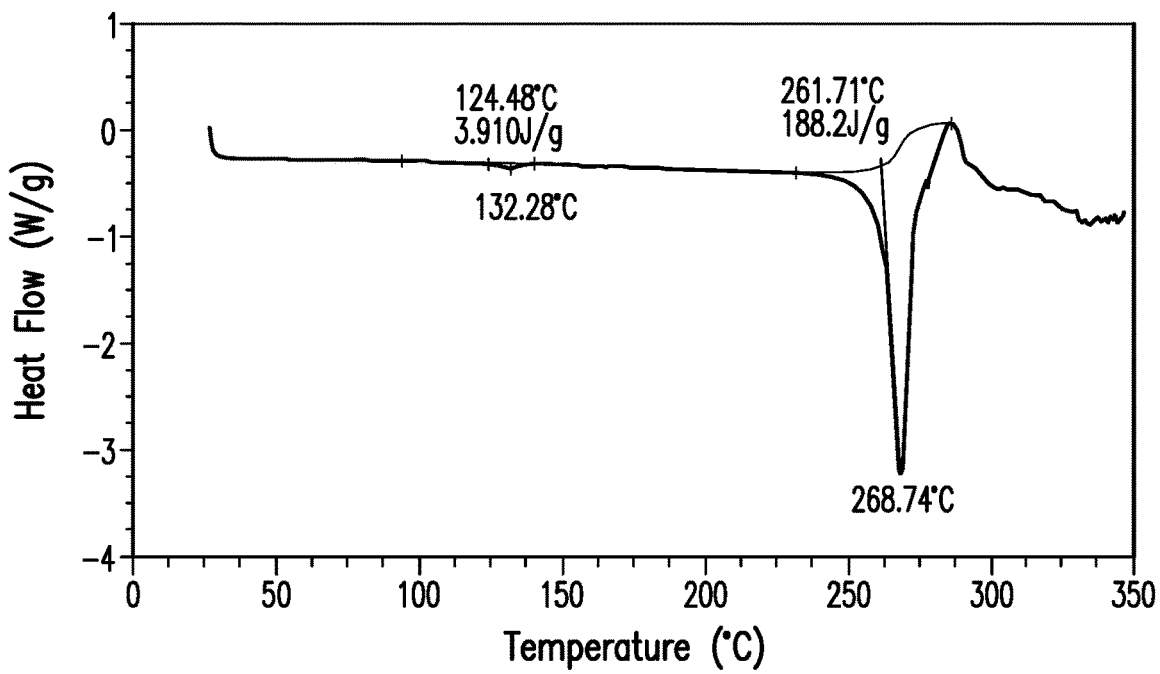

FIG. 140 provides a representative DSC thermogram of Form L of a hydrochloride salt of Compound 1.

Figure 141:
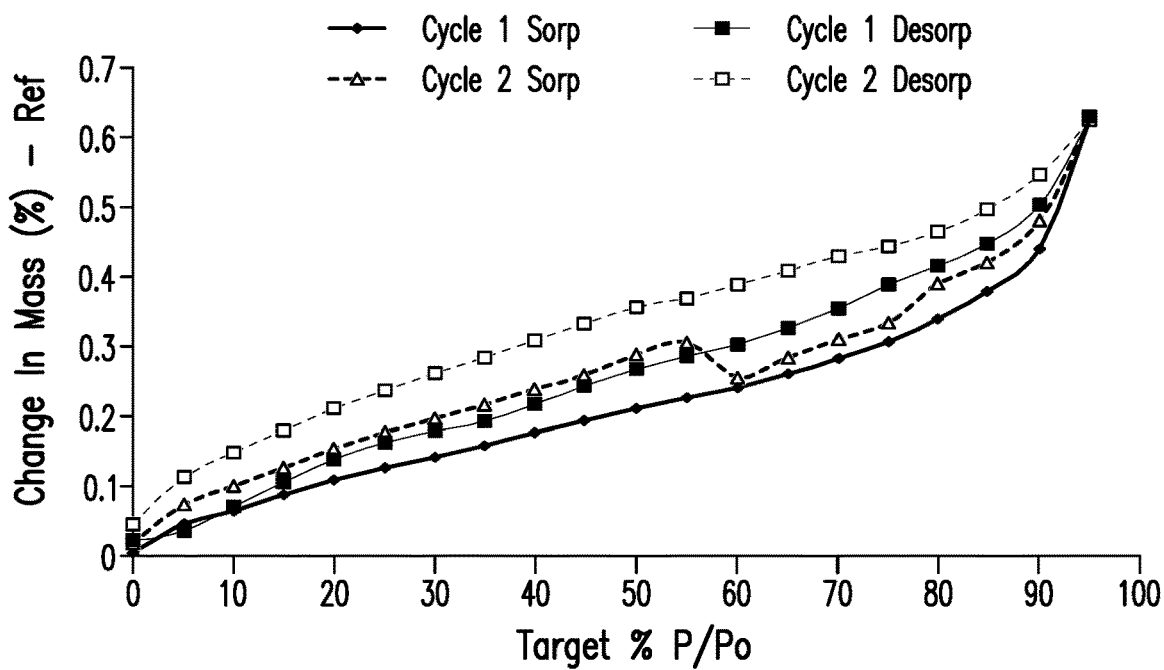

FIG. 141 provides a representative DVS isotherm plot of Form L of a hydrochloride salt of Compound 1.

Figure 142:
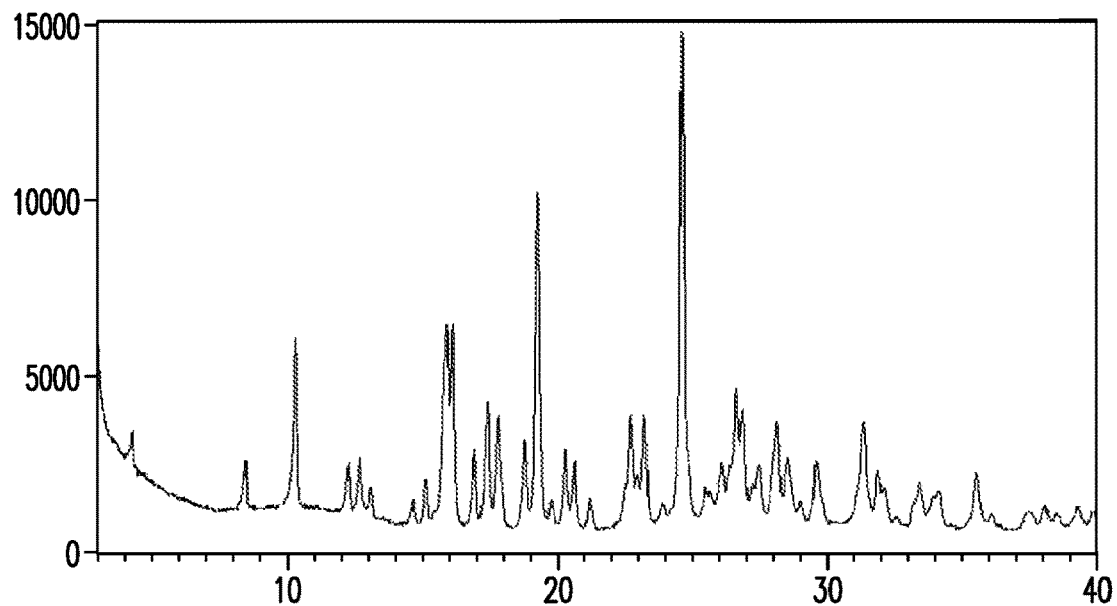

FIG. 142 provides a representative XRPD pattern of Form M of a hydrochloride salt of Compound 1.

Figure 143:
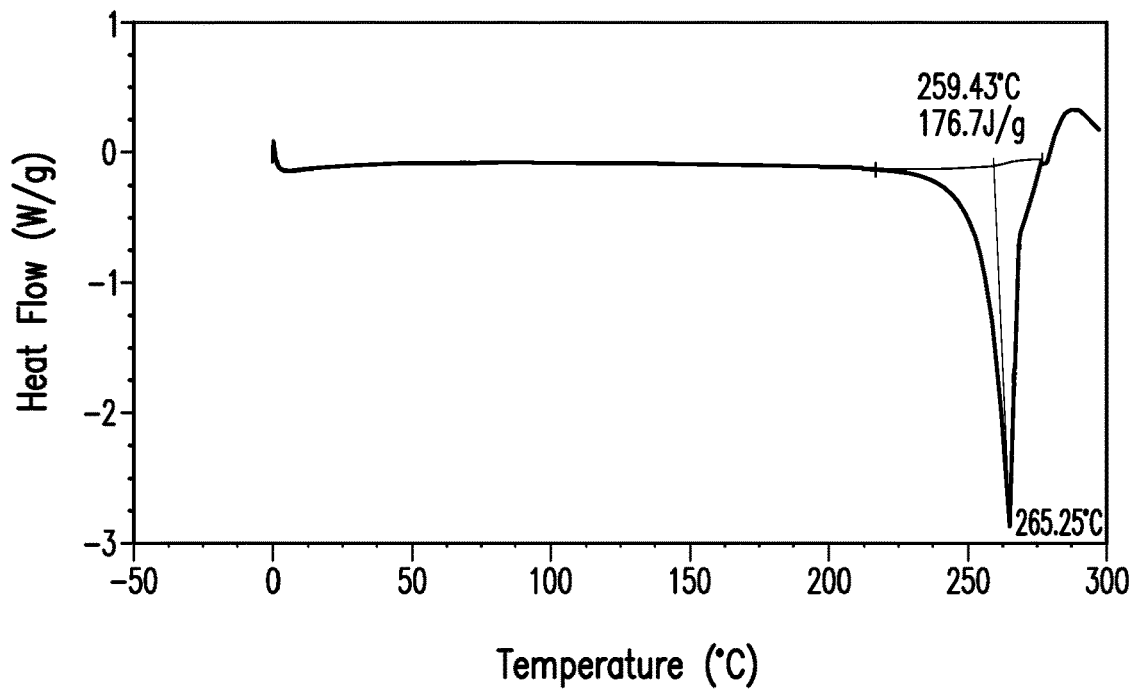

FIG. 143 provides a representative DSC thermogram of Form M of a hydrochloride salt of Compound 1.

Figure 144:
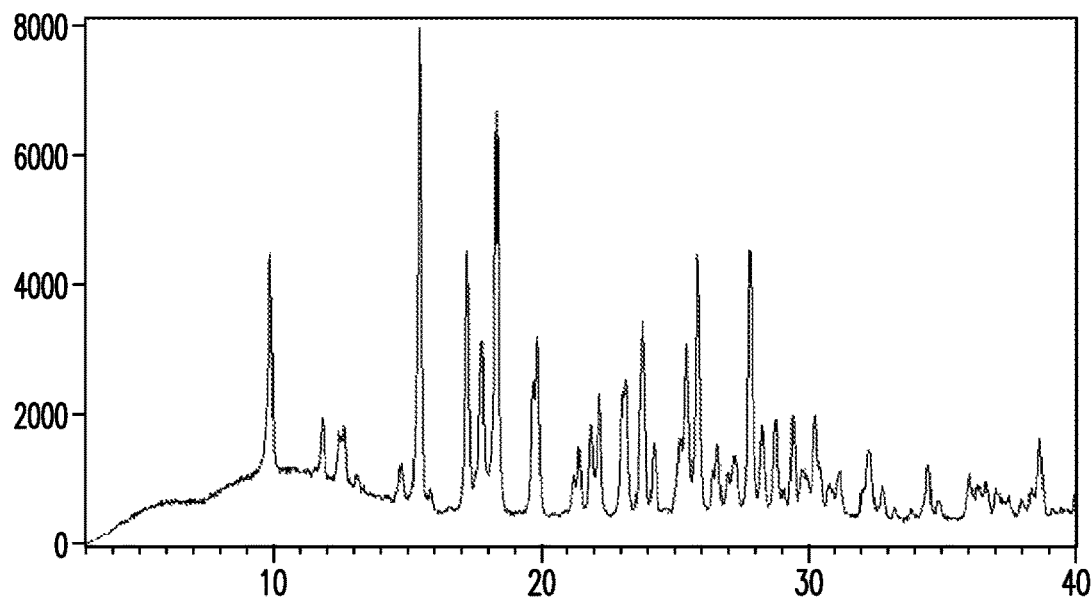

FIG. 144 provides a representative XRPD pattern of Form N of a hydrochloride salt of Compound 1.

Figure 145:
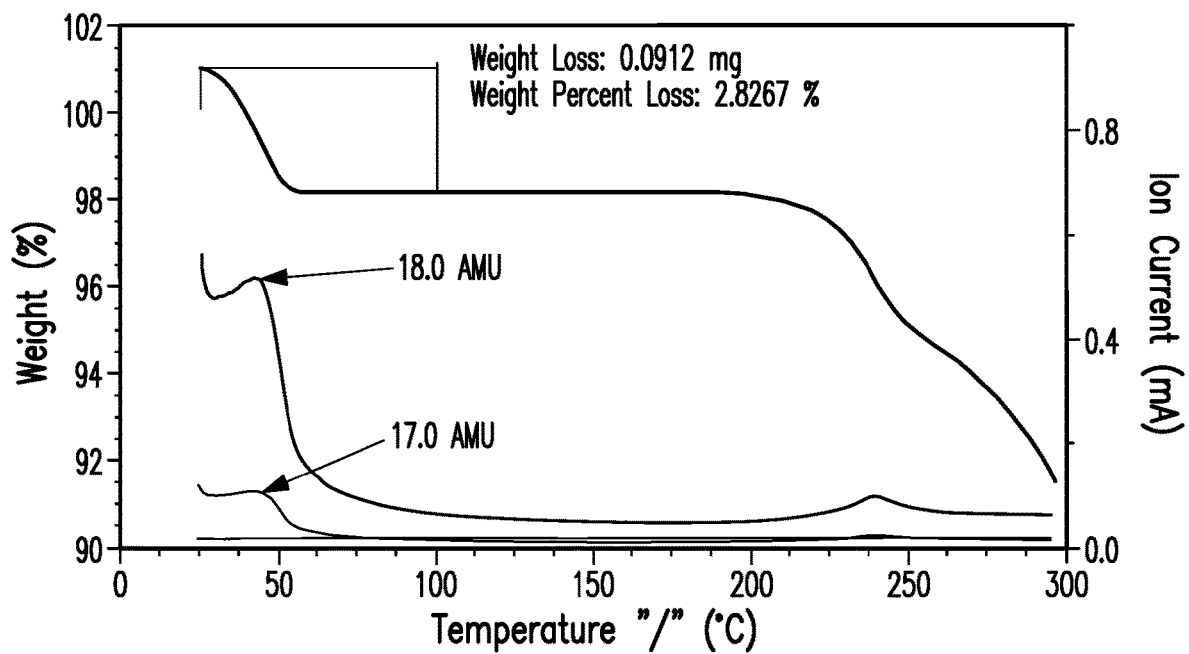

FIG. 145 provides a representative TG-MS thermogram of Form N of a hydrochloride salt of Compound 1.

Figure 146:
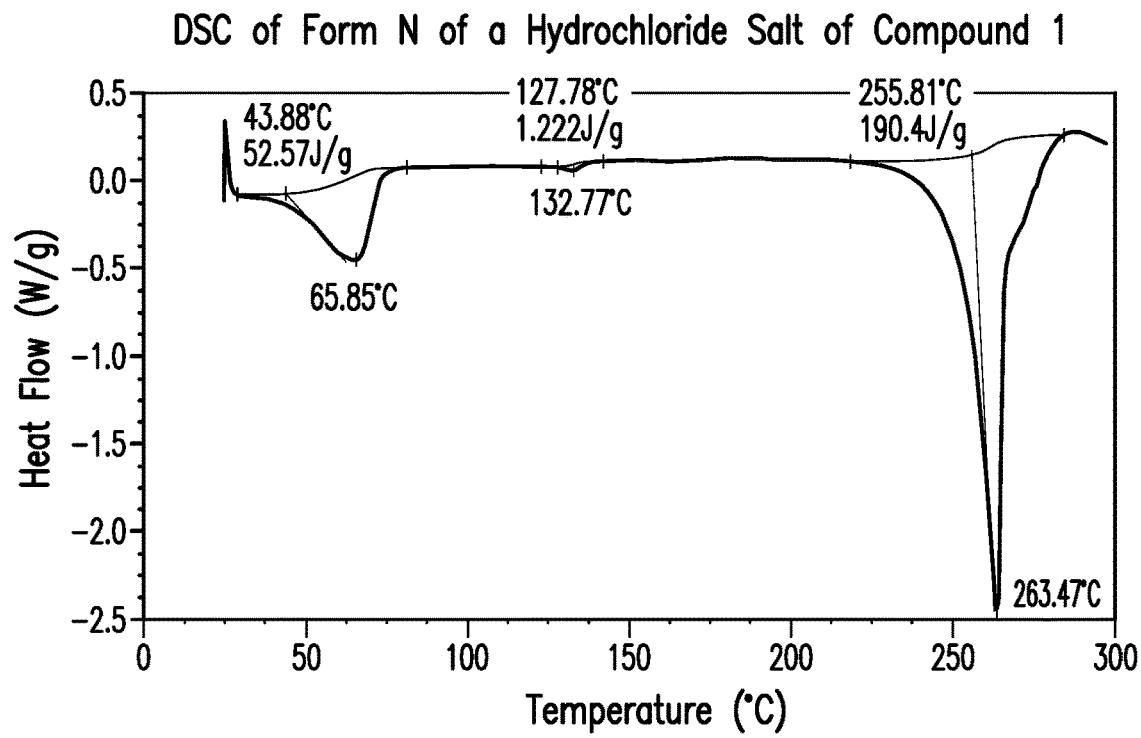

FIG. 146 provides a representative DSC thermogram of Form N of a hydrochloride salt of Compound 1.

Figure 147:
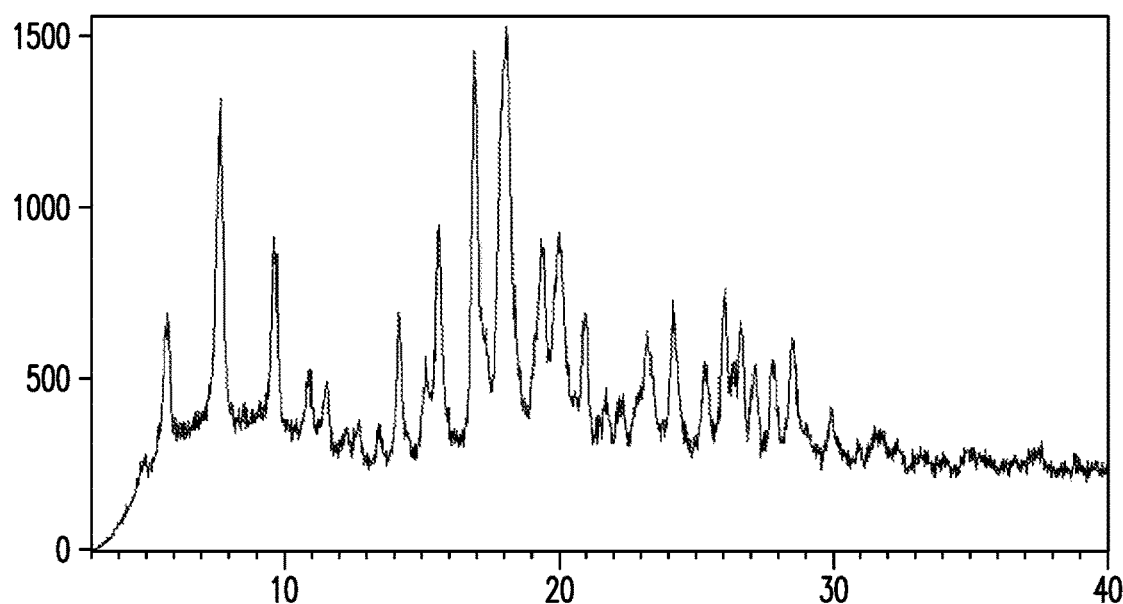

FIG. 147 provides a representative XRPD pattern of Form O of a hydrochloride salt of Compound 1.

Figure 148:
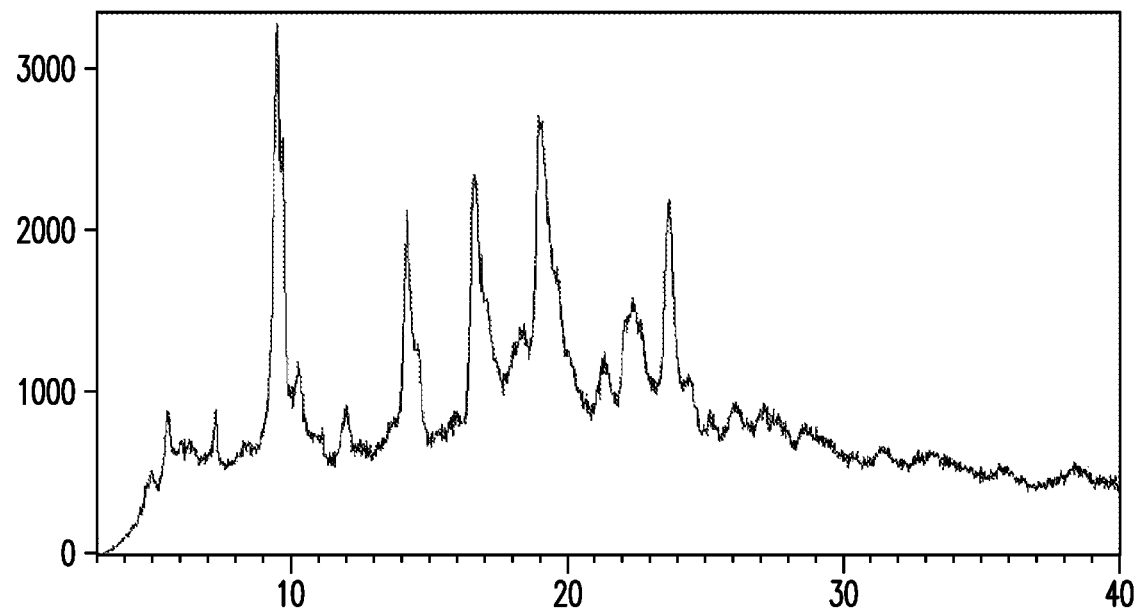

FIG. 148 provides a representative XRPD pattern of Form P of a hydrochloride salt of Compound 1.

Figure 149:
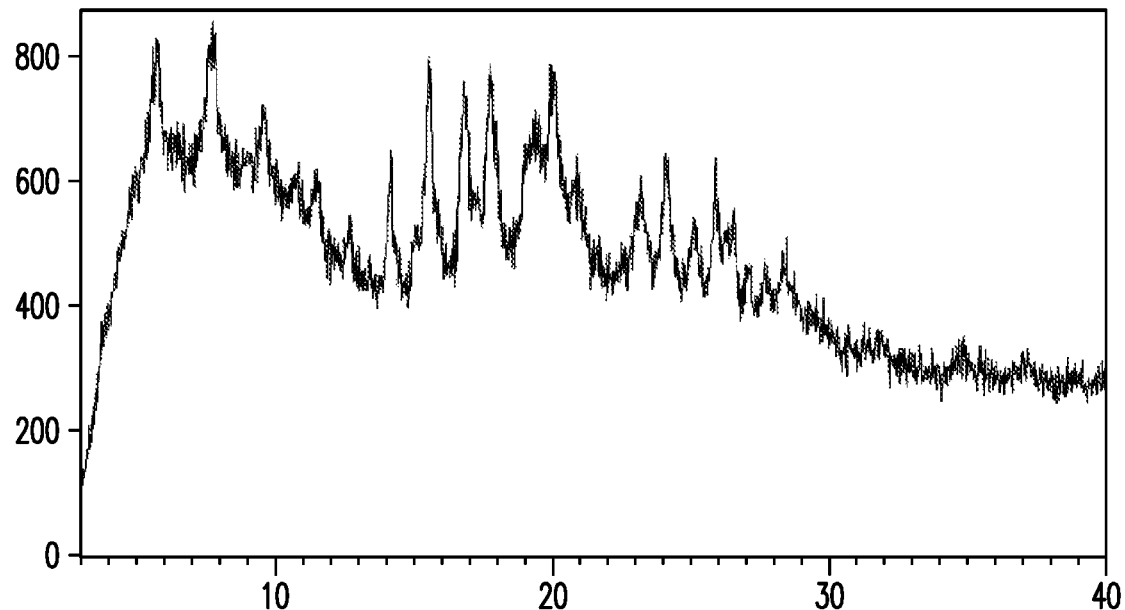

FIG. 149 provides a representative XRPD pattern of Form Q of a hydrochloride salt of Compound 1.

Figure 150:
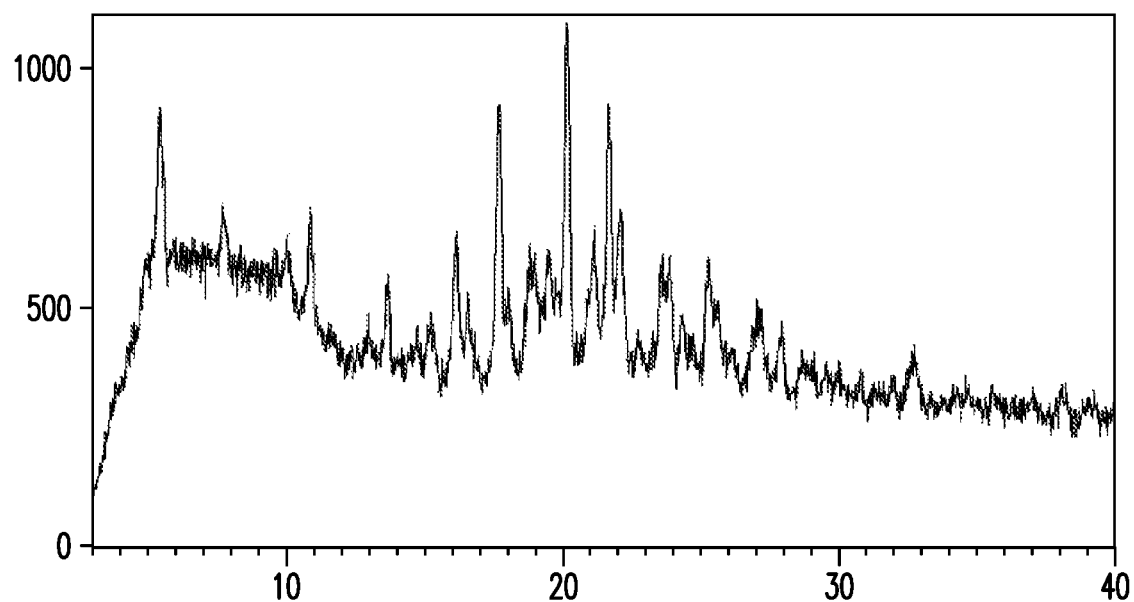

FIG. 150 provides a representative XRPD pattern of Form R of a hydrochloride salt of Compound 1.

Figure 151:
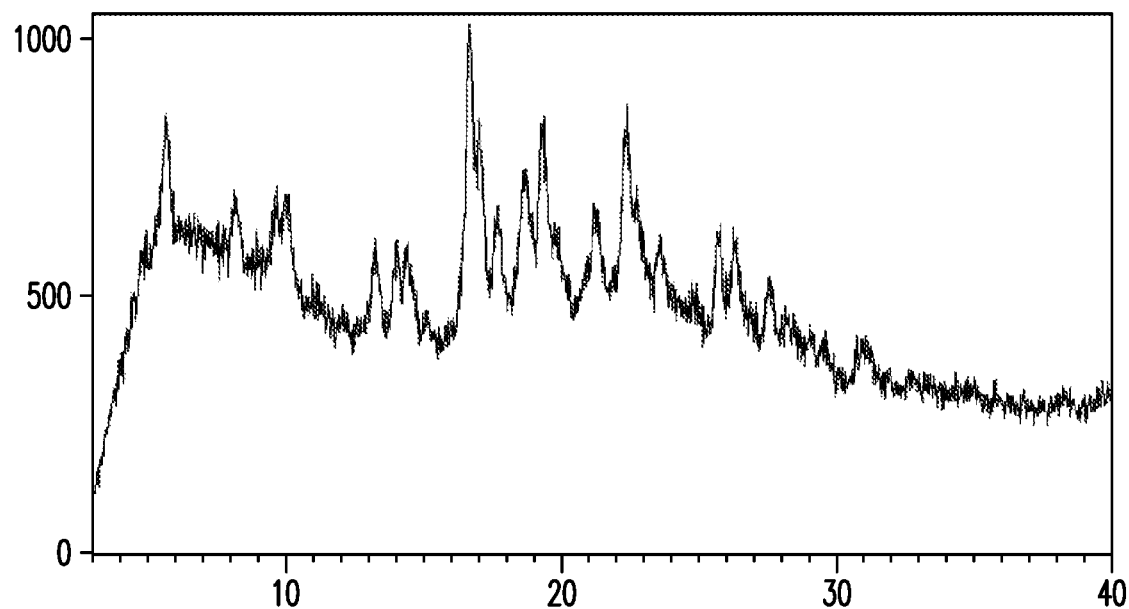

FIG. 151 provides a representative XRPD pattern of Form S of a hydrochloride salt of Compound 1.

Figure 152:
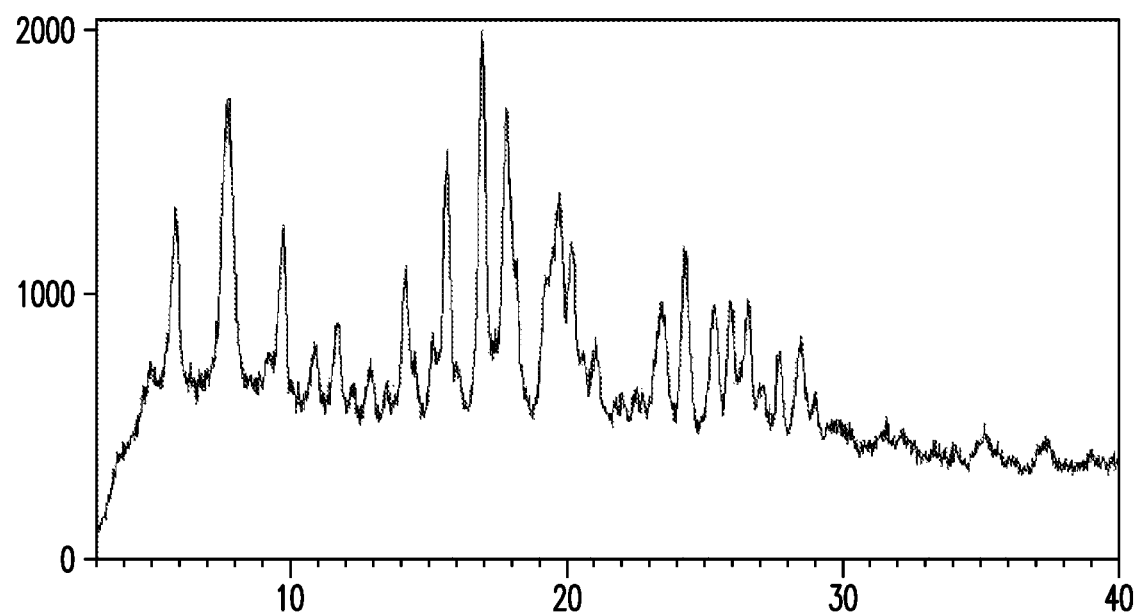

FIG. 152 provides a representative XRPD pattern of Form T of a hydrochloride salt of Compound 1.

Figure 153:
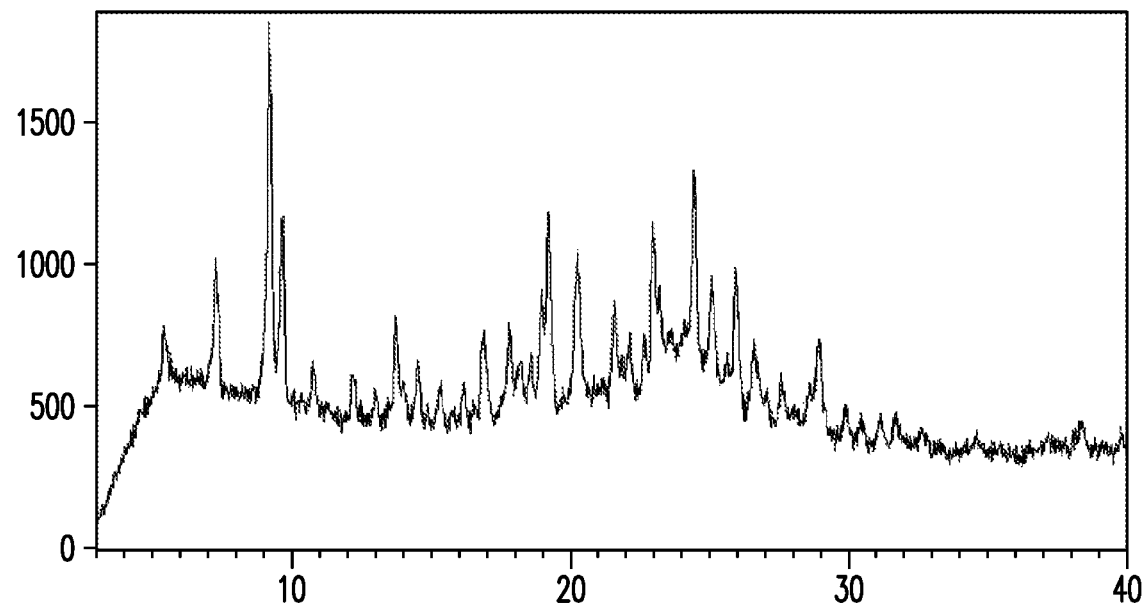

FIG. 153 provides a representative XRPD pattern of Form U of a hydrochloride salt of Compound 1.

Figure 154:
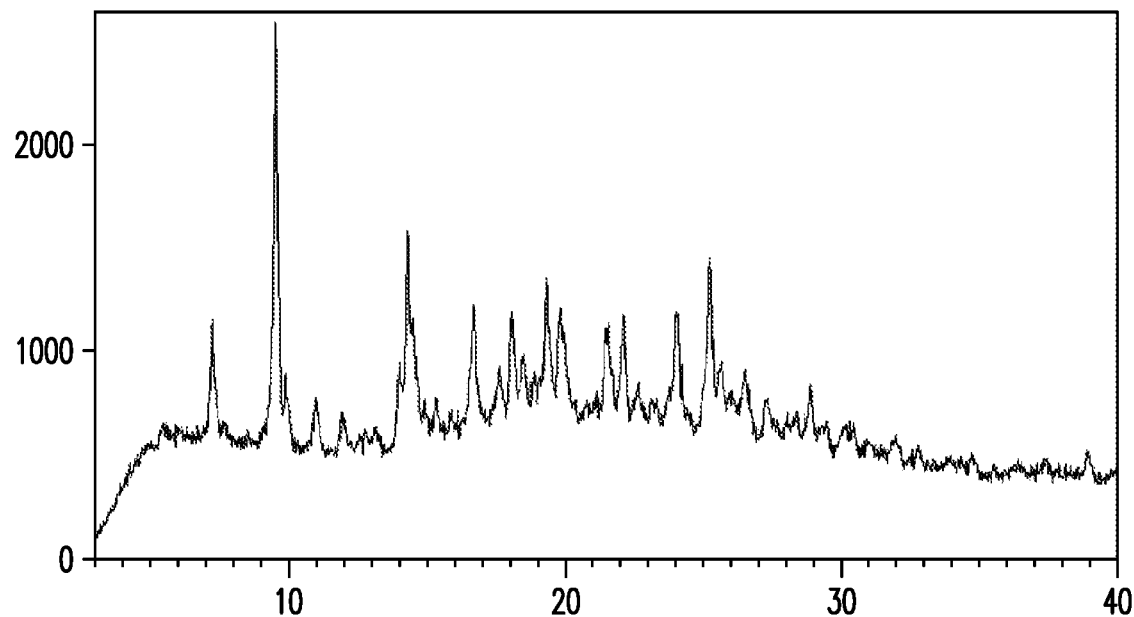

FIG. 154 provides a representative XRPD pattern of Form V of a hydrochloride salt of Compound 1.

Figure 155:
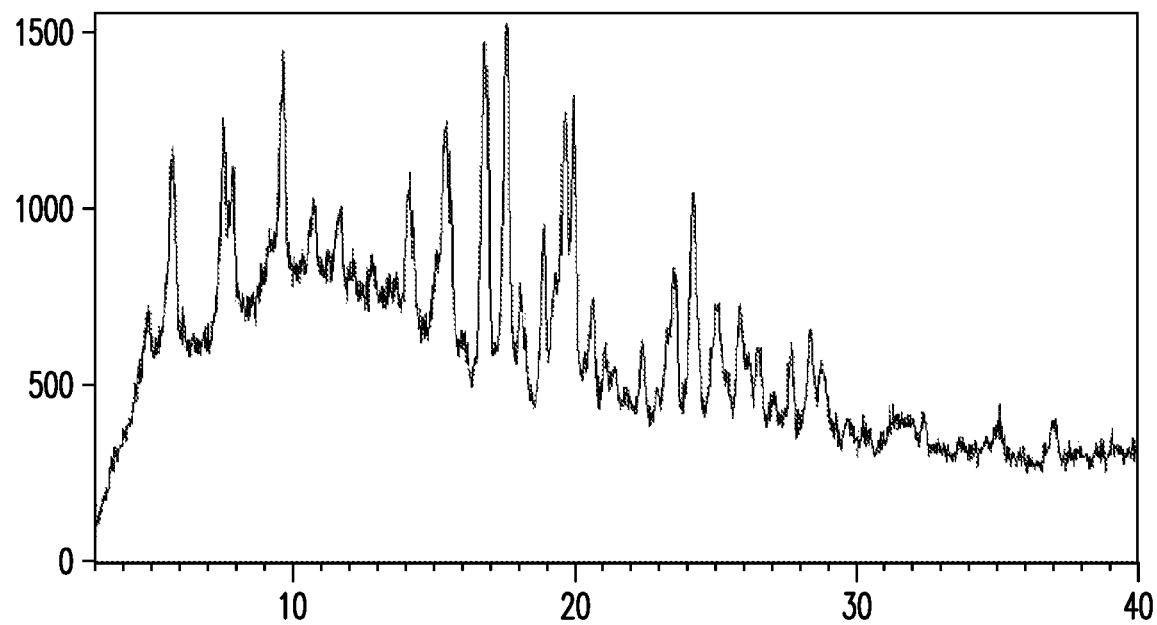

FIG. 155 provides a representative XRPD pattern of Form W of a hydrochloride salt of Compound 1.

Figure 156:
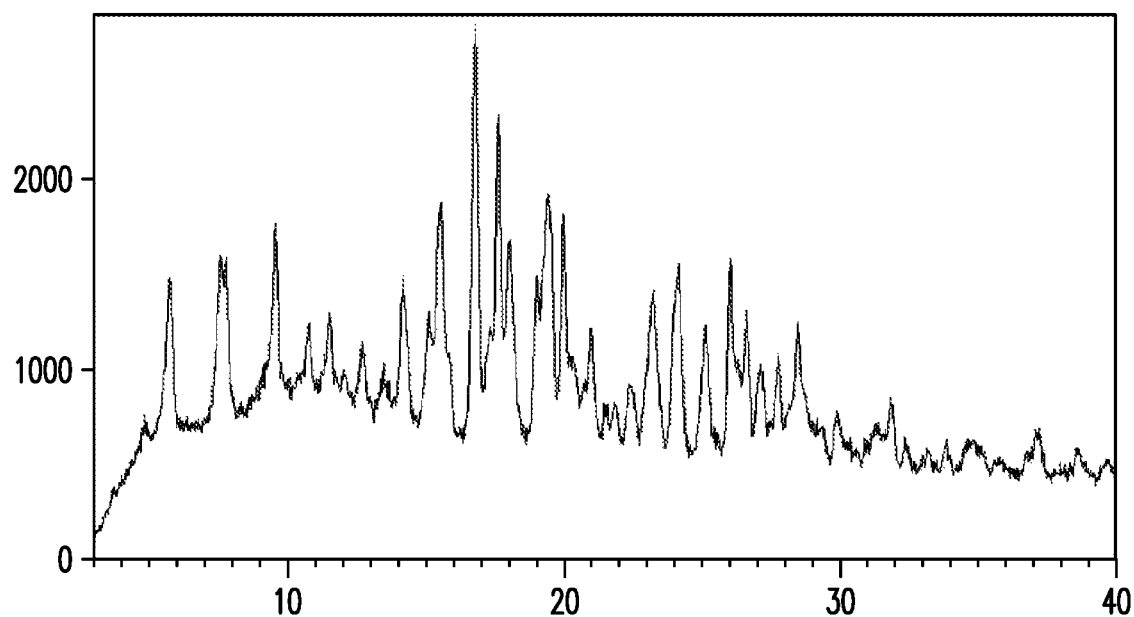

FIG. 156 provides a representative XRPD pattern of Form X of a hydrochloride salt of Compound 1.

Figure 157:
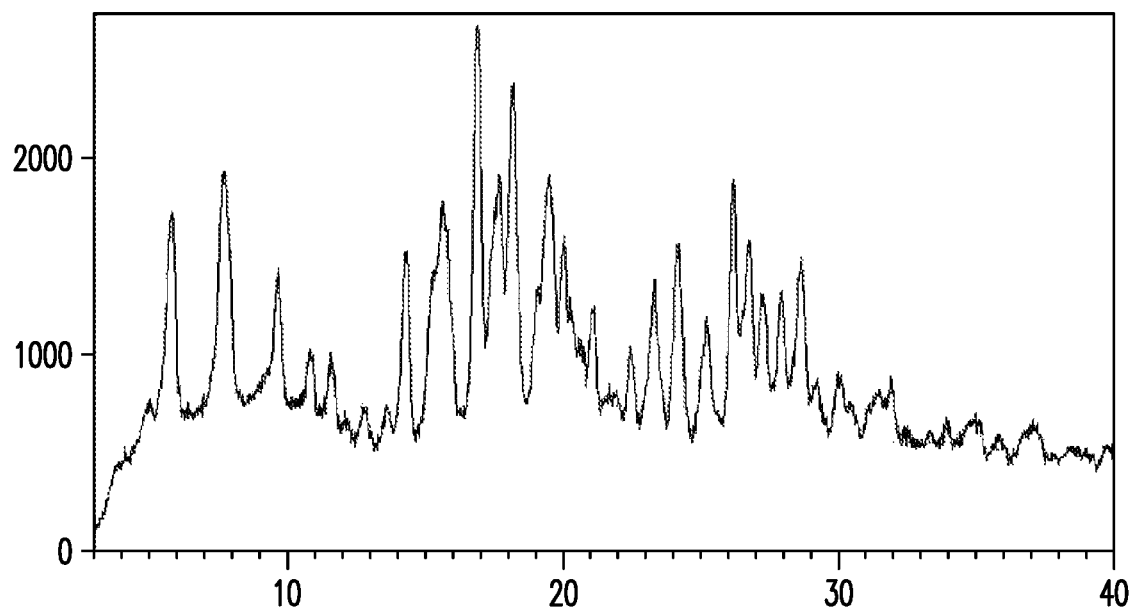

FIG. 157 provides a representative XRPD pattern of Form Y of a hydrochloride salt of Compound 1.

Figure 158:
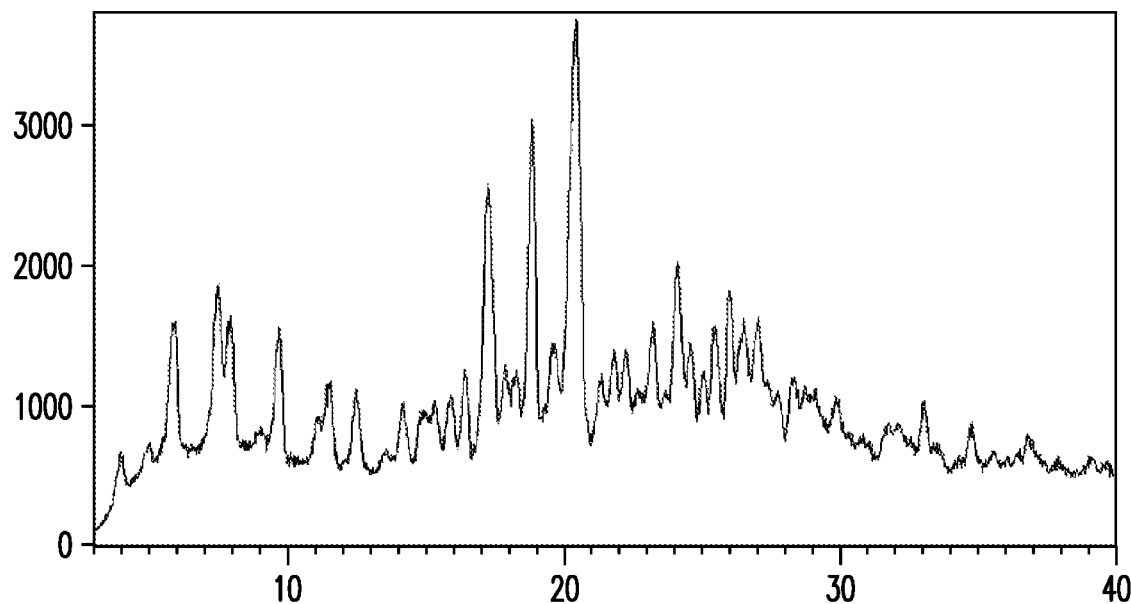

FIG. 158 provides a representative XRPD pattern of Form Z of a hydrochloride salt of Compound 1.

Figure 159:
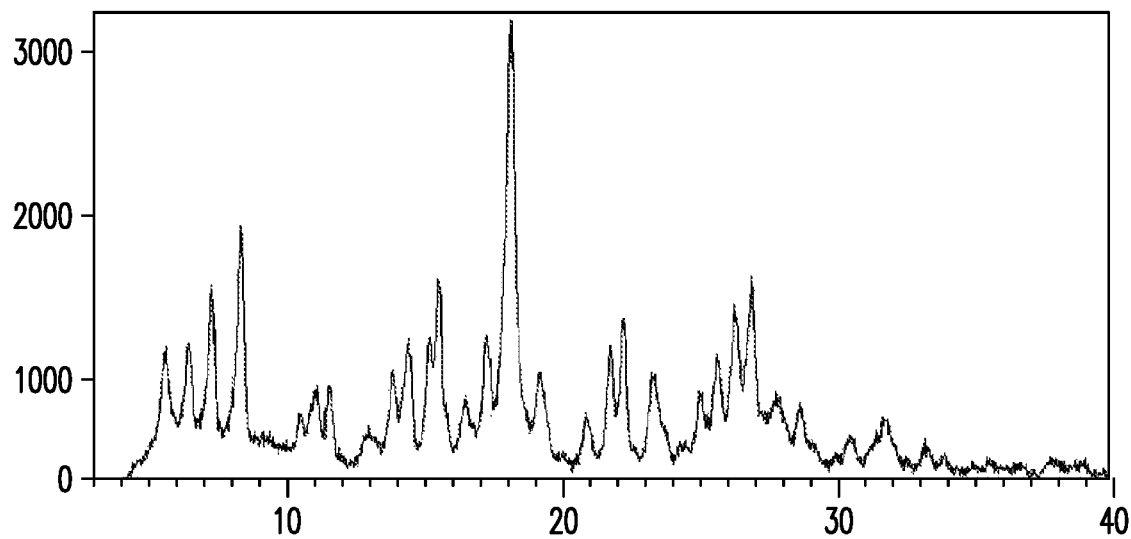

FIG. 159 provides a representative XRPD pattern of Form AA of a hydrochloride salt of Compound 1.

Figure 160:
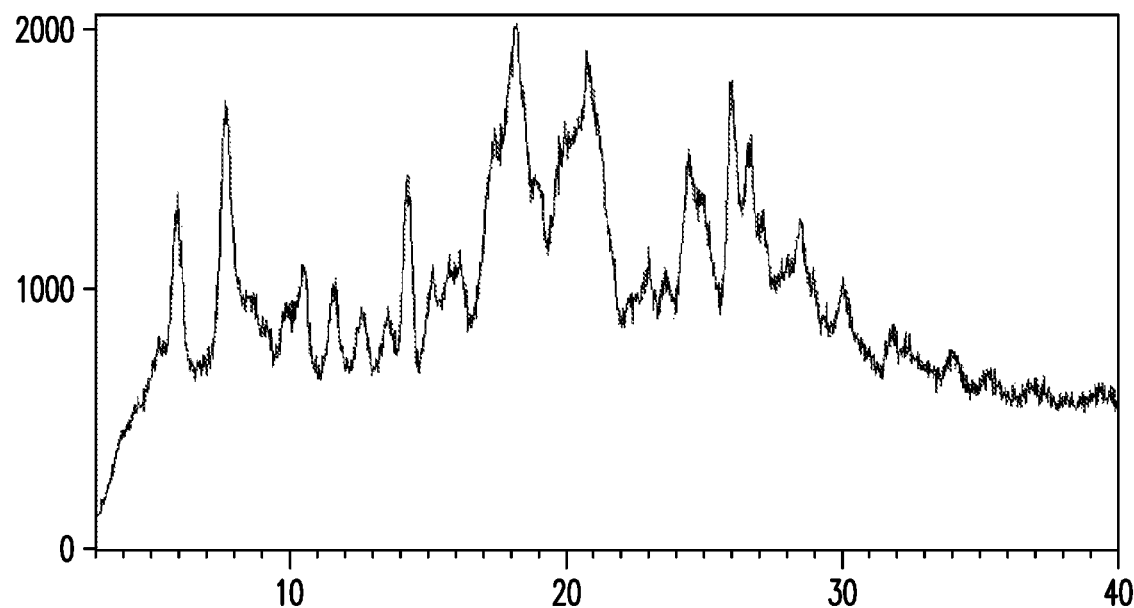

FIG. 160 provides a representative XRPD pattern of Form AB of a hydrochloride salt of Compound 1.

Figure 161:
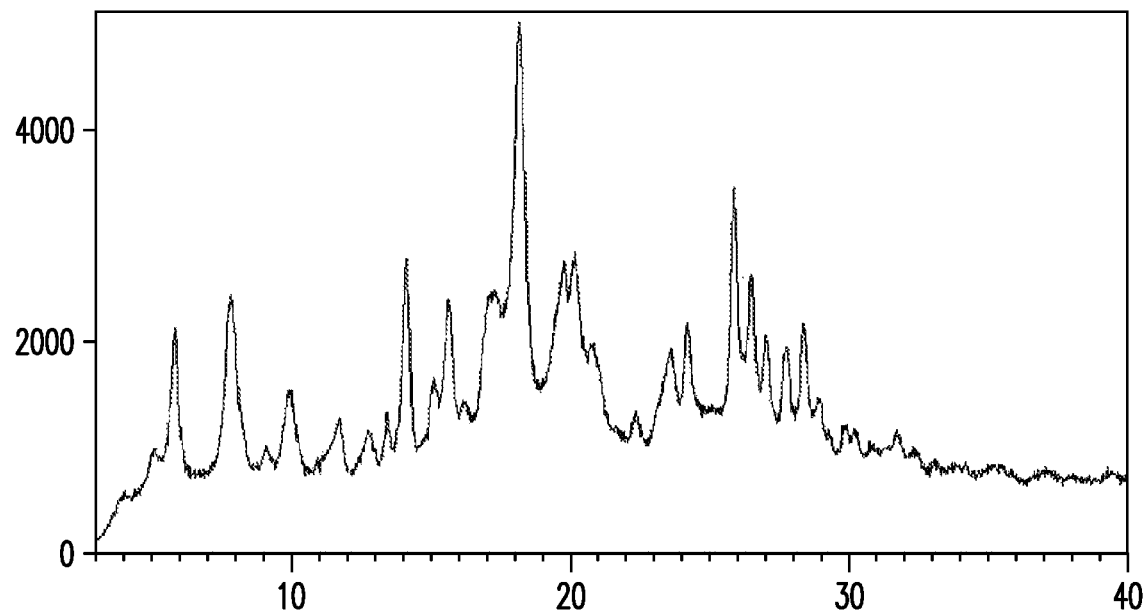

FIG. 161 provides a representative XRPD pattern of Form AC of a hydrochloride salt of Compound 1.

Figure 162:
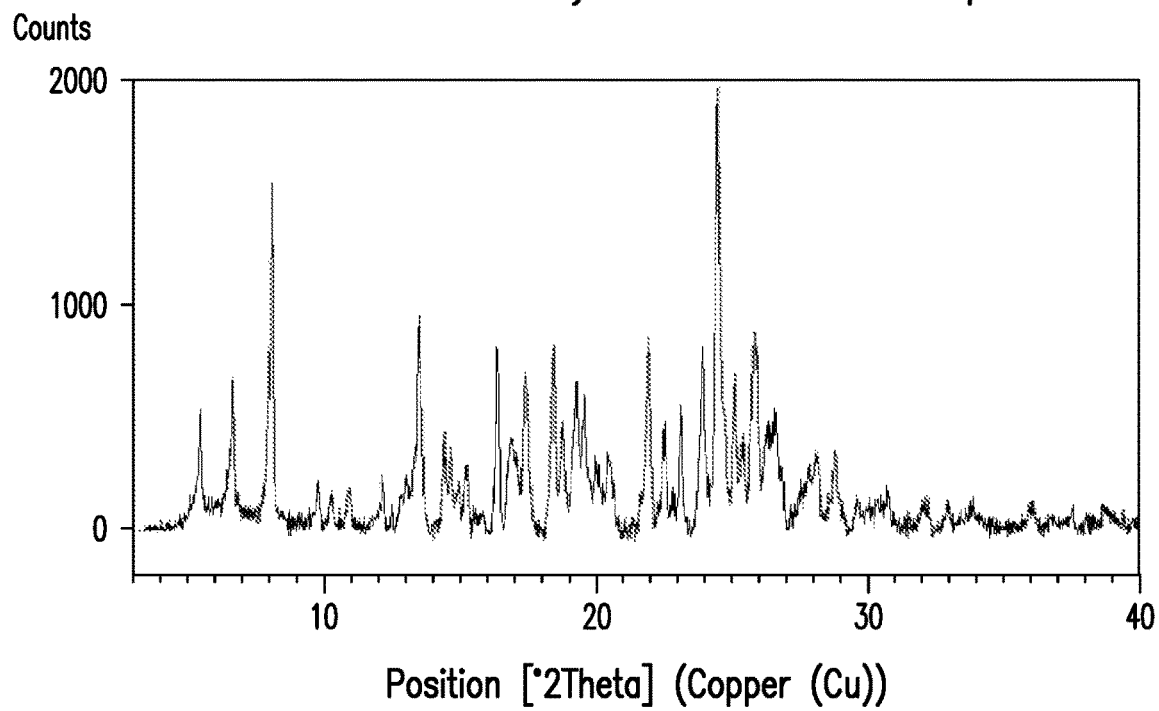

FIG. 162 provides a representative XRPD pattern of Form E of a hydrobromide salt of Compound 1.

Figure 163:
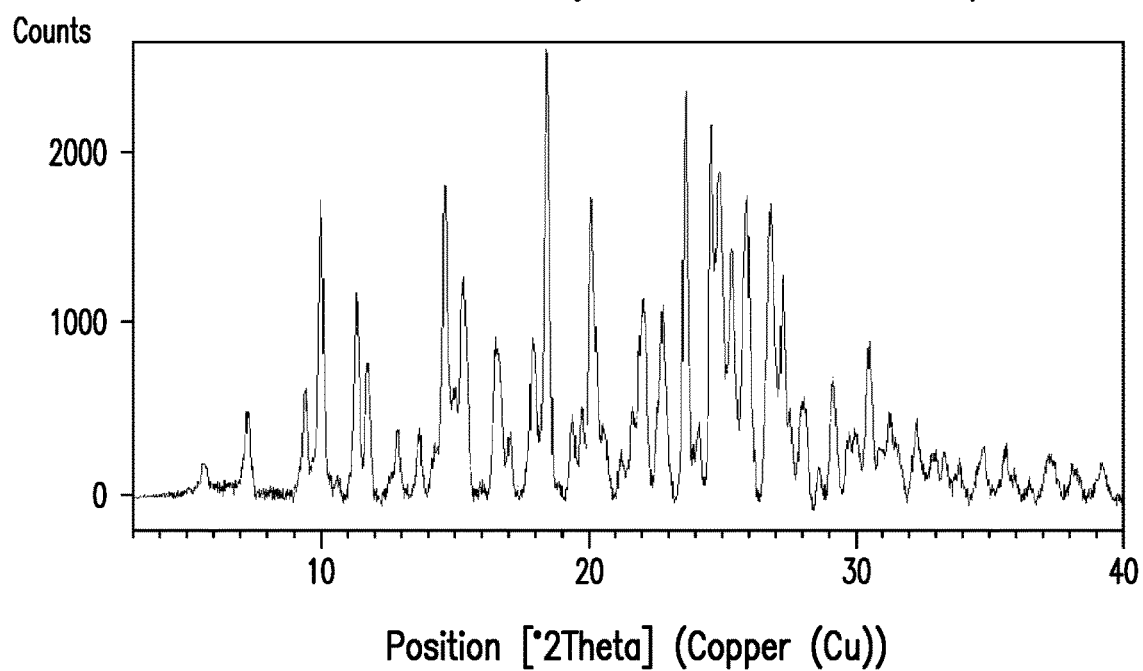

FIG. 163 provides a representative XRPD pattern of Form F of a hydrobromide salt of Compound 1.

Figure 164:
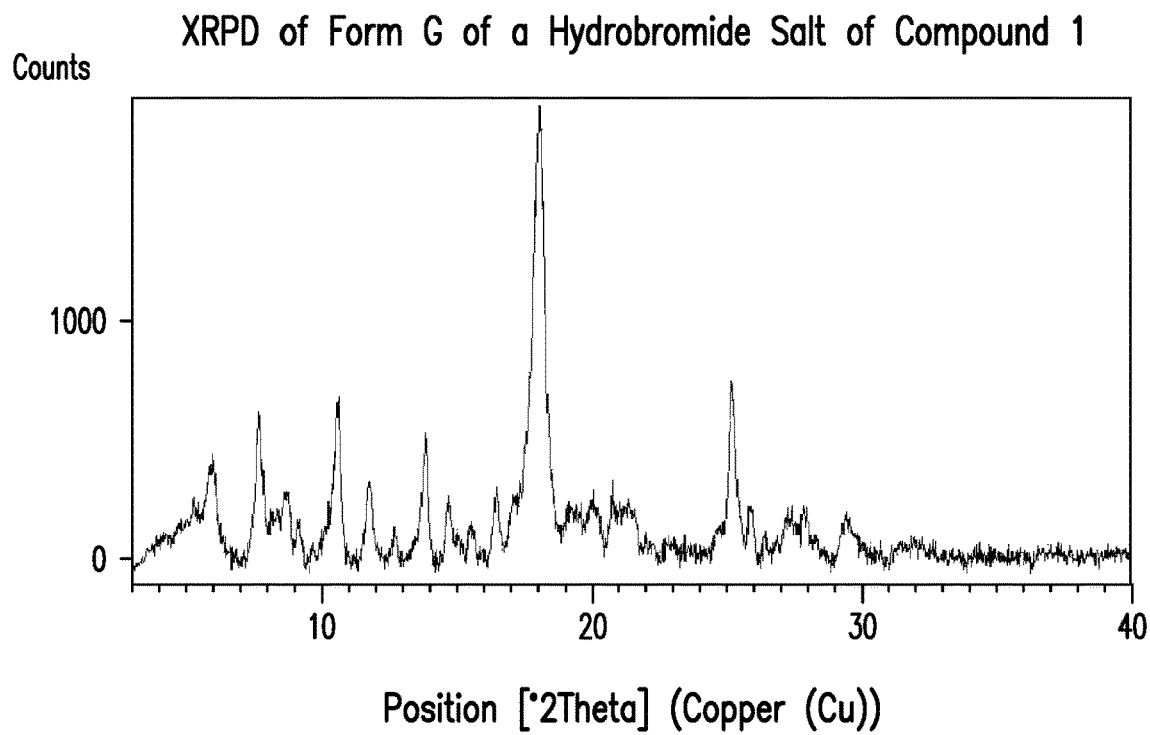

FIG. 164 provides a representative XRPD pattern of Form G of a hydrobromide salt of Compound 1.

Figure 165:
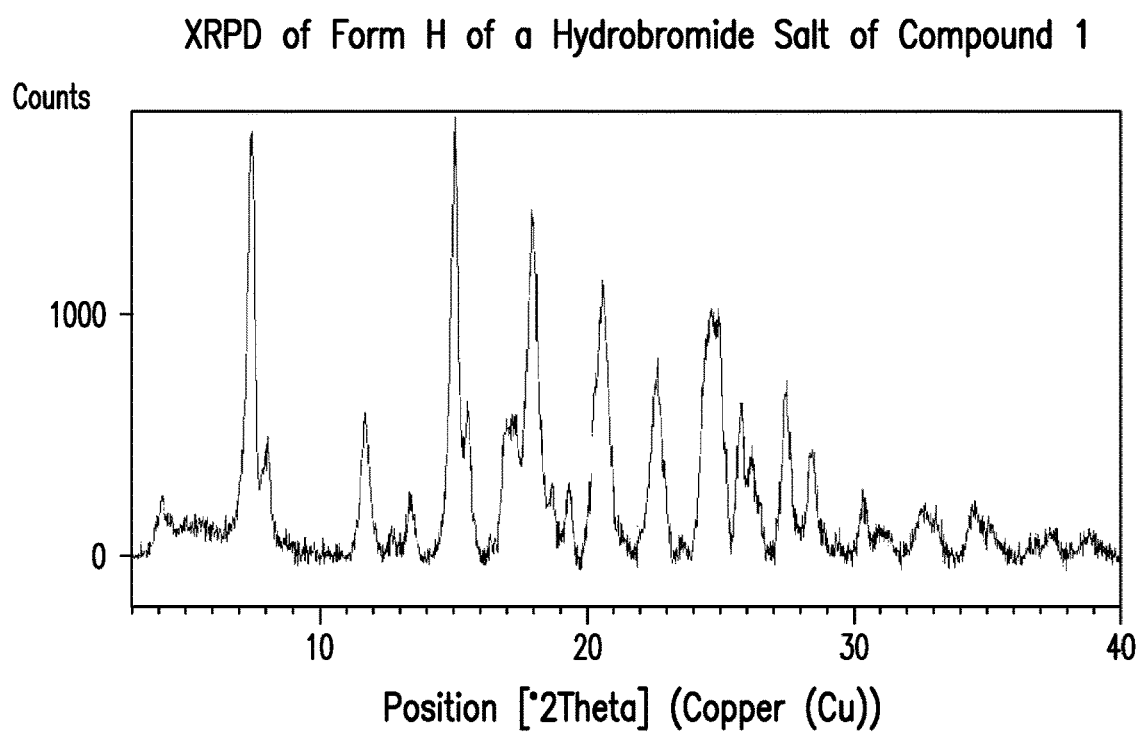

FIG. 165 provides a representative XRPD pattern of Form H of a hydrobromide salt of Compound 1.

Figure 166:
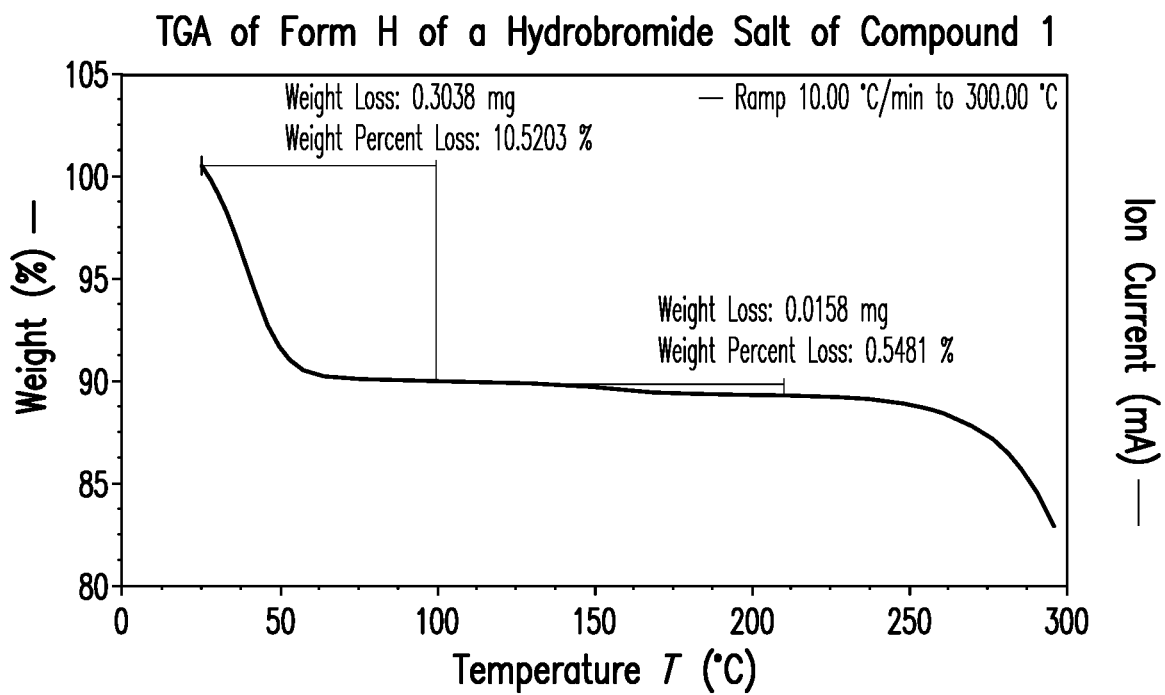

FIG. 166 provides a representative TGA pattern of Form H of a hydrobromide salt of Compound 1.

Figure 167:
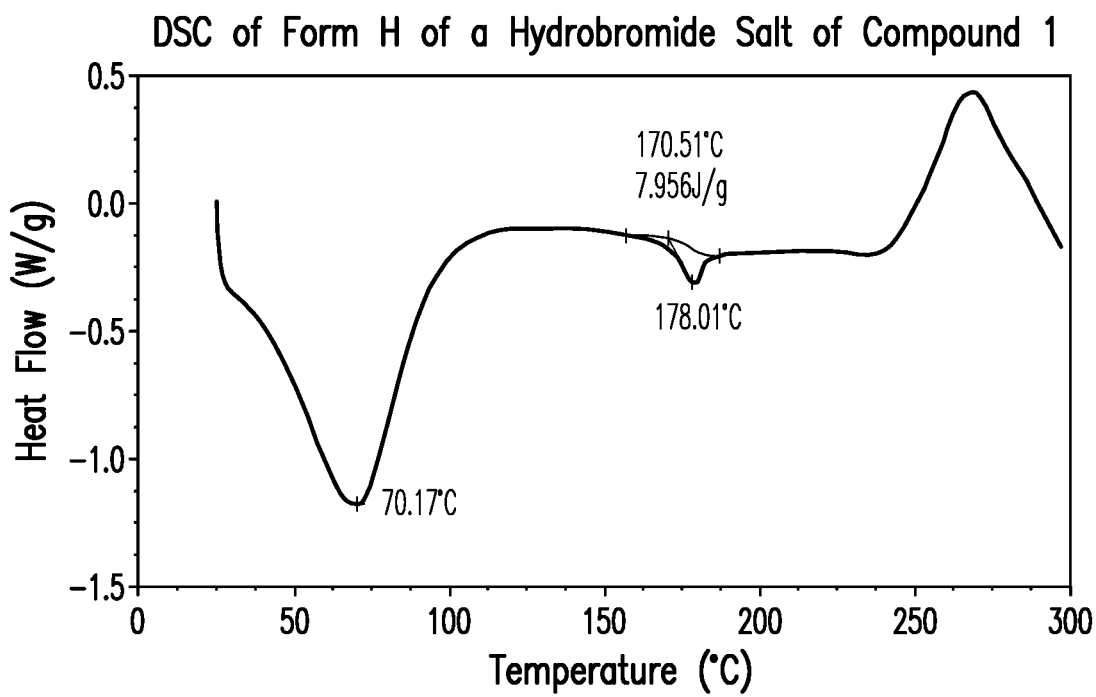

FIG. 167 provides a representative DSC pattern of Form H of a hydrobromide salt of Compound 1.

Figure 168:
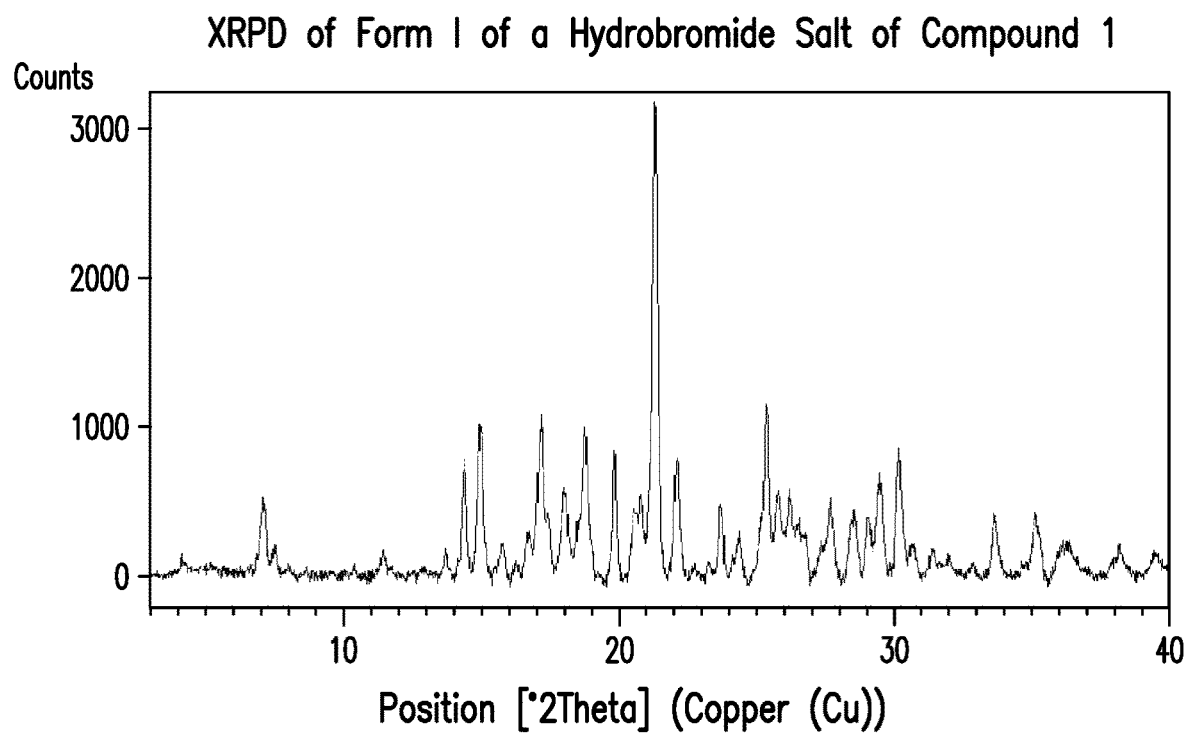

FIG. 168 provides a representative XRPD pattern of Form I of a hydrobromide salt of Compound 1.

Figure 169:
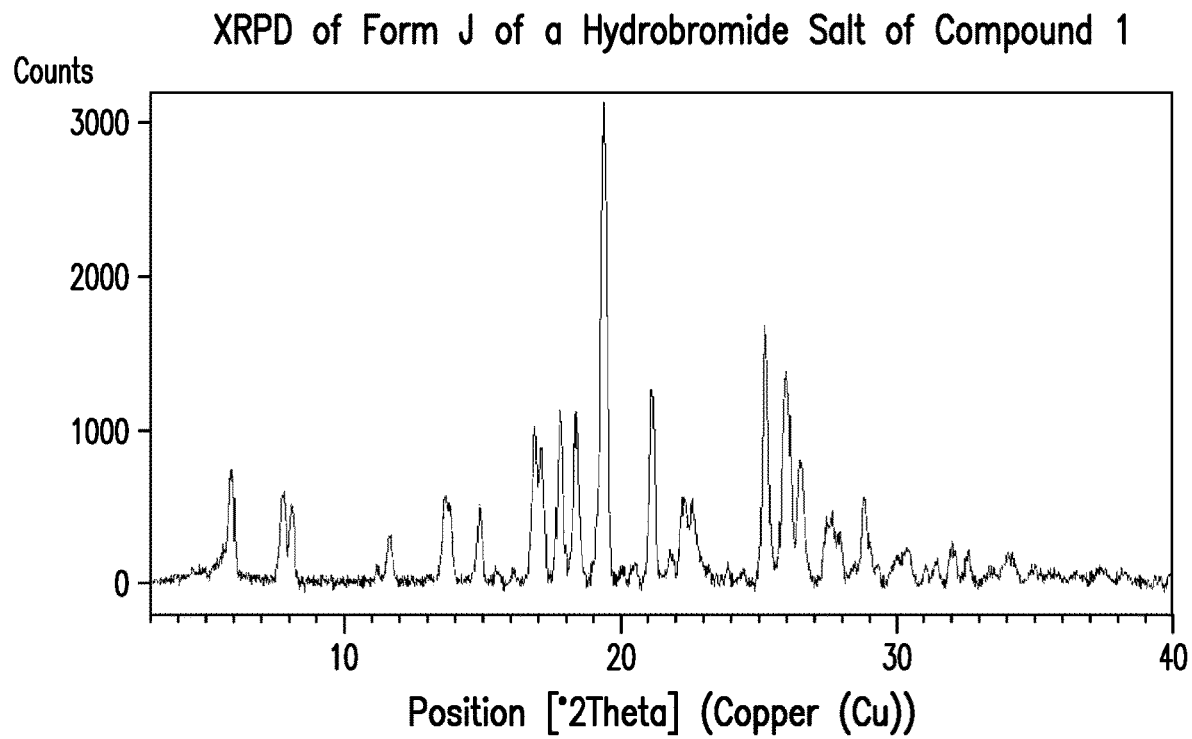

FIG. 169 provides a representative XRPD pattern of Form J of a hydrobromide salt of Compound 1.

Figure 170:
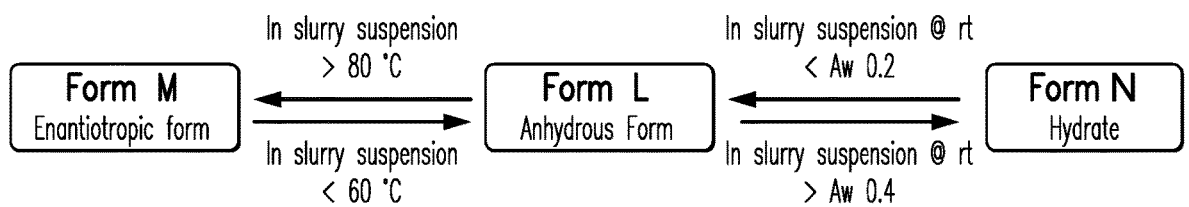

FIG. 170 shows form conversion scheme of Form L, Form M, and Form N of a hydrochloride salt of Compound 1.

5. DETAILED DESCRIPTION

5.1 Definitions

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. As used herein, a tilde (i.e., "~") preceding a numerical value or range of values indicates "about" or "approximately."

Unless otherwise specified, the terms "X-ray powder diffraction", "powder X-ray diffraction", "PXRD", and "XRPD" are used interchangeably in this application.

As used herein and unless otherwise specified, the terms "solid form" and related terms refer to a physical form which is not predominantly in a liquid or a gaseous state. As used herein, the terms "solid form" and "solid forms" encompass semi-solids. Solid forms may be crystalline, amorphous, partially crystalline, partially amorphous, or mixtures of forms.

The solid forms provided herein may have varying degrees of crystallinity or lattice order. The solid forms provided herein are not limited by any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms provided herein are about 0, 5, 10, 15, 20, 25, 30, 35, 40, 45, 50, 55, 60, 65, 70, 75, 80, 85, 90, 95 or 100% crystalline.

As used herein and unless otherwise specified, the term "crystalline" and related terms used herein, when used to describe a substance, component, product, or form, mean that the substance, component, product, or form is substantially crystalline, for example, as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ edition, 1843-1844 (1995).

As used herein and unless otherwise specified, the term "crystal form," "crystal forms," and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, co-crystals of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous form(s) and/or other crystal form(s) on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

A "single-component" solid form comprising a compound consists essentially of the compound. A "multiple-component" solid form comprising a compound comprises a significant quantity of one or more additional species, such as ions and/or molecules, within the solid form. For example, in certain embodiments, a crystalline multiple-component solid form comprising a compound further comprises one or more species non-covalently bonded at regular positions in the crystal lattice. For another example, in certain embodiments, an amorphous multiple-component solid form comprising a compound further comprises one or more polymer(s), and the compound is dispersed in a solid matrix that comprises the polymer(s).

Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to two or more crystal forms that consist essentially of the same molecule, molecules or ions. Like different crystal forms, different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing (for example, one polymorph might be more likely to form solvates or might be difficult to filter and wash free of impurities, and particle shape and size distribution might be different between polymorphs).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

Unless otherwise specified, the terms "solvate" and "solvated," as used herein, refer to a solid form of a substance which contains solvent. The terms "hydrate" and "hydrated" refer to a solvate wherein the solvent comprises water. "Polymorphs of solvates" refer to the existence of more than one solid form for a particular solvate composition. Similarly, "polymorphs of hydrates" refers to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, co-crystal, or molecular complex. The terms "hydrate" and "hydrated," as used herein, can also refer to a hydrate of a salt, co-crystal, or molecular complex.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

In certain embodiments, the solid forms, e.g., crystal or amorphous forms, provided herein are substantially pure, i.e., substantially free of other solid forms and/or of other chemical compounds, containing less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

Solid forms may exhibit distinct physical characterization data that are unique to a particular solid form, such as the crystal forms provided herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms provided herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis variation.

As used herein, and unless otherwise specified, the term "pharmaceutically acceptable salts" refers to salts prepared from pharmaceutically acceptable, relatively non-toxic acids, including inorganic acids and organic acids. In certain embodiments, suitable acids include, but are not limited to, acetic, adipic, 4-aminosalicylic, ascorbic, aspartic, benzenesulfonic, benzoic, camphoric, camphorsulfonic, capric, caproic, caprylic, cinnamic, carbonic, citric, cyclamic, dihydrogenphosphoric, 2,5-dihydroxybenzoic (gentisic), 1,2-ethanedisulfonic, ethanesulfonic, fumaric, galactunoric, gluconic, glucuronic, glutamic, glutaric, glycolic, hippuric, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, 1,5-naphthalenedisulfonic, nicotinic, nitric, oxalic, pamoic, pantothenic, phosphoric, phthalic, propionic, pyroglutamic, salicylic, suberic, succinic, sulfuric, tartaric, toluenesulfonic acid, and the like (see, e.g., S. M. Berge et al., *J. Pharm. Sci.*, 66:1-19 (1977); and *Handbook of Pharmaceutical Salts: Properties, Selection and Use*, P. H. Stahl and C. G. Wermuth, Eds., (2002), Wiley, Weinheim). In certain embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridinesulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

As used herein "multiple myeloma" refers to hematological conditions characterized by malignant plasma cells and includes the following disorders: monoclonal gammopathy of undetermined significance (MGUS); low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smouldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(11;14)(q13;q32); t(6;14)(p21;32); t(12;14)(p13;q32); or t(6;20);); MMSET translocations (for example, t(4;14)(p16;q32)); MAF translocations (for example, t(14;16)(q32;q32); t(20;22); t(16; 22)(q11;q13); or t(14;20)(q32;q11)); or other chromosome factors (for example, deletion of 17p13, or chromosome 13; del(17/17p), nonhyperdiploidy, and gain(1q)).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

The term "relapsed" refers to a situation where patients, who have had a remission of multiple myeloma after therapy, have a return of myeloma cells and/or reduced normal cells in the marrow.

The term "refractory or resistant" refers to a circumstance where patients, even after intensive treatment, have residual myeloma cells and/or reduced normal cells in the marrow.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another therapy, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

"Remission" as used herein, is a decrease in or disappearance of signs and symptoms of a cancer, for example, multiple myeloma. In partial remission, some, but not all, signs and symptoms of the cancer have disappeared. In complete remission, all signs and symptoms of the cancer have disappeared, although the cancer still may be in the body.

As used herein "transplant" refers to high-dose therapy with stem cell rescue. Hematopoietic (blood) or bone marrow stem cells are used not as treatment but to rescue the patient after the high-dose therapy, for example high dose chemotherapy and/or radiation. Transplant includes "autologous" stem cell transplant (ASCT), which refers to use of the patients' own stem cells being harvested and used as the replacement cells. In some embodiments, transplant also includes tandem transplant or multiple transplants.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with Compound 1, or an enantiomer or a mixture of enantiomers, tautomers, isotopolog or a pharmaceutically acceptable salt thereof.

The term "biological therapy" refers to administration of biological therapeutics such as cord blood, stem cells, growth factors and the like.

In the context of a cancer, such as multiple myeloma, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP, as used herein, means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response ≥partial response (PR), according to the IMWG Uniform Response Criteria. In one embodiment, duration of response (DoR) is the time from achieving a response until relapse or disease progression. In one embodiment, DoR is the time from achieving a response ≥partial response (PR) until relapse or disease progression. In one embodiment, DoR is the time from the first documentation of a response until to the first documentation of progressive disease or death. In one embodiment, DoR is the time from the first documentation of a response ≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response ≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. *Leukemia*, 2006; (10) 10: 1-7), using the response and endpoint definitions shown below:

| Response Subcategory | Response Criteria[a] |
|---|---|
| sCR | CR as defined below plus<br>Normal FLC ratio and<br>Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma |

-continued

| Response Subcategory | Response Criteria[a] |
|---|---|
| | cells is required in place of M-protein, provided baseline bone marrow plasma cell percentage was ≥30% In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response.
[a]All response categories require two consecutive assessments made at any time before the institution of any new therapy; all categories also require no known evidence of progressive or new bone lesions if radiographic studies were performed. Radiographic studies are not required to satisfy these response requirements.
[b]Confirmation with repeat bone marrow biopsy not needed.
[c]Presence/absence of clonal cells is based upon the κ/λ ratio. An abnormal κ/λ ratio by immunohistochemistry and/or immunofluorescence requires a minimum of 100 plasma cells for analysis. An abnonnal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, e.g., light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

Unless otherwise specified, to the extent that there is a discrepancy between a depicted chemical structure of a compound provided herein and a chemical name of a compound provided herein, the chemical structure shall control.

5.2 Salts and Solid Forms Comprising Compound 1

In certain embodiments, provided herein is a solid form comprising Compound 1:

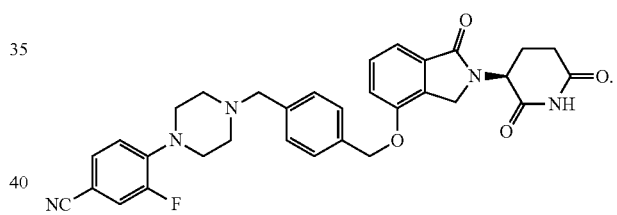

Compound 1 has the chemical name (S)-4-(4-(4-(((2-(2,6-dioxopiperidin-3-yl)-1-oxoisoindolin-4-yl)oxy)methyl)benzyl)piperazin-1-yl)-3-fluorobenzonitrile. Methods of preparing Compound 1 have been described in U.S. application Ser. No. 16/030,695, which is incorporated herein by reference in its entirety.

In one embodiment, the solid form comprises a free base of Compound 1. In one embodiment, the solid form comprises a salt of Compound 1. In one embodiment, the solid form comprises a hydrochloride salt of Compound 1. In one embodiment, the solid form comprises a mesylate salt of Compound 1. In one embodiment, the solid form comprises a hydrobromide salt of Compound 1. In one embodiment, the solid form comprises a besylate salt of Compound 1. In one embodiment, the solid form comprises a glycolate salt of Compound 1. In one embodiment, the solid form comprises an L-malate salt of Compound 1.

In one embodiment, the solid form is crystalline. In one embodiment, the solid form is a hydrate. In one embodiment, the solid form is an anhydrate. In one embodiment, the solid form is a solvate. In one embodiment, the solid form is non-solvated.

The solid forms provided may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

Also provided herein are salts of Compound 1. In one embodiment, the salt is a hydrochloride salt of Compound 1. In one embodiment, the salt is a mesylate salt of Compound 1. In one embodiment, the salt is a hydrobromide salt of Compound 1. In one embodiment, the salt is a besylate salt of Compound 1. In one embodiment, the salt is a glycolate salt of Compound 1. In one embodiment, the salt is an L-malate salt of Compound 1.

Without being limited by any particular theory, the acids are associated with one or more basic nitrogen of Compound 1. Without being limited by any particular theory, the acids are associated with a nitrogen on the piperazine ring of Compound 1.

The purity of the solid forms and salts provided herein may be determined by standard analytical methods, such as thin layer chromatography (TLC), gel electrophoresis, gas chromatography, high performance liquid chromatography (HPLC), and mass spectrometry.

While not intending to be bound by any particular theory, certain solid forms and salts are characterized by physical properties, e.g., stability, solubility and dissolution rate, appropriate for pharmaceutical and therapeutic dosage forms. Moreover, while not wishing to be bound by any particular theory, certain solid forms and salts are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms and salts suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art. While not intending to be bound by any particular theory, certain solid forms and salts provided herein exhibit suitable pharmaceutical properties, e.g., pharmaceutical kinetics, pharmaceutical dynamics, half-life, $C_{max}$, and bioavailability. Such properties can be determined using assays known to the skilled artisan.

(a) Free Base of Compound 1

In some embodiments, provided herein is a free base of Compound 1. It is contemplated that a free base of Compound 1 can exist in a variety of solid forms. Such solid forms include crystalline solids, such as polymorphs, solvates and hydrates of crystalline free base of Compound 1, as well as amorphous solids, or mixtures thereof.

In one embodiment, provided herein is a solid form comprising a free base of Compound 1. In one embodiment, the solid form is a solvate of a free base of Compound 1. In one embodiment, the solid form is a hydrate of a free base of Compound 1. In one embodiment, the solid form is a non-solvated form of a free base of Compound 1. In one embodiment, the solid form is a desolvated form of a free base of Compound 1. In one embodiment, the solid form is an anhydrous form (anhydrate) of a free base of Compound 1. In one embodiment, the solid form is a dehydrated form of a free base of Compound 1.

(i) Form A of Free Base of Compound 1

In certain embodiments, provided herein is Form A of a free base of Compound 1.

In one embodiment, Form A is crystalline. In one embodiment, Form A is substantially crystalline. In one embodiment, Form A is moderately crystalline. In one embodiment, Form A is partially crystalline.

In one embodiment, Form A is an anhydrous form of a free base of Compound 1. In one embodiment, Form A is a desolvated form of a free base of Compound 1.

A representative XRPD pattern of Form A is provided in FIG. 1.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 6.5, 7.0, 11.3, 13.1, 14.1, 16.8, 17.2, 17.4, 17.7, 18.0, 18.8, 19.7, 21.2, 21.4, 21.7, 22.2, 23.5, 23.9, 24.9, 25.8, 26.3, 27.2, and 27.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 11.3, 14.1, and 17.4° 2θ. In one embodiment, the XRPD pattern further comprises peaks at approximately 6.5, 19.7, and 25.8° 2θ. In one embodiment, the XRPD pattern further comprises peaks at approximately 13.1 and 17.2° 2θ. In one embodiment, the XRPD pattern comprises peaks at approximately 6.5, 11.3, 13.1, 14.1, 17.2, 17.4, 17.7, 18.8, 19.7, 22.2, and 25.8° 2θ.

In one embodiment, provided herein is a solid form comprising a free base of Compound 1, characterized by an XRPD pattern that matches the XRPD pattern presented in FIG. 1.

In one embodiment, the XRPD patterns are obtained using Cu Kα radiation.

A representative thermal gravimetric analysis (TGA) thermogram of Form A is provided in FIG. 2. In one embodiment, provided herein is a solid form comprising a free base of Compound 1, which exhibits a weight loss of about 0.3% upon heating from about 25° C. to about 160° C. In one embodiment, without being limited by any particular theory, the weight loss corresponds to the loss of trace amount of residual solvent or water. In one embodiment, provided herein is a solid form comprising a free base of Compound 1, characterized by a TGA thermogram that matches the TGA thermogram presented in FIG. 2.

A representative differential scanning calorimetry (DSC) thermogram of Form A is presented in FIG. 3. In one embodiment, provided herein is a solid form comprising a free base of Compound 1, which exhibits, as characterized by DSC, a first thermal event with an onset temperature of about 138° C., a second thermal event with an onset temperature of about 183° C., and a third thermal event with an onset temperature of about 217° C. In one embodiment, the first thermal event also has a peak temperature of about 146°

C., the second thermal event also has a peak temperature of about 195° C., and the third thermal event also has a peak temperature of about 225° C. In one embodiment, without being limited by any particular theory, the first thermal event corresponds to melting of Form A. In one embodiment, provided herein is a solid form comprising a free base of Compound 1, characterized by a DSC thermogram that matches the DSC thermogram presented in FIG. 3.

A representative dynamic vapor sorption (DVS) isotherm plot of the Form A is provided in FIG. 4. In one embodiment, provided herein is a solid form comprising a free base of Compound 1, which exhibits a mass increase of about 2.4% when subjected to an increase in a relative humidity (RH) from about 5% to about 95%. In one embodiment, provided herein is a solid form comprising a free base of Compound 1, characterized by a DVS isotherm plot which matches the DVS isotherm plot presented in FIG. 4. In one embodiment, Form A is slightly hygroscopic.

In one embodiment, Form A remains as Form A after being ground (e.g., by a mortar and pestle) for about two minutes.

In one embodiment, Form A of a free base of Compound 1 is prepared by drying Form E of a free base of Compound 1 (e.g., about 40° C., vacuum, about 18 hours).

In one embodiment, provided herein is a solid form comprising Form A of a free base of Compound 1 and amorphous free base of Compound 1. In one embodiment, provided herein is a solid form comprising Form A of a free base Compound 1 and one or more other crystalline forms of a free base of Compound 1 provided herein. In one embodiment, provided herein is a solid form comprising Form A of a free base of Compound 1 and one or more forms (e.g., amorphous or crystalline) of a salt of Compound 1 provided herein.

(ii) Form B of Free Base of Compound 1

In certain embodiments, provided herein is Form B of a free base of Compound 1.

In one embodiment, Form B is crystalline. In one embodiment, Form B is substantially crystalline. In one embodiment, Form B is moderately crystalline. In one embodiment, Form B is partially crystalline.

In one embodiment, Form B is a channel solvate of a free base of Compound 1. In one embodiment, Form B is a channel hydrate of a free base of Compound 1.

A representative XRPD pattern of Form B is provided in FIG. 5.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 5.5, 6.6, 9.8, 11.0, 12.8, 13.3, 14.2, 14.6, 15.9, 16.3, 17.1, 18.3, 18.6, 19.1, 19.5, 19.9, 20.6, 22.2, 23.6, 26.3, 26.9, 27.1, 28.1, and 28.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 6.6, 16.3, and 17.1° 2θ. In one embodiment, the XRPD pattern further comprises peaks at approximately 11.0 and 19.9° 2θ. In one embodiment, the XRPD pattern further comprises peaks at approximately 9.8 and 12.8° 2θ. In one embodiment, the XRPD pattern comprises peaks at approximately 6.6, 9.8, 11.0, 12.8, 16.3, 17.1, 19.1, 19.9, and 26.9° 2θ.

In one embodiment, provided herein is a solid form comprising a free base of Compound 1, characterized by an XRPD pattern that matches the XRPD pattern presented in FIG. 5.

In one embodiment, the XRPD patterns are obtained using Cu Kα radiation.

A representative thermal gravimetric analysis (TGA) thermogram of Form B is provided in FIG. 6. In one embodiment, provided herein is a solid form comprising a free base of Compound 1, which exhibits a weight loss of about 1.7% upon heating from about 25° C. to about 175° C. In one embodiment, without being limited by any particular theory, the weight loss corresponds to the loss of water. In one embodiment, provided herein is a solid form comprising a free base of Compound 1, characterized by a TGA thermogram that matches the TGA thermogram presented in FIG. 6.

A representative differential scanning calorimetry (DSC) thermogram of Form B is presented in FIG. 7. In one embodiment, provided herein is a solid form comprising a free base of Compound 1, which exhibits, as characterized by DSC, a first (broad) thermal event from about 20° C. to about 100° C., a second thermal event with an onset temperature of about 127° C., a third thermal event with an onset temperature of about 180° C., and a fourth thermal event with an onset temperature of about 224° C. In one embodiment, the second thermal event also has a peak temperature of about 138° C., the third thermal event also has a peak temperature of about 189° C., and the fourth thermal event also has a peak temperature of about 227° C. In one embodiment, without being limited by any particular theory, the first (broad) thermal event corresponds to dehydration, and the second thermal event corresponds to melting of dehydrated Form B. In alternative embodiments, Form B has a melting point in the range of about 122-129° C. (peak temperature), as characterized by DSC. In one embodiment, provided herein is a solid form comprising a free base of Compound 1, characterized by a DSC thermogram that matches the DSC thermogram presented in FIG. 7.

A representative dynamic vapor sorption (DVS) isotherm plot of the Form B is provided in FIG. 8. In one embodiment, provided herein is a solid form comprising a free base of Compound 1, which exhibits a mass increase of about 3.1% when subjected to an increase in a relative humidity (RH) from about 5% to about 95%. In one embodiment, provided herein is a solid form comprising a free base of Compound 1, characterized by a DVS isotherm plot which matches the DVS isotherm plot presented in FIG. 8. In one embodiment, Form B is slightly hygroscopic.

In one embodiment, Form B remains as Form B after being ground (e.g., by a mortar and pestle) for about two minutes.

In one embodiment, Form B of a free base of Compound 1 is prepared by desolvation of a solvate form of a free base of Compound 1. In one embodiment, Form B of a free base of Compound 1 is prepared by desolvation of Form E of a free base of Compound 1. In one embodiment, the desolvation of Form E occurs spontaneously under ambient conditions. In one embodiment, Form B of a free base of Compound 1 is prepared by drying Form E of a free base of Compound 1 (e.g., about 40° C., vacuum, about 19 to about 24 hours). In one embodiment, Form B of a free base of Compound 1 is prepared by drying Form F of a free base of Compound 1. In one embodiment, Form B of a free base of Compound 1 is prepared by drying Form G of a free base of Compound 1 (e.g., about 40° C., vacuum, about 31 hours). In one embodiment, Form B of a free base of Compound 1 is prepared by drying a mixture of Form E and Form C of a free base of Compound 1 (e.g., about 40° C., vacuum, about 25 hours).

In one embodiment, Form B of a free base of Compound 1 is prepared by crystallizing a free base of Compound 1 from MeOAc, followed by drying (e.g., about 80° C.).

In one embodiment, provided herein is a solid form comprising Form B of a free base of Compound 1 and amorphous free base of Compound 1. In one embodiment, provided herein is a solid form comprising Form B of a free base Compound 1 and one or more other crystalline forms of a free base of Compound 1 provided herein. In one embodiment, provided herein is a solid form comprising Form B of a free base of Compound 1 and one or more forms (e.g., amorphous or crystalline) of a salt of Compound 1 provided herein.

(iii) Form C of Free Base of Compound 1

In certain embodiments, provided herein is Form C of a free base of Compound 1.

In one embodiment, Form C is crystalline. In one embodiment, Form C is substantially crystalline. In one embodiment, Form C is moderately crystalline. In one embodiment, Form C is partially crystalline.

In one embodiment, Form C is a desolvated form of a free base of Compound 1. In one embodiment, Form C is an anhydrous form of a free base of Compound 1.

A representative XRPD pattern of Form C is provided in FIG. 9.

In one embodiment, provided herein is a solid form comprising a free base of Compound 1, characterized by 1, 2, 3, 4, 5, 6, 7, 8, 9, 10, 11, 12, 13, 14, 15, 16, 17, or all of the peaks located at approximately the following positions: 2.5, 9.9, 14.2, 14.6, 15.7, 15.9, 16.5, 17.2, 18.8, 19.7, 20.6, 21.5, 21.8, 22.4, 23.5, 24.5, 25.7, and 26.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 14.2, 15.9, and 21.5° 2θ. In one embodiment, the XRPD pattern further comprises peaks at approximately 2.5, 20.6, and 23.5° 2θ. In one embodiment, the XRPD pattern further comprises peaks at approximately 15.7 and 21.8° 2θ. In one embodiment, the XRPD pattern comprises peaks at approximately 2.5, 14.2, 15.7, 15.9, 16.5, 17.2, 20.6, 21.5, 21.8, and 23.5° 2θ.

In one embodiment, provided herein is a solid form comprising a free base of Compound 1, characterized by an XRPD pattern that matches the XRPD pattern presented in FIG. 9.

In one embodiment, the XRPD patterns are obtained using Cu Kα radiation.

A representative thermal gravimetric analysis (TGA) thermogram of Form C is provided in FIG. 10. In one embodiment, provided herein is a solid form comprising a free base of Compound 1, which exhibits a weight loss of about 0.6% upon heating from about 25° C. to about 210° C. In one embodiment, without being limited by any particular theory, the weight loss corresponds to the loss of trace amount of residual solvent or water. In one embodiment, provided herein is a solid form comprising a free base of Compound 1, characterized by a TGA thermogram that matches the TGA thermogram presented in FIG. 10.

A representative differential scanning calorimetry (DSC) thermogram of Form C is presented in FIG. 11. In one embodiment, provided herein is a solid form comprising a free base of Compound 1, which exhibits, as characterized by DSC, a first thermal event with an onset temperature of about 160° C., and a second thermal event with an onset temperature of about 224° C. In one embodiment, the first thermal event also has a peak temperature of about 172° C., and the second thermal event also has a peak temperature of about 226° C. In one embodiment, without being limited by any particular theory, the first thermal event corresponds to melting of Form C. In alternative embodiments, the melting peak of Form C shifts to a lower temperature (e.g., with an onset temperature of about 113° C. and a peak temperature of about 125° C.). Without being limited by any particular theory, the shifting of melting peak is caused by the plasticizing effect of residual solvent, and the complete desolvation process in a Form C sample could take up to about two months. In one embodiment, provided herein is a solid form comprising a free base of Compound 1, characterized by a DSC thermogram that matches the DSC thermogram presented in FIG. 11.

A representative dynamic vapor sorption (DVS) isotherm plot of the Form C is provided in FIG. 12. In one embodiment, provided herein is a solid form comprising a free base of Compound 1, which exhibits a mass increase of about 8.3% when subjected to an increase in a relative humidity (RH) from about 5% to about 95%. In one embodiment, provided herein is a solid form comprising a free base of Compound 1, characterized by a DVS isotherm plot which matches the DVS isotherm plot presented in FIG. 12. In one embodiment, Form C is hygroscopic at high relative humidity.

In one embodiment, Form C of a free base of Compound 1 is prepared by crystallizing a free base of Compound 1 from a mixture solvent comprising water. In one embodiment, the solvent is a mixture of 2-PrOH and water (e.g., 95:5 v/v, or 90:10 v/v). In one embodiment, the solvent is a mixture of DMSO and water (e.g., 1:3 v/v). In one embodiment, the preparation comprising suspending Compound 1 in the solvent at about 50° C. for a period of time. In one embodiment, the preparation comprising cooling the solvent containing Compound 1 from about 60° C.

In one embodiment, Form C of a free base of Compound 1 is prepared by evaporating a solution of a free base of Compound 1 in a mixture solvent of acetone and 2-PrOH under ambient condition.

In one embodiment, provided herein is a solid form comprising Form C of a free base of Compound 1 and amorphous free base of Compound 1. In one embodiment, provided herein is a solid form comprising Form C of a free base Compound 1 and one or more other crystalline forms of a free base of Compound 1 provided herein. In one embodiment, provided herein is a solid form comprising Form C of a free base of Compound 1 and one or more forms (e.g., amorphous or crystalline) of a salt of Compound 1 provided herein.

(iv) Form D of Free Base of Compound 1

In certain embodiments, provided herein is Form D of a free base of Compound 1.

In one embodiment, Form D is crystalline. In one embodiment, Form D is substantially crystalline. In one embodiment, Form D is moderately crystalline. In one embodiment, Form D is partially crystalline.

In one embodiment, Form D is a channel hydrate of a free base of Compound 1.

A representative XRPD pattern of Form D is provided in FIG. 13.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 6.1, 9.6, 11.1, 11.6, 14.2, 14.4, 15.9, 16.4, 16.9, 17.5, 17.7, 17.9, 18.5, 19.4, 20.4, 23.3, 24.7, 24.8, 26.0, 27.2, 27.4, and 29.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 6.1, 11.1, and 18.5° 2θ. In one embodiment, the XRPD pattern further comprises peaks at approximately 11.6 and 17.7° 2θ. In one embodiment, the XRPD pattern further comprises peaks at approximately 15.9 and 23.3° 2θ. In one embodiment, the XRPD pattern comprises peaks at approximately 6.1, 11.1, 11.6, 14.2, 14.4, 15.9, 17.7, 17.9, 18.5, 19.4, 23.3, and 26.0° 2θ.

In one embodiment, provided herein is a solid form comprising a free base of Compound 1, characterized by an XRPD pattern that matches the XRPD pattern presented in FIG. 13.

In one embodiment, the XRPD patterns are obtained using Cu Kα radiation.

A representative thermal gravimetric analysis (TGA) thermogram of Form D is provided in FIG. 14. In one embodiment, provided herein is a solid form comprising a free base of Compound 1, which exhibits a weight loss of about 2.0% upon heating from about 25° C. to about 150° C. In one embodiment, without being limited by any particular theory, the weight loss corresponds to the loss of water. Without being limited by any particular theory, the water molecules are weakly bound (or residual), given that the mass is released below the boiling point of water. In one embodiment, provided herein is a solid form comprising a free base of Compound 1, characterized by a TGA thermogram that matches the TGA thermogram presented in FIG. 14.

A representative differential scanning calorimetry (DSC) thermogram of Form D is presented in FIG. 15. In one embodiment, provided herein is a solid form comprising a free base of Compound 1, which exhibits, as characterized by DSC, a first (broad) thermal event from about 30° C. to about 120° C., a second thermal event with an onset temperature of about 129° C., a third thermal event with an onset temperature of about 171° C., and a fourth thermal event with an onset temperature of about 222° C. In one embodiment, the second thermal event also has a peak temperature of about 136° C., the third thermal event also has a peak temperature of about 184° C., and the fourth thermal event also has a peak temperature of about 226° C. In one embodiment, without being limited by any particular theory, the first (broad) thermal event corresponds to dehydration, and the second thermal event corresponds to melting of dehydrated Form D. In one embodiment, provided herein is a solid form comprising a free base of Compound 1, characterized by a DSC thermogram that matches the DSC thermogram presented in FIG. 15.

A representative dynamic vapor sorption (DVS) isotherm plot of the Form D is provided in FIG. 16. In one embodiment, provided herein is a solid form comprising a free base of Compound 1, which exhibits a mass increase of about 3.0% when subjected to an increase in a relative humidity (RH) from about 5% to about 95%. In one embodiment, provided herein is a solid form comprising a free base of Compound 1, characterized by a DVS isotherm plot which matches the DVS isotherm plot presented in FIG. 16. In one embodiment, Form D is slightly hygroscopic. In one embodiment, Form D converts to a mixture of Form B and Form E after the DVS humidity cycle.

In one embodiment, Form D of a free base of Compound 1 is prepared by crystallizing a free base of Compound 1 from ethanol. In one embodiment, the preparation comprising suspending Compound 1 in ethanol at about 25° C. to about 35° C. for a period of time. In one embodiment, the preparation comprising suspending Compound 1 in ethanol at room temperature for a period of time.

In one embodiment, Form D of a free base of Compound 1 is prepared by suspending Compound 1 in diglyme at about 40° C. for a period of time (e.g., about 14 days). In one embodiment, Form D of a free base of Compound 1 is prepared by suspending Compound 1 in carbitol at about 40° C. for a period of time (e.g., about 14 days).

In one embodiment, provided herein is a solid form comprising Form D of a free base of Compound 1 and amorphous free base of Compound 1. In one embodiment, provided herein is a solid form comprising Form D of a free base Compound 1 and one or more other crystalline forms of a free base of Compound 1 provided herein. In one embodiment, provided herein is a solid form comprising Form D of a free base of Compound 1 and one or more forms (e.g., amorphous or crystalline) of a salt of Compound 1 provided herein.

(v) Form E of Free Base of Compound 1

In certain embodiments, provided herein is Form E of a free base of Compound 1.

In one embodiment, Form E is crystalline. In one embodiment, Form E is substantially crystalline. In one embodiment, Form E is moderately crystalline. In one embodiment, Form E is partially crystalline.

In one embodiment, Form E is a solvate of a free base of Compound 1. In one embodiment, Form E is an isomorphic solvate of a free base of Compound 1. In one embodiment, Form E is a hydrate of a free base of Compound 1. In one embodiment, Form E is an MEK solvate of a free base of Compound 1. In one embodiment, Form E is an ethyl formate solvate of a free base of Compound 1.

A representative XRPD pattern of Form E is provided in FIG. 17.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 6.2, 9.8, 11.3, 11.7, 12.5, 13.6, 14.2, 14.3, 16.5, 16.9, 17.2, 17.7, 17.8, 18.0, 18.8, 19.6, 20.5, 21.4, 23.6, 24.0, 25.7, 26.4, and 26.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 6.2, 14.3, and 18.8° 2θ. In one embodiment, the XRPD pattern further comprises peaks at approximately 11.3 and 11.7° 2θ. In one embodiment, the XRPD pattern further comprises peaks at approximately 16.5, 17.2, and 26.4° 2θ. In one embodiment, the XRPD pattern comprises peaks at approximately 6.2, 11.3, 11.7, 14.3, 16.5, 17.2, 17.8, 18.0, 18.8, 20.5, and 26.4° 2θ.

In one embodiment, provided herein is a solid form comprising a free base of Compound 1, characterized by an XRPD pattern that matches the XRPD pattern presented in FIG. 17.

In one embodiment, the XRPD patterns are obtained using Cu Kα radiation.

A representative thermal gravimetric analysis (TGA) thermogram of Form E is provided in FIG. 18. In one embodiment, provided herein is a solid form comprising a free base of Compound 1, which exhibits a weight loss of about 9.7% upon heating from about 25° C. to about 180° C. In one embodiment, without being limited by any particular theory, the weight loss corresponds to the loss of MEK. In one embodiment, provided herein is a solid form comprising a free base of Compound 1, characterized by a TGA thermogram that matches the TGA thermogram presented in FIG. 18.

A representative differential scanning calorimetry (DSC) thermogram of Form E is presented in FIG. 19. In one embodiment, provided herein is a solid form comprising a free base of Compound 1, which exhibits, as characterized by DSC, a first thermal event with an onset temperature of about 118° C., a second thermal event with an onset temperature of about 147° C., and a third thermal event with an onset temperature of about 224° C. In one embodiment, the first thermal event also has a peak temperature of about 132° C., the second thermal event also has a peak temperature of about 170° C., and the third thermal event also has a peak temperature of about 226° C. In one embodiment, without being limited by any particular theory, the first thermal event corresponds to melting (after partial dehydration/desolvation). In one embodiment, provided herein is a solid form comprising a free base of Compound 1, characterized by a DSC thermogram that matches the DSC thermogram presented in FIG. 19.

A representative dynamic vapor sorption (DVS) isotherm plot of the Form E is provided in FIG. 20. In one embodiment, Form E loses mass during both the initial equilibration period at 50% relative humidity (RH) and the subsequent humidity cycle, even when the humidity is raised. Without being limited by any particular theory, this corresponds to replacement of many of the heavier MEK molecules by lighter $H_2O$ molecules. In one embodiment, provided herein is a solid form comprising a free base of Compound 1, characterized by a DVS isotherm plot which matches the DVS isotherm plot presented in FIG. 20. In one embodiment, Form E converts to primarily amorphous material after the DVS humidity cycle.

In one embodiment, Form E of a free base of Compound 1 is prepared by crystallizing a free base of Compound 1 from a solvent. In one embodiment, the solvent is ethyl formate, toluene, MEK, a mixture of iPrOAc and DMA, a mixture of IPE and DMF, and a mixture of IPE and NMP. In one embodiment, the solvent is MEK. In one embodiment, the preparation comprising cooling an MEK solution of Compound 1. In one embodiment, the solvent is ethyl formate. In one embodiment, the preparation comprising suspending Compound 1 in ethyl formate at about 25° C. to about 35° C. for a period of time.

In one embodiment, provided herein is a solid form comprising Form E of a free base of Compound 1 and amorphous free base of Compound 1. In one embodiment, provided herein is a solid form comprising Form E of a free base Compound 1 and one or more other crystalline forms of a free base of Compound 1 provided herein. In one embodiment, provided herein is a solid form comprising Form E of a free base of Compound 1 and one or more forms (e.g., amorphous or crystalline) of a salt of Compound 1 provided herein.

(vi) Form F of Free Base of Compound 1

In certain embodiments, provided herein is Form F of a free base of Compound 1.

In one embodiment, Form F is crystalline. In one embodiment, Form F is substantially crystalline. In one embodiment, Form F is moderately crystalline. In one embodiment, Form F is partially crystalline.

In one embodiment, Form F is a solvate of a free base of Compound 1. In one embodiment, Form F is an isomorphic solvate of a free base of Compound 1. In one embodiment, Form F is an anisole solvate of a free base of Compound 1. In one embodiment, Form F is a toluene solvate of a free base of Compound 1. In one embodiment, Form F is an ethyl formate solvate of a free base of Compound 1. In one embodiment, Form F is a methyl acetate solvate of a free base of Compound 1. In one embodiment, Form F is an ethyl acetate solvate of a free base of Compound 1. In one embodiment, Form F is an isopropyl acetate solvate of a free base of Compound 1. In one embodiment, Form F is an acetone solvate of a free base of Compound 1. In one embodiment, Form F is a dioxane solvate of a free base of Compound 1. In one embodiment, Form F is a cumene solvate of a free base of Compound 1. In one embodiment, Form F is a trifluorotoluene solvate of a free base of Compound 1. In one embodiment, Form F is a p-xylene solvate of a free base of Compound 1.

A representative XRPD pattern of Form F is provided in FIG. 21.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 5.0, 5.5, 7.8, 10.1, 13.1, 14.1, 14.3, 15.6, 16.5, 16.9, 17.3, 18.0, 18.6, 21.3, 21.7, 21.8, 22.2, 23.9, 25.8, 26.3, 26.4, 27.0, and 28.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 5.0, 14.3, and 26.3° 2θ. In one embodiment, the XRPD pattern further comprises peaks at approximately 18.0 and 26.4° 2θ. In one embodiment, the XRPD pattern further comprises peaks at approximately 7.8 and 18.6° 2θ. In one embodiment, the XRPD pattern comprises peaks at approximately 5.0, 7.8, 14.1, 14.3, 18.0, 18.6, 21.7, 21.8, 26.3, and 26.4° 2θ.

In one embodiment, provided herein is a solid form comprising a free base of Compound 1, characterized by an XRPD pattern that matches the XRPD pattern presented in FIG. 21.

In one embodiment, the XRPD patterns are obtained using Cu Kα radiation.

A representative thermal gravimetric analysis (TGA) thermogram of Form F is provided in FIG. 22. In one embodiment, provided herein is a solid form comprising a free base of Compound 1, which exhibits a weight loss of about 21.5% upon heating from about 25° C. to about 200° C. In one embodiment, without being limited by any particular theory, the weight loss corresponds to the loss of anisole and some water. In one embodiment, provided herein is a solid form comprising a free base of Compound 1, characterized by a TGA thermogram that matches the TGA thermogram presented in FIG. 22.

A representative differential scanning calorimetry (DSC) thermogram of Form F is presented in FIG. 23. In one embodiment, provided herein is a solid form comprising a free base of Compound 1, which exhibits, as characterized by DSC, a first thermal event with an onset temperature of about 113° C., and a second thermal event with an onset temperature of about 223° C. In one embodiment, the first thermal event also has a peak temperature of about 121° C., and the second thermal event also has a peak temperature of about 225° C. In one embodiment, without being limited by any particular theory, the irregular baseline in the DSC thermogram is likely due to some release of solvent below 100° C., and the first thermal event corresponds to melting of the solvate itself, while still releasing solvent. In one embodiment, provided herein is a solid form comprising a free base of Compound 1, characterized by a DSC thermogram that matches the DSC thermogram presented in FIG. 23.

In one embodiment, Form F of a free base of Compound 1 is prepared by crystallizing a free base of Compound 1 from a solvent. In one embodiment, the solvent is anisole, toluene, a mixture of acetone and water, ethyl formate, EtOAc, a mixture of iPrOAc and THF, MeOAc, a mixture of 2-propanol and water, and a mixture of dioxane and toluene. In one embodiment, the solvent is anisole. In one embodiment, the preparation comprising cooling an anisole solution of Compound 1. In one embodiment, the preparation comprising suspending Compound 1 in anisole at room temperature for a period of time. In one embodiment, the preparation comprising suspending Compound 1 in anisole at about 25° C. to about 35° C. for a period of time. In one embodiment, the solvent is toluene. In one embodiment, the preparation comprising suspending Compound 1 in toluene at about 25° C. to about 35° C. for a period of time.

In one embodiment, provided herein is a solid form comprising Form F of a free base of Compound 1 and amorphous free base of Compound 1. In one embodiment, provided herein is a solid form comprising Form F of a free base Compound 1 and one or more other crystalline forms of a free base of Compound 1 provided herein. In one embodiment, provided herein is a solid form comprising Form F of a free base of Compound 1 and one or more forms (e.g., amorphous or crystalline) of a salt of Compound 1 provided herein.

(vii) Form G of Free Base of Compound 1

In certain embodiments, provided herein is Form G of a free base of Compound 1.

In one embodiment, Form G is crystalline. In one embodiment, Form G is substantially crystalline. In one embodiment, Form G is moderately crystalline. In one embodiment, Form G is partially crystalline.

In one embodiment, Form G is a solvate of a free base of Compound 1. In one embodiment, Form G is an acetonitrile solvate of a free base of Compound 1.

A representative XRPD pattern of Form G is provided in FIG. 24.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, or all of the peaks located at approximately the following positions: 5.6, 6.4, 6.9, 9.8, 10.9, 11.2, 12.1, 13.9, 14.4, 16.0, 16.4, 16.7, 18.0, 18.7, 19.1, 19.6, 23.6, 24.3, 26.0, 26.3, 26.9, and 28.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 6.4, 19.1, and 19.6° 2θ. In one embodiment, the XRPD pattern further comprises peaks at approximately 12.1 and 13.9° 2θ. In one embodiment, the XRPD pattern further comprises peaks at approximately 14.4, 16.7, and 26.0° 2θ. In one embodiment, the XRPD pattern comprises peaks at approximately 5.6, 6.4, 11.2, 12.1, 13.9, 14.4, 16.7, 19.1, 19.6, and 26.0° 2θ.

In one embodiment, provided herein is a solid form comprising a free base of Compound 1, characterized by an XRPD pattern that matches the XRPD pattern presented in FIG. 24.

In one embodiment, the XRPD patterns are obtained using Cu Kα radiation.

A representative thermal gravimetric analysis (TGA) thermogram of Form G is provided in FIG. 25. In one embodiment, provided herein is a solid form comprising a free base of Compound 1, which exhibits a weight loss of about 6.1% upon heating from about 25° C. to about 170° C. In one embodiment, without being limited by any particular theory, the weight loss corresponds to the loss of acetonitrile. In one embodiment, provided herein is a solid form comprising a free base of Compound 1, characterized by a TGA thermogram that matches the TGA thermogram presented in FIG. 25.

A representative differential scanning calorimetry (DSC) thermogram of Form G is presented in FIG. 26. In one embodiment, provided herein is a solid form comprising a free base of Compound 1, which exhibits, as characterized by DSC, a first thermal event with an onset temperature of about 132° C., and a second thermal event with an onset temperature of about 225° C. In one embodiment, the first thermal event also has a peak temperature of about 140° C., and the second thermal event also has a peak temperature of about 226° C. In one embodiment, without being limited by any particular theory, the first thermal event corresponds to melting (after desolvation). In one embodiment, provided herein is a solid form comprising a free base of Compound 1, characterized by a DSC thermogram that matches the DSC thermogram presented in FIG. 26.

In one embodiment, Form G of a free base of Compound 1 is prepared by crystallizing a free base of Compound 1 from a solvent comprising acetonitrile. In one embodiment, the solvent is acetonitrile. In one embodiment, the solvent is a mixture of acetonitrile and water (e.g., 95:5 v/v). In one embodiment, the preparation comprising suspending Compound 1 in acetonitrile at room temperature for a period of time. In one embodiment, the preparation comprising suspending Compound 1 in acetonitrile at about 25° C. to about 35° C. for a period of time.

In one embodiment, provided herein is a solid form comprising Form G of a free base of Compound 1 and amorphous free base of Compound 1. In one embodiment, provided herein is a solid form comprising Form G of a free base Compound 1 and one or more other crystalline forms of a free base of Compound 1 provided herein. In one embodiment, provided herein is a solid form comprising Form G of a free base of Compound 1 and one or more forms (e.g., amorphous or crystalline) of a salt of Compound 1 provided herein.

(viii) Form H of Free Base of Compound 1

In certain embodiments, provided herein is Form H of a free base of Compound 1.

In one embodiment, Form H is crystalline. In one embodiment, Form H is substantially crystalline. In one embodiment, Form H is moderately crystalline. In one embodiment, Form H is partially crystalline.

In one embodiment, Form H is a solvate of a free base of Compound 1. In one embodiment, Form H is an isomorphic solvate of a free base of Compound 1. In one embodiment, Form H is a THF solvate of a free base of Compound 1. In one embodiment, Form H is a TBME solvate of a free base of Compound 1.

A representative XRPD pattern of Form H is provided in FIG. 27.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, or all of the peaks located at approximately the following positions: 5.4, 5.7, 7.5, 10.7, 13.3, 14.2, 14.5, 15.1, 15.4, 16.7, 17.2, 17.6, 18.4, 19.2, 19.6, 20.6, 26.1, 26.6, 26.8, and 27.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 5.4, 7.5, and 10.7° 2θ. In one embodiment, the XRPD pattern further comprises peaks at approximately 14.2 and 14.5° 2θ. In one embodiment, the XRPD pattern further comprises peaks at approximately 17.2, 17.6, and 26.1° 2θ. In one embodiment, the XRPD pattern comprises peaks at approximately 5.4, 7.5, 10.7, 14.2, 14.5, 17.2, 17.6, 26.1, 26.6, and 26.8° 2θ.

In one embodiment, provided herein is a solid form comprising a free base of Compound 1, characterized by an XRPD pattern that matches the XRPD pattern presented in FIG. 27.

In one embodiment, the XRPD patterns are obtained using Cu Kα radiation.

A representative thermal gravimetric analysis (TGA) thermogram of Form H is provided in FIG. 28. In one embodiment, provided herein is a solid form comprising a free base of Compound 1, which exhibits a weight loss of about 11.8% upon heating from about 25° C. to about 220° C. In one embodiment, without being limited by any particular theory, the weight loss corresponds to the loss of TBME. In one embodiment, provided herein is a solid form comprising a free base of Compound 1, characterized by a TGA thermogram that matches the TGA thermogram presented in FIG. 28.

A representative differential scanning calorimetry (DSC) thermogram of Form H is presented in FIG. 29. In one embodiment, provided herein is a solid form comprising a free base of Compound 1, which exhibits, as characterized by DSC, a first (broad) thermal event with a peak temperature of about 140° C., a second thermal event with an onset temperature of about 177° C., and a third thermal event with an onset temperature of about 221° C. In one embodiment, the second thermal event also has a peak temperature of about 193° C., and the third thermal event also has a peak temperature of about 224° C. In one embodiment, without being limited by any particular theory, the first (broad) thermal event corresponds to concomitant desolvation and melting. In one embodiment, provided herein is a solid form comprising a free base of Compound 1, characterized by a DSC thermogram that matches the DSC thermogram presented in FIG. 29.

In one embodiment, Form H of a free base of Compound 1 is prepared by evaporating a THF solution of Compound 1 at room temperature. In one embodiment, Form H of a free base of Compound 1 is prepared by suspending Compound 1 in TBME at about 25° C. to about 35° C. for a period of time. In one embodiment, Form H of a free base of Compound 1 is prepared by suspending Compound 1 in TBME at about 50° C. for a period of time.

In one embodiment, provided herein is a solid form comprising Form H of a free base of Compound 1 and amorphous free base of Compound 1. In one embodiment, provided herein is a solid form comprising Form H of a free base Compound 1 and one or more other crystalline forms of a free base of Compound 1 provided herein. In one embodiment, provided herein is a solid form comprising Form H of a free base of Compound 1 and one or more forms (e.g., amorphous or crystalline) of a salt of Compound 1 provided herein.

(ix) Form I of Free Base of Compound 1

In certain embodiments, provided herein is Form I of a free base of Compound 1.

In one embodiment, Form I is crystalline. In one embodiment, Form I is substantially crystalline. In one embodiment, Form I is moderately crystalline. In one embodiment, Form I is partially crystalline.

In one embodiment, Form I is a solvate of a free base of Compound 1. In one embodiment, Form I is a DMSO solvate of a free base of Compound 1.

A representative XRPD pattern of Form I is provided in FIG. 30.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, or all of the peaks located at approximately the following positions: 5.7, 6.2, 9.9, 11.3, 11.5, 14.9, 15.1, 15.6, 16.3, 16.6, 16.7, 17.0, 18.0, 18.4, 19.6, 21.1, 21.3, 21.6, 23.2, 26.1, 26.4, and 26.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 14.9, 15.6, and 21.3° 2θ. In one embodiment, the XRPD pattern further comprises peaks at approximately 6.2, 16.7, and 18.0° 2θ. In one embodiment, the XRPD pattern further comprises peaks at approximately 9.9 and 16.3° 2θ. In one embodiment, the XRPD pattern comprises peaks at approximately 6.2, 9.9, 14.9, 15.6, 16.3, 16.7, 17.0, 18.0, 19.6, 21.1, 21.3, and 26.1° 2θ.

In one embodiment, provided herein is a solid form comprising a free base of Compound 1, characterized by an XRPD pattern that matches the XRPD pattern presented in FIG. 30.

In one embodiment, the XRPD patterns are obtained using Cu Kα radiation.

A representative thermal gravimetric analysis (TGA) thermogram of Form I is provided in FIG. 31. In one embodiment, provided herein is a solid form comprising a free base of Compound 1, which exhibits a weight loss of about 42.2% upon heating from about 25° C. to about 300° C. In one embodiment, without being limited by any particular theory, the weight loss corresponds to the loss of DMSO (and some water). In one embodiment, provided herein is a solid form comprising a free base of Compound 1, characterized by a TGA thermogram that matches the TGA thermogram presented in FIG. 31.

In one embodiment, Form I of a free base of Compound 1 is prepared by suspending Compound 1 in a mixture of DMSO and 2-PrOH (e.g., 1:3 v/v) at about 50° C. for a period of time. In one embodiment, Form I of a free base of Compound 1 is prepared by suspending Compound 1 in a mixture of DMSO and water (e.g., 95:5 v/v) at room temperature for a period of time.

In one embodiment, provided herein is a solid form comprising Form I of a free base of Compound 1 and amorphous free base of Compound 1. In one embodiment, provided herein is a solid form comprising Form I of a free base Compound 1 and one or more other crystalline forms of a free base of Compound 1 provided herein. In one embodiment, provided herein is a solid form comprising Form I of a free base of Compound 1 and one or more forms (e.g., amorphous or crystalline) of a salt of Compound 1 provided herein.

(x) Form J of Free Base of Compound 1

In certain embodiments, provided herein is Form J of a free base of Compound 1.

In one embodiment, Form J is crystalline. In one embodiment, Form J is substantially crystalline. In one embodiment, Form J is moderately crystalline. In one embodiment, Form J is partially crystalline.

In one embodiment, Form J is a solvate of a free base of Compound 1. In one embodiment, Form J is an acetic acid solvate of a free base of Compound 1.

A representative XRPD pattern of Form J is provided in FIG. 32.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 5.9, 11.1, 11.8, 12.3, 13.5, 13.8, 14.1, 15.2, 17.0, 17.9, 20.3, 20.5, 22.0, 22.3, 23.3, 23.7, 24.3, 24.7, 25.7, 26.2, 26.4, 26.7, and 28.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 13.8, 15.2, and 22.0° 2θ. In one embodiment, the XRPD pattern further comprises peaks at approximately 23.3 and 23.7° 2θ. In one embodiment, the XRPD pattern further comprises peaks at approximately 5.9 and 25.7° 2θ. In one embodiment, the XRPD pattern comprises peaks at approximately 5.9, 11.8, 13.8, 14.1, 15.2, 20.3, 22.0, 23.3, 23.7, 24.3, 25.7, and 26.7° 2θ.

In one embodiment, provided herein is a solid form comprising a free base of Compound 1, characterized by an XRPD pattern that matches the XRPD pattern presented in FIG. 32.

In one embodiment, the XRPD patterns are obtained using Cu Kα radiation.

A representative thermal gravimetric analysis (TGA) thermogram of Form J is provided in FIG. 33. In one embodiment, provided herein is a solid form comprising a free base of Compound 1, which exhibits a weight loss of about 3.9% upon heating from about 25° C. to about 110° C., and a weight loss of about 15.3% upon heating from about 110° C. to about 250° C. In one embodiment, without being limited by any particular theory, the first weight loss corresponds to the loss of acetic acid (and trace water), and the second weight loss corresponds to the loss of acetic acid. In one embodiment, provided herein is a solid form comprising a free base of Compound 1, characterized by a TGA thermogram that matches the TGA thermogram presented in FIG. 33.

A representative differential scanning calorimetry (DSC) thermogram of Form J is presented in FIG. 34. In one embodiment, provided herein is a solid form comprising a free base of Compound 1, which exhibits, as characterized by DSC, a first thermal event with a peak temperature of about 70° C., a second thermal event with an onset temperature of about 138° C., and a third thermal event with an onset temperature of about 219° C. In one embodiment, the first thermal event also has a peak temperature of about 80° C., the second thermal event also has a peak temperature of about 155° C., and the third thermal event also has a peak temperature of about 225° C. In one embodiment, provided herein is a solid form comprising a free base of Compound 1, characterized by a DSC thermogram that matches the DSC thermogram presented in FIG. 34.

In one embodiment, Form J of a free base of Compound 1 is prepared by suspending Compound 1 in a mixture of acetic acid and isopropyl ether (e.g., 1:9 v/v) at about 25° C. to about 35° C. for a period of time.

In one embodiment, provided herein is a solid form comprising Form J of a free base of Compound 1 and amorphous free base of Compound 1. In one embodiment, provided herein is a solid form comprising Form J of a free base Compound 1 and one or more other crystalline forms of a free base of Compound 1 provided herein. In one embodiment, provided herein is a solid form comprising Form J of a free base of Compound 1 and one or more forms (e.g., amorphous or crystalline) of a salt of Compound 1 provided herein.

(xi) Forms K and K' of Free Base of Compound 1

In certain embodiments, provided herein is Form K of a free base of Compound 1, Form K' of a free base of Compound 1, an intermediate form between Form K and Form K', or a mixture thereof.

In one embodiment, Form K is crystalline. In one embodiment, Form K is substantially crystalline. In one embodiment, Form K is moderately crystalline. In one embodiment, Form K is partially crystalline. In one embodiment, Form K' is crystalline. In one embodiment, Form K' is substantially crystalline. In one embodiment, Form K' is moderately crystalline. In one embodiment, Form K' is partially crystalline.

In one embodiment, Form K is a channel hydrate of a free base of Compound 1. In one embodiment, Form K is a monohydrate of a free base of Compound 1. In one embodiment, Form K' is a dehydrated hydrate of Form K. In one embodiment, without being limited by a particular theory, Form K' converts to Form K with increasing humidity, and Form K converts to Form K' with decreasing humidity. Accordingly, intermediate forms between Form K and Form K' exist depending on the degree of humidity. Examples of the conversion between Form K and Form K', including possible intermediate forms, are provided in FIG. 132 and FIG. 133. In one embodiment, From K converts to Form K' when water activity is not higher than about 0.11. In one embodiment, From K' converts to Form K when water activity is not lower than about 0.17.

In one embodiment, provided herein is Form K, Form K', or an intermediate form between Form K and Form K', or a mixture thereof, of a free base of Compound 1, characterized by an XRPD pattern comprising peaks at approximately 14.6, 18.2, and 18.3° 2θ. In one embodiment, the XRPD pattern further comprises peaks at approximately 22.3 and 23.1° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 20.5, 20.9, 22.3, and 23.1° 2θ. In one embodiment, provided here is Form K of a free base of Compound 1, characterized by an XRPD pattern further comprising at least a peak at approximately 14.2, 18.6, or 20.3° 2θ. In one embodiment, provided here is Form K' of a free base of Compound 1, characterized by an XRPD pattern further comprising at least a peak at approximately 18.0 or 18.8° 2θ.

A representative XRPD pattern of Form K is provided in FIG. 35.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 8.6, 10.8, 14.2, 14.3, 14.6, 16.6, 17.3, 17.5, 18.2, 18.3, 18.6, 20.3, 20.5, 20.9, 21.8, 22.3, 22.5, 23.1, 24.5, 25.1, 25.7, 26.0, 27.4, 27.9, and 31.4° 2θ. In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 8.59, 10.78, 14.21, 14.32, 14.60, 16.55, 17.26, 17.45, 18.21, 18.34, 18.62, 20.25, 20.47, 20.87, 21.79, 22.28, 22.45, 23.05, 24.54, 25.05, 25.67, 26.01, 27.43, 27.89, and 31.44° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 14.2, 14.6, 18.2, and 18.3° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.2, 14.3, 14.6, 16.6, 18.2, 18.3, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, provided herein is a solid form comprising a free base of Compound 1, characterized by an XRPD pattern comprising peaks at 14.2, 14.6, 18.2, and 18.3° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, provided herein is a solid form comprising a free base of Compound 1, characterized by an XRPD pattern comprising peaks at 14.21, 14.60, 18.21, and 18.34° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, provided herein is a solid form comprising a free base of Compound 1, characterized by an XRPD pattern comprising peaks at 14.2, 14.6, 18.2, and 18.3° 2θ±0.02° 2θ. In one embodiment, the XRPD pattern further comprises peaks at 22.3, 23.1, and 24.5° 2θ±0.02° 2θ. In one embodiment, the XRPD pattern further comprises peaks at 20.5 and 20.9° 2θ±0.02° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, provided herein is a solid form comprising a free base of Compound 1, characterized by an XRPD pattern comprising peaks at 14.21, 14.60, 18.21, and 18.34° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ±0.02° 2θ.

In one embodiment, provided herein is a solid form comprising a free base of Compound 1, characterized by an XRPD pattern comprising peaks at 14.2, 14.6, 18.2, and 18.3° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.2, 14.3, 14.6, 16.6, 18.2, 18.3, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, provided herein is a solid form comprising a free base of Compound 1, characterized by an XRPD pattern comprising peaks at 14.21, 14.60, 18.21, and 18.34° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.21, 14.32, 14.60, 16.55, 18.21, 18.34, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, provided herein is a solid form comprising a free base of Compound 1, characterized by an XRPD pattern comprising peaks at approximately 14.6, 18.2, 18.3, and 18.6° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 18.6, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, provided herein is a solid form comprising a free base of Compound 1, characterized by an XRPD pattern comprising peaks at 14.6, 18.2, 18.3, and 18.6° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, provided herein is a solid form comprising a free base of Compound 1, characterized by an XRPD pattern comprising peaks at 14.60, 18.21, 18.34, and 18.62° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, provided herein is a solid form comprising a free base of Compound 1, characterized by an XRPD pattern comprising peaks at 14.6, 18.2, 18.3, and 18.6° 2θ±0.02° 2θ. In one embodiment, the XRPD pattern further comprises peaks at 22.3, 23.1, and 24.5° 2θ±0.02° 2θ. In one embodiment, the XRPD pattern further comprises peaks at 20.5 and 20.9° 2θ±0.02° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, provided herein is a solid form comprising a free base of Compound 1, characterized by an XRPD pattern comprising peaks at 14.60, 18.21, 18.34, and 18.62° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ±0.02° 2θ.

In one embodiment, provided herein is a solid form comprising a free base of Compound 1, characterized by an XRPD pattern comprising peaks at 14.6, 18.2, 18.3, and 18.6° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.3, 14.6, 16.6, 18.2, 18.3, 18.6, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, provided herein is a solid form comprising a free base of Compound 1, characterized by an XRPD pattern comprising peaks at 14.60, 18.21, 18.34, and 18.62° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.32, 14.60, 16.55, 18.21, 18.34, 18.62, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, provided herein is a solid form comprising a free base of Compound 1, characterized by an XRPD pattern comprising peaks at approximately 14.6, 18.2, 18.3, and 20.3° 2θ. In one embodiment, the XRPD pattern further comprises peaks at approximately 22.3, 23.1, and 24.5° 2θ. In one embodiment, the XRPD pattern further comprises peaks at approximately 20.5 and 20.9° 2θ. In one embodiment, the XRPD pattern comprises peaks at approximately 8.6, 14.3, 14.6, 16.6, 18.2, 18.3, 20.3, 20.5, 20.9, 22.3, 23.1, 24.5, and 26.0° 2θ. In one embodiment, the XRPD pattern does not contain a peak at approximately 18.0° 2θ. In one embodiment, the XRPD pattern does not contain a peak at approximately 18.8° 2θ.

In one embodiment, provided herein is a solid form comprising a free base of Compound 1, characterized by an XRPD pattern comprising peaks at 14.6, 18.2, 18.3, and 20.3° 2θ±0.04° 2θ. In one embodiment, the XRPD pattern further comprises peaks at 22.3, 23.1, and 24.5° 2θ±0.04° 2θ. In one embodiment, the XRPD pattern further comprises peaks at 20.5 and 20.9° 2θ±0.04° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ±0.04° 2θ. In one embodiment, the XRPD pattern does not contain a peak at 18.0° 2θ±0.04° 2θ. In one embodiment, the XRPD pattern does not contain a peak at 18.8° 2θ±0.04° 2θ. In one embodiment, provided herein is a solid form comprising a free base of Compound 1, characterized by an XRPD pattern comprising peaks at 14.60, 18.21, 18.34, and 20.3° 2θ±0.04° 2θ. In one embodiment, the XRPD pattern further comprises peaks at 22.28, 23.05, and 24.54° 2θ±0.04° 2θ. In one embodiment, the XRPD pattern further comprises peaks at 20.47 and 20.87° 2θ±0.04° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ±0.04° 2θ. In one embodiment, the XRPD pattern does not contain a peak at 18.02° 2θ±0.04° 2θ. In one embodiment, the XRPD pattern does not contain a peak at 18.75° 2θ±0.04° 2θ.

In one embodiment, provided herein is a solid form comprising a free base of Compound 1, characterized by an XRPD pattern comprising peaks at 14.6, 18.2, 18.3, and 20.3° 2θ±0.02° 2θ. In one embodiment, the XRPD pattern further comprises peaks at 22.3, 23.1, and 24.5° 2θ±0.02° 2θ. In one embodiment, the XRPD pattern further comprises peaks at 20.5 and 20.9° 2θ±0.02° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ±0.02° 2θ. In one embodiment, the XRPD pattern does not contain a peak at 18.0° 2θ±0.02° 2θ. In one embodiment, the XRPD pattern does not contain a peak at 18.8° 2θ±0.02° 2θ. In one embodiment, provided herein is a solid form comprising a free base of Compound 1, characterized by an XRPD pattern comprising peaks at 14.60, 18.21, 18.34, and 20.25° 2θ±0.02° 2θ. In one embodiment, the XRPD pattern further comprises peaks at 22.28, 23.05, and 24.54° 2θ±0.02° 2θ. In one embodiment, the XRPD pattern further comprises peaks at 20.47 and 20.87° 2θ±0.02° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ±0.02° 2θ. In one embodiment, the XRPD pattern does not contain a peak at 18.02° 2θ±0.02° 2θ. In one embodiment, the XRPD pattern does not contain a peak at 18.75° 2θ±0.02° 2θ.

In one embodiment, provided herein is a solid form comprising a free base of Compound 1, characterized by an XRPD pattern comprising peaks at 14.6, 18.2, 18.3, and 20.3° 2θ. In one embodiment, the XRPD pattern further comprises peaks at 22.3, 23.1, and 24.5° 2θ. In one embodiment, the XRPD pattern further comprises peaks at 20.5 and 20.9° 2θ. In one embodiment, the XRPD pattern comprises peaks at 8.6, 14.3, 14.6, 16.6, 18.2, 18.3, 20.3, 20.5, 20.9, 22.3, 23.1, 24.5, and 26.0° 2θ. In one embodiment, the XRPD pattern does not contain a peak at 18.0° 2θ. In one embodiment, the XRPD pattern does not contain a peak at 18.8° 2θ. In one embodiment, provided herein is a solid form comprising a free base of Compound 1, characterized by an XRPD pattern comprising peaks at 14.60, 18.21, 18.34, and 20.25° 2θ. In one embodiment, the XRPD pattern further comprises peaks at 22.28, 23.05, and 24.54° 2θ. In one embodiment, the XRPD pattern further comprises peaks at 20.47 and 20.87° 2θ. In one embodiment, the XRPD pattern comprises peaks at 8.59, 14.32, 14.60, 16.55, 18.21, 18.34, 20.25, 20.47, 20.87, 22.28, 23.05, 24.54, and 26.01° 2θ. In one embodiment, the XRPD pattern does not contain a peak at 18.02° 2θ. In one embodiment, the XRPD pattern does not contain a peak at 18.75° 2θ.

In one embodiment, provided herein is a solid form comprising a free base of Compound 1, characterized by an XRPD pattern that matches the XRPD pattern presented in FIG. 35.

A representative XRPD pattern of Form K' is provided in FIG. 36.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 8.7, 10.8, 14.4, 14.6, 16.6, 17.4, 17.5, 18.0, 18.3, 18.4, 18.8, 20.5, 20.9, 21.8, 22.4, 22.6, 23.2, 24.7, 25.2, 25.8, 26.2, 26.4, 27.5, 28.1, 31.7, and 38.4° 2θ. In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 8.65, 10.79, 14.36, 14.63, 16.55, 17.35, 17.53, 18.02, 18.25, 18.40, 18.75, 20.52, 20.92, 21.81, 22.36, 22.64, 23.19, 24.68, 25.20, 25.82, 26.17, 26.39, 27.54, 28.08, 31.69, and 38.41° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 14.6, 18.0, 18.3, and 18.4° 2θ. In one embodiment, the XRPD pattern further comprises peaks at approximately 20.9, 22.4, and 23.2° 2θ. In one embodiment, the XRPD pattern further comprises peaks at approximately 16.6 and 20.5° 2θ. In one embodiment, the XRPD pattern comprises peaks at approximately 8.7, 14.4, 14.6, 16.6, 18.0, 18.3, 18.4, 20.5, 20.9, 22.4, 23.2, and 24.7° 2θ. In one embodiment, the XRPD pattern does not contain a peak at approximately 14.2° 2θ. In one embodiment, the XRPD pattern does not contain a peak at approximately 18.6° 2θ. In one embodiment, the XRPD pattern does not contain a peak at approximately 20.3° 2θ.

In one embodiment, provided herein is a solid form comprising a free base of Compound 1, characterized by an XRPD pattern comprising peaks at 14.6, 18.0, 18.3, and 18.4° 2θ±0.04° 2θ. In one embodiment, the XRPD pattern further comprises peaks at 20.9, 22.4, and 23.2° 2θ±0.04° 2θ. In one embodiment, the XRPD pattern further comprises peaks at 16.6 and 20.5° 2θ±0.04° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ±0.04° 2θ. In one embodiment, the XRPD pattern does not contain a peak at 14.2° 2θ±0.04° 2θ. In one embodiment, the XRPD pattern does not contain a peak at 18.6° 2θ±0.04° 2θ. In one embodiment, the XRPD pattern does not contain a peak at 20.3° 2θ±0.04° 2θ. In one embodiment, provided herein is a solid form comprising a free base of Compound 1, characterized by an XRPD pattern comprising peaks at 14.63, 18.02, 18.25, and 18.40° 2θ±0.04° 2θ. In one embodiment, the XRPD pattern further comprises peaks at 20.92, 22.36, and 23.19° 2θ±0.04° 2θ. In one embodiment, the XRPD pattern further comprises peaks at 16.55 and 20.52° 2θ±0.04° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ±0.04° 2θ. In one embodiment, the XRPD pattern does not contain a peak at 14.21° 2θ±0.04° 2θ. In one embodiment, the XRPD pattern does not contain a peak at 18.62° 2θ±0.04° 2θ. In one embodiment, the XRPD pattern does not contain a peak at 20.25° 2θ±0.04° 2θ.

In one embodiment, provided herein is a solid form comprising a free base of Compound 1, characterized by an XRPD pattern comprising peaks at 14.6, 18.0, 18.3, and 18.4° 2θ±0.02° 2θ. In one embodiment, the XRPD pattern further comprises peaks at 20.9, 22.4, and 23.2° 2θ±0.02° 2θ. In one embodiment, the XRPD pattern further comprises peaks at 16.6 and 20.5° 2θ±0.02° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ±0.02° 2θ. In one embodiment, the XRPD pattern does not contain a peak at 14.2° 2θ±0.02° 2θ. In one embodiment, the XRPD pattern does not contain a peak at 18.6° 2θ±0.02° 2θ. In one embodiment, the XRPD pattern does not contain a peak at 20.3° 2θ±0.02° 2θ. In one embodiment, provided herein is a solid form comprising a free base of Compound 1, characterized by an XRPD pattern comprising peaks at 14.63, 18.02, 18.25, and 18.40° 2θ±0.02° 2θ. In one embodiment, the XRPD pattern further comprises peaks at 20.92, 22.36, and 23.19° 2θ±0.02° 2θ. In one embodiment, the XRPD pattern further comprises peaks at 16.55 and 20.52° 2θ±0.02° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ±0.02° 2θ. In one embodiment, the XRPD pattern does not contain a peak at 14.21° 2θ±0.02° 2θ. In one embodiment, the XRPD pattern does not contain a peak at 18.62° 2θ±0.02° 2θ. In one embodiment, the XRPD pattern does not contain a peak at 20.25° 2θ±0.02° 2θ.

In one embodiment, provided herein is a solid form comprising a free base of Compound 1, characterized by an XRPD pattern comprising peaks at 14.6, 18.0, 18.3, and 18.4° 2θ. In one embodiment, the XRPD pattern further comprises peaks at 20.9, 22.4, and 23.2° 2θ. In one embodiment, the XRPD pattern further comprises peaks at 16.6 and 20.5° 2θ. In one embodiment, the XRPD pattern comprises peaks at 8.7, 14.4, 14.6, 16.6, 18.0, 18.3, 18.4, 20.5, 20.9, 22.4, 23.2, and 24.7° 2θ. In one embodiment, the XRPD pattern does not contain a peak at 14.2° 2θ. In one embodiment, the XRPD pattern does not contain a peak at 18.6° 2θ. In one embodiment, the XRPD pattern does not contain a peak at 20.3° 2θ. In one embodiment, provided herein is a solid form comprising a free base of Compound 1, characterized by an XRPD pattern comprising peaks at 14.63, 18.02, 18.25, and 18.40° 2θ. In one embodiment, the XRPD pattern further comprises peaks at 20.92, 22.36, and 23.19° 2θ. In one embodiment, the XRPD pattern further comprises peaks at 16.55 and 20.52° 2θ. In one embodiment, the XRPD pattern comprises peaks at 8.65, 14.36, 14.63, 16.55, 18.02, 18.25, 18.40, 20.52, 20.92, 22.36, 23.19, and 24.68° 2θ. In one embodiment, the XRPD pattern does not contain a peak at 14.21° 2θ. In one embodiment, the XRPD pattern does not contain a peak at 18.62° 2θ. In one embodiment, the XRPD pattern does not contain a peak at 20.25° 2θ.

In one embodiment, provided herein is a solid form comprising a free base of Compound 1, characterized by an XRPD pattern comprising peaks at approximately 14.6, 18.3, 18.4, and 18.8° 2θ. In one embodiment, the XRPD pattern further comprises peaks at approximately 20.9, 22.4, and 23.2° 2θ. In one embodiment, the XRPD pattern further comprises peaks at approximately 16.6 and 20.5° 2θ. In one embodiment, the XRPD pattern comprises peaks at approximately 8.7, 14.4, 14.6, 16.6, 18.3, 18.4, 18.8, 20.5, 20.9, 22.4, 23.2, and 24.7° 2θ. In one embodiment, the XRPD pattern does not contain a peak at approximately 14.2° 2θ. In one embodiment, the XRPD pattern does not contain a peak at approximately 18.6° 2θ. In one embodiment, the XRPD pattern does not contain a peak at approximately 20.3° 2θ.

In one embodiment, provided herein is a solid form comprising a free base of Compound 1, characterized by an XRPD pattern comprising peaks at 14.6, 18.3, 18.4, and 18.8° 2θ±0.04° 2θ. In one embodiment, the XRPD pattern further comprises peaks at 20.9, 22.4, and 23.2° 2θ±0.04° 2θ. In one embodiment, the XRPD pattern further comprises peaks at 16.6 and 20.5° 2θ±0.04° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ±0.04° 2θ. In one embodiment, the XRPD pattern does not contain a peak at 14.2° 2θ±0.04° 2θ. In one embodiment, the XRPD pattern does not contain a peak at 18.6° 2θ±0.04° 2θ. In one embodiment, the XRPD pattern does not contain a peak at 20.3° 2θ±0.04° 2θ. In one embodiment, provided herein is a solid form comprising a free base of Compound 1, characterized by an XRPD pattern comprising peaks at 14.63, 18.25, 18.40, and 18.75° 2θ±0.04° 2θ. In one embodiment, the XRPD pattern further comprises peaks at 20.92, 22.36, and 23.19° 2θ±0.04° 2θ. In one embodiment, the XRPD pattern further comprises peaks at 16.55 and 20.52° 2θ±0.04° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ±0.04° 2θ. In one embodiment, the XRPD pattern does not contain a peak at 14.21° 2θ±0.04° 2θ. In one embodiment, the XRPD pattern does not contain a peak at 18.62° 2θ±0.04° 2θ. In one embodiment, the XRPD pattern does not contain a peak at 20.25° 2θ±0.04° 2θ.

In one embodiment, provided herein is a solid form comprising a free base of Compound 1, characterized by an XRPD pattern comprising peaks at 14.6, 18.3, 18.4, and 18.8° 2θ±0.02° 2θ. In one embodiment, the XRPD pattern further comprises peaks at 20.9, 22.4, and 23.2° 2θ±0.02° 2θ. In one embodiment, the XRPD pattern further comprises peaks at 16.6 and 20.5° 2θ±0.02° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ±0.02° 2θ. In one embodiment, the XRPD pattern does not contain a peak at 14.2° 2θ±0.02° 2θ. In one embodiment, the XRPD pattern does not contain a peak at 18.6° 2θ±0.02° 2θ. In one embodiment, the XRPD pattern does not contain a peak at 20.3° 2θ±0.02° 2θ. In one embodiment, provided herein is a solid form comprising a free base of Compound 1, characterized by an XRPD pattern comprising peaks at 14.63, 18.25, 18.40, and 18.75° 2θ±0.02° 2θ. In one embodiment, the XRPD pattern further comprises peaks at 20.92, 22.36, and 23.19° 2θ±0.02° 2θ. In one embodiment, the XRPD pattern further comprises peaks at 16.55 and 20.52° 2θ±0.02° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ±0.02° 2θ. In one embodiment, the XRPD pattern does not contain a peak at 14.21° 2θ±0.02° 2θ. In one embodiment, the XRPD pattern does not contain a peak at 18.62° 2θ±0.02° 2θ. In one embodiment, the XRPD pattern does not contain a peak at 20.25° 2θ±0.02° 2θ.

In one embodiment, provided herein is a solid form comprising a free base of Compound 1, characterized by an XRPD pattern comprising peaks at 14.6, 18.3, 18.4, and 18.8° 2θ. In one embodiment, the XRPD pattern further comprises peaks at 20.9, 22.4, and 23.2° 2θ. In one embodiment, the XRPD pattern further comprises peaks at 16.6 and 20.5° 2θ. In one embodiment, the XRPD pattern comprises peaks at 8.7, 14.4, 14.6, 16.6, 18.3, 18.4, 18.8, 20.5, 20.9, 22.4, 23.2, and 24.7° 2θ. In one embodiment, the XRPD pattern does not contain a peak at 14.2° 2θ. In one embodiment, the XRPD pattern does not contain a peak at 18.6° 2θ. In one embodiment, the XRPD pattern does not contain a peak at 20.3° 2θ. In one embodiment, provided herein is a solid form comprising a free base of Compound 1, characterized by an XRPD pattern comprising peaks at 14.63, 18.25, 18.40, and 18.75° 2θ. In one embodiment, the XRPD pattern further comprises peaks at 20.92, 22.36, and 23.19° 2θ. In one embodiment, the XRPD pattern further comprises peaks at 16.55 and 20.52° 2θ. In one embodiment, the XRPD pattern comprises peaks at 8.65, 14.36, 14.63, 16.55, 18.25, 18.40, 18.75, 20.52, 20.92, 22.36, 23.19, and 24.68° 2θ. In one embodiment, the XRPD pattern does not contain a peak at 14.21° 2θ. In one embodiment, the XRPD pattern does not contain a peak at 18.62° 2θ. In one embodiment, the XRPD pattern does not contain a peak at 20.25° 2θ.

In one embodiment, provided herein is a solid form comprising a free base of Compound 1, characterized by an XRPD pattern that matches the XRPD pattern presented in FIG. 36.

In one embodiment, without being limited to any particular theory, compared to Form K, the XRPD peaks in Form K' shift slightly to higher ° 2θ values, suggesting Form K' has slightly contracted lattice.

In one embodiment, the XRPD patterns are obtained using Cu Kα radiation.

A representative thermal gravimetric analysis (TGA) thermogram of Form K is provided in FIG. 37. In one embodiment, provided herein is a solid form comprising a free base of Compound 1, which exhibits a first weight loss of about 1.7% upon heating from about 25° C. to about 75° C., and a second weight loss of about 0.6% upon heating from about 120° C. to about 160° C. In one embodiment, without being limited by any particular theory, the first weight loss corresponds to the loss of channel water, and the second weight loss corresponds to the loss of the bound recrystallization solvent which is believed to be part of the crystal structure and is released only upon the melt of the enantiomer. In one embodiment, provided herein is a solid form comprising a free base of Compound 1, characterized by a TGA thermogram that matches the TGA thermogram presented in FIG. 37.

A representative differential scanning calorimetry (DSC) thermogram of Form K is presented in FIG. 38. In one embodiment, provided herein is a solid form comprising a free base of Compound 1, which exhibits, as characterized by DSC, a first (broad) thermal event with a peak temperature of about 60° C., a second thermal event with an onset temperature of about 148° C., a third (broad) thermal event with an onset temperature of about 190° C., and a fourth thermal event with an onset temperature of about 224° C. In one embodiment, the second thermal event also has a peak temperature of about 153° C., the third thermal event also has a peak temperature of about 197° C., and the fourth thermal event also has a peak temperature of about 227° C. In one embodiment, without being limited by any particular theory, the first (broad) thermal event corresponds to loss of channel water, the second thermal event corresponds to melting of dehydrated Form K (i.e., Form K'), the third thermal event corresponds to the simultaneous racemization and crystallization of the compound, and the fourth thermal event corresponds to the melt of the racemate compound. In one embodiment, provided herein is a solid form comprising a free base of Compound 1, characterized by a DSC thermogram that matches the DSC thermogram presented in FIG. 38.

A representative dynamic vapor sorption (DVS) isotherm plot of the Form K is provided in FIG. 39. In one embodiment, provided herein is a solid form comprising a free base of Compound 1, which exhibits a mass increase of about 3.2% when subjected to an increase in a relative humidity (RH) from about 5% to about 95%. In one embodiment, provided herein is a solid form comprising a free base of Compound 1, characterized by a DVS isotherm plot which matches the DVS isotherm plot presented in FIG. 39. In one embodiment, Form K is slightly hygroscopic.

In one embodiment, Form K of a free base of Compound 1 is prepared by crystallizing a free base of Compound 1 from a mixture solvent comprising water. In one embodiment, the solvent is a mixture of 2-PrOH and water. In one embodiment, the ratio of 2-PrOH to water is from about 85:15 to about 95:5 (v/v). In one embodiment, the solvent is a mixture of 2-PrOH and water at the ratio of about 85/15 (v/v). In one embodiment, the solvent is a mixture of 2-PrOH and water at the ratio of about 90/10 (v/v). In one embodiment, the solvent is a mixture of 2-PrOH and water at the ratio of about 95/5 (v/v). In one embodiment, the solvent is a mixture of acetone and water (e.g., 95:5 v/v, 90:10 v/v, 80:20 v/v). In one embodiment, the preparation comprising suspending Compound 1 in the solvent at about 60° C. for a period of time (e.g., 1 to 14 days, e.g., 5 days). In one embodiment, the preparation comprising suspending Compound 1 in the solvent at room temperature for a period of time (e.g., 1 to 14 days, e.g., 1 day, or 4 days). In one embodiment, the preparation occurs under high water activities ($a_{H2O}$). In one embodiment, the water activity is at least 0.2. In one embodiment, the water activity is at least 0.3. In one embodiment, the water activity is at least 0.5. In one embodiment, the water activity is at least 0.7. In one embodiment, the water activity is about 0.7. In one embodiment, without being limited by any particular theory, crystallizing a free base of Compound 1 from a mixture solvent comprising water results in Form B or Form C initially, which converts to Form K.

In one embodiment, Form K' of a free base of Compound 1 is prepared by dehydration of Form K. In one embodiment, From K converts to Form K' when water activity is not higher than about 0.11. In one embodiment, From K' converts to Form K when water activity is not lower than about 0.17.

In one embodiment, provided herein is a solid form comprising Form K of a free base of Compound 1 and amorphous free base of Compound 1. In one embodiment, provided herein is a solid form comprising Form K of a free base Compound 1 and one or more other crystalline forms of a free base of Compound 1 provided herein. In one embodiment, provided herein is a solid form comprising Form K of a free base of Compound 1 and one or more forms (e.g., amorphous or crystalline) of a salt of Compound 1 provided herein.

In one embodiment, provided herein is a solid form comprising Form K' of a free base of Compound 1 and amorphous free base of Compound 1. In one embodiment, provided herein is a solid form comprising Form K' of a free base Compound 1 and one or more other crystalline forms of a free base of Compound 1 provided herein. In one embodiment, provided herein is a solid form comprising Form K' of a free base of Compound 1 and one or more forms (e.g., amorphous or crystalline) of a salt of Compound 1 provided herein.

(xii) Form L of Free Base of Compound 1

In certain embodiments, provided herein is Form L of a free base of Compound 1.

In one embodiment, Form L is crystalline. In one embodiment, Form L is substantially crystalline. In one embodiment, Form L is moderately crystalline. In one embodiment, Form L is partially crystalline.

In one embodiment, Form L is a solvate of a free base of Compound 1. In one embodiment, Form L is a tetrahydrofurfuryl alcohol solvate of a free base of Compound 1.

A representative XRPD pattern of Form L is provided in FIG. 40.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, or all of the peaks located at approximately the following positions: 6.5, 11.8, 14.3, 14.7, 15.9, 16.1, 17.2, 17.9, 18.4, 19.3, 19.8, 20.0, 20.3, 21.7, 24.9, 25.7, 26.2, 26.3, 26.7, and 27.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 15.9, 17.9, and 26.2° 2θ. In one embodiment, the XRPD pattern further comprises peaks at approximately 19.8 and 20.3° 2θ. In one embodiment, the XRPD pattern further comprises peaks at approximately 14.3, 14.7, and 25.7° 2θ. In one embodiment, the XRPD pattern comprises peaks at approximately 6.5, 14.3, 14.7, 15.9, 17.9, 18.4, 19.8, 20.3, 25.7, 26.2, and 26.3° 2θ.

In one embodiment, provided herein is a solid form comprising a free base of Compound 1, characterized by an XRPD pattern that matches the XRPD pattern presented in FIG. 40.

In one embodiment, the XRPD patterns are obtained using Cu Kα radiation.

In one embodiment, Form L of a free base of Compound 1 is prepared by suspending Compound 1 in tetrahydrofurfuryl alcohol at about 40° C. for a period of time (e.g., about 14 days).

In one embodiment, provided herein is a solid form comprising Form L of a free base of Compound 1 and amorphous free base of Compound 1. In one embodiment, provided herein is a solid form comprising Form L of a free base Compound 1 and one or more other crystalline forms of a free base of Compound 1 provided herein. In one embodiment, provided herein is a solid form comprising Form L of a free base of Compound 1 and one or more forms (e.g., amorphous or crystalline) of a salt of Compound 1 provided herein.

(xiii) Form M of Free Base of Compound 1

In certain embodiments, provided herein is Form M of a free base of Compound 1.

In one embodiment, Form M is crystalline. In one embodiment, Form M is substantially crystalline. In one embodiment, Form M is moderately crystalline. In one embodiment, Form M is partially crystalline.

In one embodiment, Form M is a solvate of a free base of Compound 1. In one embodiment, Form M is a 2-pentyl acetate solvate of a free base of Compound 1. In one embodiment, Form M is a 2-pentyl acetate hemisolvate of a free base of Compound 1.

A representative XRPD pattern of Form M is provided in FIG. 41.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, or all of the peaks located at approximately the following positions: 5.1, 5.4, 5.8, 12.0, 13.3, 14.1, 15.3, 15.6, 16.4, 17.0, 18.4, 18.9, 19.3, 22.6, 24.2, 25.6, 26.1, 26.2, 26.6, and 27.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 14.1, 17.0, and 18.4° 2θ. In one embodiment, the XRPD pattern further comprises peaks at approximately 5.8 and 15.3° 2θ. In one embodiment, the XRPD pattern further comprises peaks at approximately 5.4 and 24.2° 2θ. In one embodiment, the XRPD pattern comprises peaks at approximately 5.1, 5.4, 5.8, 12.0, 14.1, 15.3, 16.4, 17.0, 18.4, 18.9, 24.2, and 26.2° 2θ.

In one embodiment, provided herein is a solid form comprising a free base of Compound 1, characterized by an XRPD pattern that matches the XRPD pattern presented in FIG. 41.

In one embodiment, the XRPD patterns are obtained using Cu Kα radiation.

A representative thermal gravimetric analysis (TGA) thermogram of Form M is provided in FIG. 42. In one embodiment, provided herein is a solid form comprising a free base of Compound 1, which exhibits a weight loss of about 10.9% upon heating from about 25° C. to about 200° C. In one embodiment, without being limited by any particular theory, the weight loss corresponds to the loss of 2-pentyl acetate (and trace water). In one embodiment, provided herein is a solid form comprising a free base of Compound 1, characterized by a TGA thermogram that matches the TGA thermogram presented in FIG. 42.

A representative differential scanning calorimetry (DSC) thermogram of Form M is presented in FIG. 43. In one embodiment, provided herein is a solid form comprising a free base of Compound 1, which exhibits, as characterized by DSC, a thermal event with an onset temperature of about 141° C. In one embodiment, the thermal event also has a peak temperature of about 155° C. In one embodiment, without being limited by any particular theory, the thermal event corresponds to melting. In one embodiment, provided herein is a solid form comprising a free base of Compound 1, characterized by a DSC thermogram that matches the DSC thermogram presented in FIG. 43.

In one embodiment, Form M of a free base of Compound 1 is prepared by suspending Compound 1 in 2-pentyl acetate at about 40° C. for a period of time (e.g., about 14 days). In one embodiment, Form M of a free base of Compound 1 is prepared by suspending Compound 1 in 2-pentyl acetate at about 60° C. for a period of time (e.g., about 7 days).

In one embodiment, provided herein is a solid form comprising Form M of a free base of Compound 1 and amorphous free base of Compound 1. In one embodiment, provided herein is a solid form comprising Form M of a free base Compound 1 and one or more other crystalline forms of a free base of Compound 1 provided herein. In one embodiment, provided herein is a solid form comprising Form M of a free base of Compound 1 and one or more forms (e.g., amorphous or crystalline) of a salt of Compound 1 provided herein.

(xiv) Form N of Free Base of Compound 1

In certain embodiments, provided herein is Form N of a free base of Compound 1.

In one embodiment, Form N is crystalline. In one embodiment, Form N is substantially crystalline. In one embodiment, Form N is moderately crystalline. In one embodiment, Form N is partially crystalline.

In one embodiment, Form N is a solvate of a free base of Compound 1. In one embodiment, Form N is a hexamethylphosphoramide solvate of a free base of Compound 1.

A representative XRPD pattern of Form N is provided in FIG. 44.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, or all of the peaks located at approximately the following positions: 3.7, 5.5, 10.5, 12.6, 12.8, 13.0, 13.7, 13.9, 14.1, 14.5, 14.7, 15.0, 15.3, 15.5, 16.4, 16.6, 16.8, 17.3, 18.8, 25.0, 25.7, and 26.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 13.0, 25.0, and 25.7° 2θ. In one embodiment, the XRPD pattern further comprises peaks at approximately 13.9, 15.0, and 26.1° 2θ. In one embodiment, the XRPD pattern further comprises peaks at approximately 3.7 and 10.5° 2θ. In one embodiment, the XRPD pattern comprises peaks at approximately 3.7, 10.5, 13.0, 13.9, 14.5, 15.0, 18.8, 25.0, 25.7, and 26.1° 2θ.

In one embodiment, provided herein is a solid form comprising a free base of Compound 1, characterized by an XRPD pattern that matches the XRPD pattern presented in FIG. 44.

In one embodiment, the XRPD patterns are obtained using Cu Kα radiation.

In one embodiment, Form N of a free base of Compound 1 is prepared by suspending Compound 1 in hexamethylphosphoramide at about 40° C. for a period of time (e.g., about 14 days), followed by evaporating the solvent.

In one embodiment, provided herein is a solid form comprising Form N of a free base of Compound 1 and amorphous free base of Compound 1. In one embodiment, provided herein is a solid form comprising Form N of a free base Compound 1 and one or more other crystalline forms of a free base of Compound 1 provided herein. In one embodiment, provided herein is a solid form comprising Form N of a free base of Compound 1 and one or more forms (e.g., amorphous or crystalline) of a salt of Compound 1 provided herein.

(xv) Form O of Free Base of Compound 1

In certain embodiments, provided herein is Form O of a free base of Compound 1.

In one embodiment, Form O is crystalline. In one embodiment, Form O is substantially crystalline. In one embodiment, Form O is moderately crystalline. In one embodiment, Form O is partially crystalline.

A representative XRPD pattern of Form O is provided in FIG. 45.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, or all of the peaks located at approximately the following positions: 6.5, 7.2, 10.7, 13.5, 14.0, 14.3, 16.5, 17.7, 18.1, 18.8, 19.0, 19.9, 20.3, 20.6, 21.5, 21.7, 22.9, 23.3, 25.8, 28.7, and 29.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 6.5, 16.5, and 20.6° 2θ. In one embodiment, the XRPD pattern further comprises peaks at approximately 14.0 and 17.7° 2θ. In one embodiment, the XRPD pattern further comprises peaks at approximately 14.3, 19.9, and 21.7° 2θ. In one embodiment, the XRPD pattern comprises peaks at approximately 6.5, 7.2, 10.7, 14.0, 14.3, 16.5, 17.7, 19.9, 20.6, 21.7, 22.9, and 25.8° 2θ.

In one embodiment, provided herein is a solid form comprising a free base of Compound 1, characterized by an XRPD pattern that matches the XRPD pattern presented in FIG. 45.

In one embodiment, the XRPD patterns are obtained using Cu Kα radiation.

Representative TG/DTA thermograms of Form O are provided in FIG. 46. In one embodiment, provided herein is a solid form comprising a free base of Compound 1, which exhibits a weight loss of about 1.5% upon heating from about 25° C. to about 75° C., and a weight loss of about 3.0% upon heating from about 75° C. to about 150° C. In one embodiment, without being limited by any particular theory, the first weight loss corresponds to the loss of unbound solvent, and the second weight loss corresponds to dehydration (about 1 equiv. of water). In one embodiment, provided herein is a solid form comprising a free base of Compound 1, characterized by a TGA thermogram that matches the TGA thermogram presented in FIG. 46.

In one embodiment, provided herein is a solid form comprising a free base of Compound 1, which exhibits, as characterized by DTA, a thermal event with an onset temperature of about 113° C. In one embodiment, the thermal event also has a peak temperature of about 117° C. In one embodiment, without being limited by any particular theory, the thermal event corresponds to dehydration. In one embodiment, provided herein is a solid form comprising a free base of Compound 1, characterized by a DTA thermogram that matches the DTA thermogram presented in FIG. 46.

In one embodiment, Form O of a free base of Compound 1 is prepared by subjecting a slurry comprising Compound 1 and L-malic acid in IPA to a temperature cycle (e.g., at room temperature for about 4 hours and then at about 40° C. for about 4 hours) for a period of time (e.g., 72 hours).

In one embodiment, provided herein is a solid form comprising Form O of a free base of Compound 1 and amorphous free base of Compound 1. In one embodiment, provided herein is a solid form comprising Form O of a free base Compound 1 and one or more other crystalline forms of a free base of Compound 1 provided herein. In one embodiment, provided herein is a solid form comprising Form O of a free base of Compound 1 and one or more forms (e.g., amorphous or crystalline) of a salt of Compound 1 provided herein.

(xvi) Form P of Free Base of Compound 1

In certain embodiments, provided herein is Form P of a free base of Compound 1.

In one embodiment, Form P is crystalline. In one embodiment, Form P is substantially crystalline. In one embodiment, Form P is moderately crystalline. In one embodiment, Form P is partially crystalline.

A representative XRPD pattern of Form P is provided in FIG. 47.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, or all of the peaks located at approximately the following positions: 7.1, 10.5, 11.6, 12.8, 13.7, 14.3, 15.5, 16.3, 16.6, 17.0, 17.8, 19.9, 21.0, 21.5, 21.7, 23.2, 27.4, 28.6, 28.9, 29.5, and 32.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 14.3, 16.3, and 21.0° 2θ. In one embodiment, the XRPD pattern further comprises peaks at approximately 16.6, 17.0, and 17.8° 2θ. In one embodiment, the XRPD pattern further comprises peaks at approximately 7.1 and 13.7° 2θ. In one embodiment, the XRPD pattern comprises peaks at approximately 7.1, 13.7, 14.3, 16.3, 16.6, 17.0, 17.8, 19.9, 21.0, 23.2, and 28.9° 2θ.

In one embodiment, provided herein is a solid form comprising a free base of Compound 1, characterized by an XRPD pattern that matches the XRPD pattern presented in FIG. 47.

In one embodiment, the XRPD patterns are obtained using Cu Kα radiation.

Representative TG/DTA thermograms of Form P are provided in FIG. 48. In one embodiment, provided herein is a solid form comprising a free base of Compound 1, which exhibits a weight loss of about 2.6% upon heating from about 25° C. to about 60° C. In one embodiment, without being limited by any particular theory, the weight loss corresponds to the loss of unbound solvent. In one embodiment, provided herein is a solid form comprising a free base of Compound 1, characterized by a TGA thermogram that matches the TGA thermogram presented in FIG. 48.

In one embodiment, provided herein is a solid form comprising a free base of Compound 1, which exhibits, as characterized by DTA, a thermal event with an onset temperature of about 132° C. In one embodiment, the thermal event also has a peak temperature of about 141° C. In one embodiment, without being limited by any particular theory, the thermal event corresponds to melting/degradation. In one embodiment, provided herein is a solid form comprising a free base of Compound 1, characterized by a DTA thermogram that matches the DTA thermogram presented in FIG. 48.

In one embodiment, Form P of a free base of Compound 1 is prepared by subjecting a slurry comprising Compound 1 and D-gluconic acid in ethanol to a temperature cycle (e.g., at room temperature for about 4 hours and then at about 40° C. for about 4 hours) for a period of time (e.g., 72 hours).

In one embodiment, provided herein is a solid form comprising Form P of a free base of Compound 1 and amorphous free base of Compound 1. In one embodiment, provided herein is a solid form comprising Form P of a free base Compound 1 and one or more other crystalline forms of a free base of Compound 1 provided herein. In one embodiment, provided herein is a solid form comprising Form P of a free base of Compound 1 and one or more forms (e.g., amorphous or crystalline) of a salt of Compound 1 provided herein.

(xvii) Form Q of Free Base of Compound 1

In certain embodiments, provided herein is Form Q of a free base of Compound 1.

In one embodiment, Form Q is crystalline. In one embodiment, Form Q is substantially crystalline. In one embodiment, Form Q is moderately crystalline. In one embodiment, Form Q is partially crystalline.

A representative XRPD pattern of Form Q is provided in FIG. 49.

In one embodiment, provided herein is a solid form comprising a free base of Compound 1, characterized by 1, 2, 3, 4, 5, 6, 7, 8, 9, 10, 11, 12, 13, 14, 15, 16, or all of the peaks located at approximately the following positions: 5.7, 12.5, 13.1, 15.2, 15.5, 15.7, 16.0, 16.8, 17.1, 17.3, 18.1, 18.4, 20.7, 22.1, 25.3, 27.0, and 31.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 5.7, 15.5, and 20.7° 2θ. In one embodiment, the XRPD pattern further comprises peaks at approximately 13.1 and 16.0° 2θ. In one embodiment, the XRPD pattern further comprises peaks at approximately 12.5 and 18.1° 2θ. In one embodiment, the XRPD pattern comprises peaks at approximately 5.7, 12.5, 13.1, 15.5, 16.0, 17.1, 18.1, 20.7, 22.1, 25.3, and 27.0° 2θ.

In one embodiment, provided herein is a solid form comprising a free base of Compound 1, characterized by an XRPD pattern that matches the XRPD pattern presented in FIG. 49.

In one embodiment, the XRPD patterns are obtained using Cu Kα radiation.

Representative TG/DTA thermograms of Form Q are provided in FIG. 50. In one embodiment, provided herein is a solid form comprising a free base of Compound 1, which exhibits a weight loss of about 0.4% upon heating from about 25° C. to about 125° C., and exhibits a weight loss of about 10.6% upon heating from about 125° C. to about 200° C. In one embodiment, without being limited by any particular theory, the second weight loss corresponds to the loss of water. In one embodiment, provided herein is a solid form comprising a free base of Compound 1, characterized by a TGA thermogram that matches the TGA thermogram presented in FIG. 50.

In one embodiment, provided herein is a solid form comprising a free base of Compound 1, which exhibits, as characterized by DTA, a thermal event with an onset temperature of about 126° C. In one embodiment, the thermal event also has a peak temperature of about 132° C. In one embodiment, without being limited by any particular theory, the thermal event corresponds to dehydration. In one embodiment, provided herein is a solid form comprising a free base of Compound 1, characterized by a DTA thermogram that matches the DTA thermogram presented in FIG. 50.

In one embodiment, Form Q of a free base of Compound 1 is prepared by subjecting a slurry comprising Compound 1 and L-glutamic acid in a mixture of THF/water (50:50 v/v)

to a temperature cycle (e.g., at room temperature for about 4 hours and then at about 40° C. for about 4 hours) for a period of time (e.g., 72 hours).

In one embodiment, provided herein is a solid form comprising Form Q of a free base of Compound 1 and amorphous free base of Compound 1. In one embodiment, provided herein is a solid form comprising Form Q of a free base Compound 1 and one or more other crystalline forms of a free base of Compound 1 provided herein. In one embodiment, provided herein is a solid form comprising Form Q of a free base of Compound 1 and one or more forms (e.g., amorphous or crystalline) of a salt of Compound 1 provided herein.

(xviii) Form R of Free Base of Compound 1

In certain embodiments, provided herein is Form R of a free base of Compound 1.

In one embodiment, Form R is crystalline. In one embodiment, Form R is substantially crystalline. In one embodiment, Form R is moderately crystalline. In one embodiment, Form R is partially crystalline.

A representative XRPD pattern of Form R is provided in FIG. 51.

In one embodiment, provided herein is a solid form comprising a free base of Compound 1, characterized by 1, 2, 3, 4, 5, or all of the peaks located at approximately the following positions: 3.7, 8.0, 13.9, 14.9, 25.4, and 26.7° 2θ. In one embodiment, the solid form is characterized by 3 of the peaks. In one embodiment, the solid form is characterized by 5 of the peaks. In one embodiment, the solid form is characterized by all of the peaks.

In one embodiment, provided herein is a solid form comprising a free base of Compound 1, characterized by an XRPD pattern comprising peaks at approximately 14.9, 25.4, and 26.7° 2θ. In one embodiment, the XRPD pattern further comprises peaks at approximately 3.7 and 13.9° 2θ. In one embodiment, the XRPD pattern further comprises a peak at approximately 8.0° 2θ. In one embodiment, the XRPD pattern comprises peaks at approximately 3.7, 8.0, 13.9, 14.9, 25.4, and 26.7° 2θ.

In one embodiment, provided herein is a solid form comprising a free base of Compound 1, characterized by an XRPD pattern that matches the XRPD pattern presented in FIG. 51.

In one embodiment, the XRPD patterns are obtained using Cu Kα radiation.

Representative TG/DTA thermograms of Form R are provided in FIG. 52. In one embodiment, provided herein is a solid form comprising a free base of Compound 1, which exhibits a weight loss of about 2.1% upon heating from about 25° C. to about 60° C., a weight loss of about 1.6% upon heating from about 60° C. to about 110° C., and a weight loss of about 18.9% upon heating from about 110° C. to about 200° C. In one embodiment, without being limited by any particular theory, the first two weight losses correspond to the loss of unbound solvent, and the third weight loss corresponds to the loss of water. In one embodiment, provided herein is a solid form comprising a free base of Compound 1, characterized by a TGA thermogram that matches the TGA thermogram presented in FIG. 52.

In one embodiment, provided herein is a solid form comprising a free base of Compound 1, which exhibits, as characterized by DTA, a first thermal event with an onset temperature of about 100° C., and a second thermal event with an onset temperature of about 140° C. In one embodiment, the first thermal event also has a peak temperature of about 106° C., and the second thermal event also has a peak temperature of about 142° C. In one embodiment, without being limited by any particular theory, the first thermal event correspond to the loss of unbound solvent, and the second thermal event corresponds to the loss of water. In one embodiment, provided herein is a solid form comprising a free base of Compound 1, characterized by a DTA thermogram that matches the DTA thermogram presented in FIG. 52.

In one embodiment, Form R of a free base of Compound 1 is prepared by subjecting a slurry comprising Compound 1 and malonic acid in DCM to a temperature cycle (e.g., at room temperature for about 4 hours and then at about 40° C. for about 4 hours) for a period of time (e.g., 72 hours).

In one embodiment, provided herein is a solid form comprising Form R of a free base of Compound 1 and amorphous free base of Compound 1. In one embodiment, provided herein is a solid form comprising Form R of a free base Compound 1 and one or more other crystalline forms of a free base of Compound 1 provided herein. In one embodiment, provided herein is a solid form comprising Form R of a free base of Compound 1 and one or more forms (e.g., amorphous or crystalline) of a salt of Compound 1 provided herein.

(xix) Form S of Free Base of Compound 1

In certain embodiments, provided herein is Form S of a free base of Compound 1.

In one embodiment, Form S is crystalline. In one embodiment, Form S is substantially crystalline. In one embodiment, Form S is moderately crystalline. In one embodiment, Form S is partially crystalline.

A representative XRPD pattern of Form S is provided in FIG. 53.

In one embodiment, provided herein is a solid form comprising a free base of Compound 1, characterized by 1, 2, 3, 4, 5, 6, 7, 8, 9, 10, 11, 12, 13, 14, 15, 16, 17, or all of the peaks located at approximately the following positions: 6.6, 7.1, 9.8, 10.9, 13.5, 14.0, 14.3, 16.5, 17.7, 20.2, 20.8, 21.7, 23.3, 26.1, 28.2, 29.0, 29.3, and 31.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern comprising peaks at approximately 6.6, 16.5, and 20.8° 2θ. In one embodiment, the XRPD pattern further comprises peaks at approximately 14.0 and 17.7° 2θ. In one embodiment, the XRPD pattern further comprises peaks at approximately 14.3, 21.7, and 23.3° 2θ. In one embodiment, the XRPD pattern comprises peaks at approximately 6.6, 7.1, 10.9, 14.0, 14.3, 16.5, 17.7, 20.8, 21.7, and 23.3° 2θ.

In one embodiment, provided herein is a solid form comprising a free base of Compound 1, characterized by an XRPD pattern that matches the XRPD pattern presented in FIG. 53.

In one embodiment, the XRPD patterns are obtained using Cu Kα radiation.

Representative TG/DTA thermograms of Form S are provided in FIG. 54. In one embodiment, provided herein is a solid form comprising a free base of Compound 1, which exhibits a weight loss of about 1.5% upon heating from about 25° C. to about 60° C. (followed by steady weight loss). In one embodiment, without being limited by any particular theory, the weight loss corresponds to the loss of unbound solvent. In one embodiment, provided herein is a solid form comprising a free base of Compound 1, characterized by a TGA thermogram that matches the TGA thermogram presented in FIG. 54.

In one embodiment, provided herein is a solid form comprising a free base of Compound 1, which exhibits, as characterized by DTA, a thermal event with an onset temperature of about 128° C. In one embodiment, the thermal event also has a peak temperature of about 136° C. In one embodiment, provided herein is a solid form comprising a free base of Compound 1, characterized by a DTA thermogram that matches the DTA thermogram presented in FIG. 54.

In one embodiment, Form S of a free base of Compound 1 is prepared by subjecting a slurry comprising Compound 1 and R-mandelic acid in ethanol to a temperature cycle (e.g., at room temperature for about 4 hours and then at about 40° C. for about 4 hours) for a period of time (e.g., 72 hours).

In one embodiment, provided herein is a solid form comprising Form S of a free base of Compound 1 and amorphous free base of Compound 1. In one embodiment, provided herein is a solid form comprising Form S of a free base Compound 1 and one or more other crystalline forms of a free base of Compound 1 provided herein. In one embodiment, provided herein is a solid form comprising Form S of a free base of Compound 1 and one or more forms (e.g., amorphous or crystalline) of a salt of Compound 1 provided herein.

(b) Hydrochloride Salt of Compound 1

In some embodiments, provided herein is a hydrochloride salt of Compound 1. It is contemplated that a hydrochloride salt of Compound 1 can exist in a variety of solid forms. Such solid forms include crystalline solids, such as polymorphs, solvates and hydrates of crystalline hydrochloride salt of Compound 1, as well as amorphous solids, or mixtures thereof.

In one embodiment, provided herein is a solid form comprising a hydrochloride salt of Compound 1. In one embodiment, the solid form is a solvate of a hydrochloride salt of Compound 1. In one embodiment, the solid form is a hydrate of a hydrochloride salt of Compound 1. In one embodiment, the solid form is a non-solvated form of a hydrochloride salt of Compound 1. In one embodiment, the solid form is a desolvated form of a hydrochloride salt of Compound 1. In one embodiment, the solid form is an anhydrous form (anhydrate) of a hydrochloride salt of Compound 1. In one embodiment, the solid form is a dehydrated form of a hydrochloride salt of Compound 1.

In some embodiments, the molar ratio of Compound 1 to hydrochloric acid in the solid form ranges from about 1:1 to about 1:2. In one embodiment, the molar ratio is about 1:2 (i.e., bis-hydrochloride salt). In another embodiment, the molar ratio is about 1:1 (i.e., mono-hydrochloride salt).

(i) Form A of Hydrochloride Salt of Compound 1

In certain embodiments, provided herein is Form A of a hydrochloride salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to hydrochloric acid in Form A is about 1:1. In one embodiment, Form A is a mono-hydrochloride salt of Compound 1.

In one embodiment, Form A is a solvate of a hydrochloride salt of Compound 1. In one embodiment, Form A is an isomorphic solvate of a hydrochloride salt of Compound 1. In one embodiment, Form A is a TBME solvate of a hydrochloride salt of Compound 1. In one embodiment, Form A is an acetone solvate of a hydrochloride salt of Compound 1. In one embodiment, Form A is an anisole solvate of a hydrochloride salt of Compound 1. In one embodiment, Form A is an ethyl formate solvate of a hydrochloride salt of Compound 1. In one embodiment, Form A is an isopropyl acetate solvate of a hydrochloride salt of Compound 1. In one embodiment, Form A is an MEK solvate of a hydrochloride salt of Compound 1. In one embodiment, Form A is a toluene solvate of a hydrochloride salt of Compound 1. In one embodiment, Form A is a DMF solvate of a hydrochloride salt of Compound 1. In one embodiment, Form A is a DMA solvate of a hydrochloride salt of Compound 1.

A representative XRPD pattern of Form A of a hydrochloride salt of Compound 1 is provided in FIG. 55.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, or all of the peaks located at approximately the following positions: 5.6, 7.4, 7.7, 9.5, 14.1, 15.0, 15.5, 15.7, 16.6, 17.3, 17.5, 17.9, 19.2, 19.4, 19.8, 20.9, 23.8, 24.0, 26.0, 26.6, 27.7, and 28.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 14.1, 16.6, and 26.0° 2θ. In one embodiment, the XRPD pattern further comprises peaks at approximately 5.6, 7.4, and 15.5° 2θ. In one embodiment, the XRPD pattern further comprises peaks at approximately 7.7 and 17.9° 2θ. In one embodiment, the XRPD pattern comprises peaks at approximately 5.6, 7.4, 7.7, 14.1, 15.5, 16.6, 17.9, 26.0, 26.6, and 27.7° 2θ.

In one embodiment, provided herein is a solid form comprising a hydrochloride salt of Compound 1, characterized by an XRPD pattern that matches the XRPD pattern presented in FIG. 55.

In one embodiment, the XRPD patterns are obtained using Cu Kα radiation.

A representative thermal gravimetric analysis (TGA) thermogram of Form A of a hydrochloride salt of Compound 1 is provided in FIG. 56. In one embodiment, provided herein is a solid form comprising a hydrochloride salt of Compound 1, which exhibits a weight loss of about 2.9% upon heating from about 25° C. to about 110° C., and a weight loss of about 8.0% upon heating from about 110° C. to about 230° C. In one embodiment, without being limited by any particular theory, the first weight loss corresponds to the loss of water (and some TBME), and the weight loss corresponds to the loss of TBME. In one embodiment, provided herein is a solid form comprising a hydrochloride salt of Compound 1, characterized by a TGA thermogram that matches the TGA thermogram presented in FIG. 56.

A representative differential scanning calorimetry (DSC) thermogram of Form A of a hydrochloride salt of Compound 1 is presented in FIG. 57. In one embodiment, provided herein is a solid form comprising a hydrochloride salt of Compound 1, which exhibits, as characterized by DSC, a first (broad) thermal event with a peak temperature of about 83° C., and a second thermal event with an onset temperature of about 189° C. In one embodiment, the second thermal event also has a peak temperature of about 202° C. In one embodiment, without being limited by any particular theory, the first thermal event corresponds to the loss of water (and some TBME), and the second thermal event corresponds to desolvation of TBME, possibly combined with simultaneous melting. In one embodiment, provided herein is a solid form comprising a hydrochloride salt of Compound 1, characterized by a DSC thermogram that matches the DSC thermogram presented in FIG. 57.

A representative dynamic vapor sorption (DVS) isotherm plot of the Form A of a hydrochloride salt of Compound 1 is provided in FIG. 58. In one embodiment, provided herein is a solid form comprising a hydrochloride salt of Compound 1, which exhibits a mass increase of about 11.7% when subjected to an increase in a relative humidity (RH) from about 5% to about 95%. In one embodiment, provided herein is a solid form comprising a hydrochloride salt of Compound 1, characterized by a DVS isotherm plot which matches the DVS isotherm plot presented in FIG. 58. In one embodiment, Form A is hygroscopic. In one embodiment, Form A remains as Form A after DVS cycle.

In one embodiment, Form A of a hydrochloride salt of Compound 1 is prepared by subjecting a mixture of Compound 1 and hydrochloric acid (e.g., about 1:1 molar ratio) in a solvent to a temperature cycle (e.g., between about 25° C. and about 35° C.) for a period of time (e.g., from about 1 day to about 14 days, e.g., about 7 days). In one embodiment, the solvent is acetone, anisole, ethyl formate, iPrOAc, MEK, TBME, toluene, a mixture of DMA and iPrOAc (e.g., 1:9 v/v), or a mixture of DMF and toluene (e.g., 1:9 v/v). In one embodiment, the solvent is TBME.

In one embodiment, Form A of a hydrochloride salt of Compound 1 is prepared by cooling a solution or suspension of Compound 1 and hydrochloric acid (e.g., about 1:1 molar ratio) in a mixture of toluene and DMF (e.g., about 9:1 v/v) from about 60° C. to room temperature (e.g., overnight).

In one embodiment, the product prepared is optionally dried (e.g., under vacuum at 40° C.) for a period of time (e.g., about 4 hours).

In one embodiment, provided herein is a solid form comprising Form A of a hydrochloride salt of Compound 1 and one or more forms of a free base of Compound 1 (e.g., amorphous form and crystalline forms). In one embodiment, provided herein is a solid form comprising Form A of a hydrochloride salt of Compound 1 and amorphous hydrochloride salt of Compound 1. In one embodiment, provided herein is a solid form comprising Form A of a hydrochloride salt Compound 1 and one or more other crystalline forms of a hydrochloride salt of Compound 1 provided herein. In one embodiment, provided herein is a solid form comprising Form A of a hydrochloride salt of Compound 1 and one or more forms (e.g., amorphous or crystalline) of a salt of Compound 1 provided herein.

(ii) Form B of Hydrochloride Salt of Compound 1

In certain embodiments, provided herein is Form B of a hydrochloride salt of Compound 1.

In one embodiment, Form B is crystalline. In one embodiment, Form B is substantially crystalline. In one embodiment, Form B is moderately crystalline. In one embodiment, Form B is partially crystalline.

In one embodiment, Form B is a solvate of a hydrochloride salt of Compound 1. In one embodiment, Form B is an isomorphic solvate of a hydrochloride salt of Compound 1. In one embodiment, Form B is an ethanol solvate of a hydrochloride salt of Compound 1. In one embodiment, Form B is a 2-propanol solvate of a hydrochloride salt of Compound 1. In one embodiment, Form B is an ethyl acetate solvate of a hydrochloride salt of Compound 1. In one embodiment, Form B is a hydrate of a hydrochloride salt of Compound 1.

A representative XRPD pattern of Form B of a hydrochloride salt of Compound 1 is provided in FIG. 59.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, or all of the peaks located at approximately the following positions: 6.1, 7.7, 10.9, 12.2, 13.4, 13.6, 15.6, 16.3, 16.6, 19.7, 22.1, 23.3, 23.4, 24.6, 24.8, 25.2, 25.7, 26.0, 27.4, and 27.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 6.1, 13.4, and 24.6° 2θ. In one embodiment, the XRPD pattern further comprises peaks at approximately 12.2 and 16.6° 2θ. In one embodiment, the XRPD pattern further comprises peaks at approximately 10.9 and 25.2° 2θ. In one embodiment, the XRPD pattern comprises peaks at approximately 6.1, 10.9, 12.2, 13.4, 13.6, 15.6, 16.6, 24.6, 25.2, 25.7, and 27.6° 2θ.

In one embodiment, provided herein is a solid form comprising a hydrochloride salt of Compound 1, characterized by an XRPD pattern that matches the XRPD pattern presented in FIG. 59.

In one embodiment, the XRPD patterns are obtained using Cu Kα radiation.

A representative thermal gravimetric analysis (TGA) thermogram of Form B of a hydrochloride salt of Compound 1 is provided in FIG. 60. In one embodiment, provided herein is a solid form comprising a hydrochloride salt of Compound 1, which exhibits a weight loss of about 3.8% upon heating from about 25° C. to about 120° C., and a weight loss of about 2.8% upon heating from about 120° C. to about 220° C. In one embodiment, without being limited by any particular theory, the first weight loss corresponds to the loss of water (and some ethanol), and the second weight loss corresponds to the loss of ethanol and water. In one embodiment, provided herein is a solid form comprising a hydrochloride salt of Compound 1, characterized by a TGA thermogram that matches the TGA thermogram presented in FIG. 60.

A representative differential scanning calorimetry (DSC) thermogram of Form B of a hydrochloride salt of Compound 1 is presented in FIG. 61. In one embodiment, provided herein is a solid form comprising a hydrochloride salt of Compound 1, which exhibits, as characterized by DSC, a first (broad) thermal event with a peak temperature of about 80° C., and a second thermal event with an onset temperature of about 200° C. In one embodiment, the second thermal event also has a peak temperature of about 210° C. In one embodiment, without being limited by any particular theory, the first thermal event corresponds to the loss of water, and the second thermal event corresponds to melting of desolvated Form B. In one embodiment, provided herein is a solid form comprising a hydrochloride salt of Compound 1, characterized by a DSC thermogram that matches the DSC thermogram presented in FIG. 61.

A representative dynamic vapor sorption (DVS) isotherm plot of the Form B of a hydrochloride salt of Compound 1 is provided in FIG. 62. In one embodiment, provided herein is a solid form comprising a hydrochloride salt of Compound 1, which exhibits a mass increase of about 15.7% when subjected to an increase in a relative humidity (RH) from about 5% to about 95%. In one embodiment, provided herein is a solid form comprising a hydrochloride salt of Compound 1, characterized by a DVS isotherm plot which matches the DVS isotherm plot presented in FIG. 62. In one embodiment, Form B is hygroscopic.

In one embodiment, Form B of a hydrochloride salt of Compound 1 is prepared by subjecting a mixture of Compound 1 and hydrochloric acid (e.g., about 1:1 molar ratio) in a solvent to a temperature cycle (e.g., between about 25° C. and about 35° C.) for a period of time (e.g., from about 1 day to about 14 days, e.g., about 7 days). In one embodiment, the solvent is a protic solvent. In one embodiment, the solvent is ethanol, a mixture of 2-PrOH and water (e.g., 95:5 v/v), or water. In one embodiment, the solvent is ethanol.

In one embodiment, Form B of a hydrochloride salt of Compound 1 is prepared by subjecting a mixture of Compound 1 and hydrochloric acid (e.g., about 1:1 molar ratio) in ethyl acetate to a temperature cycle (e.g., between about 25° C. and about 35° C.) for a period of time (e.g., from about 1 day to about 14 days, e.g., about 7 days). Although ethyl acetate is not a protic solvent, hydrolysis of ethyl acetate into ethanol and acetic acid can be expected under acidic conditions.

In one embodiment, provided herein is a solid form comprising Form B of a hydrochloride salt of Compound 1 and one or more forms of a free base of Compound 1 (e.g., amorphous form and crystalline forms). In one embodiment, provided herein is a solid form comprising Form B of a hydrochloride salt of Compound 1 and amorphous hydrochloride salt of Compound 1. In one embodiment, provided herein is a solid form comprising Form B of a hydrochloride salt Compound 1 and one or more other crystalline forms of a hydrochloride salt of Compound 1 provided herein. In one embodiment, provided herein is a solid form comprising Form B of a hydrochloride salt of Compound 1 and one or more forms (e.g., amorphous or crystalline) of a salt of Compound 1 provided herein.

(iii) Form C of Hydrochloride Salt of Compound 1

In certain embodiments, provided herein is Form C of a hydrochloride salt of Compound 1.

In one embodiment, Form C is crystalline. In one embodiment, Form C is substantially crystalline. In one embodiment, Form C is moderately crystalline. In one embodiment, Form C is partially crystalline.

In one embodiment, Form C is a solvate of a hydrochloride salt of Compound 1. In one embodiment, Form C is an acetone solvate of a hydrochloride salt of Compound 1. In one embodiment, Form C is a monoacetone solvate of a hydrochloride salt of Compound 1.

A representative XRPD pattern of Form C of a hydrochloride salt of Compound 1 is provided in FIG. 63.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 2.8, 5.4, 5.7, 6.3, 7.2, 8.2, 11.4, 13.7, 14.1, 14.3, 15.0, 15.3, 15.7, 17.0, 17.2, 18.0, 20.8, 21.6, 22.0, 25.4, 25.6, 26.1, 26.2, and 26.7° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.2, 8.2, and 15.0° 2θ. In one embodiment, the XRPD pattern further comprises peaks at approximately 2.8, 17.2, and 26.7° 2θ. In one embodiment, the XRPD pattern further comprises peaks at approximately 21.6 and 26.2° 2θ. In one embodiment, the XRPD pattern comprises peaks at approximately 2.8, 7.2, 8.2, 14.1, 15.0, 17.2, 18.0, 21.6, 25.6, 26.2, and 26.7° 2θ.

In one embodiment, provided herein is a solid form comprising a hydrochloride salt of Compound 1, characterized by an XRPD pattern that matches the XRPD pattern presented in FIG. 63.

In one embodiment, the XRPD patterns are obtained using Cu Kα radiation.

In one embodiment, Form C of a hydrochloride salt of Compound 1 is prepared by subjecting a mixture of Compound 1 and hydrochloric acid (e.g., about 1:1 molar ratio) in a mixture of acetone and heptane (e.g., about 1:1 v/v) to a temperature cycle (e.g., between about 25° C. and about 35° C.) for a period of time (e.g., from about 1 day to about 14 days, e.g., about 3 days). In another embodiment, Form C is prepared from a mixture of acetone and water (e.g., about 95:5 v/v).

In one embodiment, provided herein is a solid form comprising Form C of a hydrochloride salt of Compound 1 and one or more forms of a free base of Compound 1 (e.g., amorphous form and crystalline forms). In one embodiment, provided herein is a solid form comprising Form C of a hydrochloride salt of Compound 1 and amorphous hydrochloride salt of Compound 1. In one embodiment, provided herein is a solid form comprising Form C of a hydrochloride salt Compound 1 and one or more other crystalline forms of a hydrochloride salt of Compound 1 provided herein. In one embodiment, provided herein is a solid form comprising Form C of a hydrochloride salt of Compound 1 and one or more forms (e.g., amorphous or crystalline) of a salt of Compound 1 provided herein.

(iv) Form D of Hydrochloride Salt of Compound 1

In certain embodiments, provided herein is Form D of a hydrochloride salt of Compound 1.

In one embodiment, Form D is crystalline. In one embodiment, Form D is substantially crystalline. In one embodiment, Form D is moderately crystalline. In one embodiment, Form D is partially crystalline.

In one embodiment, Form D is a hydrate of a hydrochloride salt of Compound 1.

A representative XRPD pattern of Form D of a hydrochloride salt of Compound 1 is provided in FIG. 64.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, or all of the peaks located at approximately the following positions: 3.4, 5.1, 6.8, 7.8, 8.2, 12.7, 13.2, 13.7, 14.6, 15.3, 15.7, 16.4, 17.9, 20.0, 21.7, 22.8, 24.1, 25.1, 25.6, 26.4, and 27.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 14.6, 25.1, and 25.6° 2θ. In one embodiment, the XRPD pattern further comprises peaks at approximately 6.8, 13.7, and 26.4° 2θ. In one embodiment, the XRPD pattern further comprises peaks at approximately 8.2 and 12.7° 2θ. In one embodiment, the XRPD pattern comprises peaks at approximately 3.4, 6.8, 7.8, 8.2, 12.7, 13.7, 14.6, 16.4, 25.1, 25.6, and 26.4° 2θ.

In one embodiment, provided herein is a solid form comprising a hydrochloride salt of Compound 1, characterized by an XRPD pattern that matches the XRPD pattern presented in FIG. 64.

In one embodiment, the XRPD patterns are obtained using Cu Kα radiation.

In one embodiment, Form D of a hydrochloride salt of Compound 1 is prepared by evaporating a solution of Compound 1 and hydrochloric acid (e.g., about 1:1 molar ratio) in a mixture of DCM and water (e.g., about 55:45 v/v) under ambient conditions at room temperature.

In one embodiment, provided herein is a solid form comprising Form D of a hydrochloride salt of Compound 1 and one or more forms of a free base of Compound 1 (e.g., amorphous form and crystalline forms). In one embodiment, provided herein is a solid form comprising Form D of a hydrochloride salt of Compound 1 and amorphous hydrochloride salt of Compound 1. In one embodiment, provided herein is a solid form comprising Form D of a hydrochloride salt Compound 1 and one or more other crystalline forms of a hydrochloride salt of Compound 1 provided herein. In one embodiment, provided herein is a solid form comprising Form D of a hydrochloride salt of Compound 1 and one or more forms (e.g., amorphous or crystalline) of a salt of Compound 1 provided herein.

(v) Form E of Hydrochloride Salt of Compound 1

In certain embodiments, provided herein is Form E of a hydrochloride salt of Compound 1.

In one embodiment, Form E is crystalline. In one embodiment, Form E is substantially crystalline. In one embodiment, Form E is moderately crystalline. In one embodiment, Form E is partially crystalline.

In one embodiment, Form E is a solvate of a hydrochloride salt of Compound 1. In one embodiment, Form E is an isomorphic solvate of a hydrochloride salt of Compound 1. In one embodiment, Form E is a 2-propanol solvate of a hydrochloride salt of Compound 1. In one embodiment, Form E is an acetonitrile solvate of a hydrochloride salt of Compound 1.

A representative XRPD pattern of Form E of a hydrochloride salt of Compound 1 is provided in FIG. 65.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, or all of the peaks located at approximately the following positions: 4.8, 5.5, 9.1, 9.7, 13.3, 14.0, 14.6, 17.0, 17.6, 19.4, 22.5, 23.3, 24.1, 25.7, 26.3, 26.8, 27.5, 28.1, 28.5, 29.0, and 29.7° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 5.5, 19.4, and 25.7° 2θ. In one embodiment, the XRPD pattern further comprises peaks at approximately 4.8 and 9.7° 2θ. In one embodiment, the XRPD pattern further comprises peaks at approximately 17.0 and 26.3° 2θ. In one embodiment, the XRPD pattern comprises peaks at approximately 4.8, 5.5, 9.7, 14.0, 17.0, 17.6, 19.4, 22.5, 25.7, 26.3, and 27.5° 2θ.

In one embodiment, provided herein is a solid form comprising a hydrochloride salt of Compound 1, characterized by an XRPD pattern that matches the XRPD pattern presented in FIG. 65.

In one embodiment, the XRPD patterns are obtained using Cu Kα radiation.

In one embodiment, Form E of a hydrochloride salt of Compound 1 is prepared by subjecting a mixture of Compound 1 and hydrochloric acid (e.g., about 1:10 molar ratio) in 2-PrOH to a temperature cycle (e.g., between about 25° C. and about 35° C.) for a period of time (e.g., from about 1 day to about 14 days, e.g., about 5 days).

In one embodiment, Form E of a hydrochloride salt of Compound 1 is prepared by suspending Form C of a hydrochloride salt of Compound 1 in acetonitrile.

In one embodiment, provided herein is a solid form comprising Form E of a hydrochloride salt of Compound 1 and one or more forms of a free base of Compound 1 (e.g., amorphous form and crystalline forms). In one embodiment, provided herein is a solid form comprising Form E of a hydrochloride salt of Compound 1 and amorphous hydrochloride salt of Compound 1. In one embodiment, provided herein is a solid form comprising Form E of a hydrochloride salt Compound 1 and one or more other crystalline forms of a hydrochloride salt of Compound 1 provided herein. In one embodiment, provided herein is a solid form comprising Form E of a hydrochloride salt of Compound 1 and one or more forms (e.g., amorphous or crystalline) of a salt of Compound 1 provided herein.

(vi) Form F of Hydrochloride Salt of Compound 1

In certain embodiments, provided herein is Form F of a hydrochloride salt of Compound 1.

In one embodiment, Form F is crystalline. In one embodiment, Form F is substantially crystalline. In one embodiment, Form F is moderately crystalline. In one embodiment, Form F is partially crystalline.

In one embodiment, Form F is a solvate of a hydrochloride salt of Compound 1. In one embodiment, Form F is an acetonitrile solvate of a hydrochloride salt of Compound 1.

A representative XRPD pattern of Form F of a hydrochloride salt of Compound 1 is provided in FIG. 66.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 5.0, 5.4, 5.7, 7.4, 9.6, 10.0, 10.4, 10.6, 11.4, 11.9, 14.4, 14.8, 15.0, 17.1, 21.8, 22.9, 24.0, 24.9, 25.5, 26.0, 26.2, 28.4, and 30.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.4, 9.6, and 24.9° 2θ. In one embodiment, the XRPD pattern further comprises peaks at approximately 5.0 and 10.0° 2θ. In one embodiment, the XRPD pattern further comprises peaks at approximately 5.7, 11.4, and 11.9° 2θ. In one embodiment, the XRPD pattern comprises peaks at approximately 5.0, 5.7, 7.4, 9.6, 10.0, 11.4, 11.9, 14.4, 24.0, 24.9, and 26.0° 2θ.

In one embodiment, provided herein is a solid form comprising a hydrochloride salt of Compound 1, characterized by an XRPD pattern that matches the XRPD pattern presented in FIG. 66.

In one embodiment, the XRPD patterns are obtained using Cu Kα radiation.

In one embodiment, Form F of a hydrochloride salt of Compound 1 is prepared by subjecting a mixture of Compound 1 and hydrochloric acid (e.g., about 1:1 molar ratio) in a mixture of acetonitrile and water (e.g., 95:5 v/v) to a temperature cycle (e.g., between about 25° C. and about 35° C.) for a period of time (e.g., from about 1 day to about 14 days, e.g., about 7 days).

In one embodiment, Form F of a hydrochloride salt of Compound 1 is prepared by cooling a solution or suspension of Compound 1 and hydrochloric acid (e.g., about 1:1 molar ratio) in a mixture of acetonitrile and water (e.g., 95:5 v/v) from about 60° C. to room temperature (e.g., overnight).

In one embodiment, provided herein is a solid form comprising Form F of a hydrochloride salt of Compound 1 and one or more forms of a free base of Compound 1 (e.g., amorphous form and crystalline forms). In one embodiment, provided herein is a solid form comprising Form F of a hydrochloride salt of Compound 1 and amorphous hydrochloride salt of Compound 1. In one embodiment, provided herein is a solid form comprising Form F of a hydrochloride salt Compound 1 and one or more other crystalline forms of a hydrochloride salt of Compound 1 provided herein. In one embodiment, provided herein is a solid form comprising Form F of a hydrochloride salt of Compound 1 and one or more forms (e.g., amorphous or crystalline) of a salt of Compound 1 provided herein.

(vii) Form G of Hydrochloride Salt of Compound 1

In certain embodiments, provided herein is Form G of a hydrochloride salt of Compound 1.

In one embodiment, Form G is crystalline. In one embodiment, Form G is substantially crystalline. In one embodiment, Form G is moderately crystalline. In one embodiment, Form G is partially crystalline.

In one embodiment, Form G is a solvate of a hydrochloride salt of Compound 1. In one embodiment, Form G is an NMP solvate of a hydrochloride salt of Compound 1.

A representative XRPD pattern of Form G of a hydrochloride salt of Compound 1 is provided in FIG. 67.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, or all of the peaks located at approximately the following positions: 7.3, 9.5, 11.0, 12.7, 13.1, 13.9, 14.3, 14.5, 14.8, 16.6, 16.7, 18.4, 18.7, 19.8, 21.5, 24.0, 25.1, 25.5, 25.8, and 26.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 9.5, 13.9, and 25.1° 2θ. In one embodiment, the XRPD pattern further comprises peaks at approximately 7.3 and 25.5° 2θ. In one embodiment, the XRPD pattern further comprises peaks at approximately 12.7 and 13.1° 2θ. In one embodiment, the XRPD pattern comprises peaks at approximately 7.3, 9.5, 12.7, 13.1, 13.9, 16.6, 16.7, 21.5, 25.1, 25.5, and 25.8° 2θ.

In one embodiment, provided herein is a solid form comprising a hydrochloride salt of Compound 1, characterized by an XRPD pattern that matches the XRPD pattern presented in FIG. 67.

In one embodiment, the XRPD patterns are obtained using Cu Kα radiation.

In one embodiment, Form G of a hydrochloride salt of Compound 1 is prepared by suspending a mixture of Compound 1 and hydrochloric acid (e.g., about 1:1 molar ratio) in a mixture of IPE and NMP (e.g., 9:1 v/v) at room temperature for a period of time (e.g., from about 1 day to about 14 days, e.g., about 7 days).

In one embodiment, provided herein is a solid form comprising Form G of a hydrochloride salt of Compound 1 and one or more forms of a free base of Compound 1 (e.g., amorphous form and crystalline forms). In one embodiment, provided herein is a solid form comprising Form G of a hydrochloride salt of Compound 1 and amorphous hydrochloride salt of Compound 1. In one embodiment, provided herein is a solid form comprising Form G of a hydrochloride salt Compound 1 and one or more other crystalline forms of a hydrochloride salt of Compound 1 provided herein. In one embodiment, provided herein is a solid form comprising Form G of a hydrochloride salt of Compound 1 and one or more forms (e.g., amorphous or crystalline) of a salt of Compound 1 provided herein.

(viii) Form H of Hydrochloride Salt of Compound 1

In certain embodiments, provided herein is Form H of a hydrochloride salt of Compound 1.

In one embodiment, Form H is crystalline. In one embodiment, Form H is substantially crystalline. In one embodiment, Form H is moderately crystalline. In one embodiment, Form H is partially crystalline.

In one embodiment, Form H is a solvate of a hydrochloride salt of Compound 1. In one embodiment, Form H is an NMP solvate of a hydrochloride salt of Compound 1.

A representative XRPD pattern of Form H of a hydrochloride salt of Compound 1 is provided in FIG. 68.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, or all of the peaks located at approximately the following positions: 4.8, 6.2, 7.3, 11.4, 13.7, 14.3, 14.8, 15.9, 16.0, 16.3, 17.3, 18.0, 19.1, 19.6, 20.8, 22.1, 22.3, 23.3, 25.9, 26.7, 27.0, and 27.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.3, 16.3, and 26.7° 2θ. In one embodiment, the XRPD pattern further comprises peaks at approximately 14.8, 19.1, and 25.9° 2θ. In one embodiment, the XRPD pattern further comprises peaks at approximately 14.3 and 16.0° 2θ. In one embodiment, the XRPD pattern comprises peaks at approximately 7.3, 14.3, 14.8, 16.0, 16.3, 17.3, 19.1, 22.3, 25.9, 26.7, and 27.8° 2θ.

In one embodiment, provided herein is a solid form comprising a hydrochloride salt of Compound 1, characterized by an XRPD pattern that matches the XRPD pattern presented in FIG. 68.

In one embodiment, the XRPD patterns are obtained using Cu Kα radiation.

In one embodiment, Form H of a hydrochloride salt of Compound 1 is prepared by evaporating a solution of Compound 1 and hydrochloric acid (e.g., about 1:1 molar ratio) in a mixture of cyclohexane and NMP (e.g., about 1:1 v/v) under N$_2$ flow.

In one embodiment, provided herein is a solid form comprising Form H of a hydrochloride salt of Compound 1 and one or more forms of a free base of Compound 1 (e.g., amorphous form and crystalline forms). In one embodiment, provided herein is a solid form comprising Form H of a hydrochloride salt of Compound 1 and amorphous hydrochloride salt of Compound 1. In one embodiment, provided herein is a solid form comprising Form H of a hydrochloride salt Compound 1 and one or more other crystalline forms of a hydrochloride salt of Compound 1 provided herein. In one embodiment, provided herein is a solid form comprising Form H of a hydrochloride salt of Compound 1 and one or more forms (e.g., amorphous or crystalline) of a salt of Compound 1 provided herein.

(ix) Form I of Hydrochloride Salt of Compound 1

In certain embodiments, provided herein is Form I of a hydrochloride salt of Compound 1.

In one embodiment, Form I is crystalline. In one embodiment, Form I is substantially crystalline. In one embodiment, Form I is moderately crystalline. In one embodiment, Form I is partially crystalline.

In one embodiment, Form I is a solvate of a hydrochloride salt of Compound 1. In one embodiment, Form I is a DMSO solvate of a hydrochloride salt of Compound 1.

A representative XRPD pattern of Form I of a hydrochloride salt of Compound 1 is provided in FIG. 69.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, or all of the peaks located at approximately the following positions: 4.9, 6.3, 8.0, 9.8, 13.4, 14.4, 15.1, 16.1, 18.4, 18.7, 19.6, 19.8, 20.5, 21.5, 21.8, 23.5, 25.6, 26.5, 26.8, and 27.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 4.9, 16.1, and 21.5° 2θ. In one embodiment, the XRPD pattern further comprises peaks at approximately 14.4 and 25.6° 2θ. In one embodiment, the XRPD pattern further comprises peaks at approximately 19.8, 21.8, and 26.5° 2θ. In one embodiment, the XRPD pattern comprises peaks at approximately 4.9, 6.3, 14.4, 16.1, 19.8, 21.5, 21.8, 25.6, 26.5, and 27.5° 2θ.

In one embodiment, provided herein is a solid form comprising a hydrochloride salt of Compound 1, characterized by an XRPD pattern that matches the XRPD pattern presented in FIG. 69.

In one embodiment, the XRPD patterns are obtained using Cu Kα radiation.

In one embodiment, Form I of a hydrochloride salt of Compound 1 is prepared by evaporating a solution of Compound 1 and hydrochloric acid (e.g., about 1:1 molar ratio) in a mixture of IPE and DMSO (e.g., about 89:11 v/v) under N$_2$ flow.

In one embodiment, provided herein is a solid form comprising Form I of a hydrochloride salt of Compound 1 and one or more forms of a free base of Compound 1 (e.g., amorphous form and crystalline forms). In one embodiment, provided herein is a solid form comprising Form I of a hydrochloride salt of Compound 1 and amorphous hydrochloride salt of Compound 1. In one embodiment, provided herein is a solid form comprising Form I of a hydrochloride salt Compound 1 and one or more other crystalline forms of a hydrochloride salt of Compound 1 provided herein. In one embodiment, provided herein is a solid form comprising Form I of a hydrochloride salt of Compound 1 and one or more forms (e.g., amorphous or crystalline) of a salt of Compound 1 provided herein.

(x) Form J of Hydrochloride Salt of Compound 1

In certain embodiments, provided herein is Form J of a hydrochloride salt of Compound 1. A representative XRPD pattern of Form J of a hydrochloride salt of Compound 1 is provided in FIG. 136. In one embodiment, provided herein is a solid form comprising a hydrochloride salt of Compound 1, characterized by an XRPD pattern that matches the XRPD pattern presented in FIG. 136.

In one embodiment, provided herein is a solid form comprising Form J of a hydrochloride salt of Compound 1 and one or more forms of a free base of Compound 1 (e.g., amorphous form and crystalline forms). In one embodiment, provided herein is a solid form comprising Form J of a hydrochloride salt of Compound 1 and amorphous hydrochloride salt of Compound 1. In one embodiment, provided herein is a solid form comprising Form J of a hydrochloride salt Compound 1 and one or more other crystalline forms of a hydrochloride salt of Compound 1 provided herein. In one embodiment, provided herein is a solid form comprising Form J of a hydrochloride salt of Compound 1 and one or more forms (e.g., amorphous or crystalline) of a salt of Compound 1 provided herein.

(xi) Form K of Hydrochloride Salt of Compound 1

In certain embodiments, provided herein is Form K of a hydrochloride salt of Compound 1. A representative XRPD pattern of Form K of a hydrochloride salt of Compound 1 is provided in FIG. 137. In one embodiment, provided herein is a solid form comprising a hydrochloride salt of Compound 1, characterized by an XRPD pattern that matches the XRPD pattern presented in FIG. 137.

In one embodiment, provided herein is a solid form comprising Form K of a hydrochloride salt of Compound 1 and one or more forms of a free base of Compound 1 (e.g., amorphous form and crystalline forms). In one embodiment, provided herein is a solid form comprising Form K of a hydrochloride salt of Compound 1 and amorphous hydrochloride salt of Compound 1. In one embodiment, provided herein is a solid form comprising Form K of a hydrochloride salt Compound 1 and one or more other crystalline forms of a hydrochloride salt of Compound 1 provided herein. In one embodiment, provided herein is a solid form comprising Form K of a hydrochloride salt of Compound 1 and one or more forms (e.g., amorphous or crystalline) of a salt of Compound 1 provided herein.

(xii) Form L of Hydrochloride Salt of Compound 1

In certain embodiments, provided herein is Form L of a hydrochloride salt of Compound 1.

In one embodiment, Form L is crystalline. In one embodiment, Form L is substantially crystalline. In one embodiment, Form L is moderately crystalline. In one embodiment, Form L is partially crystalline.

In one embodiment, Form L is an anhydrous form of a hydrochloride salt of Compound 1.

A representative XRPD pattern of Form L of a hydrochloride salt of Compound 1 is provided in FIG. 138.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, or all of the peaks located at approximately the following positions: 8.4, 10.1, 12.2, 12.7, 13.1, 15.7, 16.1, 17.2, 17.9, 19.1, 19.4, 20.5, 22.6, 23.3, 23.6, 24.6, 25.7, 26.5, 26.9, 28.2, 28.6, and 29.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 10.1, 19.1, and 24.6° 2θ. In one embodiment, the XRPD pattern further comprises peaks at approximately 8.4, 15.7, and 16.1° 2θ. In one embodiment, the XRPD pattern further comprises peaks at approximately 19.4 and 26.9° 2θ. In one embodiment, the XRPD pattern comprises peaks at approximately 8.4, 10.1, 12.2, 13.1, 15.7, 16.1, 17.2, 19.1, 19.4, 20.5, 24.6, and 26.9° 2θ. In one embodiment, the XRPD pattern does not contain a peak at approximately 4.2° 2θ. In one embodiment, the XRPD pattern does not contain a peak at approximately 14.7° 2θ. In one embodiment, the XRPD pattern does not contain a peak at approximately 15.1° 2θ. In one embodiment, the XRPD pattern does not contain a peak at approximately 16.9° 2θ. In one embodiment, the XRPD pattern does not contain a peak at approximately 18.8° 2θ. In one embodiment, the XRPD pattern does not contain a peak at approximately 20.3° 2θ.

In one embodiment, provided herein is a solid form comprising a hydrochloride salt of Compound 1, characterized by an XRPD pattern comprising peaks at 10.1, 19.1, and 24.6±0.04° 2θ. In one embodiment, the XRPD pattern further comprises peaks at 8.4, 15.7, and 16.1±0.04° 2θ. In one embodiment, the XRPD pattern further comprises peaks at 19.4 and 26.9±0.04° 2θ. In one embodiment, the XRPD pattern comprises peaks at 8.4, 10.1, 12.2, 13.1, 15.7, 16.1, 17.2, 19.1, 19.4, 20.5, 24.6, and 26.9±0.04° 2θ. In one embodiment, the XRPD pattern does not contain a peak at 4.2±0.04° 2θ. In one embodiment, the XRPD pattern does not contain a peak at 14.7±0.04° 2θ. In one embodiment, the XRPD pattern does not contain a peak at 15.1±0.04° 2θ. In one embodiment, the XRPD pattern does not contain a peak at 16.9±0.04° 2θ. In one embodiment, the XRPD pattern does not contain a peak at 18.8±0.04° 2θ. In one embodiment, the XRPD pattern does not contain a peak at 20.3±0.04° 2θ.

In one embodiment, provided herein is a solid form comprising a hydrochloride salt of Compound 1, characterized by an XRPD pattern comprising peaks at 10.1, 19.1, and 24.6±0.02° 2θ. In one embodiment, the XRPD pattern further comprises peaks at 8.4, 15.7, and 16.1±0.02° 2θ. In one embodiment, the XRPD pattern further comprises peaks at 19.4 and 26.9±0.02° 2θ. In one embodiment, the XRPD pattern comprises peaks at 8.4, 10.1, 12.2, 13.1, 15.7, 16.1, 17.2, 19.1, 19.4, 20.5, 24.6, and 26.9±0.02° 2θ. In one embodiment, the XRPD pattern does not contain a peak at 4.2±0.02° 2θ. In one embodiment, the XRPD pattern does not contain a peak at 14.7±0.02° 2θ. In one embodiment, the XRPD pattern does not contain a peak at 15.1±0.02° 2θ. In one embodiment, the XRPD pattern does not contain a peak at 16.9±0.02° 2θ. In one embodiment, the XRPD pattern does not contain a peak at 18.8±0.02° 2θ. In one embodiment, the XRPD pattern does not contain a peak at 20.3±0.02° 2θ.

In one embodiment, provided herein is a solid form comprising a hydrochloride salt of Compound 1, characterized by an XRPD pattern comprising peaks at 10.1, 19.1, and 24.6° 2θ. In one embodiment, the XRPD pattern further comprises peaks at 8.4, 15.7, and 16.1° 2θ. In one embodiment, the XRPD pattern further comprises peaks at 19.4 and 26.9° 2θ. In one embodiment, the XRPD pattern comprises peaks at 8.4, 10.1, 12.2, 13.1, 15.7, 16.1, 17.2, 19.1, 19.4, 20.5, 24.6, and 26.9° 2θ. In one embodiment, the XRPD pattern does not contain a peak at 4.2° 2θ. In one embodiment, the XRPD pattern does not contain a peak at 14.7° 2θ. In one embodiment, the XRPD pattern does not contain a peak at 15.1° 2θ. In one embodiment, the XRPD pattern does not contain a peak at 16.9° 2θ. In one embodiment, the XRPD pattern does not contain a peak at 18.8° 2θ. In one embodiment, the XRPD pattern does not contain a peak at 20.3° 2θ.

In one embodiment, provided herein is a solid form comprising a hydrochloride salt of Compound 1, characterized by an XRPD pattern that matches the XRPD pattern presented in FIG. 138.

In one embodiment, the XRPD patterns are obtained using Cu Kα radiation.

A representative thermal gravimetric analysis (TGA) thermogram of Form L of a hydrochloride salt of Compound 1 is provided in FIG. 139. In one embodiment, provided herein is a solid form comprising a hydrochloride salt of Compound 1, which exhibits almost no weight loss upon heating from about 30° C. to about 200° C. In one embodiment, provided herein is a solid form comprising a hydrochloride salt of Compound 1, characterized by a TGA thermogram that matches the TGA thermogram presented in FIG. 139.

A representative differential scanning calorimetry (DSC) thermogram of Form L of a hydrochloride salt of Compound 1 is presented in FIG. 140. In one embodiment, provided herein is a solid form comprising a hydrochloride salt of Compound 1, which exhibits, as characterized by DSC, a first thermal event with an onset temperature of about 124° C., and a second thermal event with an onset temperature of about 262° C. In one embodiment, the first thermal event also has a peak temperature of about 132° C., and the second thermal event also has a peak temperature of about 269° C. In one embodiment, without being limited by any particular theory, the first thermal event corresponds to solid-solid phase transition, and the second thermal event corresponds to melting. In one embodiment, provided herein is a solid form comprising a hydrochloride salt of Compound 1, characterized by a DSC thermogram that matches the DSC thermogram presented in FIG. 140.

A representative dynamic vapor sorption (DVS) isotherm plot of the Form L of a hydrochloride salt of Compound 1 is provided in FIG. 141. In one embodiment, provided herein is a solid form comprising a hydrochloride salt of Compound 1, which exhibits a mass increase of about 0.6% when subjected to an increase in a relative humidity (RH) from about 0% to about 95%. In one embodiment, provided herein is a solid form comprising a hydrochloride salt of Compound 1, characterized by a DVS isotherm plot which matches the DVS isotherm plot presented in FIG. 141. In one embodiment, Form L is slightly hygroscopic. In one embodiment, Form L remains as Form L after DVS cycle.

In one embodiment, Form L of a hydrochloride salt of Compound 1 is prepared by a reactive crystallization process. In one embodiment, Form L of a hydrochloride salt of Compound 1 is prepared by a process comprising adding an hydrochloric acid source to a mixture (e.g., a suspension or a solution) of a free base of Compound 1 in a solvent. In one embodiment, the free base of Compound 1 is Form K of a free base of Compound 1. In one embodiment, the hydrochloric acid source is hydrochloric acid in an organic solvent. In one embodiment, the hydrochloric acid source is a hydrochloric acid aqueous solution. In one embodiment, the solvent is acetonitrile. In one embodiment, the solvent is a mixture of CPME and water. In one embodiment, the solvent is a mixture of acetone and water. In one embodiment, the solvent is a mixture of DMSO and water. In one embodiment, the solvent is isopropyl acetate. In one embodiment, the solvent is ethyl acetate. In one embodiment, the solvent is a mixture of NMP and water. In one embodiment, the solvent is a mixture of DMF and water. In one embodiment, the solvent is a mixture of DMAc and water. In one embodiment, the solvent is n-propanol. In one embodiment, the solvent is n-butanol. In one embodiment, the amount of the hydrochloric acid (relative to the amount of the free base of Compound 1) is from about 1 to about 5 molar equivalents. In one embodiment, the amount of the hydrochloric acid is from about 1.1 to about 4 molar equivalents. In one embodiment, the amount of the hydrochloric acid is about 1.1 molar equivalents. In one embodiment, the amount of the hydrochloric acid is about 1.2 molar equivalents. In one embodiment, the amount of the hydrochloric acid is about 2 molar equivalents. In one embodiment, the amount of the hydrochloric acid is about 2.5 molar equivalents. In one embodiment, the amount of the hydrochloric acid is about 4 molar equivalents. In one embodiment, the hydrochloric acid is added at a temperature of from about 0° C. to about 80° C. In one embodiment, the temperature is about 0° C. In one embodiment, the temperature is about room temperature. In one embodiment, the temperature is about 40° C. In one embodiment, the temperature is about 80° C. In one embodiment, the process further comprises subjecting the mixture (after addition of hydrochloric acid) to one or more temperature cycles (e.g., between room temperature and about 40° C.).

In one embodiment, Form L of a hydrochloride salt of Compound 1 is prepared by a process comprising adding a hydrochloric acid aqueous solution (e.g., 1N HCl solution; e.g., about 4 molar equivalents) to a suspension of Form K of a free base of Compound 1 in a mixture of acetone and water (e.g., 20% acetone/water v/v). In one embodiment, the process further comprises subjecting the mixture (after addition of hydrochloric acid) to one or more temperature cycles (e.g., between room temperature and about 40° C.).

In one embodiment, provided herein is a solid form comprising Form L of a hydrochloride salt of Compound 1 and one or more forms of a free base of Compound 1 (e.g., amorphous form and crystalline forms). In one embodiment, provided herein is a solid form comprising Form L of a hydrochloride salt of Compound 1 and amorphous hydrochloride salt of Compound 1. In one embodiment, provided herein is a solid form comprising Form L of a hydrochloride salt Compound 1 and one or more other crystalline forms of a hydrochloride salt of Compound 1 provided herein. In one embodiment, provided herein is a solid form comprising Form L of a hydrochloride salt of Compound 1 and one or more forms (e.g., amorphous or crystalline) of a salt of Compound 1 provided herein.

(xiii) Form M of Hydrochloride Salt of Compound 1

In certain embodiments, provided herein is Form M of a hydrochloride salt of Compound 1.

In one embodiment, Form M is crystalline. In one embodiment, Form M is substantially crystalline. In one embodiment, Form M is moderately crystalline. In one embodiment, Form M is partially crystalline.

In one embodiment, Form M is an anhydrous form of a hydrochloride salt of Compound 1.

A representative XRPD pattern of Form M of a hydrochloride salt of Compound 1 is provided in FIG. 142.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 4.2, 8.5, 10.3, 12.3, 12.7, 13.1, 14.7, 15.1, 15.9, 16.1, 16.9, 17.4, 17.8, 18.8, 19.3, 19.8, 20.3, 20.6, 21.2, 22.7, 23.2, 23.9, 24.6, 25.5, 26.1, and 26.6 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 10.3, 19.3, and 24.6° 2θ. In one embodiment, the XRPD pattern further comprises one or more peaks at approximately 4.2, 14.7, 15.1, and 16.9° 2θ. In one embodiment, the XRPD pattern further comprises a peak at approximately 4.2° 2θ. In one embodiment, the XRPD pattern further comprises a peak at approximately 14.7° 2θ. In one embodiment, the XRPD pattern further comprises a peak at approximately 15.1° 2θ. In one embodiment, the XRPD pattern further comprises a peak at approximately 16.9° 2θ. In one embodiment, the XRPD pattern further comprises peaks at approximately 15.9 and 16.1° 2θ. In one embodiment, the XRPD pattern further comprises peaks at approximately 17.4, 22.7, and 26.6° 2θ. In one embodiment, the XRPD pattern comprises peaks at approximately 4.2, 10.3, 12.3, 12.7, 14.7, 15.1, 15.9, 16.1, 16.9, 17.4, 17.8, 19.3, 22.7, 23.2, 24.6, and 26.6° 2θ.

In one embodiment, provided herein is a solid form comprising a hydrochloride salt of Compound 1, characterized by an XRPD pattern comprising peaks at 10.3, 19.3, and 24.6±0.04° 2θ. In one embodiment, the XRPD pattern further comprises one or more peaks at 4.2, 14.7, 15.1, and 16.9±0.04° 2θ. In one embodiment, the XRPD pattern further comprises a peak at 4.2±0.04° 2θ. In one embodiment, the XRPD pattern further comprises a peak at 14.7±0.04° 2θ. In one embodiment, the XRPD pattern further comprises a peak at 15.1±0.04° 2θ. In one embodiment, the XRPD pattern further comprises a peak at 16.9±0.04° 2θ. In one embodiment, the XRPD pattern further comprises peaks at 15.9 and 16.1±0.04° 2θ. In one embodiment, the XRPD pattern further comprises peaks at 17.4, 22.7, and 26.6±0.04° 2θ. In one embodiment, the XRPD pattern comprises peaks at 4.2, 10.3, 12.3, 12.7, 14.7, 15.1, 15.9, 16.1, 16.9, 17.4, 17.8, 19.3, 22.7, 23.2, 24.6, and 26.6±0.04° 2θ.

In one embodiment, provided herein is a solid form comprising a hydrochloride salt of Compound 1, characterized by an XRPD pattern comprising peaks at 10.3, 19.3, and 24.6±0.02° 2θ. In one embodiment, the XRPD pattern further comprises one or more peaks at 4.2, 14.7, 15.1, and 16.9±0.02° 2θ. In one embodiment, the XRPD pattern further comprises a peak at 4.2±0.02° 2θ. In one embodiment, the XRPD pattern further comprises a peak at 14.7±0.02° 2θ. In one embodiment, the XRPD pattern further comprises a peak at 15.1±0.02° 2θ. In one embodiment, the XRPD pattern further comprises a peak at 16.9±0.02° 2θ. In one embodiment, the XRPD pattern further comprises peaks at 15.9 and 16.1±0.02° 2θ. In one embodiment, the XRPD pattern further comprises peaks at 17.4, 22.7, and 26.6±0.02° 2θ. In one embodiment, the XRPD pattern comprises peaks at 4.2, 10.3, 12.3, 12.7, 14.7, 15.1, 15.9, 16.1, 16.9, 17.4, 17.8, 19.3, 22.7, 23.2, 24.6, and 26.6±0.02° 2θ.

In one embodiment, provided herein is a solid form comprising a hydrochloride salt of Compound 1, characterized by an XRPD pattern comprising peaks at 10.3, 19.3, and 24.6° 2θ. In one embodiment, the XRPD pattern further comprises one or more peaks at 4.2, 14.7, 15.1, and 16.9° 2θ. In one embodiment, the XRPD pattern further comprises a peak at 4.2° 2θ. In one embodiment, the XRPD pattern further comprises a peak at 14.7° 2θ. In one embodiment, the XRPD pattern further comprises a peak at 15.1° 2θ. In one embodiment, the XRPD pattern further comprises a peak at 16.9° 2θ. In one embodiment, the XRPD pattern further comprises peaks at 15.9 and 16.1° 2θ. In one embodiment, the XRPD pattern further comprises peaks at 17.4, 22.7, and 26.6° 2θ. In one embodiment, the XRPD pattern comprises peaks at 4.2, 10.3, 12.3, 12.7, 14.7, 15.1, 15.9, 16.1, 16.9, 17.4, 17.8, 19.3, 22.7, 23.2, 24.6, and 26.6° 2θ.

In one embodiment, provided herein is a solid form comprising a hydrochloride salt of Compound 1, characterized by an XRPD pattern that matches the XRPD pattern presented in FIG. 142.

In one embodiment, the XRPD patterns are obtained using Cu Kα radiation.

A representative differential scanning calorimetry (DSC) thermogram of Form M of a hydrochloride salt of Compound 1 is presented in FIG. 143. In one embodiment, provided herein is a solid form comprising a hydrochloride salt of Compound 1, which exhibits, as characterized by DSC, a thermal event with an onset temperature of about 259° C. In one embodiment, the thermal event also has a peak temperature of about 265° C. In one embodiment, without being limited by any particular theory, the thermal event corresponds to melting of Form M. In one embodiment, provided herein is a solid form comprising a hydrochloride salt of Compound 1, characterized by a DSC thermogram that matches the DSC thermogram presented in FIG. 143.

In one embodiment, Form M of a hydrochloride salt of Compound 1 is prepared by a process comprising heating Form L of a hydrochloride salt of Compound 1 to about 160° C. In one embodiment, the process further comprises holding the hydrochloride salt of Compound 1 at about 160° C. for about 10 minutes, and cooling it down to about room temperature.

In one embodiment, provided herein is a solid form comprising Form M of a hydrochloride salt of Compound 1 and one or more forms of a free base of Compound 1 (e.g., amorphous form and crystalline forms). In one embodiment, provided herein is a solid form comprising Form M of a hydrochloride salt of Compound 1 and amorphous hydrochloride salt of Compound 1. In one embodiment, provided herein is a solid form comprising Form M of a hydrochloride salt Compound 1 and one or more other crystalline forms of a hydrochloride salt of Compound 1 provided herein. In one embodiment, provided herein is a solid form comprising Form M of a hydrochloride salt of Compound 1 and one or more forms (e.g., amorphous or crystalline) of a salt of Compound 1 provided herein.

(xiv) Form N of Hydrochloride Salt of Compound 1

In certain embodiments, provided herein is Form N of a hydrochloride salt of Compound 1.

In one embodiment, Form N is crystalline. In one embodiment, Form N is substantially crystalline. In one embodiment, Form N is moderately crystalline. In one embodiment, Form N is partially crystalline.

In one embodiment, Form N is a hydrate of a hydrochloride salt of Compound 1.

A representative XRPD pattern of Form N of a hydrochloride salt of Compound 1 is provided in FIG. 144.

In one embodiment, provided herein is a solid form comprising a hydrochloride salt of Compound 1, characterized by 1, 2, 3, 4, 5, 6, 7, 8, 9, 10, 11, 12, 13, 14, 15, 16, 17, 18, 19, or all of the peaks located at approximately the following positions: 9.9, 11.8, 15.4, 17.2, 17.8, 18.3, 19.6, 19.9, 21.9, 22.2, 23.2, 23.8, 24.2, 25.4, 25.8, 27.2, 27.8, 28.2, 28.7, and 29.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 9.9, 15.4, and 18.3° 2θ. In one embodiment, the XRPD pattern further comprises peaks at approximately 17.2, 25.8, and 27.8° 2θ. In one embodiment, the XRPD pattern further comprises peaks at approximately 17.8, 19.9, and 23.8° 2θ. In one embodiment, the XRPD pattern comprises peaks at approximately 9.9, 11.8, 15.4, 17.2, 17.8, 18.3, 19.9, 22.2, 23.2, 23.8, 25.4, 25.8, and 27.8° 2θ.

In one embodiment, provided herein is a solid form comprising a hydrochloride salt of Compound 1, characterized by an XRPD pattern that matches the XRPD pattern presented in FIG. 144.

In one embodiment, the XRPD patterns are obtained using Cu Kα radiation.

A representative TG-MS thermogram of Form N of a hydrochloride salt of Compound 1 is provided in FIG. 145. In one embodiment, provided herein is a solid form comprising a hydrochloride salt of Compound 1, which exhibits a weight loss of about 2.8% upon heating from about 25° C. to about 100° C. In one embodiment, without being limited by any particular theory, the weight loss corresponds to the loss of water. In one embodiment, provided herein is a solid form comprising a hydrochloride salt of Compound 1, characterized by a TGA thermogram that matches the TGA thermogram presented in FIG. 145.

A representative differential scanning calorimetry (DSC) thermogram of Form N of a hydrochloride salt of Compound 1 is presented in FIG. 146. In one embodiment, provided herein is a solid form comprising a hydrochloride salt of Compound 1, which exhibits, as characterized by DSC, first thermal event with an onset temperature of about 44° C., a second thermal event with an onset temperature of about 128° C., and a third thermal event with an onset temperature of about 256° C. In one embodiment, the first thermal event also has a peak temperature of about 66° C., the second thermal event also has a peak temperature of about 133° C., and the third thermal event also has a peak temperature of about 263° C. In one embodiment, without being limited by any particular theory, the first thermal event corresponds to dehydration, the second thermal event corresponds to solid-solid state transition, and the third thermal event corresponds to melting. In one embodiment, provided herein is a solid form comprising a hydrochloride salt of Compound 1, characterized by a DSC thermogram that matches the DSC thermogram presented in FIG. 146.

In one embodiment, Form N of a hydrochloride salt of Compound 1 is prepared by heating Form L of a hydrochloride salt of Compound 1 in a mixture solvent of acetone and water (e.g., 20% acetone/water v/v) at about 60° C. for a period of time (e.g., overnight).

In one embodiment, provided herein is a solid form comprising Form N of a hydrochloride salt of Compound 1 and one or more forms of a free base of Compound 1 (e.g., amorphous form and crystalline forms). In one embodiment, provided herein is a solid form comprising Form N of a hydrochloride salt of Compound 1 and amorphous hydrochloride salt of Compound 1. In one embodiment, provided herein is a solid form comprising Form N of a hydrochloride salt Compound 1 and one or more other crystalline forms of a hydrochloride salt of Compound 1 provided herein. In one embodiment, provided herein is a solid form comprising Form N of a hydrochloride salt of Compound 1 and one or more forms (e.g., amorphous or crystalline) of a salt of Compound 1 provided herein.

(xv) Form O of Hydrochloride Salt of Compound 1

In certain embodiments, provided herein is Form O of a hydrochloride salt of Compound 1.

In one embodiment, Form O is crystalline. In one embodiment, Form O is substantially crystalline. In one embodiment, Form O is moderately crystalline. In one embodiment, Form O is partially crystalline.

In one embodiment, Form O is a solvate of a hydrochloride salt of Compound 1. In one embodiment, Form O is a THF solvate of a hydrochloride salt of Compound 1.

A representative XRPD pattern of Form O of a hydrochloride salt of Compound 1 is provided in FIG. 147.

In one embodiment, provided herein is a solid form comprising a hydrochloride salt of Compound 1, characterized by 1, 2, 3, 4, 5, 6, 7, 8, 9, 10, 11, or all of the peaks located at approximately the following positions: 5.8, 7.6, 9.6, 14.2, 15.6, 16.9, 18.1, 19.4, 20.0, 23.3, 24.2, and 25.3° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.6, 16.9, and 18.1° 2θ. In one embodiment, the XRPD pattern further comprises peaks at approximately 9.6 and 15.6° 2θ. In one embodiment, the XRPD pattern further comprises peaks at approximately 5.8, 19.4, and 20.0° 2θ. In one embodiment, the XRPD pattern comprises peaks at approximately 5.8, 7.6, 9.6, 14.2, 15.6, 16.9, 18.1, 19.4, 20.0, 23.3, 24.2, and 25.3° 2θ.

In one embodiment, provided herein is a solid form comprising a hydrochloride salt of Compound 1, characterized by an XRPD pattern that matches the XRPD pattern presented in FIG. 147.

In one embodiment, the XRPD patterns are obtained using Cu Kα radiation.

In one embodiment, Form O of a hydrochloride salt of Compound 1 is prepared by suspending Form L of a hydrochloride salt of Compound 1 in THF at room temperature for a period of time (e.g., about 7 days).

In one embodiment, provided herein is a solid form comprising Form O of a hydrochloride salt of Compound 1 and one or more forms of a free base of Compound 1 (e.g., amorphous form and crystalline forms). In one embodiment, provided herein is a solid form comprising Form O of a hydrochloride salt of Compound 1 and amorphous hydrochloride salt of Compound 1. In one embodiment, provided herein is a solid form comprising Form O of a hydrochloride salt Compound 1 and one or more other crystalline forms of a hydrochloride salt of Compound 1 provided herein. In one embodiment, provided herein is a solid form comprising Form O of a hydrochloride salt of Compound 1 and one or more forms (e.g., amorphous or crystalline) of a salt of Compound 1 provided herein.

(xvi) Form P of Hydrochloride Salt of Compound 1

In certain embodiments, provided herein is Form P of a hydrochloride salt of Compound 1.

In one embodiment, Form P is crystalline. In one embodiment, Form P is substantially crystalline. In one embodiment, Form P is moderately crystalline. In one embodiment, Form P is partially crystalline.

In one embodiment, Form P is a solvate of a hydrochloride salt of Compound 1. In one embodiment, Form P is a DMAc solvate of a hydrochloride salt of Compound 1.

A representative XRPD pattern of Form P of a hydrochloride salt of Compound 1 is provided in FIG. 148.

In one embodiment, provided herein is a solid form comprising a hydrochloride salt of Compound 1, characterized by 1, 2, 3, 4, 5, 6, or all of the peaks located at approximately the following positions: 4.8, 9.5, 14.1, 16.6, 18.9, 22.3, and 23.6° 2θ. In one embodiment, the solid form is characterized by 3 of the peaks. In one embodiment, the solid form is characterized by 5 of the peaks. In one embodiment, the solid form is characterized by all of the peaks.

In one embodiment, provided herein is a solid form comprising a hydrochloride salt of Compound 1, characterized by an XRPD pattern comprising peaks at approximately 9.5, 16.6, and 18.9° 2θ. In one embodiment, the XRPD pattern further comprises peaks at approximately 14.1 and 23.6° 2θ. In one embodiment, the XRPD pattern comprises peaks at approximately 9.5, 14.1, 16.6, 18.9, 22.3, and 23.6° 2θ.

In one embodiment, provided herein is a solid form comprising a hydrochloride salt of Compound 1, characterized by an XRPD pattern that matches the XRPD pattern presented in FIG. 148.

In one embodiment, the XRPD patterns are obtained using Cu Kα radiation.

In one embodiment, Form P of a hydrochloride salt of Compound 1 is prepared by subjecting a suspension of Form L of a hydrochloride salt of Compound 1 in DMAc to a temperature cycle (e.g., between about 4° C. and about 80° C.) for a period of time (e.g., about 7 days).

In one embodiment, provided herein is a solid form comprising Form P of a hydrochloride salt of Compound 1 and one or more forms of a free base of Compound 1 (e.g., amorphous form and crystalline forms). In one embodiment, provided herein is a solid form comprising Form P of a hydrochloride salt of Compound 1 and amorphous hydrochloride salt of Compound 1. In one embodiment, provided herein is a solid form comprising Form P of a hydrochloride salt Compound 1 and one or more other crystalline forms of a hydrochloride salt of Compound 1 provided herein. In one embodiment, provided herein is a solid form comprising Form P of a hydrochloride salt of Compound 1 and one or more forms (e.g., amorphous or crystalline) of a salt of Compound 1 provided herein.

(xvii) Form Q of Hydrochloride Salt of Compound 1

In certain embodiments, provided herein is Form Q of a hydrochloride salt of Compound 1.

In one embodiment, Form Q is crystalline. In one embodiment, Form Q is substantially crystalline. In one embodiment, Form Q is moderately crystalline. In one embodiment, Form Q is partially crystalline.

In one embodiment, Form Q is a solvate of a hydrochloride salt of Compound 1. In one embodiment, Form Q is a mixed DMSO and ethyl acetate solvate of a hydrochloride salt of Compound 1.

A representative XRPD pattern of Form Q of a hydrochloride salt of Compound 1 is provided in FIG. 149.

In one embodiment, provided herein is a solid form comprising a hydrochloride salt of Compound 1, characterized by 1, 2, 3, 4, 5, 6, 7, 8, 9, or all of the peaks located at approximately the following positions: 5.6, 7.6, 14.1, 15.5, 16.8, 17.7, 20.0, 23.1, 24.0, and 26.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.6, 15.5, and 17.7° 2θ. In one embodiment, the XRPD pattern further comprises peaks at approximately 16.8 and 20.0° 2θ. In one embodiment, the XRPD pattern further comprises peaks at approximately 5.6 and 14.1° 2θ. In one embodiment, the XRPD pattern comprises peaks at approximately 5.6, 7.6, 14.1, 15.5, 16.8, 17.7, 20.0, 24.0, and 26.0° 2θ.

In one embodiment, provided herein is a solid form comprising a hydrochloride salt of Compound 1, characterized by an XRPD pattern that matches the XRPD pattern presented in FIG. 149.

In one embodiment, the XRPD patterns are obtained using Cu Kα radiation.

In one embodiment, Form Q of a hydrochloride salt of Compound 1 is prepared by adding a solution of a hydrochloride salt of Compound 1 in DMSO into ethyl acetate, and holding the resulted suspension at about room temperature for a period of time (e.g., overnight). In one embodiment, the solution of a hydrochloride salt of Compound 1 in DMSO is prepared by dissolving Form L of a hydrochloride salt of Compound 1 in DMSO.

In one embodiment, provided herein is a solid form comprising Form Q of a hydrochloride salt of Compound 1 and one or more forms of a free base of Compound 1 (e.g., amorphous form and crystalline forms). In one embodiment, provided herein is a solid form comprising Form Q of a hydrochloride salt of Compound 1 and amorphous hydrochloride salt of Compound 1. In one embodiment, provided herein is a solid form comprising Form Q of a hydrochloride salt Compound 1 and one or more other crystalline forms of a hydrochloride salt of Compound 1 provided herein. In one embodiment, provided herein is a solid form comprising Form Q of a hydrochloride salt of Compound 1 and one or more forms (e.g., amorphous or crystalline) of a salt of Compound 1 provided herein.

(xviii) Form R of Hydrochloride Salt of Compound 1

In certain embodiments, provided herein is Form R of a hydrochloride salt of Compound 1.

In one embodiment, Form R is crystalline. In one embodiment, Form R is substantially crystalline. In one embodiment, Form R is moderately crystalline. In one embodiment, Form R is partially crystalline.

In one embodiment, Form R is a solvate of a hydrochloride salt of Compound 1. In one embodiment, Form R is a mixed DMSO and MTBE solvate of a hydrochloride salt of Compound 1.

A representative XRPD pattern of Form R of a hydrochloride salt of Compound 1 is provided in FIG. 150.

In one embodiment, provided herein is a solid form comprising a hydrochloride salt of Compound 1, characterized by 1, 2, 3, 4, 5, 6, 7, 8, or all of the peaks located at approximately the following positions: 5.4, 16.2, 17.7, 18.8, 20.1, 21.6, 22.1, 23.8, and 25.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by all of the peaks.

In one embodiment, provided herein is a solid form comprising a hydrochloride salt of Compound 1, characterized by an XRPD pattern comprising peaks at approximately 17.7, 20.1, and 21.6° 2θ. In one embodiment, the XRPD pattern further comprises peaks at approximately 5.4 and 22.1° 2θ. In one embodiment, the XRPD pattern further comprises peaks at approximately 16.2 and 18.8° 2θ. In one embodiment, the XRPD pattern comprises peaks at approximately 5.4, 16.2, 17.7, 18.8, 20.1, 21.6, 22.1, and 23.8° 2θ.

In one embodiment, provided herein is a solid form comprising a hydrochloride salt of Compound 1, characterized by an XRPD pattern that matches the XRPD pattern presented in FIG. 150.

In one embodiment, the XRPD patterns are obtained using Cu Kα radiation.

In one embodiment, Form R of a hydrochloride salt of Compound 1 is prepared by adding a solution of a hydrochloride salt of Compound 1 in DMSO into MTBE, and holding the resulted suspension at about room temperature for a period of time (e.g., overnight). In one embodiment, the solution of a hydrochloride salt of Compound 1 in DMSO is prepared by dissolving Form L of a hydrochloride salt of Compound 1 in DMSO.

In one embodiment, provided herein is a solid form comprising Form R of a hydrochloride salt of Compound 1 and one or more forms of a free base of Compound 1 (e.g., amorphous form and crystalline forms). In one embodiment, provided herein is a solid form comprising Form R of a hydrochloride salt of Compound 1 and amorphous hydrochloride salt of Compound 1. In one embodiment, provided herein is a solid form comprising Form R of a hydrochloride salt Compound 1 and one or more other crystalline forms of a hydrochloride salt of Compound 1 provided herein. In one embodiment, provided herein is a solid form comprising Form R of a hydrochloride salt of Compound 1 and one or more forms (e.g., amorphous or crystalline) of a salt of Compound 1 provided herein.

(xix) Form S of Hydrochloride Salt of Compound 1

In certain embodiments, provided herein is Form S of a hydrochloride salt of Compound 1.

In one embodiment, Form S is crystalline. In one embodiment, Form S is substantially crystalline. In one embodiment, Form S is moderately crystalline. In one embodiment, Form S is partially crystalline.

In one embodiment, Form S is a solvate of a hydrochloride salt of Compound 1. In one embodiment, Form S is a mixed DMSO and toluene solvate of a hydrochloride salt of Compound 1.

A representative XRPD pattern of Form S of a hydrochloride salt of Compound 1 is provided in FIG. 151.

In one embodiment, provided herein is a solid form comprising a hydrochloride salt of Compound 1, characterized by 1, 2, 3, 4, or all of the peaks located at approximately the following positions: 5.6, 9.9, 16.6, 18.6, and 22.4° 2θ. In one embodiment, the solid form is characterized by 3 of the peaks. In one embodiment, the solid form is characterized by all of the peaks.

In one embodiment, provided herein is a solid form comprising a hydrochloride salt of Compound 1, characterized by an XRPD pattern comprising peaks at approximately 16.6, 18.6, and 22.4° 2θ. In one embodiment, the XRPD pattern comprises peaks at approximately 5.6, 9.9, 16.6, 18.6, and 22.4° 2θ.

In one embodiment, provided herein is a solid form comprising a hydrochloride salt of Compound 1, characterized by an XRPD pattern that matches the XRPD pattern presented in FIG. 151.

In one embodiment, the XRPD patterns are obtained using Cu Kα radiation.

In one embodiment, Form S of a hydrochloride salt of Compound 1 is prepared by adding a solution of a hydrochloride salt of Compound 1 in DMSO into toluene, and holding the resulted suspension at about room temperature for a period of time (e.g., overnight). In one embodiment, the solution of a hydrochloride salt of Compound 1 in DMSO is prepared by dissolving Form L of a hydrochloride salt of Compound 1 in DMSO.

In one embodiment, provided herein is a solid form comprising Form S of a hydrochloride salt of Compound 1 and one or more forms of a free base of Compound 1 (e.g., amorphous form and crystalline forms). In one embodiment, provided herein is a solid form comprising Form S of a hydrochloride salt of Compound 1 and amorphous hydrochloride salt of Compound 1. In one embodiment, provided herein is a solid form comprising Form S of a hydrochloride salt Compound 1 and one or more other crystalline forms of a hydrochloride salt of Compound 1 provided herein. In one embodiment, provided herein is a solid form comprising Form S of a hydrochloride salt of Compound 1 and one or more forms (e.g., amorphous or crystalline) of a salt of Compound 1 provided herein.

(xx) Form T of Hydrochloride Salt of Compound 1

In certain embodiments, provided herein is Form T of a hydrochloride salt of Compound 1.

In one embodiment, Form T is crystalline. In one embodiment, Form T is substantially crystalline. In one embodiment, Form T is moderately crystalline. In one embodiment, Form T is partially crystalline.

In one embodiment, Form T is a solvate of a hydrochloride salt of Compound 1. In one embodiment, Form T is an isopropyl acetate solvate of a hydrochloride salt of Compound 1.

A representative XRPD pattern of Form T of a hydrochloride salt of Compound 1 is provided in FIG. 152.

In one embodiment, provided herein is a solid form comprising a hydrochloride salt of Compound 1, characterized by 1, 2, 3, 4, 5, 6, 7, 8, 9, 10, 11, or all of the peaks located at approximately the following positions: 5.8, 7.7, 9.7, 14.1, 15.6, 16.9, 17.8, 19.4, 23.4, 24.3, 25.3, and 28.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.7, 16.9, and 17.8° 2θ. In one embodiment, the XRPD pattern further comprises peaks at approximately 5.8 and 15.6° 2θ. In one embodiment, the XRPD pattern further comprises peaks at approximately 9.7 and 19.4° 2θ. In one embodiment, the XRPD pattern comprises peaks at approximately 5.8, 7.7, 9.7, 14.1, 15.6, 16.9, 17.8, 19.4, 23.4, and 24.3° 2θ.

In one embodiment, provided herein is a solid form comprising a hydrochloride salt of Compound 1, characterized by an XRPD pattern that matches the XRPD pattern presented in FIG. 152.

In one embodiment, the XRPD patterns are obtained using Cu Kα radiation.

In one embodiment, Form T of a hydrochloride salt of Compound 1 is prepared by suspending amorphous hydrochloride salt of Compound 1 in isopropyl acetate at about room temperature for a period of time (e.g., about 7 days).

In one embodiment, provided herein is a solid form comprising Form T of a hydrochloride salt of Compound 1 and one or more forms of a free base of Compound 1 (e.g., amorphous form and crystalline forms). In one embodiment, provided herein is a solid form comprising Form T of a hydrochloride salt of Compound 1 and amorphous hydrochloride salt of Compound 1. In one embodiment, provided herein is a solid form comprising Form T of a hydrochloride salt Compound 1 and one or more other crystalline forms of a hydrochloride salt of Compound 1 provided herein. In one embodiment, provided herein is a solid form comprising Form T of a hydrochloride salt of Compound 1 and one or more forms (e.g., amorphous or crystalline) of a salt of Compound 1 provided herein.

(xxi) Form U of Hydrochloride Salt of Compound 1

In certain embodiments, provided herein is Form U of a hydrochloride salt of Compound 1.

In one embodiment, Form U is crystalline. In one embodiment, Form U is substantially crystalline. In one embodiment, Form U is moderately crystalline. In one embodiment, Form U is partially crystalline.

In one embodiment, Form U is a solvate of a hydrochloride salt of Compound 1. In one embodiment, Form U is an acetic acid solvate of a hydrochloride salt of Compound 1.

A representative XRPD pattern of Form U of a hydrochloride salt of Compound 1 is provided in FIG. 153.

In one embodiment, provided herein is a solid form comprising a hydrochloride salt of Compound 1, characterized by 1, 2, 3, 4, 5, 6, 7, 8, 9, 10, or all of the peaks located at approximately the following positions: 7.2, 9.1, 9.6, 13.7, 16.8, 19.2, 20.2, 23.0, 24.4, 25.9, and 28.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by all of the peaks.

In one embodiment, provided herein is a solid form comprising a hydrochloride salt of Compound 1, characterized by an XRPD pattern comprising peaks at approximately 9.1, 19.2, and 24.4° 2θ. In one embodiment, the XRPD pattern further comprises peaks at approximately 9.6 and 23.0° 2θ. In one embodiment, the XRPD pattern further comprises peaks at approximately 7.2 and 20.2° 2θ. In one embodiment, the XRPD pattern comprises peaks at approximately 7.2, 9.1, 9.6, 13.7, 16.8, 19.2, 20.2, 23.0, and 24.4° 2θ.

In one embodiment, provided herein is a solid form comprising a hydrochloride salt of Compound 1, characterized by an XRPD pattern that matches the XRPD pattern presented in FIG. 153.

In one embodiment, the XRPD patterns are obtained using Cu Kα radiation.

In one embodiment, Form U of a hydrochloride salt of Compound 1 is prepared by suspending amorphous hydrochloride salt of Compound 1 in acetic acid at about room temperature for a period of time (e.g., about 7 days).

In one embodiment, provided herein is a solid form comprising Form U of a hydrochloride salt of Compound 1 and one or more forms of a free base of Compound 1 (e.g., amorphous form and crystalline forms). In one embodiment, provided herein is a solid form comprising Form U of a hydrochloride salt of Compound 1 and amorphous hydrochloride salt of Compound 1. In one embodiment, provided herein is a solid form comprising Form U of a hydrochloride salt Compound 1 and one or more other crystalline forms of a hydrochloride salt of Compound 1 provided herein. In one embodiment, provided herein is a solid form comprising Form U of a hydrochloride salt of Compound 1 and one or more forms (e.g., amorphous or crystalline) of a salt of Compound 1 provided herein.

(xxii) Form V of Hydrochloride Salt of Compound 1

In certain embodiments, provided herein is Form V of a hydrochloride salt of Compound 1.

In one embodiment, Form V is crystalline. In one embodiment, Form V is substantially crystalline. In one embodiment, Form V is moderately crystalline. In one embodiment, Form V is partially crystalline.

In one embodiment, Form V is a solvate of a hydrochloride salt of Compound 1. In one embodiment, Form V is an NMP solvate of a hydrochloride salt of Compound 1.

A representative XRPD pattern of Form V of a hydrochloride salt of Compound 1 is provided in FIG. 154.

In one embodiment, provided herein is a solid form comprising a hydrochloride salt of Compound 1, characterized by 1, 2, 3, 4, 5, 6, 7, 8, 9, 10, or all of the peaks located at approximately the following positions: 7.2, 9.5, 14.3, 16.7, 18.0, 19.3, 21.5, 22.1, 24.0, 25.2, and 26.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.2, 9.5, and 14.3° 2θ. In one embodiment, the XRPD pattern further comprises peaks at approximately 19.3 and 25.2° 2θ. In one embodiment, the XRPD pattern further comprises peaks at approximately 16.7 and 18.0° 2θ. In one embodiment, the XRPD pattern comprises peaks at approximately 7.2, 9.5, 14.3, 16.7, 18.0, 19.3, 21.5, 22.1, 24.0, and 25.2° 2θ.

In one embodiment, provided herein is a solid form comprising a hydrochloride salt of Compound 1, characterized by an XRPD pattern that matches the XRPD pattern presented in FIG. 154.

In one embodiment, the XRPD patterns are obtained using Cu Kα radiation.

In one embodiment, Form V of a hydrochloride salt of Compound 1 is prepared by suspending amorphous hydrochloride salt of Compound 1 in NMP at about room temperature for a period of time (e.g., about 7 days).

In one embodiment, provided herein is a solid form comprising Form V of a hydrochloride salt of Compound 1 and one or more forms of a free base of Compound 1 (e.g., amorphous form and crystalline forms). In one embodiment, provided herein is a solid form comprising Form V of a hydrochloride salt of Compound 1 and amorphous hydrochloride salt of Compound 1. In one embodiment, provided herein is a solid form comprising Form V of a hydrochloride salt Compound 1 and one or more other crystalline forms of a hydrochloride salt of Compound 1 provided herein. In one embodiment, provided herein is a solid form comprising Form V of a hydrochloride salt of Compound 1 and one or more forms (e.g., amorphous or crystalline) of a salt of Compound 1 provided herein.

(xxiii) Form W of Hydrochloride Salt of Compound 1

In certain embodiments, provided herein is Form W of a hydrochloride salt of Compound 1.

In one embodiment, Form W is crystalline. In one embodiment, Form W is substantially crystalline. In one embodiment, Form W is moderately crystalline. In one embodiment, Form W is partially crystalline.

In one embodiment, Form W is a solvate of a hydrochloride salt of Compound 1. In one embodiment, Form W is an anisole solvate of a hydrochloride salt of Compound 1.

A representative XRPD pattern of Form W of a hydrochloride salt of Compound 1 is provided in FIG. 155.

In one embodiment, provided herein is a solid form comprising a hydrochloride salt of Compound 1, characterized by 1, 2, 3, 4, 5, 6, 7, 8, 9, 10, 11, 12, 13, 14, or all of the peaks located at approximately the following positions: 5.7, 7.5, 9.6, 14.1, 15.4, 16.8, 17.6, 18.9, 19.6, 19.9, 23.5, 24.2, 25.0, 25.9, and 28.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 9.6, 16.8, and 17.6° 2θ. In one embodiment, the XRPD pattern further comprises peaks at approximately 7.5 and 15.4° 2θ. In one embodiment, the XRPD pattern further comprises peaks at approximately 5.7, 19.6, and 19.9° 2θ. In one embodiment, the XRPD pattern comprises peaks at approximately 5.7, 7.5, 9.6, 14.1, 15.4, 16.8, 17.6, 18.9, 19.6, 19.9, and 24.2° 2θ.

In one embodiment, provided herein is a solid form comprising a hydrochloride salt of Compound 1, characterized by an XRPD pattern that matches the XRPD pattern presented in FIG. 155.

In one embodiment, the XRPD patterns are obtained using Cu Kα radiation.

In one embodiment, Form W of a hydrochloride salt of Compound 1 is prepared by suspending amorphous hydrochloride salt of Compound 1 in anisole at about 50° C. for a period of time (e.g., about 7 days).

In one embodiment, provided herein is a solid form comprising Form W of a hydrochloride salt of Compound 1 and one or more forms of a free base of Compound 1 (e.g., amorphous form and crystalline forms). In one embodiment, provided herein is a solid form comprising Form W of a hydrochloride salt of Compound 1 and amorphous hydrochloride salt of Compound 1. In one embodiment, provided herein is a solid form comprising Form W of a hydrochloride salt Compound 1 and one or more other crystalline forms of a hydrochloride salt of Compound 1 provided herein. In one embodiment, provided herein is a solid form comprising Form W of a hydrochloride salt of Compound 1 and one or more forms (e.g., amorphous or crystalline) of a salt of Compound 1 provided herein.

(xxiv) Form X of Hydrochloride Salt of Compound 1

In certain embodiments, provided herein is Form X of a hydrochloride salt of Compound 1.

In one embodiment, Form X is crystalline. In one embodiment, Form X is substantially crystalline. In one embodiment, Form X is moderately crystalline. In one embodiment, Form X is partially crystalline.

In one embodiment, Form X is a solvate of a hydrochloride salt of Compound 1. In one embodiment, Form X is a CPME solvate of a hydrochloride salt of Compound 1. In one embodiment, Form X and Form Y of a hydrochloride salt of Compound 1 are isomorphic solvate forms. In one embodiment, Form X and Form O are also isomorphic solvate forms.

A representative XRPD pattern of Form X of a hydrochloride salt of Compound 1 is provided in FIG. 156.

In one embodiment, provided herein is a solid form comprising a hydrochloride salt of Compound 1, characterized by 1, 2, 3, 4, 5, 6, 7, 8, 9, 10, 11, 12, 13, 14, 15, 16, or all of the peaks located at approximately the following positions: 5.7, 7.6, 9.5, 12.7, 14.1, 15.4, 16.8, 17.6, 18.0, 19.5, 19.9, 23.2, 24.1, 25.1, 26.0, 26.6, and 28.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 9.5, 16.8, and 17.6° 2θ. In one embodiment, the XRPD pattern further comprises peaks at approximately 7.6, 15.4, and 19.5° 2θ. In one embodiment, the XRPD pattern further comprises peaks at approximately 5.7 and 19.9° 2θ. In one embodiment, the XRPD pattern comprises peaks at approximately 5.7, 7.6, 9.5, 14.1, 15.4, 16.8, 17.6, 18.0, 19.5, 19.9, 23.2, 24.1, and 26.0° 2θ.

In one embodiment, provided herein is a solid form comprising a hydrochloride salt of Compound 1, characterized by an XRPD pattern that matches the XRPD pattern presented in FIG. 156.

In one embodiment, the XRPD patterns are obtained using Cu Kα radiation.

In one embodiment, Form X of a hydrochloride salt of Compound 1 is prepared by suspending amorphous hydrochloride salt of Compound 1 in CPME at about 50° C. for a period of time (e.g., about 7 days).

In one embodiment, provided herein is a solid form comprising Form X of a hydrochloride salt of Compound 1 and one or more forms of a free base of Compound 1 (e.g., amorphous form and crystalline forms). In one embodiment, provided herein is a solid form comprising Form X of a hydrochloride salt of Compound 1 and amorphous hydrochloride salt of Compound 1. In one embodiment, provided herein is a solid form comprising Form X of a hydrochloride salt Compound 1 and one or more other crystalline forms of a hydrochloride salt of Compound 1 provided herein. In one embodiment, provided herein is a solid form comprising Form X of a hydrochloride salt of Compound 1 and one or more forms (e.g., amorphous or crystalline) of a salt of Compound 1 provided herein.

(xxv) Form Y of Hydrochloride Salt of Compound 1

In certain embodiments, provided herein is Form Y of a hydrochloride salt of Compound 1.

In one embodiment, Form Y is crystalline. In one embodiment, Form Y is substantially crystalline. In one embodiment, Form Y is moderately crystalline. In one embodiment, Form Y is partially crystalline.

In one embodiment, Form Y is a solvate of a hydrochloride salt of Compound 1. In one embodiment, Form Y is an MTBE solvate of a hydrochloride salt of Compound 1. In one embodiment, Form Y and Form X of a hydrochloride salt of Compound 1 are isomorphic solvate forms. In one embodiment, Form Y and Form O are also isomorphic solvate forms.

A representative XRPD pattern of Form Y of a hydrochloride salt of Compound 1 is provided in FIG. 157.

In one embodiment, provided herein is a solid form comprising a hydrochloride salt of Compound 1, characterized by 1, 2, 3, 4, 5, 6, 7, 8, 9, 10, 11, 12, 13, or all of the peaks located at approximately the following positions: 5.8, 7.6, 9.6, 14.3, 15.6, 16.7, 18.2, 19.5, 23.2, 24.1, 25.1, 26.1, 26.7, and 28.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.6, 16.7, and 18.2° 2θ. In one embodiment, the XRPD pattern further comprises peaks at approximately 5.8 and 19.5° 2θ. In one embodiment, the XRPD pattern further comprises peaks at approximately 15.6 and 26.1° 2θ. In one embodiment, the XRPD pattern comprises peaks at approximately 5.8, 7.6, 9.6, 14.3, 15.6, 16.7, 18.2, 19.5, 24.1, and 26.1° 2θ.

In one embodiment, provided herein is a solid form comprising a hydrochloride salt of Compound 1, characterized by an XRPD pattern that matches the XRPD pattern presented in FIG. 157.

In one embodiment, the XRPD patterns are obtained using Cu Kα radiation.

In one embodiment, Form Y of a hydrochloride salt of Compound 1 is prepared by suspending amorphous hydrochloride salt of Compound 1 in MTBE at about 50° C. for a period of time (e.g., about 7 days).

In one embodiment, provided herein is a solid form comprising Form Y of a hydrochloride salt of Compound 1 and one or more forms of a free base of Compound 1 (e.g., amorphous form and crystalline forms). In one embodiment, provided herein is a solid form comprising Form Y of a hydrochloride salt of Compound 1 and amorphous hydrochloride salt of Compound 1. In one embodiment, provided herein is a solid form comprising Form Y of a hydrochloride salt Compound 1 and one or more other crystalline forms of a hydrochloride salt of Compound 1 provided herein. In one embodiment, provided herein is a solid form comprising Form Y of a hydrochloride salt of Compound 1 and one or more forms (e.g., amorphous or crystalline) of a salt of Compound 1 provided herein.

(xxvi) Form Z of Hydrochloride Salt of Compound 1

In certain embodiments, provided herein is Form Z of a hydrochloride salt of Compound 1.

In one embodiment, Form Z is crystalline. In one embodiment, Form Z is substantially crystalline. In one embodiment, Form Z is moderately crystalline. In one embodiment, Form Z is partially crystalline.

In one embodiment, Form Z is a solvate of a hydrochloride salt of Compound 1. In one embodiment, Form Z is a n-butanol solvate of a hydrochloride salt of Compound 1.

A representative XRPD pattern of Form Z of a hydrochloride salt of Compound 1 is provided in FIG. 158.

In one embodiment, provided herein is a solid form comprising a hydrochloride salt of Compound 1, characterized by 1, 2, 3, 4, 5, 6, 7, 8, 9, 10, 11, 12, 13, 14, 15, or all of the peaks located at approximately the following positions: 5.9, 7.5, 8.0, 9.7, 11.3, 12.4, 14.1, 16.4, 17.3, 18.8, 20.4, 21.9, 23.2, 24.0, 25.4, and 25.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 17.3, 18.8, and 20.4° 2θ. In one embodiment, the XRPD pattern further comprises peaks at approximately 7.5 and 24.0° 2θ. In one embodiment, the XRPD pattern further comprises peaks at approximately 5.9, 8.0, and 9.7° 2θ. In one embodiment, the XRPD pattern comprises peaks at approximately 5.9, 7.5, 8.0, 9.7, 11.3, 12.4, 14.1, 16.4, 17.3, 18.8, 20.4, and 24.0° 2θ.

In one embodiment, provided herein is a solid form comprising a hydrochloride salt of Compound 1, characterized by an XRPD pattern that matches the XRPD pattern presented in FIG. 158.

In one embodiment, the XRPD patterns are obtained using Cu Kα radiation.

In one embodiment, Form Z of a hydrochloride salt of Compound 1 is prepared by suspending amorphous hydrochloride salt of Compound 1 in n-butanol at about 50° C. for a period of time (e.g., about 7 days).

In one embodiment, provided herein is a solid form comprising Form Z of a hydrochloride salt of Compound 1 and one or more forms of a free base of Compound 1 (e.g., amorphous form and crystalline forms). In one embodiment, provided herein is a solid form comprising Form Z of a hydrochloride salt of Compound 1 and amorphous hydrochloride salt of Compound 1. In one embodiment, provided herein is a solid form comprising Form Z of a hydrochloride salt Compound 1 and one or more other crystalline forms of a hydrochloride salt of Compound 1 provided herein. In one embodiment, provided herein is a solid form comprising Form Z of a hydrochloride salt of Compound 1 and one or more forms (e.g., amorphous or crystalline) of a salt of Compound 1 provided herein.

(xxvii) Form AA of Hydrochloride Salt of Compound 1

In certain embodiments, provided herein is Form AA of a hydrochloride salt of Compound 1.

In one embodiment, Form AA is crystalline. In one embodiment, Form AA is substantially crystalline. In one embodiment, Form AA is moderately crystalline. In one embodiment, Form AA is partially crystalline.

In one embodiment, Form AA is a solvate of a hydrochloride salt of Compound 1. In one embodiment, Form AA is a mixed acetone and water solvate of a hydrochloride salt of Compound 1.

A representative XRPD pattern of Form AA of a hydrochloride salt of Compound 1 is provided in FIG. 159.

In one embodiment, provided herein is a solid form comprising a hydrochloride salt of Compound 1, characterized by 1, 2, 3, 4, 5, 6, 7, 8, 9, 10, 11, 12, or all of the peaks located at approximately the following positions: 5.5, 7.2, 8.3, 11.3, 14.5, 15.5, 17.2, 18.2, 19.2, 21.7, 22.2, 23.3, and 26.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 8.3, 15.5, and 18.2° 2θ. In one embodiment, the XRPD pattern further comprises peaks at approximately 7.2 and 22.2° 2θ. In one embodiment, the XRPD pattern further comprises peaks at approximately 5.5 and 26.9° 2θ. In one embodiment, the XRPD pattern comprises peaks at approximately 5.5, 7.2, 8.3, 11.3, 14.5, 15.5, 17.2, 18.2, 19.2, 22.2, and 26.9° 2θ.

In one embodiment, provided herein is a solid form comprising a hydrochloride salt of Compound 1, characterized by an XRPD pattern that matches the XRPD pattern presented in FIG. 159.

In one embodiment, the XRPD patterns are obtained using Cu Kα radiation.

In one embodiment, Form AA of a hydrochloride salt of Compound 1 is prepared by suspending Form L of a hydrochloride salt of Compound 1 in a mixture solvent of acetone and water (e.g., about 97:3 v/v) at about room temperature for a period of time (e.g., about 14 days).

In one embodiment, provided herein is a solid form comprising Form AA of a hydrochloride salt of Compound 1 and one or more forms of a free base of Compound 1 (e.g., amorphous form and crystalline forms). In one embodiment, provided herein is a solid form comprising Form AA of a hydrochloride salt of Compound 1 and amorphous hydrochloride salt of Compound 1. In one embodiment, provided herein is a solid form comprising Form AA of a hydrochloride salt Compound 1 and one or more other crystalline forms of a hydrochloride salt of Compound 1 provided herein. In one embodiment, provided herein is a solid form comprising Form AA of a hydrochloride salt of Compound 1 and one or more forms (e.g., amorphous or crystalline) of a salt of Compound 1 provided herein.

(xxviii) Form AB of Hydrochloride Salt of Compound 1

In certain embodiments, provided herein is Form AB of a hydrochloride salt of Compound 1.

In one embodiment, Form AB is crystalline. In one embodiment, Form AB is substantially crystalline. In one embodiment, Form AB is moderately crystalline. In one embodiment, Form AB is partially crystalline.

In one embodiment, Form AB is a solvate of a hydrochloride salt of Compound 1. In one embodiment, Form AB is an ethyl acetate solvate of a hydrochloride salt of Compound 1.

A representative XRPD pattern of Form AB of a hydrochloride salt of Compound 1 is provided in FIG. 160.

In one embodiment, provided herein is a solid form comprising a hydrochloride salt of Compound 1, characterized by 1, 2, 3, 4, 5, 6, 7, or all of the peaks located at approximately the following positions: 5.9, 7.7, 10.4, 14.2, 18.2, 20.9, 24.5, and 25.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by all of the peaks.

In one embodiment, provided herein is a solid form comprising a hydrochloride salt of Compound 1, characterized by an XRPD pattern comprising peaks at approximately 7.7, 18.2, and 20.9° 2θ. In one embodiment, the XRPD pattern further comprises peaks at approximately 5.9 and 14.2° 2θ. In one embodiment, the XRPD pattern comprises peaks at approximately 5.9, 7.7, 10.4, 14.2, 18.2, 20.9, and 25.9° 2θ.

In one embodiment, provided herein is a solid form comprising a hydrochloride salt of Compound 1, characterized by an XRPD pattern that matches the XRPD pattern presented in FIG. 160.

In one embodiment, the XRPD patterns are obtained using Cu Kα radiation.

In one embodiment, Form AB of a hydrochloride salt of Compound 1 is prepared by suspending amorphous hydrochloride salt of Compound 1 in ethyl acetate at about 50° C. for a period of time (e.g., about 7 days).

In one embodiment, provided herein is a solid form comprising Form AB of a hydrochloride salt of Compound 1 and one or more forms of a free base of Compound 1 (e.g., amorphous form and crystalline forms). In one embodiment, provided herein is a solid form comprising Form AB of a hydrochloride salt of Compound 1 and amorphous hydrochloride salt of Compound 1. In one embodiment, provided herein is a solid form comprising Form AB of a hydrochloride salt Compound 1 and one or more other crystalline forms of a hydrochloride salt of Compound 1 provided herein. In one embodiment, provided herein is a solid form comprising Form AB of a hydrochloride salt of Compound 1 and one or more forms (e.g., amorphous or crystalline) of a salt of Compound 1 provided herein.

(xxix) Form AC of Hydrochloride Salt of Compound 1

In certain embodiments, provided herein is Form AC of a hydrochloride salt of Compound 1.

In one embodiment, Form AC is crystalline. In one embodiment, Form AC is substantially crystalline. In one embodiment, Form AC is moderately crystalline. In one embodiment, Form AC is partially crystalline.

In one embodiment, Form AC is a solvate of a hydrochloride salt of Compound 1. In one embodiment, Form AC is a toluene solvate of a hydrochloride salt of Compound 1.

A representative XRPD pattern of Form AC of a hydrochloride salt of Compound 1 is provided in FIG. 161.

In one embodiment, provided herein is a solid form comprising a hydrochloride salt of Compound 1, characterized by 1, 2, 3, 4, 5, 6, 7, 8, 9, 10, 11, 12, 13, 14, or all of the peaks located at approximately the following positions: 5.8, 7.8, 9.9, 14.1, 15.6, 17.0, 18.2, 20.0, 23.4, 24.2, 25.8, 26.5, 27.0, 27.7, and 28.3° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrochloride salt of Compound 1, characterized by an XRPD pattern comprising peaks at approximately 14.1, 18.2, and 25.8° 2θ. In one embodiment, the XRPD pattern further comprises peaks at approximately 7.8 and 15.6° 2θ. In one embodiment, the XRPD pattern further comprises peaks at approximately 5.8 and 20.0° 2θ. In one embodiment, the XRPD pattern comprises peaks at approximately 5.8, 7.8, 9.9, 14.1, 15.6, 17.0, 18.2, 20.0, 23.4, 24.2, and 25.8° 2θ.

In one embodiment, provided herein is a solid form comprising a hydrochloride salt of Compound 1, characterized by an XRPD pattern that matches the XRPD pattern presented in FIG. 161.

In one embodiment, the XRPD patterns are obtained using Cu Kα radiation.

In one embodiment, Form AB of a hydrochloride salt of Compound 1 is prepared by suspending amorphous hydrochloride salt of Compound 1 in toluene at about 50° C. for a period of time (e.g., about 7 days).

In one embodiment, provided herein is a solid form comprising Form AC of a hydrochloride salt of Compound 1 and one or more forms of a free base of Compound 1 (e.g., amorphous form and crystalline forms). In one embodiment, provided herein is a solid form comprising Form AC of a hydrochloride salt of Compound 1 and amorphous hydrochloride salt of Compound 1. In one embodiment, provided herein is a solid form comprising Form AC of a hydrochloride salt Compound 1 and one or more other crystalline forms of a hydrochloride salt of Compound 1 provided herein. In one embodiment, provided herein is a solid form comprising Form AC of a hydrochloride salt of Compound 1 and one or more forms (e.g., amorphous or crystalline) of a salt of Compound 1 provided herein.

(c) Mesylate Salt of Compound 1

In some embodiments, provided herein is a mesylate salt of Compound 1. It is contemplated that a mesylate salt of Compound 1 can exist in a variety of solid forms. Such solid forms include crystalline solids, such as polymorphs, solvates and hydrates of crystalline mesylate salt of Compound 1, as well as amorphous solids, or mixtures thereof.

In one embodiment, provided herein is a solid form comprising a mesylate salt of Compound 1. In one embodiment, the solid form is a solvate of a mesylate salt of Compound 1. In one embodiment, the solid form is a hydrate of a mesylate salt of Compound 1. In one embodiment, the solid form is a non-solvated form of a mesylate salt of Compound 1. In one embodiment, the solid form is a desolvated form of a mesylate salt of Compound 1. In one embodiment, the solid form is an anhydrous form (anhydrate) of a mesylate salt of Compound 1. In one embodiment, the solid form is a dehydrated form of a mesylate salt of Compound 1.

In some embodiments, the molar ratio of Compound 1 to methanesulfonic acid in the solid form ranges from about 1:1 to about 1:2. In one embodiment, the molar ratio is about 1:2 (i.e., bis-mesylate salt). In another embodiment, the molar ratio is about 1:1 (i.e., mono-mesylate salt).

(i) Form A of Mesylate Salt of Compound 1

In certain embodiments, provided herein is Form A of a mesylate salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to methanesulfonic acid in Form A is about 1:1. In one embodiment, Form A is a mono-mesylate salt of Compound 1.

In one embodiment, Form A is a solvate of a mesylate salt of Compound 1. In one embodiment, Form A is an ethyl acetate solvate of a mesylate salt of Compound 1.

A representative XRPD pattern of Form A of a mesylate salt of Compound 1 is provided in FIG. 70.

In one embodiment, provided herein is a solid form comprising a mesylate salt of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 5.5, 9.1, 12.1, 12.7, 13.2, 14.3, 15.2, 15.9, 16.6, 16.9, 17.7, 18.3, 19.0, 21.4, 21.7, 22.2, 22.7, 23.3, 23.9, 24.6, 25.6, 27.1, and 28.0° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a mesylate salt of Compound 1, characterized by an XRPD pattern comprising peaks at approximately 16.9, 17.7, and 22.7° 2θ. In one embodiment, the XRPD pattern further comprises peaks at approximately 15.2 and 23.9° 2θ. In one embodiment, the XRPD pattern further comprises peaks at approximately 9.1 and 16.6° 2θ. In one embodiment, the XRPD pattern comprises peaks at approximately 9.1, 13.2, 14.3, 15.2, 16.6, 16.9, 17.7, 21.4, 22.7, 23.3, and 23.9° 2θ.

In one embodiment, provided herein is a solid form comprising a mesylate salt of Compound 1, characterized by an XRPD pattern that matches the XRPD pattern presented in FIG. 70.

In one embodiment, the XRPD patterns are obtained using Cu Kα radiation.

A representative thermal gravimetric analysis (TGA) thermogram of Form A of a mesylate salt of Compound 1 is provided in FIG. 71. In one embodiment, provided herein is a solid form comprising a mesylate salt of Compound 1, which exhibits a weight loss of about 9.6% upon heating from about 25° C. to about 180° C. In one embodiment, without being limited by any particular theory, the weight loss corresponds to the loss of ethyl acetate (and trace water). In one embodiment, provided herein is a solid form comprising a mesylate salt of Compound 1, characterized by a TGA thermogram that matches the TGA thermogram presented in FIG. 71.

A representative differential scanning calorimetry (DSC) thermogram of Form A of a mesylate salt of Compound 1 is presented in FIG. 72. In one embodiment, provided herein is a solid form comprising a mesylate salt of Compound 1, which exhibits, as characterized by DSC, a first (broad) thermal event with a peak temperature of about 69° C., a second thermal event with an onset temperature of about 132° C., and a third thermal event with an onset temperature of about 228° C. In one embodiment, the second thermal event also has a peak temperature of about 155° C., and the third thermal event also has a peak temperature of about 264° C. In one embodiment, without being limited by any particular theory, the first thermal event corresponds to partial desolvation, and the second thermal event corresponds to melting and desolvation. In one embodiment, provided herein is a solid form comprising a mesylate salt of Compound 1, characterized by a DSC thermogram that matches the DSC thermogram presented in FIG. 72.

A representative dynamic vapor sorption (DVS) isotherm plot of the Form A of a mesylate salt of Compound 1 is provided in FIG. 73. In one embodiment, provided herein is a solid form comprising a mesylate salt of Compound 1, which exhibits a mass increase of about 20.8% when subjected to an increase in a relative humidity (RH) from about 5% to about 95%. In one embodiment, provided herein is a solid form comprising a mesylate salt of Compound 1, characterized by a DVS isotherm plot which matches the DVS isotherm plot presented in FIG. 73. In one embodiment, Form A is hygroscopic.

In one embodiment, Form A of a mesylate salt of Compound 1 is prepared by subjecting a mixture of Compound 1 and methanesulfonic acid (e.g., about 1:1 molar ratio) in ethyl acetate to a temperature cycle (e.g., between about 25° C. and about 35° C.) for a period of time (e.g., from about 1 day to about 14 days, e.g., about 5 days). In one embodiment, the product prepared is optionally dried (e.g., under vacuum at 40° C.) for a period of time (e.g., about 4.5 hours).

In one embodiment, provided herein is a solid form comprising Form A of a mesylate salt of Compound 1 and one or more forms of a free base of Compound 1 (e.g., amorphous form and crystalline forms). In one embodiment, provided herein is a solid form comprising Form A of a mesylate salt of Compound 1 and amorphous mesylate salt of Compound 1. In one embodiment, provided herein is a solid form comprising Form A of a mesylate salt Compound 1 and one or more other crystalline forms of a mesylate salt of Compound 1. In one embodiment, provided herein is a solid form comprising Form A of a mesylate salt of Compound 1 and one or more forms (e.g., amorphous or crystalline) of a salt of Compound 1 provided herein.

(ii) Form B of Mesylate Salt of Compound 1

In certain embodiments, provided herein is Form B of a mesylate salt of Compound 1.

In one embodiment, Form B is crystalline. In one embodiment, Form B is substantially crystalline. In one embodiment, Form B is moderately crystalline. In one embodiment, Form B is partially crystalline.

In one embodiment, Form B is a solvate of a mesylate salt of Compound 1. In one embodiment, Form B is a 1,4-dioxane solvate of a mesylate salt of Compound 1.

A representative XRPD pattern of Form B of a mesylate salt of Compound 1 is provided in FIG. 134.

In one embodiment, provided herein is a solid form comprising a mesylate salt of Compound 1, characterized by 1, 2, 3, 4, 5, 6, 7, 8, 9, 10, 11, 12, 13, 14, 15, 16, or all of the peaks located at approximately the following positions: 5.7, 7.8, 9.1, 10.1, 11.7, 14.2, 14.5, 15.5, 16.1, 17.1, 17.7, 19.3, 22.6, 23.5, 26.1, 26.7, and 28.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a mesylate salt of Compound 1, characterized by an XRPD pattern comprising peaks at approximately 5.7, 9.1, and 26.1° 2θ. In one embodiment, the XRPD pattern further comprises peaks at approximately 14.2, 19.3, and 26.7° 2θ. In one embodiment, the XRPD pattern further comprises peaks at approximately 14.5 and 16.1° 2θ. In one embodiment, the XRPD pattern comprises peaks at approximately 5.7, 7.8, 9.1, 11.7, 14.2, 14.5, 16.1, 19.3, 26.1, and 26.7° 2θ.

In one embodiment, provided herein is a solid form comprising a mesylate salt of Compound 1, characterized by an XRPD pattern that matches the XRPD pattern presented in FIG. 134.

In one embodiment, the XRPD patterns are obtained using Cu Kα radiation.

Representative TG/DTA thermograms of Form B of a mesylate salt of Compound 1 are provided in FIG. 135. In one embodiment, provided herein is a solid form comprising a mesylate salt of Compound 1, which exhibits a first weight loss of about 1.5% upon heating from about 25° C. to about 80° C., and a second weight loss of about 1.4% upon heating from about 80° C. to about 160° C. In one embodiment, without being limited by any particular theory, the first weight loss corresponds to the loss of unbound solvent, and the second weight loss corresponds to possible dehydration. In one embodiment, provided herein is a solid form comprising a mesylate salt of Compound 1, characterized by a TGA thermogram that matches the TGA thermogram presented in FIG. 135.

In one embodiment, provided herein is a solid form comprising a mesylate salt of Compound 1, which exhibits, as characterized by DTA, a thermal event (or a series of small thermal events) at the temperature from about 222° C. to about 249° C. In one embodiment, without being limited by any particular theory, the thermal event corresponds to degradation. In one embodiment, provided herein is a solid form comprising a mesylate salt of Compound 1, characterized by a DTA thermogram that matches the DTA thermogram presented in FIG. 135.

In one embodiment, Form B of a mesylate salt of Compound 1 is prepared by subjecting a slurry comprising Compound 1 and methanesulfonic acid in 1,4-dioxane to a temperature cycle (e.g., at room temperature for about 4 hours and then at about 40° C. for about 4 hours) for a period of time (e.g., 72 hours).

In one embodiment, provided herein is a solid form comprising Form B of a mesylate salt of Compound 1 and one or more forms of a free base of Compound 1 (e.g., amorphous form and crystalline forms). In one embodiment, provided herein is a solid form comprising Form B of a mesylate salt of Compound 1 and amorphous mesylate salt of Compound 1. In one embodiment, provided herein is a solid form comprising Form B of a mesylate salt Compound 1 and one or more other crystalline forms of a mesylate salt of Compound 1. In one embodiment, provided herein is a solid form comprising Form B of a mesylate salt of Compound 1 and one or more forms (e.g., amorphous or crystalline) of a salt of Compound 1 provided herein.

(d) Hydrobromide Salt of Compound 1

In some embodiments, provided herein is a hydrobromide salt of Compound 1. It is contemplated that a hydrobromide salt of Compound 1 can exist in a variety of solid forms. Such solid forms include crystalline solids, such as polymorphs, solvates and hydrates of crystalline hydrobromide salt of Compound 1, as well as amorphous solids, or mixtures thereof.

In one embodiment, provided herein is a solid form comprising a hydrobromide salt of Compound 1. In one embodiment, the solid form is a solvate of a hydrobromide salt of Compound 1. In one embodiment, the solid form is a hydrate of a hydrobromide salt of Compound 1. In one embodiment, the solid form is a non-solvated form of a hydrobromide salt of Compound 1. In one embodiment, the solid form is a desolvated form of a hydrobromide salt of Compound 1. In one embodiment, the solid form is an anhydrous form (anhydrate) of a hydrobromide salt of Compound 1. In one embodiment, the solid form is a dehydrated form of a hydrobromide salt of Compound 1.

In some embodiments, the molar ratio of Compound 1 to hydrobromic acid in the solid form ranges from about 1:1 to about 1:2. In one embodiment, the molar ratio is about 1:2 (i.e., bis-hydrobromide salt). In another embodiment, the molar ratio is about 1:1 (i.e., mono-hydrobromide salt).

(i) Form B of Hydrobromide Salt of Compound 1

In certain embodiments, provided herein is Form B of a hydrobromide salt of Compound 1.

In one embodiment, Form B is crystalline. In one embodiment, Form B is substantially crystalline. In one embodiment, Form B is moderately crystalline. In one embodiment, Form B is partially crystalline.

In one embodiment, Form B is a hydrate of a hydrobromide salt of Compound 1.

A representative XRPD pattern of Form B of a hydrobromide salt of Compound 1 is provided in FIG. 74.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, or all of the peaks located at approximately the following positions: 3.8, 5.8, 7.6, 9.9, 10.5, 11.7, 13.9, 14.8, 15.5, 17.1, 18.0, 19.9, 20.6, 25.3, 26.0, 26.6, 27.3, 27.9, and 29.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 5.8, 13.9, and 25.3° 2θ. In one embodiment, the XRPD pattern further comprises peaks at approximately 3.8 and 7.6° 2θ. In one embodiment, the XRPD pattern further comprises peaks at approximately 14.8, 19.9, and 26.0° 2θ. In one embodiment, the XRPD pattern comprises peaks at approximately 3.8, 5.8, 7.6, 10.5, 13.9, 14.8, 19.9, 20.6, 25.3, 26.0, and 27.9° 2θ.

In one embodiment, provided herein is a solid form comprising a hydrobromide salt of Compound 1, characterized by an XRPD pattern that matches the XRPD pattern presented in FIG. 74.

In one embodiment, the XRPD patterns are obtained using Cu Kα radiation.

Representative TG/DTA thermograms of Form B of a hydrobromide salt of Compound 1 are provided in FIG. 75. In one embodiment, provided herein is a solid form comprising a hydrobromide salt of Compound 1, which exhibits a weight loss of about 12.7% upon heating from about 25° C. to about 190° C. In one embodiment, without being limited by any particular theory, the weight loss corresponds to the loss of water (e.g., about 5 equiv. of water). In one embodiment, provided herein is a solid form comprising a hydrobromide salt of Compound 1, characterized by a TGA thermogram that matches the TGA thermogram presented in FIG. 75.

In one embodiment, provided herein is a solid form comprising a hydrobromide salt of Compound 1, which exhibits, as characterized by DTA, a thermal event with an onset temperature of about 169° C. In one embodiment, the thermal event also has a peak temperature of about 193° C. In one embodiment, without being limited by any particular theory, the thermal event corresponds to degradation. In one embodiment, provided herein is a solid form comprising a hydrobromide salt of Compound 1, characterized by a DTA thermogram that matches the DTA thermogram presented in FIG. 75.

In one embodiment, Form B of a hydrobromide salt of Compound 1 is prepared by subjecting a mixture of Compound 1 and hydrobromic acid (e.g., about 1:1 molar ratio) in a solvent to a temperature cycle (e.g., between about 25° C. and about 35° C.) for a period of time (e.g., from about 1 day to about 14 days, e.g., about 7 days). In one embodiment, the solvent is acetone, anisole, ethyl formate, iPrOAc, MEK, TBME, toluene, a mixture of DMA and iPrOAc (e.g., 1:9 v/v), or a mixture of DMF and toluene (e.g., 1:9 v/v). In one embodiment, the solvent is TBME.

In one embodiment, Form B of a hydrobromide salt of Compound 1 is prepared by subjecting a slurry comprising Compound 1 and hydrobromic acid in a solvent to a temperature cycle (e.g., at room temperature for about 4 hours and then at about 40° C. for about 4 hours) for a period of time (e.g., 72 hours). In one embodiment, the solvent is 1,4-dioxane, acetone, ethyl acetate, MEK, THF, a mixture of THF and water (e.g., about 1:1 v/v), toluene, or water. In one embodiment, the solvent is MEK.

In one embodiment, provided herein is a solid form comprising Form B of a hydrobromide salt of Compound 1 and one or more forms of a free base of Compound 1 (e.g., amorphous form and crystalline forms). In one embodiment, provided herein is a solid form comprising Form B of a hydrobromide salt of Compound 1 and amorphous hydrobromide salt of Compound 1. In one embodiment, provided herein is a solid form comprising Form B of a hydrobromide salt Compound 1 and one or more other crystalline forms of a hydrobromide salt of Compound 1 provided herein. In one embodiment, provided herein is a solid form comprising Form B of a hydrobromide salt of Compound 1 and one or more forms (e.g., amorphous or crystalline) of a salt of Compound 1 provided herein.

(ii) Form A of Hydrobromide Salt of Compound 1

In certain embodiments, provided herein is Form A of a hydrobromide salt of Compound 1.

In one embodiment, Form A is crystalline. In one embodiment, Form A is substantially crystalline. In one embodiment, Form A is moderately crystalline. In one embodiment, Form A is partially crystalline.

In one embodiment, the molar ratio of Compound 1 to hydrobromic acid in Form A is about 1:1. In one embodiment, Form A is a mono-hydrobromide salt of Compound 1.

In one embodiment, Form A is a non-solvated form of a hydrobromide salt of Compound 1. In one embodiment, Form A is an anhydrate of a hydrobromide salt of Compound 1.

A representative XRPD pattern of Form A of a hydrobromide salt of Compound 1 is provided in FIG. 76.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 4.3, 10.3, 11.9, 12.8, 14.4, 15.6, 15.9, 17.1, 17.6, 18.8, 19.3, 20.2, 20.7, 22.4, 22.8, 23.3, 24.0, 26.0, 26.4, 26.9, 27.7, 28.5, 29.6, and 31.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, 19, 20, 21, 22, 23, 24, 25, or all of the peaks located at approximately the following positions: 4.3, 10.3, 11.9, 12.8, 15.7, 15.9, 17.1, 17.2, 17.7, 18.8, 19.3, 19.5, 19.6, 20.2, 20.3, 20.7, 22.5, 22.8, 23.3, 23.9, 24.1, 26.0, 26.3, 26.8, 27.7, and 31.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 10.3, 19.3, and 24.0° 2θ. In one embodiment, the XRPD pattern further comprises peaks at approximately 17.1 and 20.7° 2θ. In one embodiment, the XRPD pattern further comprises peaks at approximately 12.8 and 15.6° 2θ. In one embodiment, the XRPD pattern comprises peaks at approximately 10.3, 12.8, 15.6, 15.9, 17.1, 17.6, 19.3, 20.7, 24.0, and 26.0° 2θ.

In one embodiment, provided herein is a solid form comprising a hydrobromide salt of Compound 1, characterized by an XRPD pattern that matches the XRPD pattern presented in FIG. 76.

In one embodiment, the XRPD patterns are obtained using Cu Kα radiation.

Representative TG/DSC thermograms of Form A of a hydrobromide salt of Compound 1 are provided in FIG. 77. In one embodiment, provided herein is a solid form comprising a hydrobromide salt of Compound 1, which exhibits a weight loss of about 0.1% upon heating from about 25° C. to about 150° C. In one embodiment, provided herein is a solid form comprising a hydrobromide salt of Compound 1, characterized by a TGA thermogram that matches the TGA thermogram presented in FIG. 77.

In one embodiment, provided herein is a solid form comprising a hydrobromide salt of Compound 1, which exhibits, as characterized by DSC, a thermal event with an onset temperature of about 283° C. In one embodiment, the thermal event also has a peak temperature of about 285° C. In one embodiment, without being limited by any particular theory, the thermal event corresponds to melting. In one embodiment, provided herein is a solid form comprising a hydrobromide salt of Compound 1, characterized by a DSC thermogram that matches the DTA thermogram presented in FIG. 77.

In one alternative embodiment, provided herein is a solid form comprising a hydrobromide salt of Compound 1, which exhibits a weight loss of about 1.8% upon heating from about 25° C. to about 270° C. In one embodiment, without being limited by any particular theory, the weight loss corresponds to the loss of unbound solvent.

In one alternative embodiment, provided herein is a solid form comprising a hydrobromide salt of Compound 1, which exhibits, as characterized by DTA, a thermal event with an onset temperature of about 277° C. In one embodiment, the thermal event also has a peak temperature of about 282° C. In one embodiment, without being limited by any particular theory, the thermal event corresponds to melting.

A representative dynamic vapor sorption (DVS) isotherm plot of the Form A of a hydrobromide salt of Compound 1 is provided in FIG. 78. In one embodiment, provided herein is a solid form comprising a hydrobromide salt of Compound 1, which exhibits a mass increase of about 0.7% when subjected to an increase in a relative humidity (RH) from about 0% to about 95%. In one embodiment, provided herein is a solid form comprising a hydrobromide salt of Compound 1, characterized by a DVS isotherm plot which matches the DVS isotherm plot presented in FIG. 78. In one embodiment, Form A is slightly hygroscopic. In one embodiment, Form A remains as Form A after DVS cycle.

In one alternative embodiment, provided herein is a solid form comprising a hydrobromide salt of Compound 1, which exhibits a mass increase of about 0.7% when subjected to an increase in a relative humidity (RH) from about 5% to about 90%. In one embodiment, Form A is slightly hygroscopic. In one embodiment, Form A remains as Form A after DVS cycle.

In one embodiment, Form A of a hydrobromide salt of Compound 1 is prepared by subjecting a slurry comprising Compound 1 and hydrobromic acid in a solvent to a temperature cycle (e.g., at room temperature for about 4 hours and then at about 40° C. for about 4 hours) for a period of time (e.g., 72 hours). In one embodiment, the solvent is IPA, a mixture of acetone and water (e.g., about 1:1 v/v), a mixture of acetonitrile and water (e.g., about 1:1 v/v), ethanol, or a mixture of ethanol and water (e.g., about 1:1 v/v).

In one embodiment, provided herein is a solid form comprising Form A of a hydrobromide salt of Compound 1 and one or more forms of a free base of Compound 1 (e.g., amorphous form and crystalline forms). In one embodiment, provided herein is a solid form comprising Form A of a hydrobromide salt of Compound 1 and amorphous hydrobromide salt of Compound 1. In one embodiment, provided herein is a solid form comprising Form A of a hydrobromide salt Compound 1 and one or more other crystalline forms of a hydrobromide salt of Compound 1 provided herein. In one embodiment, provided herein is a solid form comprising Form A of a hydrobromide salt of Compound 1 and one or more forms (e.g., amorphous or crystalline) of a salt of Compound 1 provided herein.

(iii) Form C of Hydrobromide Salt of Compound 1

In certain embodiments, provided herein is Form C of a hydrobromide salt of Compound 1.

In one embodiment, Form C is crystalline. In one embodiment, Form C is substantially crystalline. In one embodiment, Form C is moderately crystalline. In one embodiment, Form C is partially crystalline.

In one embodiment, Form C is an anhydrous form of a hydrobromide salt of Compound 1.

A representative XRPD pattern of Form C of a hydrobromide salt of Compound 1 is provided in FIG. 79.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, or all of the peaks located at approximately the following positions: 5.7, 7.5, 9.6, 9.7, 10.1, 10.9, 11.5, 12.1, 13.5, 15.0, 16.5, 17.2, 18.7, 20.4, 22.0, 23.1, 24.6, 25.8, and 28.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 9.7, 10.1, and 12.1° 2θ. In one embodiment, the XRPD pattern further comprises peaks at approximately 5.7, 7.5, and 24.6° 2θ. In one embodiment, the XRPD pattern further comprises peaks at approximately 15.0 and 25.8° 2θ. In one embodiment, the XRPD pattern comprises peaks at approximately 5.7, 7.5, 9.7, 10.1, 11.5, 12.1, 15.0, 17.2, 24.6, and 25.8° 2θ.

In one embodiment, provided herein is a solid form comprising a hydrobromide salt of Compound 1, characterized by an XRPD pattern that matches the XRPD pattern presented in FIG. 79.

In one embodiment, the XRPD patterns are obtained using Cu Kα radiation.

Representative TG/DTA thermograms of Form C of a hydrobromide salt of Compound 1 are provided in FIG. 80. In one embodiment, provided herein is a solid form comprising a hydrobromide salt of Compound 1, which exhibits a weight loss of about 1.1% upon heating from about 25° C. to about 250° C. In one embodiment, without being limited by any particular theory, the weight loss corresponds to the loss of unbound solvent. In one embodiment, provided herein is a solid form comprising a hydrobromide salt of Compound 1, characterized by a TGA thermogram that matches the TGA thermogram presented in FIG. 80.

In one embodiment, provided herein is a solid form comprising a hydrobromide salt of Compound 1, which exhibits, as characterized by DTA, a thermal event with an onset temperature of about 275° C. In one embodiment, the thermal event also has a peak temperature of about 279° C. In one embodiment, without being limited by any particular theory, the thermal event corresponds to melting. In one embodiment, provided herein is a solid form comprising a hydrobromide salt of Compound 1, characterized by a DTA thermogram that matches the DTA thermogram presented in FIG. 80.

In one embodiment, Form C of a hydrobromide salt of Compound 1 is prepared by subjecting a slurry comprising Compound 1 and hydrobromic acid in acetonitrile to a temperature cycle (e.g., at room temperature for about 4 hours and then at about 40° C. for about 4 hours) for a period of time (e.g., 72 hours).

In one embodiment, provided herein is a solid form comprising Form C of a hydrobromide salt of Compound 1 and one or more forms of a free base of Compound 1 (e.g., amorphous form and crystalline forms). In one embodiment, provided herein is a solid form comprising Form C of a hydrobromide salt of Compound 1 and amorphous hydrobromide salt of Compound 1. In one embodiment, provided herein is a solid form comprising Form C of a hydrobromide salt Compound 1 and one or more other crystalline forms of a hydrobromide salt of Compound 1 provided herein. In one embodiment, provided herein is a solid form comprising Form C of a hydrobromide salt of Compound 1 and one or more forms (e.g., amorphous or crystalline) of a salt of Compound 1 provided herein.

(iv) Form D of Hydrobromide Salt of Compound 1

In certain embodiments, provided herein is Form D of a hydrobromide salt of Compound 1.

In one embodiment, Form D is crystalline. In one embodiment, Form D is substantially crystalline. In one embodiment, Form D is moderately crystalline. In one embodiment, Form D is partially crystalline.

In one embodiment, Form D is a solvate of a hydrobromide salt of Compound 1. In one embodiment, Form D is a methanol solvate of a hydrobromide salt of Compound 1.

A representative XRPD pattern of Form D of a hydrobromide salt of Compound 1 is provided in FIG. 81.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, 19, or all of the peaks located at approximately the following positions: 6.2, 7.8, 11.1, 12.2, 12.4, 13.3, 13.8, 14.5, 15.5, 15.7, 17.0, 17.2, 17.6, 19.8, 20.0, 22.5, 23.4, 24.5, 25.7, and 27.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 12.2, 12.4, and 24.5° 2θ. In one embodiment, the XRPD pattern further comprises peaks at approximately 11.1 and 15.5° 2θ. In one embodiment, the XRPD pattern further comprises peaks at approximately 6.2, 17.0, and 25.7° 2θ. In one embodiment, the XRPD pattern comprises peaks at approximately 6.2, 11.1, 12.2, 12.4, 13.3, 13.8, 15.5, 15.7, 17.0, 24.5, 25.7, and 27.5° 2θ.

In one embodiment, provided herein is a solid form comprising a hydrobromide salt of Compound 1, characterized by an XRPD pattern that matches the XRPD pattern presented in FIG. 81.

In one embodiment, the XRPD patterns are obtained using Cu Kα radiation.

Representative TG/DTA thermograms of Form D of a hydrobromide salt of Compound 1 are provided in FIG. 82. In one embodiment, provided herein is a solid form comprising a hydrobromide salt of Compound 1, which exhibits a weight loss of about 0.95% upon heating from about 25° C. to about 60° C., a weight loss of about 2.2% upon heating from about 60° C. to about 140° C., and a weight loss of about 7.8% upon heating from about 140° C. to about 220° C. In one embodiment, without being limited by any particular theory, the first weight loss corresponds to the loss of unbound solvent, the second weight loss corresponds to desolvation or dehydration, and the third weight loss corresponds to degradation. In one embodiment, provided herein is a solid form comprising a hydrobromide salt of Compound 1, characterized by a TGA thermogram that matches the TGA thermogram presented in FIG. 82.

In one embodiment, provided herein is a solid form comprising a hydrobromide salt of Compound 1, which exhibits, as characterized by DTA, a first (broad) thermal event (or two overlapping thermal events) with a peak temperature from about 192° C. to about 210° C., a second thermal event with an onset temperature of about 216° C., and a third thermal event with an onset temperature of about 268° C. In one embodiment, the second thermal event also has a peak temperature of about 221° C., and the third thermal event also has a peak temperature of about 274° C. In one embodiment, without being limited by any particular theory, the thermal event corresponds to recrystallization, and the third thermal event corresponds to melting. In one embodiment, provided herein is a solid form comprising a hydrobromide salt of Compound 1, characterized by a DTA thermogram that matches the DTA thermogram presented in FIG. 82.

In one embodiment, Form D of a hydrobromide salt of Compound 1 is prepared by subjecting a slurry comprising Compound 1 and hydrobromic acid in methanol to a temperature cycle (e.g., at room temperature for about 4 hours and then at about 40° C. for about 4 hours) for a period of time (e.g., 72 hours).

In one embodiment, provided herein is a solid form comprising Form D of a hydrobromide salt of Compound 1 and one or more forms of a free base of Compound 1 (e.g., amorphous form and crystalline forms). In one embodiment, provided herein is a solid form comprising Form D of a hydrobromide salt of Compound 1 and amorphous hydrobromide salt of Compound 1. In one embodiment, provided herein is a solid form comprising Form D of a hydrobromide salt Compound 1 and one or more other crystalline forms of a hydrobromide salt of Compound 1 provided herein. In one embodiment, provided herein is a solid form comprising Form D of a hydrobromide salt of Compound 1 and one or more forms (e.g., amorphous or crystalline) of a salt of Compound 1 provided herein.

(v) Form E of Hydrobromide Salt of Compound 1

In certain embodiments, provided herein is Form E of a hydrobromide salt of Compound 1.

In one embodiment, Form E is crystalline. In one embodiment, Form E is substantially crystalline. In one embodiment, Form E is moderately crystalline. In one embodiment, Form E is partially crystalline.

In one embodiment, Form E is a solvate of a hydrobromide salt of Compound 1. In one embodiment, Form E is an isomorphic solvate of a hydrobromide salt of Compound 1. In one embodiment, Form E is a DMAc solvate of a hydrobromide salt of Compound 1. In one embodiment, Form E is a DMF solvate of a hydrobromide salt of Compound 1.

A representative XRPD pattern of Form E of a hydrobromide salt of Compound 1 is provided in FIG. 162.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, or all of the peaks located at approximately the following positions: 5.5, 6.7, 8.1, 9.8, 10.9, 12.1, 13.5, 14.4, 15.2, 16.4, 16.7, 17.4, 18.5, 18.8, 19.2, 20.0, 20.5, 21.9, 22.5, 23.1, 23.9, 24.4, 25.1, 25.8, 26.6, 28.1, and 28.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 8.1, 13.5, and 24.4° 2θ. In one embodiment, the XRPD pattern further comprises peaks at approximately 21.9 and 25.8° 2θ. In one embodiment, the XRPD pattern further comprises peaks at approximately 16.4 and 18.5° 2θ. In one embodiment, the XRPD pattern comprises peaks at approximately 5.5, 6.7, 8.1, 13.5, 16.4, 17.4, 18.5, 19.2, 21.9, 23.9, 24.4, and 25.8° 2θ.

In one embodiment, provided herein is a solid form comprising a hydrobromide salt of Compound 1, characterized by an XRPD pattern that matches the XRPD pattern presented in FIG. 162.

In one embodiment, the XRPD patterns are obtained using Cu Kα radiation.

In one embodiment, Form E of a hydrobromide salt of Compound 1 is prepared by slowly (e.g., over a period of time of overnight or longer) evaporating a solution of a hydrobromide salt of Compound 1 in DMAc or DMF.

In one embodiment, provided herein is a solid form comprising Form E of a hydrobromide salt of Compound 1 and one or more forms of a free base of Compound 1 (e.g., amorphous form and crystalline forms). In one embodiment, provided herein is a solid form comprising Form E of a hydrobromide salt of Compound 1 and amorphous hydrobromide salt of Compound 1. In one embodiment, provided herein is a solid form comprising Form E of a hydrobromide salt Compound 1 and one or more other crystalline forms of a hydrobromide salt of Compound 1 provided herein. In one embodiment, provided herein is a solid form comprising Form E of a hydrobromide salt of Compound 1 and one or more forms (e.g., amorphous or crystalline) of a salt of Compound 1 provided herein.

(vi) Form F of Hydrobromide Salt of Compound 1

In certain embodiments, provided herein is Form F of a hydrobromide salt of Compound 1.

In one embodiment, Form F is crystalline. In one embodiment, Form F is substantially crystalline. In one embodiment, Form F is moderately crystalline. In one embodiment, Form F is partially crystalline.

In one embodiment, Form F is a solvate of a hydrobromide salt of Compound 1. In one embodiment, Form F is an NMP solvate of a hydrobromide salt of Compound 1.

A representative XRPD pattern of Form F of a hydrobromide salt of Compound 1 is provided in FIG. 163.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, 18, 19, 20, 21, 22, 23, 24, or all of the peaks located at approximately the following positions: 7.3, 9.4, 10.0, 11.3, 11.8, 12.9, 13.7, 14.6, 15.3, 16.5, 17.9, 18.4, 19.4, 20.0, 20.6, 22.1, 22.8, 23.6, 24.1, 24.5, 24.9, 25.3, 25.9, 26.7, and 27.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 18.4, 23.6, and 24.5° 2θ. In one embodiment, the XRPD pattern further comprises peaks at approximately 14.6 and 24.9° 2θ. In one embodiment, the XRPD pattern further comprises peaks at approximately 10.0 and 20.0° 2θ. In one embodiment, the XRPD pattern comprises peaks at approximately 10.0, 11.3, 14.6, 15.3, 18.4, 20.0, 23.6, 24.5, 24.9, 25.3, 25.9, 26.7, and 27.2° 2θ.

In one embodiment, provided herein is a solid form comprising a hydrobromide salt of Compound 1, characterized by an XRPD pattern that matches the XRPD pattern presented in FIG. 163.

In one embodiment, the XRPD patterns are obtained using Cu Kα radiation.

In one embodiment, Form F of a hydrobromide salt of Compound 1 is prepared by slowly (e.g., over a period of time of overnight or longer) evaporating a solution of a hydrobromide salt of Compound 1 in NMP.

In one embodiment, provided herein is a solid form comprising Form F of a hydrobromide salt of Compound 1 and one or more forms of a free base of Compound 1 (e.g., amorphous form and crystalline forms). In one embodiment, provided herein is a solid form comprising Form F of a hydrobromide salt of Compound 1 and amorphous hydrobromide salt of Compound 1. In one embodiment, provided herein is a solid form comprising Form F of a hydrobromide salt Compound 1 and one or more other crystalline forms of a hydrobromide salt of Compound 1 provided herein. In one embodiment, provided herein is a solid form comprising Form F of a hydrobromide salt of Compound 1 and one or more forms (e.g., amorphous or crystalline) of a salt of Compound 1 provided herein.

(vii) Form G of Hydrobromide Salt of Compound 1

In certain embodiments, provided herein is Form G of a hydrobromide salt of Compound 1.

In one embodiment, Form G is crystalline. In one embodiment, Form G is substantially crystalline. In one embodiment, Form G is moderately crystalline. In one embodiment, Form G is partially crystalline.

In one embodiment, Form G is a solvate of a hydrobromide salt of Compound 1. In one embodiment, Form G is a toluene solvate of a hydrobromide salt of Compound 1. In one embodiment, Form G is a hydrate of a toluene solvate of a hydrobromide salt of Compound 1.

A representative XRPD pattern of Form G of a hydrobromide salt of Compound 1 is provided in FIG. 164.

In one embodiment, provided herein is a solid form comprising a hydrobromide salt of Compound 1, characterized by 1, 2, 3, 4, 5, 6, 7, 8, 9, 10, 11, 12, 13, 14, 15, or all of the peaks located at approximately the following positions: 6.0, 7.7, 8.8, 9.1, 10.6, 11.8, 12.7, 13.9, 14.7, 16.4, 18.1, 20.1, 21.5, 25.1, 25.8, and 27.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 10.6, 18.1, and 25.1° 2θ. In one embodiment, the XRPD pattern further comprises peaks at approximately 7.7 and 13.9° 2θ. In one embodiment, the XRPD pattern further comprises peaks at approximately 6.0 and 11.8° 2θ. In one embodiment, the XRPD pattern comprises peaks at approximately 6.0, 7.7, 8.8, 10.6, 11.8, 13.9, 14.7, 16.4, 18.1, and 25.1° 2θ.

In one embodiment, provided herein is a solid form comprising a hydrobromide salt of Compound 1, characterized by an XRPD pattern that matches the XRPD pattern presented in FIG. 164.

In one embodiment, the XRPD patterns are obtained using Cu Kα radiation.

In one embodiment, Form G of a hydrobromide salt of Compound 1 is prepared by subjecting a suspension of amorphous hydrobromide salt of Compound 1 in toluene to one or more temperature cycles (e.g., between about room temperature and about 50° C.) for a period of time (e.g., about 7 days).

In one embodiment, provided herein is a solid form comprising Form G of a hydrobromide salt of Compound 1 and one or more forms of a free base of Compound 1 (e.g., amorphous form and crystalline forms). In one embodiment, provided herein is a solid form comprising Form G of a hydrobromide salt of Compound 1 and amorphous hydrobromide salt of Compound 1. In one embodiment, provided herein is a solid form comprising Form G of a hydrobromide salt Compound 1 and one or more other crystalline forms of a hydrobromide salt of Compound 1 provided herein. In one embodiment, provided herein is a solid form comprising Form G of a hydrobromide salt of Compound 1 and one or more forms (e.g., amorphous or crystalline) of a salt of Compound 1 provided herein.

(viii) Form H of Hydrobromide Salt of Compound 1

In certain embodiments, provided herein is Form H of a hydrobromide salt of Compound 1.

In one embodiment, Form H is crystalline. In one embodiment, Form H is substantially crystalline. In one embodiment, Form H is moderately crystalline. In one embodiment, Form H is partially crystalline.

In one embodiment, Form H is a solvate of a hydrobromide salt of Compound 1. In one embodiment, Form H is a hydrate of a hydrobromide salt of Compound 1. In one embodiment, Form H is a tetrahydrate of a hydrobromide salt of Compound 1.

A representative XRPD pattern of Form H of a hydrobromide salt of Compound 1 is provided in FIG. 165.

In one embodiment, provided herein is a solid form comprising a hydrobromide salt of Compound 1, characterized by 1, 2, 3, 4, 5, 6, 7, 8, 9, 10, 11, 12, 13, 14, 15, 16, or all of the peaks located at approximately the following positions: 7.5, 8.1, 11.7, 13.4, 15.1, 15.6, 16.9, 18.0, 19.3, 20.6, 22.6, 24.4, 25.0, 25.8, 26.5, 27.5, and 28.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 7.5, 15.1, and 18.0° 2θ. In one embodiment, the XRPD pattern further comprises peaks at approximately 20.6 and 24.4° 2θ. In one embodiment, the XRPD pattern further comprises peaks at approximately 22.6 and 27.5° 2θ. In one embodiment, the XRPD pattern comprises peaks at approximately 7.5, 8.1, 11.7, 15.1, 15.6, 16.9, 18.0, 20.6, 22.6, 24.4, and 27.5° 2θ.

In one embodiment, provided herein is a solid form comprising a hydrobromide salt of Compound 1, characterized by an XRPD pattern that matches the XRPD pattern presented in FIG. 165.

In one embodiment, the XRPD patterns are obtained using Cu Kα radiation.

A representative thermal gravimetric analysis (TGA) thermogram of Form H is provided in FIG. 166. In one embodiment, provided herein is a solid form comprising a hydrobromide salt of Compound 1, which exhibits a weight loss of about 10.5% upon heating from about 25° C. to about 100° C. In one embodiment, without being limited by any particular theory, the weight loss corresponds to the loss of water (about 4 equivalents). In one embodiment, the solid form further exhibits a weight loss of about 0.5% upon heating from about 100° C. to about 210° C. In one embodiment, without being limited by any particular theory, the weight loss corresponds to the loss of residue solvent of chloroform. In one embodiment, provided herein is a solid form comprising a hydrobromide salt of Compound 1, characterized by a TGA thermogram that matches the TGA thermogram presented in FIG. 166.

A representative differential scanning calorimetry (DSC) thermogram of Form H is presented in FIG. 167. In one embodiment, provided herein is a solid form comprising a hydrobromide salt of Compound 1, which exhibits, as characterized by DSC, a first thermal event with a peak temperature of about 70° C., and a second thermal event with an onset temperature of about 171° C. In one embodiment, the second thermal event also has a peak temperature of about 178° C. In one embodiment, provided herein is a solid form comprising a hydrobromide salt of Compound 1, characterized by a DSC thermogram that matches the DSC thermogram presented in FIG. 167.

In one embodiment, Form H of a hydrobromide salt of Compound 1 is prepared by drying (e.g., ambient drying overnight) Form I of a hydrobromide salt of Compound 1.

In one embodiment, provided herein is a solid form comprising Form H of a hydrobromide salt of Compound 1 and one or more forms of a free base of Compound 1 (e.g., amorphous form and crystalline forms). In one embodiment, provided herein is a solid form comprising Form H of a hydrobromide salt of Compound 1 and amorphous hydrobromide salt of Compound 1. In one embodiment, provided herein is a solid form comprising Form H of a hydrobromide salt Compound 1 and one or more other crystalline forms of a hydrobromide salt of Compound 1 provided herein. In one embodiment, provided herein is a solid form comprising Form H of a hydrobromide salt of Compound 1 and one or more forms (e.g., amorphous or crystalline) of a salt of Compound 1 provided herein.

(ix) Form I of Hydrobromide Salt of Compound 1

In certain embodiments, provided herein is Form I of a hydrobromide salt of Compound 1.

In one embodiment, Form I is crystalline. In one embodiment, Form I is substantially crystalline. In one embodiment, Form I is moderately crystalline. In one embodiment, Form I is partially crystalline.

In one embodiment, Form I is a solvate of a hydrobromide salt of Compound 1. In one embodiment, Form I is a chloroform solvate of a hydrobromide salt of Compound 1.

A representative XRPD pattern of Form I of a hydrobromide salt of Compound 1 is provided in FIG. 168.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, or all of the peaks located at approximately the following positions: 7.2, 14.4, 15.0, 17.2, 18.0, 18.8, 19.8, 20.6, 21.4, 22.1, 23.7, 25.4, 25.8, 26.2, 27.7, 28.5, 29.5, and 30.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 18.8, 21.4, and 25.4° 2θ. In one embodiment, the XRPD pattern further comprises peaks at approximately 15.0 and 17.2° 2θ. In one embodiment, the XRPD pattern further comprises peaks at approximately 14.4 and 19.8° 2θ. In one embodiment, the XRPD pattern comprises peaks at approximately 7.2, 14.4, 15.0, 17.2, 18.0, 18.8, 19.8, 20.6, 21.4, 22.1, 23.7, and 25.4° 2θ.

In one embodiment, provided herein is a solid form comprising a hydrobromide salt of Compound 1, characterized by an XRPD pattern that matches the XRPD pattern presented in FIG. 168.

In one embodiment, the XRPD patterns are obtained using Cu Kα radiation.

In one embodiment, Form I of a hydrobromide salt of Compound 1 is prepared by subjecting a suspension of amorphous hydrobromide salt of Compound 1 in chloroform to one or more temperature cycles (e.g., between about room temperature and about 50° C.) for a period of time (e.g., about 7 days).

In one embodiment, provided herein is a solid form comprising Form I of a hydrobromide salt of Compound 1 and one or more forms of a free base of Compound 1 (e.g., amorphous form and crystalline forms). In one embodiment, provided herein is a solid form comprising Form I of a hydrobromide salt of Compound 1 and amorphous hydrobromide salt of Compound 1. In one embodiment, provided herein is a solid form comprising Form I of a hydrobromide salt Compound 1 and one or more other crystalline forms of a hydrobromide salt of Compound 1 provided herein. In one embodiment, provided herein is a solid form comprising Form I of a hydrobromide salt of Compound 1 and one or more forms (e.g., amorphous or crystalline) of a salt of Compound 1 provided herein.

(x) Form J of Hydrobromide Salt of Compound 1

In certain embodiments, provided herein is Form J of a hydrobromide salt of Compound 1.

In one embodiment, Form J is crystalline. In one embodiment, Form J is substantially crystalline. In one embodiment, Form J is moderately crystalline. In one embodiment, Form J is partially crystalline.

In one embodiment, Form J is a solvate of a hydrobromide salt of Compound 1. In one embodiment, Form J is a 1,4-dioxane solvate of a hydrobromide salt of Compound 1.

A representative XRPD pattern of Form J of a hydrobromide salt of Compound 1 is provided in FIG. 169.

In one embodiment, provided herein is a solid form comprising a hydrobromide salt of Compound 1, characterized by 1, 2, 3, 4, 5, 6, 7, 8, 9, 10, 11, 12, 13, 14, 15, 16, 17, or all of the peaks located at approximately the following positions: 5.9, 7.8, 8.1, 11.6, 13.6, 14.9, 16.9, 17.2, 17.8, 18.4, 19.4, 21.1, 22.2, 25.2, 25.9, 26.4, 27.4, and 28.7° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a hydrobromide salt of Compound 1, characterized by an XRPD pattern comprising peaks at approximately 19.4, 25.2, and 25.9° 2θ. In one embodiment, the XRPD pattern further comprises peaks at approximately 17.8 and 21.1° 2θ. In one embodiment, the XRPD pattern further comprises peaks at approximately 16.9 and 18.4° 2θ. In one embodiment, the XRPD pattern comprises peaks at approximately 5.9, 7.8, 8.1, 13.6, 14.9, 16.9, 17.2, 17.8, 18.4, 19.4, 21.1, 25.2, and 25.9° 2θ.

In one embodiment, provided herein is a solid form comprising a hydrobromide salt of Compound 1, characterized by an XRPD pattern that matches the XRPD pattern presented in FIG. 169.

In one embodiment, the XRPD patterns are obtained using Cu Kα radiation.

In one embodiment, Form J of a hydrobromide salt of Compound 1 is prepared by subjecting a suspension of amorphous hydrobromide salt of Compound 1 in 1,4-dioxane to one or more temperature cycles (e.g., between about room temperature and about 50° C.) for a period of time (e.g., about 7 days).

In one embodiment, provided herein is a solid form comprising Form J of a hydrobromide salt of Compound 1 and one or more forms of a free base of Compound 1 (e.g., amorphous form and crystalline forms). In one embodiment, provided herein is a solid form comprising Form J of a hydrobromide salt of Compound 1 and amorphous hydrobromide salt of Compound 1. In one embodiment, provided herein is a solid form comprising Form J of a hydrobromide salt Compound 1 and one or more other crystalline forms of a hydrobromide salt of Compound 1 provided herein. In one embodiment, provided herein is a solid form comprising Form J of a hydrobromide salt of Compound 1 and one or more forms (e.g., amorphous or crystalline) of a salt of Compound 1 provided herein.

(e) Besylate Salt of Compound 1

In some embodiments, provided herein is a besylate salt of Compound 1. It is contemplated that a besylate salt of Compound 1 can exist in a variety of solid forms. Such solid forms include crystalline solids, such as polymorphs, solvates and hydrates of crystalline besylate salt of Compound 1, as well as amorphous solids, or mixtures thereof.

In one embodiment, provided herein is a solid form comprising a besylate salt of Compound 1. In one embodiment, the solid form is a solvate of a besylate salt of Compound 1. In one embodiment, the solid form is a hydrate of a besylate salt of Compound 1. In one embodiment, the solid form is a non-solvated form of a besylate salt of Compound 1. In one embodiment, the solid form is a desolvated form of a besylate salt of Compound 1. In one embodiment, the solid form is an anhydrous form (anhydrate) of a besylate salt of Compound 1. In one embodiment, the solid form is a dehydrated form of a besylate salt of Compound 1.

In some embodiments, the molar ratio of Compound 1 to benzenesulfonic acid in the solid form ranges from about 1:1 to about 1:2. In one embodiment, the molar ratio is about 1:2 (i.e., bis-besylate salt). In another embodiment, the molar ratio is about 1:1 (i.e., mono-besylate salt).

(i) Form A of Besylate Salt of Compound 1

In certain embodiments, provided herein is Form A of a besylate salt of Compound 1.

In one embodiment, Form A is crystalline. In one embodiment, Form A is substantially crystalline. In one embodiment, Form A is moderately crystalline. In one embodiment, Form A is partially crystalline.

A representative XRPD pattern of Form A of a besylate salt of Compound 1 is provided in FIG. 83.

In one embodiment, provided herein is a solid form comprising a besylate salt of Compound 1, characterized by 1, 2, 3, 4, 5, 6, 7, 8, 9, 10, 11, 12, 13, 14, 15, 16, 17, 18, 19, or all of the peaks located at approximately the following positions: 8.8, 8.9, 13.0, 13.2, 13.7, 13.9, 14.9, 15.1, 15.6, 16.5, 16.9, 18.9, 20.8, 21.1, 24.3, 24.5, 25.0, 25.3, 27.6, and 30.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a besylate salt of Compound 1, characterized by an XRPD pattern comprising peaks at approximately 13.2, 21.1, and 24.3° 2θ. In one embodiment, the XRPD pattern further comprises peaks at approximately 15.1 and 27.6° 2θ. In one embodiment, the XRPD pattern further comprises peaks at approximately 14.9, 16.5, and 20.8° 2θ. In one embodiment, the XRPD pattern comprises peaks at approximately 8.9, 13.2, 14.9, 15.1, 15.6, 16.5, 20.8, 21.1, 24.3, 24.5, and 27.6° 2θ.

In one embodiment, provided herein is a solid form comprising a besylate salt of Compound 1, characterized by an XRPD pattern that matches the XRPD pattern presented in FIG. 83.

In one embodiment, the XRPD patterns are obtained using Cu Kα radiation.

Representative TG/DTA thermograms of Form A of a besylate salt of Compound 1 are provided in FIG. 84. In one embodiment, provided herein is a solid form comprising a besylate salt of Compound 1, which exhibits a weight loss of about 5.8% upon heating from about 25° C. to about 80° C. In one embodiment, without being limited by any particular theory, the weight loss corresponds to the loss of 1,4-dioxane (e.g., about 0.5 equiv.). In one embodiment, provided herein is a solid form comprising a besylate salt of Compound 1, characterized by a TGA thermogram that matches the TGA thermogram presented in FIG. 84.

In one embodiment, provided herein is a solid form comprising a besylate salt of Compound 1, which exhibits, as characterized by DTA, a first (broad) thermal event with a peak temperature of about 50° C., and a second thermal event with an onset temperature of about 272° C. In one embodiment, the second thermal event also has a peak temperature of about 306° C. In one embodiment, without being limited by any particular theory, the first thermal event corresponds to desolvation, and the second thermal event corresponds to degradation. In one embodiment, provided herein is a solid form comprising a besylate salt of Compound 1, characterized by a DTA thermogram that matches the DTA thermogram presented in FIG. 84.

In one embodiment, Form A of a besylate salt of Compound 1 is prepared by subjecting a mixture of Compound 1 and benzenesulfonic acid (e.g., about 1:1 molar ratio) in a solvent to a temperature cycle (e.g., between about 25° C. and about 35° C.) for a period of time (e.g., from about 1 day to about 14 days, e.g., about 7 days). In one embodiment, the solvent is a mixture of acetone and water (e.g., about 1:1 v/v), a mixture of THF and water (e.g., about 1:1 v/v), or 1,4-dioxane.

In one embodiment, provided herein is a solid form comprising Form A of a besylate salt of Compound 1 and one or more forms of a free base of Compound 1 (e.g., amorphous form and crystalline forms). In one embodiment, provided herein is a solid form comprising Form A of a besylate salt of Compound 1 and amorphous besylate salt of Compound 1. In one embodiment, provided herein is a solid form comprising Form A of a besylate salt Compound 1 and one or more other crystalline forms of a besylate salt of Compound 1 provided herein. In one embodiment, provided herein is a solid form comprising Form A of a besylate salt of Compound 1 and one or more forms (e.g., amorphous or crystalline) of a salt of Compound 1 provided herein.

(ii) Form B of Besylate Salt of Compound 1

In certain embodiments, provided herein is Form B of a besylate salt of Compound 1.

In one embodiment, Form B is crystalline. In one embodiment, Form B is substantially crystalline. In one embodiment, Form B is moderately crystalline. In one embodiment, Form B is partially crystalline.

In one embodiment, the molar ratio of Compound 1 to benzenesulfonic acid in Form B is about 1:1. In one embodiment, Form B is a mono-besylate salt of Compound 1.

In one embodiment, Form B is a non-solvated form of a besylate salt of Compound 1. In one embodiment, Form B is an anhydrate of a besylate salt of Compound 1.

A representative XRPD pattern of Form B of a besylate salt of Compound 1 is provided in FIG. 85.

In one embodiment, provided herein is a solid form comprising a besylate salt of Compound 1, characterized by 1, 2, 3, 4, 5, 6, 7, 8, 9, 10, 11, 12, 13, 14, 15, 16, 17, 18, 19, 20, 21, 22, 23, 24, 25, 26, 27, or all of the peaks located at approximately the following positions: 7.3, 10.3, 10.9, 11.2, 13.9, 14.3, 14.7, 16.2, 16.6, 16.9, 17.2, 17.6, 17.7, 18.5, 19.5, 19.7, 20.1, 20.8, 21.7, 21.9, 22.5, 23.0, 23.3, 23.5, 24.6, 25.4, 26.6, and 28.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a besylate salt of Compound 1, characterized by an XRPD pattern comprising peaks at approximately 16.9, 17.7, and 21.9° 2θ. In one embodiment, the XRPD pattern further comprises peaks at approximately 11.2, 17.6, and 23.0° 2θ. In one embodiment, the XRPD pattern further comprises peaks at approximately 7.3 and 25.4° 2θ. In one embodiment, the XRPD pattern comprises peaks at approximately 7.3, 11.2, 16.2, 16.9, 17.6, 17.7, 20.8, 21.9, 23.0, 23.3, 24.6, and 25.4° 2θ.

In one embodiment, provided herein is a solid form comprising a besylate salt of Compound 1, characterized by an XRPD pattern that matches the XRPD pattern presented in FIG. 85.

In one embodiment, the XRPD patterns are obtained using Cu Kα radiation.

A representative differential scanning calorimetry (DSC) thermogram of Form B of a besylate salt of Compound 1 is presented in FIG. 86A. In one embodiment, provided herein is a solid form comprising a besylate salt of Compound 1, which exhibits, as characterized by DSC, a first thermal event with an onset temperature of about 255° C., and a second thermal event with an onset temperature of about 265° C. In one embodiment, the first thermal event also has a peak temperature of about 261° C., and the second thermal event also has a peak temperature of about 268° C. In one embodiment, provided herein is a solid form comprising a besylate salt of Compound 1, characterized by a DSC thermogram that matches the DSC thermogram presented in FIG. 86A.

A representative thermal gravimetric analysis (TGA) thermogram of Form B of a besylate salt of Compound 1 is provided in FIG. 86B. In one embodiment, provided herein is a solid form comprising a besylate salt of Compound 1, which exhibits a weight loss of about 0.37% upon heating from about 25° C. to about 150° C., or a weight loss of about 0.84% upon heating from about 25° C. to about 200° C. In one embodiment, provided herein is a solid form comprising a besylate salt of Compound 1, characterized by a TGA thermogram that matches the TGA thermogram presented in FIG. 86B.

A representative dynamic vapor sorption (DVS) isotherm plot of the Form B of a besylate salt of Compound 1 is provided in FIG. 87. In one embodiment, provided herein is a solid form comprising a besylate salt of Compound 1, which exhibits a mass increase of about 1.75% when subjected to an increase in a relative humidity (RH) from about 5% to about 95%. In one embodiment, provided herein is a solid form comprising a besylate salt of Compound 1, characterized by a DVS isotherm plot which matches the DVS isotherm plot presented in FIG. 87. In one embodiment, Form B is slightly hygroscopic. In one embodiment, Form B remains as Form B after DVS cycle.

In one embodiment, Form B of a besylate salt of Compound 1 is prepared by crystallization from acetonitrile. In one embodiment, Form B of a besylate salt of Compound 1 is prepared by slurrying a mixture of Compound 1 and benzenesulfonic acid in acetonitrile at room temperature for a period of time (e.g., overnight). In one embodiment, Form B of a besylate salt of Compound 1 is prepared by adding benzenesulfonic acid to a slurry of Compound 1 in acetonitrile to form a solution, optionally seeding with Form B, and stirring the mixture at room temperature for a period of time (e.g., overnight).

In one embodiment, provided herein is a solid form comprising Form B of a besylate salt of Compound 1 and one or more forms of a free base of Compound 1 (e.g., amorphous form and crystalline forms). In one embodiment, provided herein is a solid form comprising Form B of a besylate salt of Compound 1 and amorphous besylate salt of Compound 1. In one embodiment, provided herein is a solid form comprising Form B of a besylate salt Compound 1 and one or more other crystalline forms of a besylate salt of Compound 1 provided herein. In one embodiment, provided herein is a solid form comprising Form B of a besylate salt of Compound 1 and one or more forms (e.g., amorphous or crystalline) of a salt of Compound 1 provided herein.

(f) Glycolate Salt of Compound 1

In some embodiments, provided herein is a glycolate salt of Compound 1. It is contemplated that a glycolate salt of Compound 1 can exist in a variety of solid forms. Such solid forms include crystalline solids, such as polymorphs, solvates and hydrates of crystalline glycolate salt of Compound 1, as well as amorphous solids, or mixtures thereof.

In one embodiment, provided herein is a solid form comprising a glycolate salt of Compound 1. In one embodiment, the solid form is a solvate of a glycolate salt of Compound 1. In one embodiment, the solid form is a hydrate of a glycolate salt of Compound 1. In one embodiment, the solid form is a non-solvated form of a glycolate salt of Compound 1. In one embodiment, the solid form is a desolvated form of a glycolate salt of Compound 1. In one embodiment, the solid form is an anhydrous form (anhydrate) of a glycolate salt of Compound 1. In one embodiment, the solid form is a dehydrated form of a glycolate salt of Compound 1.

In some embodiments, the molar ratio of Compound 1 to glycolic acid in the solid form ranges from about 1:1 to about 1:2. In one embodiment, the molar ratio is about 1:2 (i.e., bis-glycolate salt). In another embodiment, the molar ratio is about 1:1 (i.e., mono-glycolate salt).

(i) Form A of Glycolate Salt of Compound 1

In certain embodiments, provided herein is Form A of a glycolate salt of Compound 1.

In one embodiment, Form A is crystalline. In one embodiment, Form A is substantially crystalline. In one embodiment, Form A is moderately crystalline. In one embodiment, Form A is partially crystalline.

A representative XRPD pattern of Form A of a glycolate salt of Compound 1 is provided in FIG. 88.

In one embodiment, provided herein is a solid form comprising a glycolate salt of Compound 1, characterized by 1, 2, 3, 4, 5, 6, 7, 8, 9, 10, 11, 12, 13, 14, 15, 16, 17, 18, 19, 20, 21, 22, 23, or all of the peaks located at approximately the following positions: 6.2, 6.6, 7.1, 7.3, 13.6, 14.0, 14.3, 14.8, 15.2, 15.3, 16.4, 17.6, 18.1, 18.9, 19.7, 20.8, 21.0, 21.7, 22.2, 22.6, 24.2, 27.0, 27.3, and 28.1° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a glycolate salt of Compound 1, characterized by an XRPD pattern comprising peaks at approximately 13.6, 17.6, and 22.2° 2θ. In one embodiment, the XRPD pattern further comprises peaks at approximately 6.6, 14.8, and 20.8° 2θ. In one embodiment, the XRPD pattern further comprises peaks at approximately 7.3 and 21.7° 2θ. In one embodiment, the XRPD pattern comprises peaks at approximately 6.2, 6.6, 7.1, 7.3, 13.6, 14.8, 16.4, 17.6, 20.8, 21.7, 22.2, and 24.2° 2θ.

In one embodiment, provided herein is a solid form comprising a glycolate salt of Compound 1, characterized by an XRPD pattern that matches the XRPD pattern presented in FIG. 88.

In one embodiment, the XRPD patterns are obtained using Cu Kα radiation.

Representative TG/DTA thermograms of Form A of a glycolate salt of Compound 1 are provided in FIG. 89. In one embodiment, provided herein is a solid form comprising a glycolate salt of Compound 1, which exhibits a weight loss of about 2.4% upon heating from about 25° C. to about 60° C., and a weight loss of about 1.0% upon heating from about 60° C. to about 140° C. In one embodiment, without being limited by any particular theory, the first weight loss corresponds to the loss of unbound solvent, and the second weight loss corresponds to the loss of ethanol and water. In one embodiment, provided herein is a solid form comprising a glycolate salt of Compound 1, characterized by a TGA thermogram that matches the TGA thermogram presented in FIG. 89.

In one embodiment, provided herein is a solid form comprising a glycolate salt of Compound 1, which exhibits, as characterized by DTA, a first (broad) thermal event with a peak temperature of about 52° C., and a second thermal event with an onset temperature of about 140° C. In one embodiment, the second thermal event also has a peak temperature of about 144° C. In one embodiment, provided herein is a solid form comprising a glycolate salt of Compound 1, characterized by a DTA thermogram that matches the DTA thermogram presented in FIG. 89.

In one embodiment, Form A of a glycolate salt of Compound 1 is prepared by subjecting a mixture of Compound 1 and glycolic acid (e.g., about 1:1 molar ratio) in a solvent to a temperature cycle (e.g., between about 25° C. and about 35° C.) for a period of time (e.g., from about 1 day to about 14 days, e.g., about 7 days). In one embodiment, the solvent is IPA. In one embodiment, the solvent is ethanol.

In one embodiment, provided herein is a solid form comprising Form A of a glycolate salt of Compound 1 and one or more forms of a free base of Compound 1 (e.g., amorphous form and crystalline forms). In one embodiment, provided herein is a solid form comprising Form A of a glycolate salt of Compound 1 and amorphous glycolate salt of Compound 1. In one embodiment, provided herein is a solid form comprising Form A of a glycolate salt Compound 1 and one or more other crystalline forms of a glycolate salt of Compound 1. In one embodiment, provided herein is a solid form comprising Form A of a glycolate salt of Compound 1 and one or more forms (e.g., amorphous or crystalline) of a salt of Compound 1 provided herein.

(g) L-Malate (L-Malic Acid) Salt of Compound 1

In some embodiments, provided herein is an L-malate salt of Compound 1. It is contemplated that an L-malate salt of Compound 1 can exist in a variety of solid forms. Such solid forms include crystalline solids, such as polymorphs, solvates and hydrates of crystalline L-malate salt of Compound 1, as well as amorphous solids, or mixtures thereof.

In one embodiment, provided herein is a solid form comprising an L-malate salt of Compound 1. In one embodiment, the solid form is a solvate of an L-malate salt of Compound 1. In one embodiment, the solid form is a hydrate of an L-malate salt of Compound 1. In one embodiment, the solid form is a non-solvated form of an L-malate salt of Compound 1. In one embodiment, the solid form is a desolvated form of an L-malate salt of Compound 1. In one embodiment, the solid form is an anhydrous form (anhydrate) of an L-malate salt of Compound 1. In one embodiment, the solid form is a dehydrated form of an L-malate salt of Compound 1.

In some embodiments, the molar ratio of Compound 1 to L-malic acid in the solid form ranges from about 1:1 to about 1:2. In one embodiment, the molar ratio is about 1:2 (i.e., bis-L-malate salt). In another embodiment, the molar ratio is about 1:1 (i.e., mono-L-malate salt).

(i) Form A of L-Malate Salt of Compound 1

In certain embodiments, provided herein is Form A of an L-malate salt of Compound 1.

In one embodiment, Form A is crystalline. In one embodiment, Form A is substantially crystalline. In one embodiment, Form A is moderately crystalline. In one embodiment, Form A is partially crystalline.

A representative XRPD pattern of Form A of an L-malate salt of Compound 1 is provided in FIG. 90.

In one embodiment, provided herein is a solid form comprising an L-malate salt of Compound 1, characterized by 1, 2, 3, 4, 5, 6, 7, 8, 9, 10, 11, 12, 13, 14, 15, 16, 17, 18, 19, 20, 21, 22, or all of the peaks located at approximately the following positions: 5.1, 5.7, 7.2, 8.1, 11.4, 13.0, 13.8, 14.4, 14.7, 15.3, 15.5, 16.4, 17.9, 18.1, 18.6, 19.5, 20.6, 21.9, 22.9, 23.6, 25.3, 25.8, and 26.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising an L-malate salt of Compound 1, characterized by an XRPD pattern comprising peaks at approximately 8.1, 14.7, and 25.3° 2θ. In one embodiment, the XRPD pattern further comprises peaks at approximately 17.9, 20.6, and 26.6° 2θ. In one embodiment, the XRPD pattern further comprises peaks at approximately 7.2 and 14.4° 2θ. In one embodiment, the XRPD pattern comprises peaks at approximately 5.7, 7.2, 8.1, 14.4, 14.7, 15.3, 16.4, 17.9, 18.1, 19.5, 20.6, 25.3, and 26.6° 2θ.

In one embodiment, provided herein is a solid form comprising an L-malate salt of Compound 1, characterized by an XRPD pattern that matches the XRPD pattern presented in FIG. 90.

In one embodiment, the XRPD patterns are obtained using Cu Kα radiation.

Representative TG/DTA thermograms of Form A of an L-malate salt of Compound 1 are provided in FIG. 91. In one embodiment, provided herein is a solid form comprising an L-malate salt of Compound 1, which exhibits a weight loss of about 2.1% upon heating from about 25° C. to about 75° C. In one embodiment, without being limited by any particular theory, the weight loss corresponds to the loss of unbound solvent. In one embodiment, provided herein is a solid form comprising an L-malate salt of Compound 1, characterized by a TGA thermogram that matches the TGA thermogram presented in FIG. 91.

In one embodiment, provided herein is a solid form comprising an L-malate salt of Compound 1, which exhibits, as characterized by DTA, a first thermal event with an onset temperature of about 105° C., and a second thermal event with an onset temperature of about 185° C. In one embodiment, the first thermal event also has a peak temperature of about 111° C., and the second thermal event also has a peak temperature of about 206° C. In one embodiment, provided herein is a solid form comprising an L-malate salt of Compound 1, characterized by a DTA thermogram that matches the DTA thermogram presented in FIG. 91.

In one embodiment, Form A of an L-malate salt of Compound 1 is prepared by subjecting a mixture of Compound 1 and L-malic acid (e.g., about 1:1 molar ratio) in DCM to a temperature cycle (e.g., between about 25° C. and about 35° C.) for a period of time (e.g., from about 1 day to about 14 days, e.g., about 7 days).

In one embodiment, provided herein is a solid form comprising Form A of an L-malate salt of Compound 1 and one or more forms of a free base of Compound 1 (e.g., amorphous form and crystalline forms). In one embodiment, provided herein is a solid form comprising Form A of an L-malate salt of Compound 1 and amorphous L-malate salt of Compound 1. In one embodiment, provided herein is a solid form comprising Form A of an L-malate salt Compound 1 and one or more other crystalline forms of an L-malate salt of Compound 1. In one embodiment, provided herein is a solid form comprising Form A of an L-malate salt of Compound 1 and one or more forms (e.g., amorphous or crystalline) of a salt of Compound 1 provided herein.

(h) Other Salts of Compound 1

In one embodiment, provided herein is a napadisylate salt of Compound 1. In one embodiment, provided herein is Form A of a napadisylate salt of Compound 1. In one embodiment, provided herein is a solid form comprising a napadisylate salt of Compound 1, characterized by an XRPD pattern that matches the XRPD pattern presented in FIG. 92. In one embodiment, Form A of a napadisylate salt of Compound 1 is prepared by subjecting a slurry comprising Compound 1 and 1,5-naphthalenedisulfonic acid in a solvent to a temperature cycle (e.g., at room temperature for about 4 hours and then at about 40° C. for about 4 hours) for a period of time (e.g., 72 hours). In one embodiment, the solvent is 1,4-dioxane, 2-propanol, acetone, a mixture of acetone and water (e.g., about 50:50 v/v), acetonitrile, a mixture of acetonitrile and water (e.g., about 50:50 v/v), dichloromethane, diisopropyl ether, ethanol, a mixture of ethanol and water (e.g., about 50:50 v/v), ethyl acetate, heptane, isopropyl acetate, methanol, methyl ethyl ketone, tert-butyl methyl ether, tetrahydrofuran, a mixture of tetrahydrofuran and water (e.g., about 50:50 v/v), toluene, or water.

In one embodiment, provided herein is a sulfate salt of Compound 1. In one embodiment, provided herein is an amorphous sulfate salt of Compound 1.

In one embodiment, provided herein is a tosylate salt of Compound 1. In one embodiment, provided herein is Form A of a tosylate salt of Compound 1. In one embodiment, provided herein is a solid form comprising a tosylate salt of Compound 1, characterized by an XRPD pattern that matches the XRPD pattern presented in FIG. 93. In one embodiment, Form A of a tosylate salt of Compound 1 is prepared by subjecting a slurry comprising Compound 1 and toluenesulfonic acid acid in a solvent to a temperature cycle (e.g., at room temperature for about 4 hours and then at about 40° C. for about 4 hours) for a period of time (e.g., 72 hours). In one embodiment, the solvent is 1,4-dioxane.

In one embodiment, provided herein is an oxalate salt of Compound 1. In one embodiment, provided herein is Form A of an oxalate salt of Compound 1. In one embodiment, provided herein is a solid form comprising an oxalate salt of Compound 1, characterized by an XRPD pattern that matches the XRPD pattern presented in FIG. 94. In one embodiment, Form A of an oxalate salt of Compound 1 is prepared by subjecting a slurry comprising Compound 1 and oxalic acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v), a mixture of acetonitrile and water (e.g., about 50:50 v/v), methanol, or a mixture of tetrahydrofuran and water (e.g., about 50:50 v/v). In one embodiment, isopropyl acetate is added as an antisolvent.

In one embodiment, provided herein is an isethionate salt of Compound 1. In one embodiment, provided herein is Form A of an isethionate salt of Compound 1. In one embodiment, provided herein is a solid form comprising an isethionate salt of Compound 1, characterized by an XRPD pattern that matches the XRPD pattern presented in FIG. 95. In one embodiment, Form A of an isethionate salt of Compound 1 is prepared by subjecting a slurry comprising Compound 1 and isethionic acid in a solvent to a temperature cycle (e.g., at room temperature for about 4 hours and then at about 40° C. for about 4 hours) for a period of time (e.g., 72 hours). In one embodiment, the solvent is acetone.

In one embodiment, provided herein is Form B of an isethionate salt of Compound 1. In one embodiment, provided herein is a solid form comprising an isethionate salt of Compound 1, characterized by an XRPD pattern that matches the XRPD pattern presented in FIG. 96. In one embodiment, Form B of an isethionate salt of Compound 1 is prepared by subjecting a slurry comprising Compound 1 and isethionic acid in a solvent to a temperature cycle (e.g., at room temperature for about 4 hours and then at about 40° C. for about 4 hours) for a period of time (e.g., 72 hours). In one embodiment, the solvent is diisopropyl ether or heptane.

In one embodiment, provided herein is a maleate salt of Compound 1. In one embodiment, provided herein is Form A of a maleate salt of Compound 1. In one embodiment, provided herein is a solid form comprising a maleate salt of Compound 1, characterized by an XRPD pattern that matches the XRPD pattern presented in FIG. 97. In one embodiment, Form A of a maleate salt of Compound 1 is prepared by subjecting a slurry comprising Compound 1 and maleic acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v) or a mixture of acetonitrile and water (e.g., about 50:50 v/v). In one embodiment, isopropyl acetate is added as an antisolvent. In one embodiment, the solvent is evaporated.

In one embodiment, provided herein is Form B of a maleate salt of Compound 1. In one embodiment, provided herein is a solid form comprising a maleate salt of Compound 1, characterized by an XRPD pattern that matches the XRPD pattern presented in FIG. 98. In one embodiment, Form B of a maleate salt of Compound 1 is prepared by subjecting a slurry comprising Compound 1 and maleic acid in a solvent to a temperature cycle (e.g., at room temperature for about 4 hours and then at about 40° C. for about 4 hours) for a period of time (e.g., 72 hours). In one embodiment, the solvent is methanol.

In one embodiment, provided herein is a phosphate salt of Compound 1. In one embodiment, provided herein is Form A of a phosphate salt of Compound 1. In one embodiment, provided herein is a solid form comprising a phosphate salt of Compound 1, characterized by an XRPD pattern that matches the XRPD pattern presented in FIG. 99. In one embodiment, Form A of a phosphate salt of Compound 1 is prepared by subjecting a slurry comprising Compound 1 and phosphoric acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v).

In one embodiment, provided herein is a malonate salt of Compound 1. In one embodiment, provided herein is Form A of a malonate salt of Compound 1. In one embodiment, provided herein is a solid form comprising a malonate salt of Compound 1, characterized by an XRPD pattern that matches the XRPD pattern presented in FIG. 100. In one embodiment, Form A of a malonate salt of Compound 1 is prepared by subjecting a slurry comprising Compound 1 and malonic acid in a solvent to a temperature cycle (e.g., at room temperature for about 4 hours and then at about 40° C. for about 4 hours) for a period of time (e.g., 72 hours). In one embodiment, the solvent is water.

In one embodiment, provided herein is a gentisate salt of Compound 1. In one embodiment, provided herein is Form A of a gentisate salt of Compound 1. In one embodiment, provided herein is a solid form comprising a gentisate salt of Compound 1, characterized by an XRPD pattern that matches the XRPD pattern presented in FIG. 101. In one embodiment, Form A of a gentisate salt of Compound 1 is prepared by subjecting a slurry comprising Compound 1 and 2,5-dihydroxybenzoic acid in a solvent to a temperature cycle (e.g., at room temperature for about 4 hours and then at about 40° C. for about 4 hours) for a period of time (e.g., 72 hours). In one embodiment, the solvent is 1,4-dioxane, a mixture of acetone and water (e.g., about 50:50 v/v), a mixture of acetonitrile and water (e.g., about 50:50 v/v), a mixture of ethanol and water (e.g., about 50:50 v/v), tetrahydrofuran, or a mixture of tetrahydrofuran and water (e.g., about 50:50 v/v). In one embodiment, the solvent is evaporated.

In one embodiment, provided herein is Form B of a gentisate salt of Compound 1. In one embodiment, provided herein is a solid form comprising a gentisate salt of Compound 1, characterized by an XRPD pattern that matches the XRPD pattern presented in FIG. 102. In one embodiment, Form B of a gentisate salt of Compound 1 is prepared by subjecting a slurry comprising Compound 1 and 2,5-dihydroxybenzoic acid in a solvent to a temperature cycle (e.g., at room temperature for about 4 hours and then at about 40° C. for about 4 hours) for a period of time (e.g., 72 hours). In one embodiment, the solvent is acetonitrile, dichloromethane, ethanol, ethyl acetate, methyl ethyl ketone, or water.

In one embodiment, provided herein is Form C of a gentisate salt of Compound 1. In one embodiment, provided herein is a solid form comprising a gentisate salt of Compound 1, characterized by an XRPD pattern that matches the XRPD pattern presented in FIG. 103. In one embodiment, Form C of a gentisate salt of Compound 1 is prepared by subjecting a slurry comprising Compound 1 and 2,5-dihydroxybenzoic acid in a solvent to a temperature cycle (e.g., at room temperature for about 4 hours and then at about 40° C. for about 4 hours) for a period of time (e.g., 72 hours). In one embodiment, the solvent is methanol.

In one embodiment, provided herein is an L-tartrate salt of Compound 1. In one embodiment, provided herein is Form A of an L-tartrate salt of Compound 1. In one embodiment, provided herein is a solid form comprising an L-tartrate salt of Compound 1, characterized by an XRPD pattern that matches the XRPD pattern presented in FIG. 104. In one embodiment, Form A of an L-tartrate salt of Compound 1 is prepared by subjecting a slurry comprising Compound 1 and L-tartaric acid in a solvent to a temperature cycle (e.g., at room temperature for about 4 hours and then at about 40° C. for about 4 hours) for a period of time (e.g., 72 hours). In one embodiment, the solvent is 1,4-dioxane, tetrahydrofuran, or a mixture of tetrahydrofuran and water (e.g., about 50:50 v/v). In one embodiment, the solvent is evaporated.

In one embodiment, provided herein is a fumarate salt of Compound 1. In one embodiment, provided herein is Form A of a fumarate salt of Compound 1. In one embodiment, provided herein is a solid form comprising a fumarate salt of Compound 1, characterized by an XRPD pattern that matches the XRPD pattern presented in FIG. 105. In one embodiment, Form A of a fumarate salt of Compound 1 is prepared by subjecting a slurry comprising Compound 1 and fumaric acid in a solvent to a temperature cycle (e.g., at room temperature for about 4 hours and then at about 40° C. for about 4 hours) for a period of time (e.g., 72 hours). In one embodiment, the solvent is dichloromethane.

In one embodiment, provided herein is a citrate salt of Compound 1. In one embodiment, provided herein is an amorphous citrate salt of Compound 1.

In one embodiment, provided herein is an R-mandelate salt of Compound 1. In one embodiment, provided herein is Form A of an R-mandelate salt of Compound 1. In one embodiment, provided herein is a solid form comprising an R-mandelate salt of Compound 1, characterized by an XRPD pattern that matches the XRPD pattern presented in FIG. 106. In one embodiment, Form A of an R-mandelate salt of Compound 1 is prepared by subjecting a slurry comprising Compound 1 and R-mandelic acid in a solvent to a temperature cycle (e.g., at room temperature for about 4 hours and then at about 40° C. for about 4 hours) for a period of time (e.g., 72 hours). In one embodiment, the solvent is water.

In one embodiment, provided herein is an L-ascorbate salt of Compound 1. In one embodiment, provided herein is Form A of an L-ascorbate salt of Compound 1. In one embodiment, provided herein is a solid form comprising an L-ascorbate salt of Compound 1, characterized by an XRPD pattern that matches the XRPD pattern presented in FIG. 107. In one embodiment, Form A of an L-ascorbate salt of Compound 1 is prepared by subjecting a slurry comprising Compound 1 and L-ascorbic acid in a solvent to a temperature cycle (e.g., at room temperature for about 4 hours and then at about 40° C. for about 4 hours) for a period of time (e.g., 72 hours). In one embodiment, the solvent is 1,4-dioxane. In one embodiment, the solvent is evaporated.

In one embodiment, provided herein is a succinate salt of Compound 1. In one embodiment, provided herein is Form A of a succinate salt of Compound 1. In one embodiment, provided herein is a solid form comprising a succinate salt of Compound 1, characterized by an XRPD pattern that matches the XRPD pattern presented in FIG. 108. In one embodiment, Form A of a succinate salt of Compound 1 is prepared by subjecting a slurry comprising Compound 1 and succinic acid in a solvent to a temperature cycle (e.g., at room temperature for about 4 hours and then at about 40° C. for about 4 hours) for a period of time (e.g., 72 hours). In one embodiment, the solvent is 1,4-dioxane. In one embodiment, the solvent is evaporated.

In one embodiment, provided herein is a nitrate salt of Compound 1. In one embodiment, provided herein is Form A of a nitrate salt of Compound 1. In one embodiment, provided herein is a solid form comprising a nitrate salt of Compound 1, characterized by an XRPD pattern that matches the XRPD pattern presented in FIG. 109. In one embodiment, Form A of a nitrate salt of Compound 1 is prepared by subjecting a slurry comprising Compound 1 and nitric acid in a solvent to a temperature cycle (e.g., at room temperature for about 4 hours and then at about 40° C. for about 4 hours) for a period of time (e.g., 72 hours). In one embodiment, the solvent is 2-propanol, acetone, a mixture of acetone and water (e.g., about 50:50 v/v), acetonitrile, dichloromethane, diisopropyl ether, ethanol, a mixture of ethanol and water (e.g., about 50:50 v/v), ethyl acetate, heptane, isopropyl acetate, methanol, methyl ethyl ketone, tert-butyl methyl ether, tetrahydrofuran, a mixture of tetrahydrofuran and water (e.g., about 50:50 v/v), toluene, or water.

In one embodiment, provided herein is a salicylate salt of Compound 1. In one embodiment, provided herein is Form A of a salicylate salt of Compound 1. In one embodiment, provided herein is a solid form comprising a salicylate salt of Compound 1, characterized by an XRPD pattern that matches the XRPD pattern presented in FIG. 110. In one embodiment, Form A of a salicylate salt of Compound 1 is prepared by subjecting a slurry comprising Compound 1 and salicylic acid in a solvent to a temperature cycle (e.g., at room temperature for about 4 hours and then at about 40° C. for about 4 hours) for a period of time (e.g., 72 hours). In one embodiment, the solvent is acetonitrile, dichloromethane, heptane, tert-butyl methyl ether, tetrahydrofuran, a mixture of tetrahydrofuran and water (e.g., about 50:50 v/v), or water.

In one embodiment, provided herein is Form B of a salicylate salt of Compound 1. In one embodiment, provided herein is a solid form comprising a salicylate salt of Compound 1, characterized by an XRPD pattern that matches the XRPD pattern presented in FIG. 111. In one embodiment, Form B of a salicylate salt of Compound 1 is prepared by subjecting a slurry comprising Compound 1 and salicylic acid in a solvent to a temperature cycle (e.g., at room temperature for about 4 hours and then at about 40° C. for about 4 hours) for a period of time (e.g., 72 hours). In one embodiment, the solvent is ethanol or ethyl acetate.

In one embodiment, provided herein is Form C of a salicylate salt of Compound 1. In one embodiment, provided herein is a solid form comprising a salicylate salt of Compound 1, characterized by an XRPD pattern that matches the XRPD pattern presented in FIG. 112. In one embodiment, Form C of a salicylate salt of Compound 1 is prepared by subjecting a slurry comprising Compound 1 and salicylic acid in a solvent to a temperature cycle (e.g., at room temperature for about 4 hours and then at about 40° C. for about 4 hours) for a period of time (e.g., 72 hours). In one embodiment, the solvent is acetone or methyl ethyl ketone.

In one embodiment, provided herein is an edisylate salt of Compound 1. In one embodiment, provided herein is Form A of an edisylate salt of Compound 1. In one embodiment, provided herein is a solid form comprising an edisylate salt of Compound 1, characterized by an XRPD pattern that matches the XRPD pattern presented in FIG. 113. In one embodiment, Form A of an edisylate salt of Compound 1 is prepared by subjecting a slurry comprising Compound 1 and 1,2-ethanedisulfonic acid in a solvent to a temperature cycle (e.g., at room temperature for about 4 hours and then at about 40° C. for about 4 hours) for a period of time (e.g., 72 hours). In one embodiment, the solvent is 1,4-dioxane.

In one embodiment, provided herein is Form B of an edisylate salt of Compound 1. In one embodiment, provided herein is a solid form comprising an edisylate salt of Compound 1, characterized by an XRPD pattern that matches the XRPD pattern presented in FIG. 114. In one embodiment, Form B of an edisylate salt of Compound 1 is prepared by subjecting a slurry comprising Compound 1 and 1,2-ethanedisulfonic acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v), acetonitrile, a mixture of acetonitrile and water (e.g., about 50:50 v/v), diisopropyl ether, a mixture of ethanol and water (e.g., about 50:50 v/v), heptane, isopropyl acetate, methyl ethyl ketone, tert-butyl methyl ether, tetrahydrofuran, or toluene. In one embodiment, isopropyl acetate is added as an antisolvent. In one embodiment, the solvent is evaporated.

In one embodiment, provided herein is a cyclamate salt of Compound 1. In one embodiment, provided herein is Form A of a cyclamate salt of Compound 1. In one embodiment, provided herein is a solid form comprising a cyclamate salt of Compound 1, characterized by an XRPD pattern that matches the XRPD pattern presented in FIG. 115. In one embodiment, Form A of a cyclamate salt of Compound 1 is prepared by subjecting a slurry comprising Compound 1 and cyclamic acid in a solvent to a temperature cycle (e.g., at room temperature for about 4 hours and then at about 40° C. for about 4 hours) for a period of time (e.g., 72 hours). In one embodiment, the solvent is 1,4-dioxane, methyl ethyl ketone, or tetrahydrofuran.

In one embodiment, provided herein is Form B of a cyclamate salt of Compound 1. In one embodiment, provided herein is a solid form comprising a cyclamate salt of Compound 1, characterized by an XRPD pattern that matches the XRPD pattern presented in FIG. 116. In one embodiment, Form B of a cyclamate salt of Compound 1 is prepared by subjecting a slurry comprising Compound 1 and cyclamic acid in a solvent to a temperature cycle (e.g., at room temperature for about 4 hours and then at about 40° C. for about 4 hours) for a period of time (e.g., 72 hours). In one embodiment, the solvent is acetonitrile.

In one embodiment, provided herein is Form C of a cyclamate salt of Compound 1. In one embodiment, provided herein is a solid form comprising a cyclamate salt of Compound 1, characterized by an XRPD pattern that matches the XRPD pattern presented in FIG. 117. In one embodiment, Form C of a cyclamate salt of Compound 1 is prepared by subjecting a slurry comprising Compound 1 and cyclamic acid in a solvent to a temperature cycle (e.g., at room temperature for about 4 hours and then at about 40° C. for about 4 hours) for a period of time (e.g., 72 hours). In one embodiment, the solvent is dichloromethane.

In one embodiment, provided herein is Form D of a cyclamate salt of Compound 1. In one embodiment, provided herein is a solid form comprising a cyclamate salt of Compound 1, characterized by an XRPD pattern that matches the XRPD pattern presented in FIG. 118. In one embodiment, Form D of a cyclamate salt of Compound 1 is prepared by subjecting a slurry comprising Compound 1 and cyclamic acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v). In one embodiment, isopropyl acetate is added as an antisolvent.

In one embodiment, provided herein is Form E of a cyclamate salt of Compound 1. In one embodiment, provided herein is a solid form comprising a cyclamate salt of Compound 1, characterized by an XRPD pattern that matches the XRPD pattern presented in FIG. 119. In one embodiment, Form E of a cyclamate salt of Compound 1 is prepared by subjecting a slurry comprising Compound 1 and cyclamic acid in a solvent to a temperature cycle (e.g., at room temperature for about 4 hours and then at about 40° C. for about 4 hours) for a period of time (e.g., 72 hours). In one embodiment, the solvent is methanol. In one embodiment, isopropyl acetate is added as an antisolvent.

In one embodiment, provided herein is an esylate salt of Compound 1. In one embodiment, provided herein is Form A of an esylate salt of Compound 1. In one embodiment, provided herein is a solid form comprising an esylate salt of Compound 1, characterized by an XRPD pattern that matches the XRPD pattern presented in FIG. 120. In one embodiment, Form A of an esylate salt of Compound 1 is prepared by subjecting a slurry comprising Compound 1 and ethanesulfonic acid in a solvent to a temperature cycle (e.g., at room temperature for about 4 hours and then at about 40° C. for about 4 hours) for a period of time (e.g., 72 hours). In one embodiment, the solvent is 1,4-dioxane.

In one embodiment, provided herein is Form B of an esylate salt of Compound 1. In one embodiment, provided herein is a solid form comprising an esylate salt of Compound 1, characterized by an XRPD pattern that matches the XRPD pattern presented in FIG. 121. In one embodiment, Form B of an esylate salt of Compound 1 is prepared by subjecting a slurry comprising Compound 1 and ethanesulfonic acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v), a mixture of acetonitrile and water (e.g., about 50:50 v/v), tetrahydrofuran, or a mixture of tetrahydrofuran and water (e.g., about 50:50 v/v). In one embodiment, isopropyl acetate is added as an antisolvent. In one embodiment, the solvent is evaporated.

In one embodiment, provided herein is a D-glucuronate salt of Compound 1. In one embodiment, provided herein is Form A of a D-glucuronate salt of Compound 1. In one embodiment, provided herein is a solid form comprising a D-glucuronate salt of Compound 1, characterized by an XRPD pattern that matches the XRPD pattern presented in FIG. 122. In one embodiment, Form A of a D-glucuronate salt of Compound 1 is prepared by subjecting a slurry comprising Compound 1 and D-glucuronic acid in a solvent to a temperature cycle (e.g., at room temperature for about 4 hours and then at about 40° C. for about 4 hours) for a period of time (e.g., 72 hours). In one embodiment, the solvent is a mixture of tetrahydrofuran and water (e.g., about 50:50 v/v).

In one embodiment, provided herein is a 4-aminosalicylate salt of Compound 1. In one embodiment, provided herein is Form A of a 4-aminosalicylate salt of Compound 1. In one embodiment, provided herein is a solid form comprising a 4-aminosalicylate salt of Compound 1, characterized by an XRPD pattern that matches the XRPD pattern presented in FIG. 123. In one embodiment, Form A of a 4-aminosalicylate salt of Compound 1 is prepared by subjecting a slurry comprising Compound 1 and 4-aminosalicylic acid in a solvent to a temperature cycle (e.g., at room temperature for about 4 hours and then at about 40° C. for about 4 hours) for a period of time (e.g., 72 hours). In one embodiment, the solvent is water.

In one embodiment, provided herein is a caproate salt of Compound 1. In one embodiment, provided herein is Form A of a caproate salt of Compound 1. In one embodiment, provided herein is a solid form comprising a caproate salt of Compound 1, characterized by an XRPD pattern that matches the XRPD pattern presented in FIG. 124. In one embodiment, Form A of a caproate salt of Compound 1 is prepared by subjecting a slurry comprising Compound 1 and caproic acid in a solvent to a temperature cycle (e.g., at room temperature for about 4 hours and then at about 40° C. for about 4 hours) for a period of time (e.g., 72 hours). In one embodiment, the solvent is a mixture of tetrahydrofuran and water (e.g., about 50:50 v/v).

In one embodiment, provided herein is a cinnamate salt of Compound 1. In one embodiment, provided herein is Form A of a cinnamate salt of Compound 1. In one embodiment, provided herein is a solid form comprising a cinnamate salt of Compound 1, characterized by an XRPD pattern that matches the XRPD pattern presented in FIG. 125. In one embodiment, Form A of a cinnamate salt of Compound 1 is prepared by subjecting a slurry comprising Compound 1 and cinnamic acid in a solvent to a temperature cycle (e.g., at room temperature for about 4 hours and then at about 40° C. for about 4 hours) for a period of time (e.g., 72 hours). In one embodiment, the solvent is tert-butyl methyl ether.

In one embodiment, provided herein is Form B of a cinnamate salt of Compound 1. In one embodiment, provided herein is a solid form comprising a cinnamate salt of Compound 1, characterized by an XRPD pattern that matches the XRPD pattern presented in FIG. 126. In one embodiment, Form B of a cinnamate salt of Compound 1 is prepared by subjecting a slurry comprising Compound 1 and cinnamic acid in a solvent to a temperature cycle (e.g., at room temperature for about 4 hours and then at about 40° C. for about 4 hours) for a period of time (e.g., 72 hours). In one embodiment, the solvent is a mixture of tetrahydrofuran and water (e.g., about 50:50 v/v).

In one embodiment, provided herein is a caprylate salt of Compound 1. In one embodiment, provided herein is Form A of a caprylate salt of Compound 1. In one embodiment, provided herein is a solid form comprising a caprylate salt of Compound 1, characterized by an XRPD pattern that matches the XRPD pattern presented in FIG. 127. In one embodiment, Form A of a caprylate salt of Compound 1 is prepared by subjecting a slurry comprising Compound 1 and caprylic acid in a solvent to a temperature cycle (e.g., at room temperature for about 4 hours and then at about 40° C. for about 4 hours) for a period of time (e.g., 72 hours). In one embodiment, the solvent is a mixture of tetrahydrofuran and water (e.g., about 50:50 v/v).

In one embodiment, provided herein is a camphorate salt of Compound 1. In one embodiment, provided herein is Form A of a camphorate salt of Compound 1. In one embodiment, provided herein is a solid form comprising a camphorate salt of Compound 1, characterized by an XRPD pattern that matches the XRPD pattern presented in FIG. 128. In one embodiment, Form A of a camphorate salt of Compound 1 is prepared by subjecting a slurry comprising Compound 1 and camphoric acid in a solvent to a temperature cycle (e.g., at room temperature for about 4 hours and then at about 40° C. for about 4 hours) for a period of time (e.g., 72 hours). In one embodiment, the solvent is acetonitrile or methanol.

In one embodiment, provided herein is a D-aspartate salt of Compound 1. In one embodiment, provided herein is Form A of a D-aspartate salt of Compound 1. In one embodiment, provided herein is a solid form comprising a D-aspartate salt of Compound 1, characterized by an XRPD pattern that matches the XRPD pattern presented in FIG. 129. In one embodiment, Form A of a D-aspartate salt of Compound 1 is prepared by subjecting a slurry comprising Compound 1 and D-aspartic acid in a solvent to a temperature cycle (e.g., at room temperature for about 4 hours and then at about 40° C. for about 4 hours) for a period of time (e.g., 72 hours). In one embodiment, the solvent is a mixture of acetone and water (e.g., about 50:50 v/v).

In one embodiment, provided herein is Form B of a D-aspartate salt of Compound 1. In one embodiment, provided herein is a solid form comprising a D-aspartate salt of Compound 1, characterized by an XRPD pattern that matches the XRPD pattern presented in FIG. 130. In one embodiment, Form B of a D-aspartate salt of Compound 1 is prepared by subjecting a slurry comprising Compound 1 and D-aspartic acid in a solvent to a temperature cycle (e.g., at room temperature for about 4 hours and then at about 40° C. for about 4 hours) for a period of time (e.g., 72 hours). In one embodiment, the solvent is diisopropyl ether or heptane.

In one embodiment, provided herein is a D-glutamate salt of Compound 1. In one embodiment, provided herein is Form A of a D-glutamate salt of Compound 1. In one embodiment, provided herein is a solid form comprising a D-glutamate salt of Compound 1, characterized by an XRPD pattern that matches the XRPD pattern presented in FIG. 131. In one embodiment, Form A of a D-glutamate salt of Compound 1 is prepared by subjecting a slurry comprising Compound 1 and D-glutamic acid in a solvent to a temperature cycle (e.g., at room temperature for about 4 hours and then at about 40° C. for about 4 hours) for a period of time (e.g., 72 hours). In one embodiment, the solvent is a mixture of tetrahydrofuran and water (e.g., about 50:50 v/v).

5.3 Methods of Use

In one embodiment, provided herein is a method of treating multiple myeloma, which comprises administering to a patient a solid form or salt of Compound 1 provided herein. In one embodiment, provided herein is a method of treating multiple myeloma, which comprises administering to a patient a solid form comprising Compound 1 provided herein. In one embodiment, provided herein is a method of treating multiple myeloma, which comprises administering to a patient a salt of Compound 1 provided herein. In one embodiment, provided herein is a solid form or salt of Compound 1 provided herein for use in a method of treating multiple myeloma, wherein the method comprises administering said solid form or salt to a patient.

In one embodiment, provided herein is a method of preventing multiple myeloma, which comprises administering to a patient a solid form or salt of Compound 1 provided herein. In one embodiment, provided herein is a method of preventing multiple myeloma, which comprises administering to a patient a solid form comprising Compound 1 provided herein. In one embodiment, provided herein is a method of preventing multiple myeloma, which comprises administering to a patient a salt of Compound 1 provided herein. In one embodiment, provided herein is a solid form or salt of Compound 1 provided herein for use in a method of preventing multiple myeloma, wherein the method comprises said compound to a patient.

In one embodiment, provided herein is a method of managing multiple myeloma, which comprises administering to a patient a solid form or salt of Compound 1 provided herein. In one embodiment, provided herein is a method of managing multiple myeloma, which comprises administering to a patient a solid form comprising Compound 1 provided herein. In one embodiment, provided herein is a method of managing multiple myeloma, which comprises administering to a patient a salt of Compound 1 provided herein. In one embodiment, provided herein is a solid form or salt of Compound 1 provided herein for use in a method of managing multiple myeloma, wherein the method comprises administering said compound to a patient.

In one embodiment, also provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. *Leukemia,* 2006; (10) 10: 1-7) of a patient, comprising administering an effective amount of a solid form or salt of Compound 1 provided herein to a patient having multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a solid form or salt of Compound 1 provided herein to patient having multiple myeloma. In another embodiment, provided herein are methods for achieving an increase in overall survival, progression-free survival, event-free survival, time to progression, or disease-free survival in a patient, comprising administering an effective amount of a solid form or salt of Compound 1 provided herein to patient having multiple myeloma. In another embodiment, provided herein are methods for achieving an increase in overall survival in a patient, comprising administering an effective amount of a solid form or salt of Compound 1 provided herein to patient having multiple myeloma. In another embodiment, provided herein are methods for achieving an increase in progression-free survival in a patient, comprising administering an effective amount of a solid form or salt of Compound 1 provided herein to patient having multiple myeloma. In another embodiment, provided herein are methods for achieving an increase in event-free survival in a patient, comprising administering an effective amount of a solid form or salt of Compound 1 provided herein to patient having multiple myeloma. In another embodiment, provided herein are methods for achieving an increase in time to progression in a patient, comprising administering an effective amount of a solid form or salt of Compound 1 provided herein to patient having multiple myeloma. In another embodiment, provided herein are methods for achieving an increase in disease-free survival in a patient, comprising administering an effective amount of a solid form or salt of Compound 1 provided herein to patient having multiple myeloma.

Also provided herein are methods of treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not.

The methods provided herein include treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma. In one embodiment, the methods provided herein reduce, maintain or eliminate minimal residual disease (MRD). In one embodiment, methods provided herein encompass treating, preventing or managing various types of multiple myeloma, such as monoclonal gammopathy of undetermined significance (MGUS), low risk, intermediate risk, and high risk multiple myeloma, newly diagnosed multiple myeloma (including low risk, intermediate risk, and high risk newly diagnosed multiple myeloma), transplant eligible and transplant ineligible multiple myeloma, smoldering (indolent) multiple myeloma (including low risk, intermediate risk, and high risk smouldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a solid form or salt of Compound 1 provided herein. In another embodiment, methods provided herein encompass treating, preventing or managing multiple myeloma characterized by genetic abnormalities, such as Cyclin D translocations (for example, t(11;14)(q13;q32); t(6;14)(p21;32); t(12;14)(p13;q32); or t(6;20);); MMSET translocations (for example, t(4;14)(p16;q32)); MAF translocations (for example, t(14;16)(q32;q32); t(20;22); t(16;22)(q11;q13); or t(14;20)(q32;q11)); or other chromosome factors (for example, deletion of 17p13, or chromosome 13; del(17/17p), nonhyperdiploidy, and gain(1q)), by administering a therapeutically effective amount of a solid form or salt of Compound 1 provided herein.

In some embodiments, the methods comprise administering a therapeutically effective amount of a solid form or salt of Compound 1 provided herein as induction therapy. In some embodiments, the methods comprise administering a therapeutically effective amount of a solid form or salt of Compound 1 provided herein as consolidation therapy. In some embodiments, the methods comprise administering a therapeutically effective amount of a solid form or salt of Compound 1 provided herein as maintenance therapy.

In one particular embodiment of the methods described herein, the multiple myeloma is plasma cell leukemia.

In one embodiment of the methods described herein, the multiple myeloma is high risk multiple myeloma. In some such embodiments, the high risk multiple myeloma is relapsed or refractory. In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p) and t(14;16)(q32;q32). In some such embodiments, the high risk multiple myeloma is relapsed or refractory to one, two or three previous treatments.

In one embodiment, the multiple myeloma is characterized by a p53 mutation. In one embodiment, the p53 mutation is a Q331 mutation. In one embodiment, the p53 mutation is an R273H mutation. In one embodiment, the p53 mutation is a K132 mutation. In one embodiment, the p53 mutation is a K132N mutation. In one embodiment, the p53 mutation is an R337 mutation. In one embodiment, the p53 mutation is an R337L mutation. In one embodiment, the p53 mutation is a W146 mutation. In one embodiment, the p53 mutation is an S261 mutation. In one embodiment, the p53 mutation is an S261T mutation. In one embodiment, the p53 mutation is an E286 mutation. In one embodiment, the p53 mutation is an E286K mutation. In one embodiment, the p53 mutation is an R175 mutation. In one embodiment, the p53 mutation is an R175H mutation. In one embodiment, the p53 mutation is an E258 mutation. In one embodiment, the p53 mutation is an E258K mutation. In one embodiment, the p53 mutation is an A161 mutation. In one embodiment, the p53 mutation is an A161T mutation.

In one embodiment, the multiple myeloma is characterized by homozygous deletion of p53. In one embodiment, the multiple myeloma is characterized by homozygous deletion of wild type p53.

In one embodiment, the multiple myeloma is characterized by wild type p53.

In one embodiment, the multiple myeloma is characterized by activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma is characterized by activation of C-MAF. In one embodiment, the multiple myeloma is characterized by activation of MAFB. In one embodiment, the multiple myeloma is characterized by activation of FGFR3 and MMset. In one embodiment, the multiple myeloma is characterized by activation of C-MAF, FGFR3, and MMset. In one embodiment, the multiple myeloma is characterized by activation of Cyclin D1. In one embodiment, the multiple myeloma is characterized by activation of MAFB and Cyclin D1. In one embodiment, the multiple myeloma is characterized by activation of Cyclin D.

In one embodiment, the multiple myeloma is characterized by one or more chromosomal translocations. In one embodiment, the chromosomal translocation is t(14;16). In one embodiment, the chromosomal translocation is t(14;20). In one embodiment, the chromosomal translocation is t(4;14). In one embodiment, the chromosomal translocations are t(4;14) and t(14;16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14;16) and t(16;22). In one embodiment, the chromosomal translocations are t(14;20) and t(11;14).

In one embodiment, the multiple myeloma is characterized by a Q331 p53 mutation, by activation of C-MAF, and by a chromosomal translocation at t(14;16). In one embodiment, the multiple myeloma is characterized by homozygous deletion of p53, by activation of C-MAF, and by a chromosomal translocation at t(14;16). In one embodiment, the multiple myeloma is characterized by a K132N p53 mutation, by activation of MAFB, and by a chromosomal translocation at t(14;20). In one embodiment, the multiple myeloma is characterized by wild type p53, by activation of FGFR3 and MMset, and by a chromosomal translocation at t(4;14). In one embodiment, the multiple myeloma is characterized by wild type p53, by activation of C-MAF, and by a chromosomal translocation at t(14;16). In one embodiment, the multiple myeloma is characterized by homozygous deletion of p53, by activation of FGFR3, MMset, and C-MAF, and by chromosomal translocations at t(4;14) and t(14;16). In one embodiment, the multiple myeloma is characterized by homozygous deletion of p53, by activation of Cyclin D1, and by a chromosomal translocation at t(11;14). In one embodiment, the multiple myeloma is characterized by an R337L p53 mutation, by activation of Cyclin D1, and by a chromosomal translocation at t(11;14). In one embodiment, the multiple myeloma is characterized by a W146 p53 mutation, by activation of FGFR3 and MMset, and by a chromosomal translocation at t(4;14). In one embodiment, the multiple myeloma is characterized by an S261T p53 mutation, by activation of MAFB, and by chromosomal translocations at t(6;20) and t(20;22). In one embodiment, the multiple myeloma is characterized by an E286K p53 mutation, by activation of FGFR3 and MMset, and by a chromosomal translocation at t(4;14). In one embodiment, the multiple myeloma is characterized by an R175H p53 mutation, by activation of FGFR3 and MMset, and by a chromosomal translocation at t(4;14). In one embodiment, the multiple myeloma is characterized by an E258K p53 mutation, by activation of C-MAF, and by chromosomal translocations at t(14;16) and t(16;22). In one embodiment, the multiple myeloma is characterized by wild type p53, by activation of MAFB and Cyclin D1, and by chromosomal translocations at t(14;20) and t(11;14). In one embodiment, the multiple myeloma is characterized by an A161T p53 mutation, by activation of Cyclin D, and by a chromosomal translocation at t(11;14).

In some embodiments of the methods described herein, the multiple myeloma is transplant eligible newly diagnosed multiple myeloma. In another embodiment, the multiple myeloma is transplant ineligible newly diagnosed multiple myeloma.

In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In certain embodiments, provided herein are methods of treating, preventing, and/or managing multiple myeloma, including relapsed/refractory multiple myeloma in patients with impaired renal function or a symptom thereof, comprising administering a therapeutically effective amount of a solid form or salt of Compound 1 provided herein to a patient having relapsed/refractory multiple myeloma with impaired renal function.

In certain embodiments, provided herein are methods of treating, preventing, and/or managing multiple myeloma, including relapsed or refractory multiple myeloma in frail patients or a symptom thereof, comprising administering a therapeutically effective amount of a solid form or salt of Compound 1 provided herein to a frail patient having multiple myeloma. In some such embodiments, the frail patient is characterized by ineligibility for induction therapy, or intolerance to dexamethasone treatment. In some such embodiment the frail patient is elderly, for example, older than 65 years old.

In certain embodiments, provided herein are methods of treating, preventing or managing multiple myeloma, comprising administering to a patient a therapeutically effective amount of a solid form or salt of Compound 1 provided herein wherein the multiple myeloma is fourth line relapsed/refractory multiple myeloma.

In certain embodiments, provided herein are methods of treating, preventing or managing multiple myeloma, comprising administering to a patient a therapeutically effective amount of a solid form or salt of Compound 1 provided herein as induction therapy, wherein the multiple myeloma is newly diagnosed, transplant-eligible multiple myeloma.

In certain embodiments, provided herein are methods of treating, preventing or managing multiple myeloma, comprising administering to a patient a therapeutically effective amount of a solid form or salt of Compound 1 provided herein as maintenance therapy after other therapy or transplant, wherein the multiple myeloma is newly diagnosed, transplant-eligible multiple myeloma prior to the other therapy or transplant.

In certain embodiments, provided herein are methods of treating, preventing or managing multiple myeloma, comprising administering to a patient a therapeutically effective amount of a solid form or salt of Compound 1 provided herein as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1.

In certain embodiments, provided herein are methods of treating, preventing or managing multiple myeloma, comprising administering to a patient a therapeutically effective amount of a solid form or salt of Compound 1 provided herein, wherein the multiple myeloma is high risk multiple myeloma, that is relapsed or refractory to one, two or three previous treatments.

In certain embodiments, provided herein are methods of treating, preventing or managing multiple myeloma, comprising administering to a patient a therapeutically effective amount of a solid form or salt of Compound 1 provided herein, wherein the multiple myeloma is newly diagnosed, transplant-ineligible multiple myeloma.

In certain embodiments, a therapeutically or prophylactically effective amount of the compound is from about from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of Compound 1 is from about 0.1 mg per day to about 0.4 mg per day.

In certain embodiments, the therapeutically or prophylactically effective amount is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day.

In one embodiment, the recommended daily dose range of Compound 1 for the conditions described herein lie within the range of from about 0.1 mg to about 25 mg per day, preferably given as a single once-a-day dose, or in divided doses throughout a day. In other embodiments, the dosage ranges from about 0.1 to about 10 mg per day. Specific doses per day include 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day.

In a specific embodiment, the recommended starting dosage may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the patient to be treated with one of the methods provided herein has not been treated with multiple myeloma therapy prior to the administration of a solid form or salt of Compound 1 provided herein. In certain embodiments, the patient to be treated with one of the methods provided herein has been treated with multiple myeloma therapy prior to the administration of a solid form or salt of Compound 1 provided herein. In certain embodiments, the patient to be treated with one of the methods provided herein has developed drug resistance to the anti-multiple myeloma therapy. In some such embodiments, the patient has developed resistance to one, two, or three anti-multiple myeloma therapies, wherein the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

Depending on the state of the disease to be treated and the subject's condition, a solid form or salt of Compound 1 provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A solid form or salt of Compound 1 provided herein may be formulated, alone or together, in suitable dosage unit with pharmaceutically acceptable excipients, carriers, adjuvants and vehicles, appropriate for each route of administration.

In one embodiment, a solid form or salt of Compound 1 provided herein is administered orally. In another embodiment, a solid form or salt of Compound 1 provided herein is administered parenterally. In yet another embodiment, a solid form or salt of Compound 1 provided herein is administered intravenously.

A solid form or salt of Compound 1 provided herein can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A solid form or salt of Compound 1 provided herein can be administered once daily (QD or qd), or divided into multiple daily doses such as twice daily (BID or bid), three times daily (TID or tid), and four times daily (QID or qid). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 7 days to 52 weeks. The term "intermittent" or "intermittently" as used herein is intended to mean stopping and starting at either regular or irregular intervals. For example, intermittent administration of a solid form or salt of Compound 1 provided herein, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a solid form or salt of Compound 1 provided herein is administered once a day. In another embodiment, a solid form or salt of Compound 1 provided herein is administered twice a day. In yet another embodiment, a solid form or salt of Compound 1 provided herein is administered three times a day. In still another embodiment, a solid form or salt of Compound 1 provided herein is administered four times a day.

In one embodiment, a therapeutically effective amount of a solid form or salt of Compound 1 provided herein is administered in a treatment cycle which includes an administration period of up to 20 days followed by a rest period. In one embodiment, a therapeutically effective amount of a solid form or salt of Compound 1 provided herein is administered in a treatment cycle which includes an administration period of up to 15 days followed by a rest period. In one embodiment, a therapeutically effective amount of a solid form or salt of Compound 1 provided herein is administered in a treatment cycle which includes an administration period of up to 10 days followed by a rest period. In one embodiment, a therapeutically effective amount of a solid form or salt of Compound 1 provided herein is administered in a treatment cycle which includes an administration period of up to 7 days followed by a rest period. In one embodiment, a therapeutically effective amount of a solid form or salt of Compound 1 provided herein is administered in a treatment cycle which includes an administration period of up to 5 days followed by a rest period. In one embodiment, a therapeutically effective amount of a solid form or salt of Compound 1 provided herein is administered in a treatment cycle which includes an administration period of up to 4 days followed by a rest period. In one embodiment, a therapeutically effective amount of a solid form or salt of Compound 1 provided herein is administered in a treatment cycle which includes an administration period of up to 3 days followed by a rest period.

In one embodiment, the treatment cycle includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days. In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle includes an administration of a therapeutically effective amount of a solid form or salt of Compound 1 provided herein on days 1 to 5 of a 28 day cycle. In another embodiment, the treatment cycle includes an administration of a solid form or salt of Compound 1 provided herein on days 1 to 10 of a 28 day cycle. In one embodiment, the treatment cycle includes an administration of a therapeutically effective amount of a solid form or salt of Compound 1 provided herein on days 1 to 21 of a 28 day cycle. In another embodiment, the treatment cycle includes an administration of a therapeutically effective amount of a solid form or salt of Compound 1 provided herein on days 1 to 5 of a 7 day cycle. In another embodiment, the treatment cycle includes an administration of a therapeutically effective amount of a solid form or salt of Compound 1 provided herein on days 1 to 7 of a 7 day cycle. In one embodiment, the treatment cycle includes an administration of a therapeutically effective amount of a solid form or salt of Compound 1 provided herein on days 1 to 10 and days 15 to 24 of a 28 day cycle (herein referred to as 20/28 dosing cycle). In one embodiment, the treatment cycle includes an administration of a therapeutically effective amount of a solid form or salt of Compound 1 provided herein on days 1 to 3 and days 15 to 18 of a 28 day cycle. In one embodiment, the treatment cycle includes an administration of a therapeutically effective amount of a solid form or salt of Compound 1 provided herein on days 1 to 7 and days 15 to 21 of a 28 day cycle (herein referred to as 14/28 dosing cycle). In one embodiment, the treatment cycle includes an administration of a therapeutically effective amount of a solid form or salt of Compound 1 provided herein on days 1 to 5 and days 15 to 19 of a 28 day cycle (herein referred to as 10/28 dosing cycle). In one embodiment, the treatment cycle includes an administration of a therapeutically effective amount of a solid form or salt of Compound 1 provided herein on days 1 to 3 and days 15 to 17 of a 28 day cycle (herein referred to as 6/28 dosing cycle).

In one embodiment, the treatment cycle includes an administration of a therapeutically effective amount of a solid form or salt of Compound 1 provided herein on days 1 to 14 of a 21 day cycle. In another embodiment, the treatment cycle includes an administration of a solid form or salt of Compound 1 provided herein on days 1 to 4 and 8 to 11 of a 21 day cycle. In one embodiment, the treatment cycle includes an administration of a therapeutically effective amount of a solid form or salt of Compound 1 provided herein on days 1 to 5 and 8 to 12 of a 21 day cycle. In another embodiment, the treatment cycle includes an administration of a therapeutically effective amount of a solid form or salt of Compound 1 provided herein on days 1 to 5 and 11 to 15 of a 21 day cycle. In another embodiment, the treatment cycle includes an administration of a therapeutically effective amount of a solid form or salt of Compound 1 provided herein on days 1 to 5, 8 to 12 and 15 to 19 of a 21 day cycle. In another embodiment, the treatment cycle includes an administration of a therapeutically effective amount of a solid form or salt of Compound 1 provided herein on days 1 to 4, 8 to 11 and 15 to 18 of a 21 day cycle. In another embodiment, the treatment cycle includes an administration of a therapeutically effective amount of a solid form or salt of Compound 1 provided herein on days 1 to 4, 8 to 10 and 15 to 17 of a 21 day cycle. In another embodiment, the treatment cycle includes an administration of a therapeutically effective amount of a solid form or salt of Compound 1 provided herein on days 1 to 3, and 8 to 11 of a 21 day cycle. In another embodiment, the treatment cycle includes an administration of a therapeutically effective amount of a solid form or salt of Compound 1 provided herein on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of a solid form or salt of Compound 1 provided herein is administered for 1 to 13 cycles of 28 days (e.g., about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering a solid form or salt of Compound 1 provided herein at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day, administered once per day. In one embodiment the treatment cycle includes administering a solid form or salt of Compound 1 provided herein at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering a solid form or salt of Compound 1 provided herein once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering a solid form or salt of Compound 1 provided herein once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering a solid form or salt of Compound 1 provided herein once a day at a dosage amount of about 0.1 mg on days 1 to 10 and 15 to 24 of a 28 day cycle. In other embodiments, the treatment cycle includes administering a solid form or salt of Compound 1 provided herein twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering a solid form or salt of Compound 1 provided herein twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering a solid form or salt of Compound 1 provided herein twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering a solid form or salt of Compound 1 provided herein twice a day at a dosage amount of about 0.2 mg on days 1 to 3 and 15 to 17 of a 28 day cycle. In one such embodiment, the compound is administered on days 1 to 3 (morning and evening), day 14 (evening only), days 15 and 16 (morning and evening), and day 17 (morning only) of a 28 day cycle, for example in Cycle 1.

For clarity reasons, it is noted that, unless otherwise specified, the Compound 1 doses referred to herein refer to the amount of Compound 1 in its free base form. In case that for example a pharmaceutically acceptable salt of Compound 1 is used, the amounts given above will need to be adapted accordingly.

5.4 Combination Therapy with a Second Active Agent

A solid form or salt of Compound 1 provided herein can also be combined or used in conjunction with (e.g. before, during, or after) conventional therapy including, but not limited to, surgery, biological therapy (including immunotherapy, for example with checkpoint inhibitors), radiation therapy, chemotherapy, stem cell transplantation, cell therapy, or other non-drug based therapy presently used to treat, prevent or manage multiple myeloma. The combined use of the compound provided herein and conventional therapy may provide a unique treatment regimen that is unexpectedly effective in certain patients. Without being limited by theory, it is believed that a solid form or salt of Compound 1 provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A solid form or salt of Compound 1 provided herein and other active ingredient can be administered to a patient prior to, during, or after the occurrence of the adverse effect associated with conventional therapy.

A solid form or salt of Compound 1 provided herein can also be combined or used in combination with other therapeutic agents useful in the treatment and/or prevention of multiple myeloma described herein.

In one embodiment, provided herein is a method of treating, preventing, or managing multiple myeloma, comprising administering to a patient a solid form or salt of Compound 1 provided herein in combination with one or more second active agents, and optionally in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a solid form or salt of Compound 1 provided herein can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein, as is quadruple therapy. In one embodiment, the second therapy is dexamethasone.

Administration of a solid form or salt of Compound 1 provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of a solid form or salt of Compound 1 provided herein is independent of the route of administration of a second therapy. In one embodiment, a solid form or salt of Compound 1 provided herein is administered orally. In another embodiment, a solid form or salt of Compound 1 provided herein is administered intravenously. Thus, in accordance with these embodiments, a solid form or salt of Compound 1 provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a solid form or salt of Compound 1 provided herein and a second therapy are administered by the same mode of administration, orally or by IV. In another embodiment, a solid form or salt of Compound 1 provided herein is administered by one mode of administration, e.g., by IV, whereas the second agent (an anti-multiple myeloma agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of multiple myeloma being treated or managed, the severity and stage of disease, and the amount of a solid form or salt of Compound 1 provided herein and any optional additional active agents concurrently administered to the patient.

One or more second active ingredients or agents can be used together with a solid form or salt of Compound 1 provided herein in the methods and compositions provided herein. Second active agents can be large molecules (e.g., proteins), small molecules (e.g., synthetic inorganic, organometallic, or organic molecules), or cell therapies (e.g., CAR cells).

Examples of second active agents that can be used in the methods and compositions described herein include one or more of melphalan, vincristine, cyclophosphamide, etoposide, doxorubicin, bendamustine, obinutuzmab, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336), a BCL2 inhibitor (for example, venetoclax or navitoclax), an MCL-1 inhibitor (for example, AZD5991, AMG176, MIK665, 564315, or S63845), an LSD-1 inhibitor (for example, ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile or a salt thereof), a corticosteroid (for example, prednisone), dexamethasone; an antibody (for example, a CS1 antibody, such as elotuzumab; a CD38 antibody, such as daratumumab or isatuximab; or a BCMA antibody or antibody-conjugate, such as GSK2857916 or BI 836909), a checkpoint inhibitor (as described herein), or CAR cells (as described herein).

In one embodiment, the second active agent used together with a solid form or salt of Compound 1 provided herein in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1.

In some other embodiments, the dexamethasone is administered at an 8 mg dose on days 1 and 8 of a 21 day cycle. In some other embodiments, the dexamethasone is administered at an 8 mg dose on days 1, 4, 8 and 11 of a 21 day cycle. In some embodiments, the dexamethasone is administered at an 8 mg dose on days 1, 8, and 15 of a 28 day cycle. In some other embodiments, the dexamethasone is administered at an 8 mg dose on days 1, 4, 8, 11, 15 and 18 of a 28 day cycle. In some embodiments, the dexamethasone is administered at an 8 mg dose on days 1, 8, 15, and 22 of a 28 day cycle. In one such embodiment, the dexamethasone is administered at an 8 mg dose on days 1, 10, 15, and 22 of Cycle 1. In some embodiments, the dexamethasone is administered at an 8 mg dose on days 1, 3, 15, and 17 of a 28 day cycle. In one such embodiment, the dexamethasone is administered at an 8 mg dose on days 1, 3, 14, and 17 of Cycle 1.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15 and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15 and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1.

In another embodiment, the second active agent used together with a solid form or salt of Compound 1 provided herein in the methods and compositions described herein is bortezomib. In yet another embodiment, the second active agent used together with a solid form or salt of Compound 1 provided herein in the methods and compositions described herein is daratumumab. In some such embodiments, the methods additionally comprise administration of dexamethasone. In some embodiments, the methods comprise administration of a solid form or salt of Compound 1 provided herein with a proteasome inhibitor as described herein, a CD38 inhibitor as described herein and a corticosteroid as described herein.

In another embodiment, the second active agent used together with a solid form or salt of Compound 1 provided herein in the methods and compositions described herein is panobinostat. In some such embodiments, the methods additionally comprise administration of dexamethasone.

In another embodiment, the second active agent used together with a solid form or salt of Compound 1 provided herein in the methods and compositions described herein is ACY241. In some such embodiments, the methods additionally comprise administration of dexamethasone.

In another embodiment, the second active agent used together with a solid form or salt of Compound 1 provided herein in the methods and compositions described herein is vincristine. In some such embodiments, the methods additionally comprise administration of dexamethasone.

In another embodiment, the second active agent used together with a solid form or salt of Compound 1 provided herein in the methods and compositions described herein is cyclophosphamide. In some such embodiments, the methods additionally comprise administration of dexamethasone.

In another embodiment, the second active agent used together with a solid form or salt of Compound 1 provided herein in the methods and compositions described herein is etoposide. In some such embodiments, the methods additionally comprise administration of dexamethasone.

In another embodiment, the second active agent used together with a solid form or salt of Compound 1 provided herein in the methods and compositions described herein is doxorubicin. In some such embodiments, the methods additionally comprise administration of dexamethasone.

In another embodiment, the second active agent used together with a solid form or salt of Compound 1 provided herein in the methods and compositions described herein is venetoclax. In some such embodiments, the methods additionally comprise administration of dexamethasone.

In another embodiment, the second active agent used together with a solid form or salt of Compound 1 provided herein in the methods and compositions described herein is AMG176. In some such embodiments, the methods additionally comprise administration of dexamethasone.

In another embodiment, the second active agent used together with a solid form or salt of Compound 1 provided herein in the methods and compositions described herein is MIK665. In some such embodiments, the methods additionally comprise administration of dexamethasone.

In another embodiment, the second active agent used together with a solid form or salt of Compound 1 provided herein in the methods and compositions described herein is GSK525762A. In some such embodiments, the methods additionally comprise administration of dexamethasone.

In another embodiment, the second active agent used together with a solid form or salt of Compound 1 provided herein in the methods and compositions described herein is OTX015. In some such embodiments, the methods additionally comprise administration of dexamethasone.

In another embodiment, the second active agent used together with a solid form or salt of Compound 1 provided herein in the methods and compositions described herein is 4-[2-(cyclopropylmethoxy)-5-(methanesulfonyl)phenyl]-2-methylisoquinolin-1(2H)-one. In some such embodiments, the methods additionally comprise administration of dexamethasone.

In another embodiment, the second active agent used together with a solid form or salt of Compound 1 provided herein in the methods and compositions described herein is 4-[2-(4-amino-piperidin-1-yl)-5-(3-fluoro-4-methoxy-phenyl)-1-methyl-6-oxo-1,6-dihydropyrimidin-4-yl]-2-fluorobenzonitrile, or a salt thereof (for example a besylate salt). In some such embodiments, the methods additionally comprise administration of dexamethasone.

In certain embodiments, a solid form or salt of Compound 1 provided herein is administered in combination with checkpoint inhibitors. In one embodiment, one checkpoint inhibitor is used in combination with a solid form or salt of Compound 1 provided herein in connection with the methods provided herein. In another embodiment, two checkpoint inhibitors are used in combination with a solid form or salt of Compound 1 provided herein in connection with the methods provided herein. In yet another embodiment, three or more checkpoint inhibitors are used in combination with a solid form or salt of Compound 1 provided herein in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer,* 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.,* 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.,* 2012, 3834).

In one embodiment, the checkpoint inhibitors is a TIM3 (T-cell immunoglobulin domain and mucin domain 3) inhibitor (Fourcade et al., *J. Exp. Med.,* 2010, 207, 2175-86; Sakuishi et al., *J. Exp. Med.,* 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, a solid form or salt of Compound 1 provided herein can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AMU fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pme117), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, C0-029, FGF-5, G250, Ga733 (EpCAM), HTgp-175, M344, MA-50, MG7-Ag, MOV18, NB\70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3) or ITAM-containing portions thereof. In a specific embodiment, the intracellular domain is a CD3 intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3t signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 1 05(11):4247-4254 (2005).

In certain embodiments, a solid form or salt of Compound 1 provided herein is administered to patients with various types or stages of multiple myeloma in combination with chimeric antigen receptor (CAR) T-cells. In certain embodiments the CAR T cell in the combination targets B cell maturation antigen (BCMA), and in more specific embodiments, the CAR T cell is bb2121 or bb21217. In some embodiments, the CAR T cell is JCARH125.

5.5 Pharmaceutical Compositions

The pharmaceutical compositions provided herein contain therapeutically effective amounts of one or more of compounds provided herein and optionally a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

6. EXAMPLES

Certain embodiments of the invention are illustrated by the following non-limiting examples.

6.1 Synthesis of (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1)

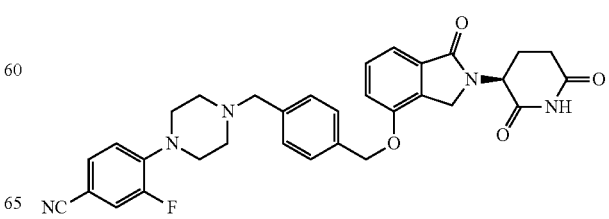

Tert-Butyl (4S)-5-amino-4-(benzyloxycarbonylamino)-5-oxo-pentanoate.

To a solution of (2S)-2-(benzyloxycarbonylamino)-5-tert-butoxy-5-oxo-pentanoic acid (150 g, 445 mmol) in 1,4-dioxane (1.50 L) was added di-tert-butyl dicarbonate (155 g, 711 mmol), pyridine (70.3 g, 889 mmol) and ammonium bicarbonate (105 g, 1.33 mol). The reaction mixture was stirred at 18° C. for 16 h and then concentrated. The residue was dissolved in ethyl acetate (5.0 L) and water (5.0 L), the organic layer was separated and washed with HCl (3.0 mL, 1 N), saturated sodium bicarbonate (3.0 L), brine (3.0 L), dried over anhydrous sodium sulfate, filtered and concentrated to give crude tert-butyl (4S)-5-amino-4-(benzyloxycarbonylamino)-5-oxo-pentanoate (450 g, crude) as a white solid, which was used in the next step without further purification. $^1$H NMR 400 MHz DMSO-$d_6$ δ: 7.35-7.30 (m, 5H), 7.02 (s, 1H), 5.01 (d, J=3.2 Hz, 1H), 3.93-3.90 (m, 1H), 2.20 (t, J=8.0 Hz, 2H), 1.88-1.84 (m, 1H), 1.72-1.69 (m, 1H), 1.35 (s, 9H).

Tert-Butyl (4S)-4,5-diamino-5-oxo-pentanoate

To a solution of tert-butyl (4S)-5-amino-4-(benzyloxycarbonylamino)-5-oxo-pentanoate (112 g, 333 mmol) in methanol (1.0 L) was added 10% palladium on carbon (15 g) under nitrogen. The suspension was degassed under vacuum and purged with hydrogen several times. The mixture was stirred under hydrogen gas (40 psi) at 30° C. for 16 h. The reaction mixture was filtered and the filtrate was concentrated to give crude tert-butyl (4S)-4,5-diamino-5-oxo-pentanoate as a colorless oil. $^1$H NMR 400 MHz DMSO-$d_6$ δ: 7.30 (s, 1H), 6.95 (s, 1H), 3.10-3.07 (m, 1H), 2.27-2.23 (m, 2H), 1.69-1.78 (m, 1H), 1.59-1.55 (m, 1H), 1.38 (s, 9H).

Methyl 3-hydroxy-2-methyl-benzoate

Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) or until the filtrate had pH >3. The solid was dried under vacuum at 45° C. to give methyl 3-hydroxy-2-methyl-benzoate (700 g, 80.4% yield) as a gray solid. $^1$H NMR: 400 MHz DMSO-$d_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate

Two batches (240 g each) were run in parallel. To a solution of methyl 3-hydroxy-2-methyl-benzoate (240 g, 1.44 mol) in N,N-dimethylformamide (1.40 L) were added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred followed by separation of the organic phase. The combined organics (two batches combined) were washed with water (1700 mL×3) and concentrated to 1500 mL (KF<0.05%). The product was stored as an isopropyl acetate solution which was used in the next step without further purification.

Methyl 2-(bromomethyl)-3-[tert-butyl(dimethyl)silyl]oxy-benzoate

Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) were removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. 41 NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

Tert-Butyl (4S)-5-amino-4-[4-[tert-butyl)dimethyl]silyl]oxy-1-oxo-isoindolin-2-yl]-5-oxo-pentanoate To a solution of tert-butyl (4S)-4,5-diamino-5-oxo-pentanoate (130 g, 643 mmol) in acetonitrile (4.0 L) was added methyl 2-(bromomethyl)-3-[tert-butyl(dimethyl)silyl]oxy-benzoate (210 g, 584 mmol) and diisopropylethylamine (113 g, 877 mmol). The reaction mixture was stirred at 50° C. for 16 h. The reaction mixture was concentrated to remove most of the acetonitrile, the residue was dissolved in methyl tert-butyl ether (2.0 L) and water (1.5 L), the organic layer was washed with saturated monopotassium phosphate (1.0 L×2), brine (1.0 L), dried over anhydrous sodium sulfate, filtered and concentrated to give crude tert-butyl (4S)-5-amino-4-[4-[tert-butyl(dimethyl)silyl]oxy-1-oxo-isoindolin-2-yl]-5-oxo-pentanoate (524 g), which was used into next step without further purification.

Tert-Butyl (4S)-5-amino-4-(4-hydroxy-1-oxo-isoindolin-2-yl)-5-oxo-pentanoate

To a solution of tert-butyl (4S)-5-amino-4-[4-[tert-butyl(dimethyl)silyl]oxy-1-oxo-isoindolin-2-yl]-5-oxo-pentanoate (275 g, 613 mmol,) in methanol (2.0 L) was added tetrabutylammonium fluoride trihydrate (38.7 g, 123 mmol). The mixture was stirred at 18° C. for 16 h. The reaction mixture was concentrated to remove most of the methanol, and the residue was dissolved in dichloromethane/water (3 L/2 L). The organic layer was separated and washed with brine (1.0 L), dried over anhydrous sodium sulfate, filtered, and concentrated to give crude product, which was purified by silica gel column to give product (260 g). Product was added into acetonitrile (750 mL) and the mixture was stirred at 60° C. for 2 h, cooled to 18° C., and stirred for another 2 h. The solid was filtered and the cake was dried to give tert-butyl (4S)-5-amino-4-(4-hydroxy-1-oxo-isoindolin-2-yl)-5-oxo-pentanoate (248 g, 60.5% yield) as a gray solid. $^1$H NMR 400 MHz DMSO-$d_6$ δ: 10.00 (s, 1H), 7.54 (s, 1H), 7.29 (t, J=7.6 Hz, 1H), 7.14 (d, J=4.8 Hz, 2H), 4.72-4.68 (m, 1H), 4.49-4.28 (m, 2H), 2.17-1.97 (m, 4H), 1.31 (s, 9H).

4-(4-(4-(chloromethyl)benzyl)piperazin-1-yl)-3-fluorobenzonitrile 1,4-bis(chloromethyl)benzene (51.2 g, 292 mmol) was placed in a flask with acetonitrile (195 mL) and N,N-dimethylformamide (195 mL). The reaction mixture was stirred at ambient temperature until all the solids dissolved. Diisopropylamine (51.1 mL, 292 mmol) was then added along with 3-fluoro-4-(piperazin-1-yl)benzonitrile (20 g, 97 mmol). The reaction was heated to 60° C. for 1 h. The acetonitrile was removed under reduced pressure. The remaining mixture was partitioned between ethyl acetate (1.0 L), water (700 mL), and brine (300 mL). The organic layer was separated and the aqueous layer was extracted with ethyl acetate twice. Volatile organics were combined and removed under reduced pressure. The solid was dissolved in minimal dichloromethane and purified on silica gel column (0-100% ethyl acetate in hexanes over 3 L). Fractions containing desired product were combined and volatile organics were removed under reduced pressure. The residue was dissolved in minimal dichloromethane and purified a second time on silica gel column (10% isocratic ethyl acteate in hexanes over 800 mL followed by 20-80% ethyl acetate in hexanes over 4 L). Fractions containing desired product were combined and volatile organics were removed under reduced pressure to afford 44444-(chloromethyl)benzyl)piperazin-1-yl)-3-fluorobenzonitrile (22.7 g, 66.0 mmol, 67.7% yield) as an off-white solid. $^1$H NMR (400 MHz, CDCl$_3$) δ ppm 7.33-7.39 (m, 5H) 7.29 (d, J=1.96 Hz, 1H) 7.25 (d, J=1.96 Hz, 1H) 6.91 (t, J=8.56 Hz, 1H) 4.60 (s, 2H) 3.58 (s, 2H) 3.19-3.27 (m, 4H) 2.58-2.66 (m, 4H). MS (ESI) m/z 344.2 [M+1]$^+$.

(S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (S)-tert-butyl 5-amino-4-(4-hydroxy-1-oxoisoindolin-2-yl)-5-oxopentanoate (22.05 g, 65.9 mmol) was placed in a flask with 4-(4-(4-(chloromethyl)benzyl)piperazin-1-yl)-3-fluorobenzonitrile (22.67 g, 65.9 mmol), potassium carbonate (18.23 g, 132 mmol), and N,N-dimethylformamide (330 mL). The reaction mixture was heated to 45° C. for 16 h. The reaction was diluted with ethyl acetate (50 mL) and filtered. The filtrate was partitioned with ethyl acetate (900 mL) and water (600 mL) and brine (200 mL). The organic layer was isolated and washed with water (600 mL). The organic layer was dried over sodium sulfate, and volatiles were removed under reduced pressure. The residue was treated with 20% ethyl acetate in hexanes and volatiles were removed under reduced pressure to afford (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (44.02 g, 68.6 mmol, 104% yield) as an off-white solid. Yield was slightly over quantitative as some DMF remained. $^1$H NMR (400 MHz, CDCl$_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H). MS (ESI) m/z 642.4 [M+1]$^+$.

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile (Compound 1)

(S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (12.1 g, 18.86 mmol) was placed in a vial with acetonitrile (189 mL) and benzenesulfonic acid (3.96 g, 24.51 mmol). The reaction mixture was placed under vacuum and purged with nitrogen. This was repeated once more and the mixture was then heated to 85° C. overnight under a nitrogen atmosphere. The warm reaction mixture was poured directly into 2 separatory funnels containing dichloromethane (1000 mL) and ethyl acetate (300 mL). To this mixture a saturated solution of sodium bicarbonate (900 mL), water (100 mL), and brine (450 mL) was added. The organic layer was isolated and the aqueous layer was extracted with dichloromethane (800 mL) and ethyl acetate (200 mL). The combined organic layers were dried over anhydrous magnesium sulfate, and concentrated. Purification by standard methods provided the title compound. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

Recrystallization to Prepare Form K of Compound 1

(S)-4-(4-(4-(((2-(2,6-dioxopiperidin-3-yl)-1-oxoisoindolin-4-yl)oxy)methyl)benzyl)piperazin-1-yl)-3-fluorobenzonitrile was dissolved in acetone (35 L/Kg) and filtered to upgrade chiral purity. The filtrate was passed through a 0.45 µM filter into a clean reactor. After distillation (target volume 15 L/Kg), water (2 L/Kg) was charged to generate supersaturation. The batch was seeded with Form K and held at constant temperature with wet-milling through a recirculation loop at 40° C. Water (6 L/Kg) was charged at a constant rate of 1 (L/Kg)/h, with wet-milling at a reduced tip speed. The batch was cooled to 25° C. and then held for 3 h. The batch was filtered, washed and dried. Humid aging was performed followed by comilling to delump yielding (S)-4-(4-(4-(((2-(2,6-dioxopiperidin-3-yl)-1-oxoisoindolin-4-yl)oxy)methyl)benzyl)piperazin-1-yl)-3-fluorobenzonitrile as Form K. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

6.2 Antiproliferative Effects on Multiple Myeloma

Cell Culture Materials: Human multiple myeloma cell lines were purchased from the vendors and cultured at 37° C. with 5% CO$_2$ in the media as indicated in Table 1. Lenalidomide and pomalidomide resistant cell lines were obtained by methods as generally described previously (Lopez-Girona et al *Leukemia* 2012; 26(11): 2335). All cell lines were kept in log phase, and cell density and viability were monitored by trypan blue exclusion using the Vi-cell XR cell viability analyzer (Beckman Coulter, Brea, Calif.).

TABLE 1

Multiple Myeloma Cell Lines Tested

| MM Cell Line | Vendor/Source | Catalog Number | Culture Conditions |
|---|---|---|---|
| NCI-H929 | ATCC (Manassas, VA) | CRL-9068 | RPMI-1640, 10% FBS |
| NCI-H929-1051 | developed in-house, made resistant to lenalidomide | NA | RPMI-1640, 10% FBS |
| OPM2 | DSMZ (Braunschweig, Germany) | ACC-50 | RPMI-1640, 10% FBS |
| OPM2-P10 | developed in-house, made resistant to 10 µM pomalidomide | NA | RPMI-1640, 10% FBS |

Preparation of Solutions of Test Article:

Compound 1 was plated into black 384-well plates (Corning Inc.) to a final DMSO volume of 0.1% assuming a maximal volume of 50 µL. A 10-point dose response starting at 10 µM with a 1:3 dilution was printed in duplicate by acoustic dispense using the EDC ATS-100 platform. Alternatively, the 10-point dose response starting at 10 µM with a 1:10 dilution, or starting at 100 nM with a 1:3 dilutions were used.

Cell Proliferation Assays:

The effect of Compound 1 on the proliferation/viability of the hematological cell lines (Table 1), was assessed after 120 h incubation using CTG (Promega), according to manufacturer's instructions. Hematological cell lines were dispensed into compound plates by a Multidrop Combi Reagent Dispenser (Thermo Scientific, Waltham, Mass.) at a concentration of $0.1 \times 10^6$ cells per mL in a 50 µL total volume. At 120 h, 25 µL per well of CTG was dispensed by a Multidrop Combi Reagent Dispenser and adenosine triphosphate (ATP) release by viable cells was measured as relative luminescence units after 30 minutes using the Envision platform.

Results. Compound 1 Demonstrates Antiproliferative Activity Against MM Cell Lines.

The MM cell lines selected for this study were lines sensitive and resistant to lenalidomide and/or pomalidomide (Table 1), two agents approved to treat myeloma patients. Proliferation was assessed using the CellTitreGlo® assay. Results for cultures incubated with Compound 1 were normalized to results for control cultures for each cell line. The $IC_{50}$ for inhibition of cell growth by Compound 1 was determined for each cell line using ActivityBase software. Compound 1 potently inhibited cell proliferation in the four cell lines, as determined by the quantitative assessment of ATP levels present in the media after 120 h. The antiproliferative $IC_{50}$ values of Compound 1 ranged between 0.07 nM and 4.3 nM (Table 2). Compound 1 showed very potent multiple myeloma anti-proliferative activity even on cell lines that were lenalidomide- and/or pomalidomide-resistant.

TABLE 2

Inhibition of Cell Growth by Compound 1 in a MM Cell Lines in Liquid Culture

| Compd. No. | NCI-H929 120 h $IC_{50}$ | NCI-H929.1051 120 h $IC_{50}$ | OPM-2 120 h $IC_{50}$ | OPM-2.P10 120 h $IC_{50}$ |
|---|---|---|---|---|
| 1 | 0.07 nM | 1.0 nM | 0.07 nM | 4.3 nM |

6.3 Off-Target Effects of Compound 1

α1 Adrenergic and Dopamine D2 Receptors. Methods:

Binding and functional assays for α1 adrenergic and dopamine D2 receptors were performed by Eurofins Cerep according to their methods.

α1 Adrenergic Receptor.

Binding at 10 µM. The binding assay evaluated the affinity of test article for the non-selective α1 adrenergic receptor in rat cerebral cortex. Membrane homogenates of cerebral cortex were incubated in duplicate for 60 minutes at room temperature with 0.25 nM [$^3$H]prazosin in the absence or presence of test articles at 10 µM. After the incubation period, samples were filtered through glass fiber filters, the filters dried and then counted for radioactivity using a scintillation counter. Results are expressed as mean percent inhibition of control radioligand binding.

Binding $IC_{50}$. To determine the binding $IC_{50}$ for the non-selective α1 adrenergic receptor, varying concentrations of test article were incubated in duplicate with 0.25 nM [$^3$H]prazosin. Previously reported compound 3-(4-((4-((4-(2,4-difluorophenyl)piperazin-1-yl)methyl)benzyl)oxy)-1-oxoisoindolin-2-yl)piperidine-2,6-dione (Example 5.285 in U.S. Pat. No. 8,518,972) (Compound A) was tested at 0.01-30 µM. Compound B, the S-enantiomer of Compound A, was tested at 0.0003-10 µM. Compound 1 was assayed at 0.03-100 µM. Radioactivity was measured as described above. The $IC_{50}$ was defined as the concentration causing a half-maximum inhibition of control specific binding.

Antagonist activity. The antagonistic effects of test compounds on the $α_{1A}$ and adrenergic receptors were measured using human receptor-transfected Chinese hamster ovary (CHO) cells. Antagonist activity was determined by measuring compound effect on agonist (epinephrine)-induced calcium mobilization in the $α_{1A}$ receptor assay or cAMP levels in the $α_{1B}$ receptor assay. In these experiments, CHO cells were incubated in duplicate at room temperature with test article and epinephrine at 3 nM in the $α_{1A}$ receptor assays or at 3000 nM in the $α_{1B}$ receptor assay. Compound A was tested in the $α_{1A}$ receptor assay at 0.01-30 µM. Compound B was tested in the $α_{1A}$ and $α_{1B}$ receptor assays at 0.0003-30 µM. Compound 1 was assayed at 0.03 to 30 µM in the $α_{1A}$ receptor assay and 0.03 to 100 µM in the $α_{1B}$ receptor assay. In the $α_{1A}$ receptor assay, cytosolic calcium levels were measured fluorometrically using the fluorescent probe, Fluo4 Direct. Intracellular cAMP levels in the $α_{1B}$ adrenergic receptor assay were measured by homogenous time-resolved fluorescence (HTRF). The antagonism $IC_{50}$ was defined as the concentration causing a half-maximum inhibition of control agonist response.

Dopamine D2 Receptor.

Binding at 10 µM. The binding assay evaluated the affinity of test articles for the dopamine D2 receptor in transfected human embryonic kidney (HEK)-293 cells. For determining the binding in the $D_{2S}$ receptor assay, test article was incubated with 0.3 nM [$^3$H] methylspiperone or 1 nM [$^3$H] 7-hydroxy-2-N,N-dipropylaminotetralin (7-OH-DPAT). [$^3$H] Methylspiperone at 0.3 nM also was used as control ligand in the $D_{2L}$ binding assay. Cell membrane homogenates were incubated in duplicate at room temperature for 60 minutes with ligand in the absence or presence of test articles at 10 µM. After the incubation period, samples were filtered through glass fiber filters, the filters dried and then counted for radioactivity using a scintillation counter. Results are expressed as mean percent inhibition of control radioligand binding.

Binding IC$_{50}$. To determine the binding IC$_{50}$ in the D2 receptor assays, HEK-293 were tested as described above but with varying concentrations of test article. Compound A was tested at 0.01-30 μM in the D$_{2S}$ radioligand binding assay. Compound B was tested at 0.0003-10 μM in both the D$_{2S}$ and D$_{2L}$ binding assays. Compound 1 was tested at 0.03-100 μM in the D$_{2S}$ assay and 0.01-100 μM in the D$_{2L}$ assays. The IC$_{50}$ was defined as the concentration causing a half-maximum inhibition of control specific binding.

Agonist activity. The agonism of test compounds on the dopamine D$_{2S}$ receptor was assessed using human receptor-transfected HEK-293 cells. Agonist activity was determined by measuring compound effect on impedance modulation. In these experiments, HEK-293 cells were incubated in duplicate at 28° C. with test article. Compound A was tested at 0.01-30 μM. Compound B was tested at 0.0003-10 μM, while Compound 1 was assayed at 0.01-10 μM. Dopamine (3 μM) was used as an agonist control. Impedance measurements were monitored for 10 minutes after ligand addition using cellular dielectric spectroscopy. The EC$_{50}$ was defined as the concentration causing a half-maximum response, compared to the control agonist (dopamine) response.

Results.

Binding at 10 μM at the α1 adrenergic and dopamine D2 receptors was evaluated for Compound 1, Compound A, Compound B and a number of compounds exemplified in U.S. Pat. No. 8,518,972 (as indicated by their example number Ex.) (Table 3). While the previously disclosed compounds fully inhibited binding of ligand at both receptors, surprisingly, Compound 1 showed greatly diminished ability to inhibit ligand binding, showing only 67/62% (α1 adrenergic receptor) and 55/52% (dopamine D$_{2S}$) inhibition of ligand binding, respectively.

Dynamic Vapor Sorption

Projekt Messtechnik (now ProUmid) SPS11-100n. The sample was placed on an aluminum holder on top of a microbalance and allowed to equilibrate at 50% r.h. before starting one of the following pre-defined humidity programs (1 cycle):
  hold 2 h at 50% r.h.,
  decrease humidity −5% r.h. h$^{-1}$ for 10 h (i.e., from 50% r.h. to 0% r.h.),
  hold 5 h at 0% r.h.,
  increase humidity+5% r.h. h$^{-1}$ for 19 h (i.e., from 0% r.h. to 95% r.h.),
  hold 5 h at 95% r.h.,
  decrease humidity −5% r.h. h$^{-1}$ for 9 h (i.e., from 95% r.h. to 50% r.h.),
  hold 2 h at 50% r.h.
or
  hold 2 h at 50% r.h.,
  increase humidity+5% r.h. h$^{-1}$ for 9 h (i.e., from 50% r.h. to 95% r.h.),
  hold 5 h at 95% r.h.,
  decrease humidity −5% r.h. h$^{-1}$ for 19 h (i.e., from 95% r.h. to 0% r.h.),
  hold 5 h at 0% r.h.,
  increase humidity+5% r.h. h$^{-1}$ for 10 h (i.e., from 0% r.h. to 50% r.h.),
  hold 2 h at 50% r.h.

The hygroscopicity was classified based on the mass gain at 85% r.h. relative to the initial mass as follows: deliquescent (sufficient water adsorbed to form a liquid), very hygroscopic (mass increase of ≥15%), hygroscopic (mass increase of <15% but ≥2%), slightly hygroscopic (mass increase of <2% but ≥0.2%), or non-hygroscopic (mass increase of <0.2%).

TABLE 3

Effects of Compound A, Compound B, Compound 1 and previously reported compounds on α1 Adrenergic and Dopamine D2 Receptor

| Cmpd No. | R$^1$ | R$^2$ | X | Stereo | Adrenergic α1 % Inh. (@10 μM) | Dopamine D$_{2S}$ % Inh. (@10 μM) |
|---|---|---|---|---|---|---|
| 1 | CN | F | CH$_2$ | S | 62 | 52 |
| A | F | F | CH$_2$ | rac | 102 | 99 |
| B | F | F | CH$_2$ | S | 98 | 99 |
| Ex. 5.229 | H | H | CH$_2$ | rac | 98.3 | 98.7 |
| Ex. 5.273 | F | H | CH$_2$ | rac | 100.3 | 94.7 |
| Ex. 5.289 | F | H | CO | rac | 97.9 | 92.4 |

6.4 Analytical Methods

Typical measurement conditions are provided below:

Differential Scanning Calorimetry

Thermal Analysis Q2000. Closed (hermetically sealed) gold crucibles or aluminum crucibles with a pinhole; sample filled under ambient conditions; heating rate of 5 or 10 K min$^{-1}$; −50 to 300° C. range (sometimes terminated earlier).

FT-Raman Spectroscopy

Bruker MultiRAM (with OPUS 7.0 software). Nd:YAG 1064-nm excitation, 300 mW nominal laser power, Ge detector, 64 scans, 3500-100 cm$^{-1}$ spectral range used for analysis, 2 cm$^{-1}$ resolution. Samples were measured through truncated, glass NMR tubes.

$^1$H NMR

Bruker DPX300. $^1$H NMR spectra were recorded using a proton frequency of 300.13 MHz, a 30° excitation pulse, and a recycle delay of 1 s. Sixteen scans were accumulated, and deuterated DMSO was used as the solvent.

HPLC

Agilent Series 1100 HPLC instrument with an Agilent 1260 Infinity degasser and Chromeleon Version 6.8 software.

Powder X-Ray Diffraction

Stoe Stadi P. Copper Kα1 radiation, 40 kV/40 mA. Mythen1K detector, transmission mode, curved Ge monochromator, 0.02° 2θ step size, 12 s step time, 1.5-50.5° 2θ scanning range with 1° 2θ detector step in step-scan mode.

Each sample (25-40 mg of powder) was placed between two cellulose acetate foils that were spaced with a metal washer (0.4-mm thick, 12-mm inner diameter). This sandwich element was transferred to a special sample holder for highly potent substances (SCell), which again was sealed with acetate foils. No special treatment was used in preparing the samples. An ambient air atmosphere was used for all measurements, and each sample was rotated during the measurement.

Indexing of diffractograms was carried out using the X'Pert HighScore Plus package from PANalytical. Tables of peaks for diffractograms were generated using Bruker's EVA (Version 14, 0, 0, 0) software and performing a background subtraction followed by a peak search. Only peaks with ° 2θ values below 40° 2θ that have significant intensity are reported.

Solubility Determination 1 mL of buffer or of ultrapure (resistivity ≥18.2 MΩcm) water was added to a pre-weighed, approximately twenty milligram aliquot of the substance to be measured. The resulting suspensions were stirred for 15 minutes at room temperature with magnetic stirrers. The suspensions were centrifuged and filtered through Millipore 0.2 μm PVDF filters, and the concentration of each filtrate (i.e., saturated solution) was determined using a general HPLC method. The pH of each saturated solution was measured with a Metrohm 713 pH meter.

TG-FTIR

Netzsch Thermo-Microbalance TG 209 with Bruker FT-IR Spectrometer IFS28 or Vector 22. Al crucible (with microhole), $N_2$ atmosphere, 10 K min$^{-1}$ heating rate, 25° C. to 350° C. range.

TG/DTA

Approximately, 5 mg of material was weighed into an open aluminium pan and loaded into a simultaneous thermogravimetric/differential thermal analyser (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm³/min.

6.5 Free Base Polymorphism Screening No. 1

A search for the polymorphic forms of free base Compound 1 was conducted from fifteen solvents and twenty-one solvent mixtures using methods such as suspension equilibration (at various temperatures), evaporation, cooling crystallization, precipitation, vapor diffusion, and vapor off-diffusion. In addition, many drying/desolvation experiments were attempted, and mechanical and thermal treatments were also applied.

Suspension equilibration experiments were carried out using a variety of solvents, temperatures, and durations. Experiments at lower temperatures are conducive to solvate formation while experiments at higher temperatures can help overcome kinetic barriers to interconversion. After completion of the experiments, the freshly filtered samples were generally characterized by Raman spectroscopy with selected samples subsequently being characterized by PXRD, TG-FTIR, $^1$H-NMR spectroscopy, and/or DSC.

Evaporation experiments were carried out from five solvents and one mixture under ambient laboratory conditions. Although very slow evaporation rates were used, four of the products were amorphous.

Cooling crystallization experiments: hot saturated solutions of Compound 1 were prepared in seven different solvents/mixtures. Upon cooling at an uncontrolled rate, relatively rapid precipitation (within less than a day) was observed in most experiments.

Precipitation experiments were attempted both by adding antisolvent to concentrated solutions of Compound 1 as well as by adding a concentrated solution of Compound 1 to an antisolvent bath. Immediate precipitation was not observed in any of the cases. In one experiment (MEK as solvent, and TBME as antisolvent), precipitation (Form H) was ultimately observed after eleven days of subsequent stirring at room temperature. In the remaining experiments, the clear solutions were used as starting materials for the vapor off-diffusion experiments.

Vapor diffusion experiments were performed by dissolving Compound 1 in a solvent in an open vial and placing that vial in a bath of a more volatile antisolvent that is miscible with the solvent. The entire system was then closed to generate an atmosphere that is saturated with the antisolvent at room temperature. Diffusion of the volatile antisolvent into the solution should reduce the solubility of the compound and potentially lead to slow precipitation.

A vapor off-diffusion (reversed vapor diffusion) experiment was carried out by dissolving Compound 1 in a solvent/antisolvent mixture in which the solvent was the more volatile component. The sample was left open under ambient conditions to allow partial evaporation, and since the more volatile solvent evaporates faster, the solubility should decrease over time, leading to precipitation.

Drying/desolvation experiments: Due to the solvophilic nature of Compound 1, most products contained residual solvent, making it difficult to distinguish solvates (whether stable or labile) from potential unsolvated forms that had been incompletely dried. In an attempt to identify true anhydrous forms, selected classes were reproduced and subsequently dried at 40° C. under vacuum overnight. The samples were dried separately to avoid cross-contamination. The resulting products were analyzed by PXRD and TG-FTIR. The drying procedure was successful in many cases but often led to loss of crystallinity and/or a change in solid form, indicating that most of the initial samples were indeed solvates that were not stable under the drying conditions. However, the Form H solvates were found to be quite stable and did not change form upon drying, and the Form K hydrate only showed slight shifts in the positions of the reflections, corresponding to dehydration into Form K'.

Storage at controlled relative humidities: the following table describes the results of storage of Form K and Form K' of Compound 1 at 17% r.h. to help narrow down the critical water activity range for interconversion between the hydrated and dehydrated forms. The range was later narrowed down to $a_{H2O}$=0.11-0.22, with Form K' being more stable at lower water activities ($a_{H2O}$≤0.11) and Form K at higher ($a_{H2O}$≥0.22).

TABLE 4

Controlled humidity storage experiments on Compound 1

| Starting material | Storage condition | PXRD result |
|---|---|---|
| Form K' | stored at 17% r.h. and r.t. for 2.5 d | Form K |
| Form K | stored at 17% r.h. and r.t. for 5.5 d | Form K |

Thermal treatment of solid forms: the following table summarizes two experiments carried out using solvent-free thermal treatment of forms of Compound 1. The goal of these experiments was to determine whether the endotherm at 225° C. observed in many DSC experiments corresponded to the melting of the racemate of Compound 1 or whether it was a polymorphic form of Compound 1. Two experiments involved generation of different solid forms of Compound 1, the amorphous form and Form E. The resulting products were subsequently heated to temperatures where exothermic events had been observed in DSC thermograms. Both experiments confirmed that the racemate was generated by heating.

TABLE 5

Thermal treatment of solid Compound 1

| Starting material | Thermal treatment | PXRD result |
|---|---|---|
| amorphous | heated under $N_2$ flow to 180° C. and held for 10 min; cooled quickly to r.t.; heated to 200° C. and held for 10 min; cooled quickly to r.t. | racemate form |
| Form E | heated under $N_2$ flow to 200° C. and held for several minutes; cooled quickly to r.t. | racemate form |

Racemization of Compound 1 during the DSC analysis was confirmed by heating the samples to various temperatures and analyzing these samples by a chiral HPLC method as well as by comparison of the melting point with a pure sample of the racemate of Compound 1. Upon heating the sample to 160° C., the chiral purity was essentially unchanged (96.1 area % at 160° C. vs. 97.1% initial). This supports the interpretation of the sharp endotherm seen in the DSC thermogram at about 152.6° C. as the melt of the enantiomer. Between 160-218° C. a gradual conversion of the enantiomer to the racemate occurs along with the recrystallization of the racemate. This explains the unsteady baseline over this temperature range and the small broad endotherm observed at about 197.1° C. The racemization is almost complete by 218° C. and is followed by the melt of the racemate corresponding to the second sharp endotherm observed in the DSC thermogram at about 226.7° C. This melting point matches the peak melting point (about 225.6° C.) of the pure racemate of Compound 1.

Racemization of Compound 1 during the DSC analysis was also confirmed by hot stage microscopy. The microscopy images upon heating a sample of Compound 1 on a hot stage showed the following: The individual particles of Compound 1 in the dry state were difficult to separate individually and were visualized as dark clumps. No remarkable changes were noticed upon heating the sample up to 151° C. when some of the smaller clumps started to melt. The compound completely melted as the temperature was increased to 153° C. This corresponds to the melt of the enantiomer. Between 170 to 212° C. racemization and recrystallization of the drug occurred as alluded to in the DSC experiment. Upon further heating to 220° C., a complete melt of the racemate was observed. The hot stage microscopy results are in reasonably good agreement with the thermal events observed by DSC and corroborated by chiral chromatography described above.

Mechanical stressing experiment: the following table describes three experiments involving mechanical stressing of Form A and/or Form B of free base Compound 1 by grinding with a mortar and pestle. No change in polymorphic form was observed when a single polymorph was ground for two minutes. When both polymorphs were ground together for ten minutes, the crystallinity diminished significantly, but the crystalline part of the sample remained a mixture of the two forms.

TABLE 6

Mechanical treatment of Compound 1

| Starting material | Mechanical treatment | PXRD result |
|---|---|---|
| Form A | ground with a mortar and pestle for 2 min | no change in polymorphic form; possible slight decrease in crystallinity |
| Form B | ground with a mortar and pestle for 2 min | no change in polymorphic form |
| Form A and Form B | ground with a mortar and pestle for 10 min | loss of crystallinity; remained a mixture of the two polymorphs |

Summary of the Results from Free Base Polymorphism Screening No. 1

The endotherm near 225° C. that was observed in many DSC thermograms is attributed to melting of the racemate of Compound 1. Such an endotherm is generally preceded by an exothermic event, which is presumably attributable to crystallization of the racemate and possibly includes racemization itself.

Form A of a free base of Compound 1 is likely an anhydrous and slightly hygroscopic polymorph with a melting point of approximately 146.4° C. (onset at 137.7° C., $\Delta H=49.7$ J g$^{-1}$). It converts into other forms when suspended in all solvent systems tested and has only been obtained by desolvation of the Form E solvate/hydrate (although other solid forms can also be obtained from desolvation of Form E samples). Grinding of Form A with a mortar and pestle for two minutes does not lead to polymorphic transformation.

Form B of a free base of Compound 1 is probably a channel hydrate that is slightly hygroscopic. It is sometimes obtained from crystallization experiments but likely only via desolvation of an intermediate solvate such as Form E, Form F, or Form G. DSC analyses of samples of Form B gave melting points (of the dehydrated form) typically in the range of 122-129° C., but the driest Form B sample observed in this project has a melting point of 138.0° C. (onset at 127.3° C., $\Delta H \approx 23.1$ J g$^{-1}$). Grinding of Form B with a mortar and pestle for two minutes does not lead to polymorphic transformation.

Form C of a free base of Compound is associated with a high melting point of 171.9° C. (onset at 160.4° C., $\Delta H \approx 41.1$ J g$^{-1}$) but is hygroscopic at high relative humidities. Although often correlated with TG-FTIR thermograms with a low solvent content (as low as 0.5 wt.-%), drying of a Form C sample (obtained from an experiment involving 2PrOH/ $H_2O$) showed a loss of crystallinity. This suggests that Form C likely arises from desolvation of solvated forms, even if these solvates were not always explicitly observed.

Form D of a free base of Compound 1 is a hydrated form that is relatively labile and converts in the direction of Form B upon drying. It was obtained initially only from suspension equilibration experiments involving ethanol and might involve a transitional solvated state. Form D has a melting point (after dehydration) of 136.1° C. (onset at 129.3° C., $\Delta H \approx 17.7$ J g$^{-1}$). While its DVS isotherm resembled that of a channel solvate, the sample converted into a mixture of Forms B and E during the humidity cycle.

Form E of a free base of Compound 1 is also likely a hydrated form although it appears to be isomorphic with solvates of MEK and ethyl formate. A typical Form E sample has a melting point (after partial dehydration/desolvation) of 132.0° C. (onset at 117.6° C., $\Delta H \approx 64.1$ J g$^{-1}$).

Form F of a free base of Compound 1 consists of nearly isomorphic solvates from many solvents including anisole, toluene, ethyl formate, ethyl acetate, methyl acetate, isopropyl acetate, and possibly acetone and dioxane. Drying of Form F samples either leads to loss of crystallinity and shifts of the reflections in the PXRD patterns (e.g., for the anisole and toluene solvates) or, in cases such as that of the MeOAc solvate, to conversion into Form B. Thus, despite the isomorphicity of various Form F solvate structures, they undergo different mechanisms of desolvation under the same conditions, presumably due to differences in the strength of the host-guest interactions.

Form G of a free base of Compound 1 appears to be a monosolvate of acetonitrile with a melting point of 139.5° C. (onset at 131.7° C., $\Delta H \approx 19.2$ J g$^{-1}$). Desolvation of this form by drying under vacuum at 40° C. overnight led to conversion into a highly crystalline sample of Form B.

Form H of a free base of Compound 1 corresponds to nearly isomorphic solvates of TBME and THF with a desolvation/melting point near 140° C. Both solvates are relatively stable and do not desolvate even after drying under vacuum at 40° C. overnight. The THF solvates generally exhibited higher crystallinity than the TBME solvates.

Form I of a free base of Compound 1 is a solvate of DMSO.

Form J of a free base of Compound 1 is a solvate of acetic acid that desolvates in two steps as the temperature is raised.

Form K of a free base of Compound 1 is probably a channel hydrate that is slightly hygroscopic. The corresponding dehydrated/desolvated form has been designated as Form K'. When dehydrated, its melting point is approximately 157.0° C. (onset at 152.9° C., $\Delta H \approx 73.4$ J g$^{-1}$). Form K is the most stable form in mixtures of water and organic solvents (such as acetone and 2PrOH) with a water activity of $a_{H2O} \geq 0.17$. Form K is also stable with respect to application of a DVS cycle. Its powder X-ray diffractogram appears to be indexable, implying that Form K corresponds to a pure phase rather than a mixture of multiple solid forms. Indexing of the Form K' diffractogram confirms that it is a slightly compressed version of the same lattice. The solubilities of Form K and Form K' after fifteen minutes at pH 2.0 are essentially identical, suggesting that the two forms should have the same bioavailability.

Desolvation processes were not always predictable, and isomorphic solvates did not always yield the same product upon drying, possibly due to differences in the strength of the interaction between different types of solvent molecules and the compound and to the details of the drying process, which were not always easy to control. Desolvation of Form E samples generally led to Form B, Form A, or mixture of Form A and B, but Form B could also be obtained by desolvation of Form G. Most Form F samples just lost crystallinity upon drying, but one (obtained from MeOAc) changed into Form B and another (obtained from 2PrOH) into Form C.

Heating of both amorphous and Form E samples to 180-200° C. and holding for several minutes led to formation of the racemate of Compound 1, confirming the assignment of the melting peak near 225° C. in the DSC endotherms to this racemate.

Both Forms A and B are mechanically stable with respect to two minutes of grinding with a mortar and pestle. Grinding of a mixture of Forms A and B for ten minutes led to partial amorphization but to no clear conversion in either direction.

6.6 Free Base Polymorphism Screening No. 2

A second search for polymorphic forms of the Compound 1 free base was conducted from twenty high-molecular-weight and/or sterically hindered solvents. The goal of these experiments was to see whether the use of solvents that were likely not to be as easily incorporated into a host-guest structure as the previously screened solvents would lead to the generation of a true anhydrous form (as opposed to a desolvated solvate). Most of the high-molecular-weight and sterically hindered solvents used in this project led to forms identified in the first screening, but three new solid forms were isolated.

Suspension equilibration (slurry) experiments were carried out using twenty high-molecular-weight and/or sterically hindered solvents. Experiments were conducted by preparing suspensions of approximately 55-68 mg of Compound 1 in 0.8-1.0 mL of the selected solvent using 4-mL Supelco glass vials. The suspensions were stirred with a magnetic stirrer for fourteen days at 40° C. A temperature higher than room temperature was chosen with the hope of decreasing the propensity towards solvate formation. The solid samples were recovered by filter centrifugation (20 min, 40° C., 5000 rpm, 0.45 μm PTFE membrane) and characterized by PXRD without further drying. This procedure should provide an indication of the most stable form in a given solvent. However, in the case of solvate or hydrate formation, the solid form might change as the sample is dried, and metastable forms might with time convert into more stable forms under ambient laboratory conditions. In two cases, no solid product was obtained so the solvents were subsequently evaporated.

Diffractograms similar to a few forms from previous screening were obtained for many products, suggesting that the use of high-molecular-weight and/or sterically hindered solvents did not inhibit solvate formation. In addition, three new solid forms (designated as Form L, Form M, and Form N) were identified.

Due to the solvophilic nature of Compound 1, most products contained residual solvent, making it difficult to distinguish solvates (whether stable or labile) from potential unsolvated forms that had been incompletely dried. In attempts either to identify true anhydrous forms or to see whether previously observed desolvation trends also held for samples from the current screening that had similar lattice structures, selected solid forms were dried at elevated temperature under vacuum overnight. The samples were dried separately to avoid cross-contamination. The resulting products were analyzed by PXRD and TG-FTIR. Form N was stable towards drying, but the other three samples lost some crystallinity and sometimes underwent a solid-form transformation as well.

Summary of the Results from Free Base Polymorphism Screening No. 2

Samples of Form B, Form C, Form D, Form E, and Form F were obtained from several of the high-molecular-weight and/or sterically hindered solvents. Slight shifts in the positions of the PXRD reflections of these products suggest that the crystal lattice often expanded to accommodate the larger molecules.

A sample of Form B was obtained from an experiment involving glycerol.

Form C, an anhydrous or desolvated form, was obtained from experiments involving 50% (w/v) choline dihydrogen phosphate in water, 50% (w/v) choline acetate in water, and Tween 20.

Forms D and E were previously associated with hydrated forms. Form D had only been obtained from ethanol in previous screening and only contained water, suggesting that it was a hydrate that formed via an intermediate solvated state. Form E had been previously shown to be a hydrate that was likely isomorphic with solvates of ethyl formate, DMA, NMP, and MEK. In the current screening, samples similar to Form D or intermediate between Forms D and E were obtained from Carbitol, diglyme, dodecane, isopropyl myristate, 1-octanol, and possibly propylene carbonate. No water was observed in any of these samples although many of them contained large amounts of residual solvent that it might not have been possible to detect any water due to limitations on the dynamic range of the TG-FTIR instrument.

Form F had previously been associated with nearly isomorphic solvates of anisole, toluene, and acetates (EtOAc, iPrOAc, and MeOAc) as well as possibly with solvates of dioxane, DMF, and 2-propanol. In the current screening, it was found to be linked with cumene, 1,3-dimethyl-2-imidazolidinone, triacetin, trifluorotoluene, and p-xylene as well. The solvent 2-pentyl acetate might also form a solvate with this structure.

Form K was not obtained from any of the experiments in this screening. There was also no evidence for a true anhydrous solid form of free base Compound 1 that was not obtained via desolvation or dehydration of a solvated form.

Form L was obtained from a single experiment involving tetrahydrofurfuryl alcohol. Tetrahydrofurfuryl alcohol is also associated with Form H, which was previously known to correspond to nearly isomorphic solvates of THF and TBME.

Form M was obtained from experiments involving 2-pentyl acetate. This form is likely a hemisolvate.

Form N was obtained from a single experiment involving hexamethylphosphoramide.

Additional Free Base Forms

Throughout a salt screen described in section 6.9 below, 5 new patterns were produced from several different free base/acidic salt former combinations and in a range of solvents. As such, these 5 new patterns were likely new polymorphs of the free base. These 5 new patterns were classified as Form O, Form P, Form Q, Form R, and Form S of a free base of Compound 1.

The properties of the solid forms of a free base of Compound 1 are summarized in the following table.

TABLE 7

Summary of solid forms of a free base of Compound 1

| Form | Solvation state | Melting point (approx.) | Other aspects |
|---|---|---|---|
| A | anhydrous (desolvated solvate) | 146.4° C. | anhydrous starting material that readily converts into solvates; obtained from desolvation of selected Form E solvates |
| B | channel hydrate | 138.0° C. | obtained from desolvation of Form G (MeCN solvate) and of selected Form E and Form F solvates (e.g., MeOAc, p-xylene) |
| C | anhydrous (desolvated solvate) | 171.9° C. | solvophilic; obtained from 2-propanol/water and ethyl formate, possibly via desolvation of labile solvates |
| D | hydrate or hygroscopic anhydrous form that is isomorphic with solvates | 136.1° C. | obtained from experiments involving Carbitol, diglyme, dodecane, EtOH, isopropyl myristate, 1-octanol, and possibly propylene carbonate; converted in the direction of Form B upon drying under vacuum at 40° C. overnight |
| E | hydrate isomorphic with solvates (e.g., of MEK) | 132.0° C. [a] | obtained from experiments involving ethyl formate, DMA, NMP, and MEK; presumably isomorphic with solvates from some of these solvents but also appears to exist as a hydrate; converts into Form A or Form B upon drying under vacuum at 40° C. overnight |
| F | nearly isomorphic solvates of acetates (iPrOAc, EtOAc, MeOAc), acetone, anisole, cumene, 1,3-dimethyl-2-imidazolidinone, toluene, triacetin, trifluorotoluene, and p-xylene | 121.2° C. [b] | moderately stable solvates that lose some crystallinity upon drying under vacuum at 40° C. overnight; possibly also forms solvates with dioxane, DMF, 2-propanol, and 2-pentyl acetate |
| G | acetonitrile (mono)solvate | 129.0° C. | converts into Form B upon drying under vacuum at 40° C. overnight |
| H | nearly isomorphic solvates of TBME and THF (and possibly MIBK and tetrahydrofurfuryl alcohol) | 141.4° C. [c] | relatively stable solvates that are not desolvated by drying under vacuum at 40° C. overnight |
| I | DMSO solvate | — [d] | |

TABLE 7-continued

Summary of solid forms of a free base of Compound 1

| Form | Solvation state | Melting point (approx.) | Other aspects |
|---|---|---|---|
| J | AcOH solvate | 79.6° C. | loses some crystallinity upon drying under vacuum at 40° C. overnight |
| K | channel hydrate | 157.0° C. | stable when dried overnight; more stable than Forms B and C in 2PrOH/H$_2$O mixtures with a$_{H2O}$ ≥ 0.3 and in acetone/H$_2$O mixtures with a$_{H2O}$ ≥ 0.5 |
| L | tetrahydrofurfuryl alcohol solvate | — | possible solvated form, but no TG-FTIR was carried out |
| M | 2-pentyl acetate solvate | 154.9° C. $^{e)}$ | probable hemisolvated form |
| N | hexamethylphosphor-amide solvate | — | possible hexamethylphosphoramide solvate |
| O | possible hydrate | — | obtained from salt screen, highly crystalline |
| P | | 132° C. | obtained from salt screen, highly crystalline |
| Q | possible hydrate | — | obtained from salt screen, highly crystalline |
| R | possible hydrate | — | obtained from salt screen, possibly a highly hydrated and hygroscopic material |
| S | | — | obtained from salt screen, highly crystalline |

$^{a)}$ The sample on which DSC was measured was found to be a solvate of MEK.
$^{b)}$ The melting point was measured on an anisole solvate.
$^{c)}$ This temperature likely corresponds to combined melting and dehydration events.
$^{d)}$ The DMSO solvate was not characterized further due to the low vapor pressure and high boiling point of DMSO.
$^{e)}$ The melting point was not resolved from the desolvation event.

6.7 Salts Screening No. 1

A search for possible co-crystals and salts of Compound 1 was conducted from four solvents (acetone, THF, MeCN, and DCM) and twenty-two potential salt/co-crystal formers (L-ascorbic acid, L-aspartic acid, benzoic acid, citric acid, ethanesulfonic acid, fumaric acid, D-gluconic acid, D-glucuronic acid, L-glutamic acid, glutaric acid, glycolic acid, hippuric acid, hydrochloric acid, DL-lactic acid, L-malic acid, maleic acid, methanesulfonic acid, phosphoric acid, succinic acid, sulfuric acid, L-tartaric acid, and toluenesulfonic acid) in a 96-well microtiter plate. A 1:1 ratio of the free drug to the salt/co-crystal former was used in all cases, and the solvents were subsequently evaporated. Upon completion of the Raman measurements on the products of the evaporation experiments, each solid residue was suspended in one of four solvents/mixtures (EtOAc, anisole, 95:5 (v/v) 2PrOH/H$_2$O, or TBME) and temperature cycled between 25 and 35° C. for thirty hours. The solvents were subsequently evaporated, and the solid residues were re-examined by Raman microscopy. In addition, benzenesulfonic acid and α-glycerophosphoric acid were screened in parallel, laboratory-scale experiments.

Based on these experiments, several potential leads were identified, including the mesylate, the D-gluconate, the besylate and the hydrochloride. The L-ascorbate, the esylate, the fumarate, the glutarate, the sulfate, and the tosylate were possible amorphous forms that showed spectral changes that might be attributable to complexation.

Attempts were made to scale up the hydrochloride salt. A total of five new diffractograms was obtained. Form A of hydrochloride salt of Compound 1 appeared to be a TBME solvate and likely had a melting point (after in-situ desolvation) of 202.2° C. (onset at 189.1° C., ΔH≈54.6 J g$^{-1}$). Both elemental analysis and $^1$H-NMR spectroscopy were consistent with the expected structure. Form A was found to be hygroscopic, but it did not change its solid form during the DVS cycle. Its aqueous solubility was measured to be 4.1 mg/mL (7.2 mM) for the free base component. Since the sample underwent solid-form transformation during the solubility measurement, this solubility value may not represent Form A of the hydrochloride salt itself.

Form B of hydrochloride salt of Compound 1 was commonly obtained from protic solvents including alcohol/water mixtures. When dried overnight, the sample only lost some of its crystallinity, and its presumed melting point after (partial) desolvation was 209.8° C. (onset at 200.4° C., ΔH=48.8 J g$^{-1}$). DVS shows that Form B is hygroscopic. $^1$H NMR is consistent with the expected structure.

Form C of hydrochloride salt of Compound 1 appears to be a monoacetone solvate. $^1$H-NMR spectroscopy confirmed that no degradation occurred.

Form D of hydrochloride salt of Compound 1 was obtained from a single evaporation experiment involving the immiscible solvents DCM and water.

A sample of Form E of hydrochloride salt of Compound 1 obtained from 1-propanol contained a significant 2-propanol contribution, suggesting that it was likely a solvated form. Another sample of Form E was obtained from suspension equilibration of a Form C sample in acetonitrile. Form E likely corresponds to isomorphic solvates.

Attempts were made to scale up the mesylate salt. Amorphous products were obtained in several experiments. The Form F anisole solvate of the free base was also frequently obtained. A degradation product was also observed in a few experiments. Two experiments involving ethyl acetate led to the formation of an ethyl acetate solvate of the mesylate salt. Both elemental analysis and $^1$H-NMR spectroscopy of the ethyl acetate solvate confirmed the expected 1:1 stoichiometry of the mesylate salt. The ethyl acetate solvate of the mesylate salt exhibited a broad desolvation endotherm at 69° C. followed by a second broad endotherm (presumably corresponding to melting of the desolvated solvate) near 154.9° C., but the sample was hygroscopic during the DVS measurement. While a relatively high solubility value of 14.9 mg/mL (26.2 mM) for the free base component was obtained, the product had formed a gel. This measured value thus may not represent the initial form itself.

6.8 Polymorphism Screening No. 1 of Hydrochloride Salt of Compound 1

A search for polymorphic forms of the hydrochloride salt of Compound 1 was conducted from sixteen solvents and ten solvent mixtures. The substance was found to have a tendency towards polymorphism, with at least eleven crystalline forms of the salt being identified. Most of these forms correspond to solvates, and in the case of several solvents (acetone, MeCN, and NMP), multiple solvated forms likely exist.

Suspension equilibration (slurry) experiments were carried out using thirteen solvents and seven solvent mixtures. All mixtures are listed as ratios by volume (v/v), and the organic component of each mixture with water was pre-dried over molecular sieves to obtain a defined water activity for the mixture. Experiments were conducted by preparing suspensions of approximately 60-65 mg of a Compound 1 hydrochloride starting material batch (determined to be a mixture of Form A and Form B) in 0.6-2.0 mL of the selected solvent using 4-mL Supelco glass vials. The suspensions were stirred with a magnetic stirrer for seven days at room temperature. The solid samples were recovered by filter centrifugation (5 min, 5000 rpm, 0.22 μm PTFE membrane) and characterized by PXRD without further drying. This procedure should provide an indication of the most stable form in a given solvent. However, in the case of solvate or hydrate formation, the solid form might change as the sample is dried, and metastable forms might with time convert into more stable forms under ambient laboratory conditions. Form A, Form B, Form F, and Form G of the hydrochloride salt were obtained from the slurries.

Evaporation experiments were carried out from three solvents and three solvent mixtures under ambient laboratory conditions. While four of the evaporation experiments led to primarily amorphous material, new solid forms (Form I and Form H) were obtained in two cases.

Heating/cooling experiments: Hot, nearly saturated solutions of Compound 1 hydrochloride were prepared in one solvent and three solvent mixtures. After at least thirty minutes of equilibration at 60° C., the samples were cooled to r.t. at an uncontrolled rate.

Summary of the Results from Polymorphism Screening of Hydrochloride Salt

The most commonly obtained solid form from suspension equilibration experiments was Form A of hydrochloride salt of Compound 1, which appears to correspond to isomorphic solvates with multiple solvents including acetone, anisole, ethyl formate, isopropyl acetate, MEK, TBME, toluene, and likely DMA and DMF.

Form F of hydrochloride salt of Compound 1 was obtained from two experiments involving acetonitrile/water mixtures. The sample appears to correspond to an acetonitrile solvate.

Form G of hydrochloride salt of Compound 1 was obtained from an experiment involving an IPE/NMP mixture. It is likely an NMP solvate.

Form H of hydrochloride salt of Compound 1 was obtained from an experiment involving cyclohexane and NMP and appears to be another NMP solvate with a different structure from that of Form G.

Form I of hydrochloride salt of Compound 1 was obtained from a single experiment involving an IPE/DMSO mixture. It is likely a DMSO solvate.

Neither Form J nor Form K of hydrochloride salt of Compound 1 was obtained in this study. In other studies, Form J of hydrochloride salt of Compound 1 had been obtained from acetonitrile, dichloromethane, 95:5 (v/v) EtOAc/H$_2$O, and heptane; while Form K of hydrochloride salt of Compound 1 had been obtained from hexane and TBME.

No anhydrous form of hydrochloride salt of Compound 1 was discovered within this study. No hydrate form of the hydrochloride salt of Compound 1 was isolated in this study, and suspension equilibration in pure water led to significant amorphization.

The following table summarizes the solid forms of a hydrochloride salt of Compound 1 (Form A to Form K).

TABLE 8

Summary of solid forms of a hydrochloride salt of Compound 1

| Name | Description |
| --- | --- |
| Form A | isomorphic solvates with acetone, anisole, ethyl formate, iPrOAc, MEK, TBME, toluene, and possibly DMA and DMF |
| Form B | isomorphic solvates obtained from protic solvents (e.g., alcohol-water mixtures) |
| Form C | probable acetone solvate |
| Form D | obtained from DCM/H$_2$O mixture; possibly a hydrated form |
| Form E | obtained from 2PrOH and from suspension of Form C in MeCN; likely isomorphic solvates |
| Form F | probable MeCN solvate |
| Form G | probable NMP solvate |
| Form H | probable NMP solvate |
| Form I | probable DMSO solvate |
| Form J | obtained from MeCN, DCM, 95:5 EtOAc/H$_2$O, and heptane |
| Form K | obtained from hexane and TBME |

6.9 Salts Screening No. 2

A salt screen was carried out on Compound 1 using 48 different acidic counterions (1 equiv.) and 20 different solvent systems in the following tables.

TABLE 9

Acidic counterions used in the salt screen

| Counterion | Counterion |
| --- | --- |
| Hydrobromic acid | DL-Lactic acid |
| Hydrochloric acid | L-Ascorbic acid |
| 1,5-Naphthalenedisulfonic acid | Benzoic acid |
| Sulfuric acid | Succinic acid |
| Toluenesulfonic acid | Glutaric acid |
| Methanesulfonic acid | Adipic acid |
| Benzenesulfonic acid | Acetic acid |
| Oxalic acid | Nicotinic acid |
| Isethionic acid | Propionic acid |
| L-Aspartic acid | Nitric acid |
| Maleic acid | Salicylic acid |
| Phosphoric acid | 1,2-Ethanedisulfonic acid |
| L-Glutamic acid | Cyclamic acid |
| Malonic acid | Ethanesulfonic acid |
| 2,5-Dihydroxybenzoic acid (Gentisic acid) | Mucic acid |
| L-Tartaric acid | D-Glucuronic acid |
| Fumaric acid | 4-Aminosalicylic acid |
| Citric acid | Caproic (Hexanoic) acid |
| L-Pyroglutamic acid | Cinnamic acid |
| R-Mandelic acid | Capric (Decanoic) acid |
| L-Malic acid | Caprylic (Octanoic) acid |
| Hippuric acid | Camphoric acid |
| D-Gluconic acid | D-Aspartic acid |
| Glycolic acid | D-Glutamic acid |

TABLE 10

Selected solvents used in the salt screen

| | Solvent | ICH Class | Volume Added (µL) |
|---|---|---|---|
| 1 | 1,4-Dioxane | 2 | 1000 |
| 2 | 2-Propanol | 3 | 1000 |
| 3 | Acetone | 3 | 1000 |
| 4 | Acetone/water (50:50 v/v) | 3 | 1000 |
| 5 | Acetonitrile | 2 | 1000 |
| 6 | Acetonitrile/water (50:50 v/v) | 2 | 700 |
| 7 | Dichloromethane | 2 | 1000 |
| 8 | Diisopropyl ether | n/a | 1000 |
| 9 | Ethanol | 3 | 1000 |
| 10 | Ethanol/water (50:50 v/v) | 3 | 1000 |
| 11 | Ethyl acetate | 3 | 1000 |
| 12 | Heptane | 3 | 1000 |
| 13 | Isopropyl acetate | 3 | 1000 |
| 14 | Methanol | 2 | 800 |
| 15 | Methyl ethyl ketone | 3 | 1000 |
| 16 | tert-Butyl methyl ether | 3 | 1000 |
| 17 | Tetrahydrofuran | 2 | 1000 |
| 18 | Tetrahydrofuran/water (50:50 v/v) | 2 | 800 |
| 19 | Toluene | 2 | 1000 |
| 20 | Water | n/a | 1000 |

For the primary salt screen, 40 mg of free base was used per sample and 20 solvents were used for each free base/counterion combination. 21 samples were lyophilised and one sample was stored at 40° C./75% RH for 72 h upon removal from the freeze dryer before being analyzed by XRPD. The remaining 20 samples (per salt) were thermally cycled (with agitation) for 72 h after the addition of selected solvents to prepare slurries/solutions. The thermal cycle consisted of 4 h at r.t. and then 40° C. for 4 h.

Upon removal from temperature cycling, any solid material present was isolated by centrifuge filtration (0.2 µm) and retained for analysis. All solids were analyzed by XRPD. Any crystalline salts were analyzed by TG/DTA.

If upon removal from the thermal cycle, no solid material was present, the mother liquor was split into 3 equal parts and stored under the following conditions: freezer (−18° C.), evaporation, and antisolvent addition (isopropyl acetate used for all samples unless specified otherwise). Any solids recovered were analyzed by XRPD and if crystalline patterns were identified, the solids were also analyzed by TG/DTA.

Of the 48 acidic counterions tested in the screen, salts were produced from 34 acidic counterions, as summarized in the following table:

TABLE 11

Summary of salt screening

| Counterion | Summary |
|---|---|
| HBr | 4 salts |
| | Form B was the most commonly produced form |
| | Form A and Form C appeared to be non-solvated forms. |
| HCl | 2 salts |
| Napadisylate | 1 salt produced from all solvent systems tested |
| Sulfate | Only amorphous solids produced |
| Tosylate | 1 salt produced from 1,4-dioxane only |
| Mesylate | 1 salt produced from 1,4-dioxane only |
| Besylate | 1 salt produced when isopropyl acetate was added as an antisolvent to acetone/water (50:50 v/v) and THF/water (50:50 v/v) |
| Oxalate | 1 salt |
| Isethionate | 2 salts |
| | Form A is possibly a non-solvated form |
| Maleate | 2 salts |
| | Form A is possibly a non-solvated form |
| Phosphate: | 1 salt from acetone/water (50:50 v/v) only |
| | Form A is possibly a non-solvated form |
| Malonate | 1 salt from water only |
| Gentisate | 3 salts |
| | most solids produced were either Form B or Form C |
| Tartrate | 1 salt |
| Fumarate | 1 salt from DCM only |
| Citrate | Only amorphous solids produced |
| Mandelate | 1 salt from water only |
| Malate | 1 salt from DCM only |
| | Form A appeared to be a non-solvated form |
| Glycolate | 1 salt from IPA only |
| Ascorbate (from L-ascorbic acid) | 1 salt from the evaporation of 1,4-dioxane only Form A is possibly a non-solvated form |
| Succinate | 1 salt from the evaporation of 1,4-dioxane only Form A is possibly a non-solvated form |
| Nitrate | 1 salt from all solvent systems tested except 1,4-dioxane and MeCN/water (50:50 v/v) |
| Salicylate | 3 salts |
| | Form A was most commonly produced |
| | Form B is possibly a non-solvated form |
| Edisylate | 2 salts |
| | Form B was most commonly produced |
| Cyclamate | 5 salts |
| Esylate | 2 salts |
| | Form B was most commonly produced |
| | Form B appeared to be a non-solvated form |
| Glucuronate (from D-glucuronic acid) | 1 salts Form A appeared to be a non-solvated form |
| 4-Amino salicylate | 1 salt from water only |
| Caproate | 1 salt from THF/water (50:50 v/v) only |
| Cinnamate | 2 salts |
| Caprylate | 1 salt from THF/water (50:50 v/v) only |
| Camphorate | 1 salt from MeCN and MeOH |
| Aspartate (from D-aspartic acid) | 2 salts |
| Glutamate (from D-glutamic acid) | 1 salt |

6.10 Evaluation of Forms (a) Evaluation of Form A of a Free Base of Compound 1

Form A was not isolated directly as a wet cake but formed only upon drying of Form E in polymorphism studies. Moreover, it appears that Form E can generate, during drying, either Form A, Form B or a mixture of the two, suggesting that what form is obtained depends on the drying kinetics. Small quantities of Form A were generated by dissolving a crude Compound 1 in MEK at high temperature, followed by fast cooling to room temperature, filtration and drying. DSC and TGA data were obtained for samples of Form A and following storage for 1 week at 60° C. and 60° C./75% RH. The DSC trace for the sample stored at 60° C. was quite similar to the initial condition, however, changes in physical form were observed in the sample stored at 60° C./75% RH. The melting endotherm was broader in this sample and had a peak temperature which was shifted by ~3.7° C. to 140.7° C. compared to 144.4° C. in the original sample. Also, another broad endotherm in the temperature range of 50-75° C. was seen in this sample which was absent in the original sample. TGA analysis confirmed that this broad endotherm was most likely due to moisture uptake under the accelerated storage conditions. Most of the weight loss of 0.82% in this sample occurred in a single step at less than 75° C. By contrast, weigh loss was a two-step process at the initial time point. A weight loss of ~0.26% was seen between 25 to 75% RH in the first step and approximately 0.36% additional weight loss was seen in the second step at the initial time point. The residual solvent initially present in the sample was lost upon storage of the sample at 60° C. (0.13% weight loss between 25 to 150° C.).

(b) Evaluation of Form B of a Free Base of Compound 1

Form B could be obtained from a process involving methyl acetate. Color change was observed in the sample stored at 60° C. from an initially white sample to light brown. HPLC traces were taken of the samples of Form B and following storage for 2 week at 60° C. and 60° C./75% RH. The area % chemical purity of the sample initially was 98.4%, which decreased to 97.71 and 97.92% following storage for 2 week at 60° C. and 60° C./75% RH respectively. Several small degradation products were seen to grow especially in the sample stored at 60° C. Chiral instability was also observed in the sample stored at 60° C./75% RH. Chiral purity changed from an initial value of 97.96 area % to 96.54 area % in the sample stored at 60° C./75% RH but remained unchanged in the sample stored at 60° C. after 2 week storage under the accelerated conditions.

(c) Evaluation of Form C of a Free Base of Compound 1

Form C could be isolated from a limited number of solvents. In particular, it could be obtained through reslurries in IPA or through hot relurries in acetone. Form C was found to be physically and chemically stable under accelerated stability conditions. During scale-up of this form, a new Form (Form K) was obtained. A comparison of the DSC heat of fusion values and sharpness of the PXRD peak data for Form C and K showed that the latter was relatively more crystalline.

Competitive slurry experiments between Form C, Form B and Form A showed that in binary as well as ternary mixtures containing Form C, Form B and Form A rapidly converted to Form C within 24 hr in an aqueous slurry at room temperature. In the absence of Form C, mixture of Form A and B remained unchanged in the aqueous slurry over a 24 hr period. This data clearly shows that of the three forms, Form C is the relatively more thermodynamically stable form.

Like Form C, Form K was also shown to be chemically and physically stable in accelerated stability studies. Competitive slurry experiments in water were performed with mixtures of both forms, and a gradual conversion of Form C to Form K occurred over prolonged stirring suggesting that Form K was the more thermodynamically stable Form.

(d) Evaluation of Form K of a Free Base of Compound 1

Form K was first discovered in IPA-water mixtures. Seeded slurry to slurry solvent mediated transformations in IPA-water (90:10), starting from Form C, consistently generated Form K. Subsequent preliminary protocols involved dissolution in acetone, followed by addition of water, seeding and charge of additional water to reduce concentration. This process also consistently produced Form K.

To study the space in which Form K is the most stable form in acetone/water, competitive slurry studies starting from a mixture of Form B, Form C and Form K were carried out in acetone/water under different conditions. Form K was found to be the most stable form for water contents (% vol.) of 5% and higher, both at room temperature and at 45° C. Form B was obtained at room temperature while form C was obtained at 45° C. in acetone alone.

Based on the results, the following process is developed for the preparation of Form K: charge Compound 1 to reactor R-1; charge acetone (15×vol) and start agitation at room temperature; heat batch to 40° C.; age batch for no less than 1 h at 40° C.; cool batch to 22.5° C. over no less than 50 min; charge acetone (15×vol); age batch for 2 h; transfer batch from R-1 to R-2 through polish filter; concentrate batch in R-2 to a total volume of ~15×vol under partial vacuum; heat batch to 42.5° C.; charge water (2×vol) to batch; seed with 5% Compound 1 Form K; perform IKA milling through a recirculation loop at 23 m/s for 8 hours; cool to 22.5° C. over no less than 4 hours; age for 3 h; charge water (6×vol) over 8 h; age for 4 h; transfer batch to filter F-1; wash filter cake three times with acetone:water (66:34 v/v); dry filter cake with vacuum under nitrogen sweep at no more than 45° C.; perform humid aging of cake for no less than 12 h, under a humidity of 70%; and assay and package the product.

It was noticed that after Form K was dried, the XRPD peaks of Form K shifted to a higher value and the resulting XRPD pattern is called Form K'. To further understand the relationships between the two forms, free base Form K and Form K' were placed on XRPD sample holders and stored in a closed Jars with saturated salt solutions for RH controls at ambient temperature, respectively. The samples were analyzed after 2-day and 6-day storages. for the following RH at ambient temperature. The salts used are lithium chloride for 11% RH, potassium acetate for 22% RH, magnesium chloride for 33% RH, and potassium carbonate for 43% RH. The XRPD diffractograms of the samples after 2-day storage are presented in FIG. 132 and FIG. 133, respectively. The results indicate that Form K converts to K' under 11% RH, and form K' converts to K at 22% RH or above. Since the peaks of Form K shifted to higher 2-theta value as Form K loses water molecules to Form K', Form K and Form K' are on a continuum.

To assess whether Form K and Form K' are likely to have different bioavailabilities, comparative solubility measurements were carried out in physiologically relevant media. Samples of Form K and Form K' were separately equilibrated in pure water, pH 2.0 buffer, and pH 6.8 buffer for fifteen minutes, and the solids were then separated from the solvents. The concentration of the compound in the filtrate (i.e., the solubility) was assessed in each case, and the solid residues were also monitored by powder X-ray diffraction. All six solid residues correspond to Form K, confirming that Form K' rapidly incorporates water into its lattice when suspended in an aqueous environment even when the solubility is low. While the solubilities in pure water and at pH 6.8 were below the limit of quantitation of 0.0001 mg/mL, the solubilities at pH 2.0 could be measured. Both were found to be essentially the same: namely, 0.93 mg/mL for Form K' and 0.96 mg/mL for Form K, and no evidence of solubility enhancement for Form K' was discernible. Thus, the bioavailabilities of the two forms are expected to be similar, and precise control of the water content (and, thereby, the solid form) is presumably not necessary from a scientific point of view. Given that the critical water activity is in the range $a_{H2O}$=0.11-0.17, the hydrated Form K is likely to be the more easily stabilized of the two forms under ambient laboratory conditions.

Hygroscopicity:

Form K picks up water at very low humidities. Water sorption continues to occur at all humidities gradually reaching a plateau in uptake of ~3.2% w/w corresponding to ~1 mole of water. The adsorbed water was released in the desorption phase with no hysteresis observed in the drying phase.

Physical Stability:

Visually, all samples of Form K were white colored powder with no apparent change in color in the samples stored under accelerated conditions (40° C., 40° C./75% RH, 60° C., 60° C./75% RH and sample stored in light chamber in clear vials exposed to light and covered in aluminum foil) for 14 d relative to the sample stored refrigerated and under ambient conditions. No visual change in color was observed in any of the samples stored under the accelerated stability conditions. Based on the DSC, PXRD and TGA data, there does not appear to be any major change in the crystal form and water content for From K under the accelerated conditions of temperature, humidity and exposure to light.

Solid State Chemical Stability:

HPLC analysis were performed on Form K samples stored under the accelerated stability conditions. Overall, no significant degradation was observed in the neat drug under accelerated storage conditions. Minor degradation was seen in the sample exposed to light (1.2 million lux). Based on the HPLC analysis data, there is a measurable but small change in the chemical stability of Form K under the accelerated conditions of temperature, humidity and exposure to light over the 14 d period. Form K is considered physically and chemically stable.

Solid State Chiral Stability:

Chiral stability of Form K samples stored under accelerated stability conditions was tested. There was ~2.9% of the R-enantiomer (97.1 area % of the active S-isomer) in the initial sample. Following storage under the accelerated conditions, there was no change in the chiral stability of the compound under accelerated conditions and the results are within analytical variability.

Shear Sensitivity:

Form K was compressed under 2000 psi for 1 minute and analyzed by XRPD. The solid form remained as Form K.

(e) Evaluation of Form A of a Hydrobromide Salt of Compound 1

Form C of a hydrobromide salt of Compound 1 was produced in the salt screen from MeCN only. As Form C had favourable thermal properties, it was selected for scale up. The HBr salt was prepared using the same method as that used in the salt screen but with all amounts scaled up to prepare a salt from 500 mg of free base: 500 mg of free base Compound 1 was dissolved in 60 mL 1,4-dioxane before 1.05 equivalents of 1 M hydrobromic acid in water was added. A further 5 mL water was added to aid dissolution for freeze drying. The material was then freeze dried. Upon removal from the freeze dryer, 12.5 mL of acetonitrile was added to prepare a slurry. The slurry was then thermally cycled for ~72 h (with agitation). The thermal cycle consisted of 4 h at r.t. and then 40° C. for 4 h. Form C was not produced successfully at 500 mg scale. Form A was produced instead.

In an attempt to reproduce Form C, the material was re-lyohphilized to produce an amorphous starting point and then 12.5 mL of acetonitrile was added to form a slurry and the resulting slurry was thermally cycled again for ~72 h. Form A was produced again. Likely that Form A is a more stable form of the HBr salt than Form C. Form A was used in the following analysis.

The material had no clear morphology, consisted of various sized aggregates and appeared birefringent (PLM). The material had an average 98.8% purity. The chemical structure was confirmed by $^1$H NMR-non solvated salt.

Thermal analyses showed an initial ~1.8% loss in mass (TGA) likely due to unbound solvent loss and both TG/DTA and DSC showed melt onsets at ~277 and 280° C., respectively. The material was found to be slightly hygroscopic by DVS, with a ~0.69% mass increase observed up to 90% RH—minimal hysteresis observed. No bulk change in crystalline form observed by XRPD post-DVS. The material was found to be both physically and chemically stable when stored at 40° C./75% RH, 80° C. and under ambient light/temperature for 1 week—no bulk change in the diffraction pattern (XRPD) or chemical purity (HPLC).

The HBr salt was largely insoluble in various buffers when 1 mg/mL slurries were prepared and the mother liquor concentration determined (by HPLC): <0.05 mg/mL in all buffers tested. When slurried in acetone/water mixtures with various water activities, the HBr salt displayed no bulk change in the diffraction pattern produced from the isolated solids—no hydrate formation evident. The HBr salt did not appear to disproportionate back to the free base when slurried in water for ~24 h.

(f) Evaluation of Form B of a Besylate Salt of Compound 1

The salt screen only produced one besylate salt of Compound 1 (Form A) when isopropyl acetate was added as an antisolvent to acetone/water (50:50 v/v) and THF/water (50:50 v/v).

Form B of a besylate salt of Compound 1 (a form not produced in the salt screen) was scaled up for a 10 g batch of free base Compound 1 according to the following procedure: 10 g of free base Compound 1 was weighed into a sample bottle and 220 mL of acetonitrile was added to form a slurry. The slurry was stirred with moderate speed at room temperature. Benzenesulfonic acid (6.14 g) was added to the slurry to form a homogeneous solution. ~20 to 30 mg of seeds were added (with stirring) and a large amount of precipitate was visible after 30 min. The slurry was left to stir overnight before the solid was isolate via Buchner filtration. An XRPD was collected of the filtered solid and of the remaining seeds to check that the desired salt form had been produced. The material was then dried in a vacuum oven at 40° C. for ~72 h before any other analysis was carried out.

Form B of the besylate salt was successfully produced on a 10 g scale. The material had no clear morphology, consisted of various sized aggregates and appeared birefringent (PLM). The yield of salt produced was ~82.4%. The material had an average 99.2% purity. The chemical structure was confirmed by $^1$H NMR-non solvated salt (1:1 Compound 1:besylate-monosalt).

Thermal analyses showed a steady ~1.5% loss in mass above ~120° C. (TGA) likely due to bound solvent loss or perhaps slow degradation and both TG/DTA and DSC showed melt/degradation onsets at ~251 and 252° C., respectively.

The material was found to be physically stable under accelerated stability conditions (40° C., 40° C./75% RH, 60° C., 60° C./75% RH, and under light for 14 days)—no bulk change in the diffraction pattern (XRPD). Chemical purity (HPLC) showed degradation peak (likely hydrolysis of —CN group) with trend in growth with temperature and humidity. The chiral purity (area % of S-isomer) remained above 99% under the accelerated stability conditions.

Solubility data of the several polymorphic forms of Compound 1 in physiologically relevant media and the final pH of these solutions are summarized in the following tables.

TABLE 12

Solubilities of different forms at different pHs

| Medium | Solubility (mg/ml) | | | | | | |
|---|---|---|---|---|---|---|---|
| | Close to Form A | Form C | Form A | Form B | Form K | HCl Salt | HBr salt |
| pH 1 buffer HCl/NaCl) | 0.107 | 0.108 | 0.088 | 0.085 | 0.133 | 0.071 | 0.018 |
| pH 3 buffer (phosphate) | 0.212 | 0.277 | 0.280 | 0.125 | 0.090 | 0.149 | 0.032 |
| pH 4 buffer (acetate) | 0.120 | 0.065 | 0.159 | 0.115 | 0.011 | 0.124 | 0.038 |
| pH 5 buffer (acetate) | 0.004 | 0.003 | 0.008 | 0.007 | 0.001 | 0.017 | 0.004 |
| SGF with pepsin | 0.391 | 0.427 | 0.429 | 0.406 | 0.420 | 0.295 | 0.077 |
| FaSSIF | 0.001 | 0.001 | 0.001 | 0.001 | 0.001 | 0.001 | <LOQ |
| FeSSiF | 0.064 | 0.031 | 0.086 | 0.077 | 0.005 | 0.094 | 0.111 |
| Water | — | <LOQ | <LOQ | <LOQ | <LOQ | — | 0.301(t0), 0.212(t24) |

TABLE 13 pHs for Correspondent Samples in the above table

| Medium | Final pH | | | | | | |
|---|---|---|---|---|---|---|---|
| | Close to Form A | Form C | Form A | Form B | Form K | HCl Salt | HBr salt |
| pH 1 buffer HCl/NaCl) | 1.29 | 1.07 | 1.14 | 1.09 | 1.20 | 1.05 | 0.95 |
| pH 3 buffer (phosphate) | 3.96 | 3.31 | 3.70 | 4.05 | 3.09 | 3.05 | 3.11 |
| pH 4 buffer (acetate) | 4.13 | 4.14 | 4.11 | 4.11 | 3.98 | 4.00 | 4.18 |
| pH 5 buffer (acetate) | 5.04 | 5.11 | 5.03 | 5.05 | 5.01 | 4.83 | 5.08 |
| SGF with pepsin | 1.49 | 1.29 | 1.34 | 1.29 | 1.47 | 1.28 | 1.15 |
| FaSSIF | 6.40 | 6.44 | 6.44 | 6.43 | 6.33 | 5.96 | 6.40 |
| FeSSiF | 5.05 | 5.05 | 5.05 | 5.03 | 5.02 | 4.99 | 5.16 |
| Water | — | 6.86 | 6.77 | 6.46 | 6.71 | — | 4.53 |

6.11 Polymorphism Screening No. 2 of Hydrochloride Salt of Compound 1

Additional studies for polymorphic forms of the hydrochloride salt of Compound 1 were conducted, given that no anhydrous form or hydrate form of hydrochloride salt of Compound 1 was discovered in polymorphism screening No. 1 of Hydrochloride Salt of Compound 1. Eventually, an anhydrous Form L was identified from multiple reactive crystallization experiments. A wide range of factors, including 1) solvents, 2) HCl sources (organic and aqueous), 3) temperature (0° C., room temperature, and 80° C.), and 4) HCl stoichiometry were screened, and the results are listed in the following table.

TABLE 14

Polymorph screening for Form L of a hydrochloride salt of Compound 1
Experiments with addition of 1.1 eq. of HCl in an organic solvent. No water added.

| Solvents | HCl (mol eq) | Solvent | Solid State | KF (%) | XRPD |
|---|---|---|---|---|---|
| CPME | N.D. | >>2 | Crystalline | x | Form A variant |
| MeOH | No salt was formed | | | x | |
| 1,4-Dioxane | 0.64 | 0.27 | Low crystallinity | 3 | |
| CPME after heat/cool cycle | 1 | 0.59 | Low crystallinity | 2.5 | |
| Heptane | 0.89 | 0.02 | Partially crystalline | 4 | |
| Toluene | 0.9 | 0.49 | Partially crystalline | 1.7 | |
| Acetone | N.D. | 0.03 | Partially crystalline | 1.1 | |
| Acetonitrile | 0.91 | 0.08 | Crystalline | 0.2 | Form L |
| 2,2-Dimethoxypropane | N.D. | 0.01 | Partially crystalline | 1.5 | |
| MTBE | 0.6 | 0.84 | Crystalline | 1 | Form A variant |

TABLE 14-continued

Polymorph screening for Form L of a hydrochloride salt of Compound 1
Experiments with addition of 1.1 eq. of HCl in an organic solvent. No water added.

| Solvents | HCl (mol eq) | Solvent | Solid State | KF (%) | XRPD |
|---|---|---|---|---|---|
| Reslurries containing water | | | | | |
| CPME solids reslurred in water | 1 | N.D | Crystalline | x | Form L |
| CPME solids reslurred in 20% acetone/water | N.D. | 0.01 | Crystalline | 0.4 | Form L |
| Experiments with addition of 1.2 eq. of HCl 1N HCl aq. | | | | | |
| DMSO:water (1:7.5 - 34X) | 0.93 | 0.04 | Crystalline | 0.4 | Form L |
| 2-MeTHF | N.D. | 0.69 | Partially crystalline | 1.8 | |
| THF | 0.88 | 0.47 | Partially crystalline | 1.6 | |
| Acetone | solution | | N/A | | |
| EtOH | N.D. | 0.01 | Crystalline | 3.2 | Form B |
| MeCN | solution | | N/A | | |
| IPAc | 0.85 | <0.01 | Crystalline | 0.4 | Form L |
| DMAc | solution | | N/A | | |
| EtOAc | N.D. | 0.01 | Crystalline | 0.1 | Form L |
| NMP/water (3:7) | 0.89 | 0.03 | Crystalline | 0.3 | Form L |
| DMF/water (3:7) | 0.93 | 0.04 | Crystalline | 0.4 | Form L |
| DMAc/water (3:6) | 0.93 | 0.03 | Crystalline | 0.2 | Form L |
| Experiments with 2 eq. and 4 eq. HCl aq. | | | | | |
| 20% acetone in water + 2 eq. HCl | 0.94 | 0.01 | Crystalline | 0.3 | Form L |
| 20% acetone in water + 4 eq. HCl | 0.87 | 0.01 | Crystalline | 0.2 | Form L |
| CPME + 2 or 4 eq. HCl | Formed a gum | | N/A | | |
| Experiment with 2.5 eq. of HCl. No water added. | | | | | |
| CPME | 0.85 | 0.44 | Partially crystalline | 1.4 | |
| Experiments at 0° C. | | | | | |
| CPME | | | Weakly crystalline | | Form L + other |
| DMSO:water (1:4) | | | Weakly crystalline | | Form L |
| Experiments at 80° C. | | | | | |
| CPME | 0.81 | ND | Crystalline | | Form L |
| DMSO:water (1:4) | | | Crystalline | | Form L |
| Alcoholic solvents + 2 eq. of HCl aq | | | | | |
| IPA | | | Crystalline | | Form B as an isomorphous solvate |
| 1-propanol | | | Crystalline | | Form L |
| 1-butanol | | | Crystalline | | Form L |
| 2-methyl-2-butanol | | | Crystalline | | Form B as an isomorphous solvate |

Stress Polymorph Screening Using Form L as Starting Form:

Form L was suspended in different solvents at different temperature for a week. XRPD patterns were collected for both wet and ambient dried cakes. The results are listed in the following table:

TABLE 15

Stress polymorph slurry screen - Form L of Compound 1 HCl as starting form

| Solvent | Temp (° C.) | XRPD wet | XRPD dry |
|---|---|---|---|
| EtOAc | 50° C. | Form L | Form L |
| IPA | 50° C. | Form L | N/A |
| Acetone | RT | Form L | Form L |
| DCM | 4° C. | weakly crystalline | weakly crystalline |
| MeCN | 50° C. | Form L | N/A |
| THF | RT | Form O | Form O* |
| Water | 50° C. | Form N | N/A |
| H₂O/MeOH 1:3 v/v (Aw = 0.5) | RT | Form B | Form B* |
| H₂O/MeCN 1:3 v/v (Aw = 0.9) | 4° C. | Form N | Form N |

TABLE 15-continued

Stress polymorph slurry screen - Form
L of Compound 1 HCl as starting form

| Solvent | Temp (° C.) | XRPD wet | XRPD dry |
| --- | --- | --- | --- |
| Ethanol | 50° C. | Form L | N/A |
| MTBE | RT | weakly crystalline | weakly crystalline |
| anisole | 50° C. | Form L + other | Form L + other |
| Toluene | 50° C. | Form L | N/A |
| DMAc | RT to 80° C. to 4° C. | Form P | Form P* |
| DMSO to water (crush precipitation) | RT | Form N | Form N |

*peak shifts and differences were seen during drying

Polymorph Screening by Crush Precipitation:

200 mg Form L of hydrochloride salt of Compound 1 was dissolved in 1 ml DMSO. 200 µl of DMSO solution was added to each of the anti-solvent (EtOAc, MTBE, toluene, MeCN and acetone). The results are listed in the following table:

TABLE 16

Compound 1 HCl polymorph screen by crush precipitation

| Solvent | Temp (° C.) | XRPD wet | XRPD dry |
| --- | --- | --- | --- |
| DMSO/EtOAc (1:5 v/v) | RT | Form Q | Form Q |
| DMSO/MTBE (1:5 v/v) | RT | Form R | Form R |
| DMSO/Toluene (1:5 v/v) | RT | Form S | Form S |
| DMSO/MeCN (1:5 v/v) | RT | Form S | Form S |
| DMSO/acetone (1:5 v/v) | RT | Form N + other | Form N |

Polymorph Screening Using Amorphous Hydrochloride Salt of Compound 1:

about 50-100 mg of amorphous hydrochloride salt of Compound 1 was suspended in 15 different organic solvents for 1 week. Five of them were seeded with 5 mg Form L, aged at 50° C. for a week and checked by XRPD. The results are listed in the following table:

TABLE 17

Compound 1 HCl polymorph screen with amorphous material

| Solvent | Temp (° C.) | XRPD wet | XRPD dry | XRPD wet (seeded with Form L) |
| --- | --- | --- | --- | --- |
| iPAc | RT | Form T | Form T* | N/A |
| AcOH | RT | Form U | Form U* | N/A |
| NMP | RT | Form H | Form V | Form H |
| anisole | 50° C. | Form W | Form W* | Form W |
| CPME | 50° C. | Form X | Form X* | Form L |
| MTBE | 50° C. | Form Y | Form Y | N/A |
| nBuOH | 50° C. | Form Z | Form Z | Form L |
| acetone | 50° C. | Low crystalline | Low crystalline | Form L |
| MeCN | 50° C. | Form L | Form L | N/A |
| EtOAc | 50° C. | Form AB | Form AB* | N/A |
| EtOH | 50° C. | Form L | Form L | N/A |
| Toluene | 50° C. | Form AC | Form AC | N/A |
| Nitromethane | 50° C. | Form L | Form L | N/A |
| MeOH | 50° C. | Form L | Form L | N/A |
| water | 50° C. | Form N | Form N | N/A |

*dry XRPD pattern is slightly different from the wet XRPD pattern.

Form M Scale Up:

150 mg Form L was heated to 160° C., hold at this temperature for 10 min and cool down to RT. XRPD and DSC confirmed the thermal annealed material converted to Form M.

Determination of Phase Transition Temperature for Form L and Form M:

4 suspensions of 1:1 Form M/L mixture in different solvents were stirred at different temperature (60, 80, 100 and 120° C.). The results (as shown in the follow table) show that Form M/L transition temperature is between 60-100° C. and it is likely in the range of 60-80° C. Form L and Form M are enantiotropically related (Form L is more stable at room temperature and Form M is more stable at high temperature).

TABLE 18

Phase transition study for Form L and Form M

| Solvent | Temp (° C.) | XRPD result |
| --- | --- | --- |
| MeCN | 60° C. | L |
| MeCN | 80° C. | M/L * |
| Toluene | 100° C. | Form M |
| p-xylene | 120° C. | Form M |

* slurry remained Form M/L mixture after 2 weeks. Form M peak increased overtime.

Determination of Critical Water Activity for Form L and Form N:

50 mg of Form L was suspended in 0.5-1 ml of water/acetone solution with specific water activity. The solutions were stirred at RT or 60° C. Form conversion was monitored by XRPD over 2 weeks. The results (as shown in the follow table) show that 1) critical water activity at RT is between 0.2-0.4; and 2) critical water at 60° C. is between 0.4-0.5. Under high water activity conditions, Form L is converted to Form N. Form N is stable under ambient condition, while upon drying in vacuum oven at 40° C., Form N readily converts to Form L.

TABLE 19

Phase transition study for Form L and Form M

| | | Aw | | | | |
| --- | --- | --- | --- | --- | --- | --- |
| | | 0.1 | 0.2 | 0.3 | 0.4 | 0.5 |
| Temp | RT | Form L | Form L | Form AA | Form N | Form N |
| | 60° C. | — | Form L | Form L | Form L | Form N |

Form conversion scheme for Form L, Form M, and Form N is shown in FIG. 170.

The discovery conditions for Form L to Form AC are summarized in the following table:

TABLE 20

Discovery conditions for Form L to Form AC of hydrochloride salt of Compound 1

| Polymorph | Discovery conditions |
|---|---|
| Form L | suspending free base Form K into 20% acetone/water, then charging 4 eq. of 1N HCl aqueous solution and performing multiple heating (40° C.) and cooling (RT) cycles |
| Form M | 150 mg Form L was heated to 160° C., isothermal for 10 min and cool down to RT |
| Form N | Form L was suspended in 20% acetone in water (v/v) at 60° C. overnight |
| Form O | 50 mg Form L was suspended in 1 ml THF at RT for a week |
| Form P | 50 mg Form L was suspended in 1 ml DMAc for a week with temperature cycling from RT to 80° C. to 4° C. |
| Form Q | 50 mg Form L dissolved in 200 ul DMSO, which was dropped into a solution of 1 ml EtOAc and suspended at RT overnight |
| Form R | 50 mg Form L dissolved in 200 ul DMSO, which was dropped into a solution of 1 ml MTBE and suspended at RT overnight |
| Form S | 50 mg Form L dissolved in 200 ul DMSO, which was dropped into a solution of 1 ml toluene and suspended at RT overnight |
| Form T | 50-100 mg of amorphous HCl salt was suspended in iPAc at RT for a week |
| Form U | 50-100 mg of amorphous HCl salt was suspended in AcOH at RT for a week |
| Form V | 50-100 mg of amorphous HCl salt was suspended in NMP at RT for a week |
| Form W | 50-100 mg of amorphous HCl salt was suspended in anisole at 50° C. for a week |
| Form X | 50-100 mg of amorphous HCl salt was suspended in CPME at 50° C. for a week |
| Form Y | 50-100 mg of amorphous HCl salt was suspended in MTBE at 50° C. for a week |
| Form Z | 50-100 mg of amorphous HCl salt was suspended in nBuOH at 50° C. for a week |
| Form AA | 50 mg of Form L was suspended in 1 ml acetone/water (97:3 v/v) solution at RT for 2 weeks |
| Form AB | 50-100 mg of amorphous HCl salt was suspended in EtOAc at 50° C. for a week |
| Form AC | 50-100 mg of amorphous HCl salt was suspended in toluene at 50° C. for a week |

The following table summarizes the solid forms of a hydrochloride salt of Compound 1 (Form L to Form AC).

TABLE 21

Summary of solid forms of a hydrochloride salt of Compound 1

| Name | Description |
|---|---|
| Form L | anhydrous form. DSC: 1st endo at 124° C. for solid-state transition and 2nd endo at 262° C. for melt. |
| Form M | anhydrous form. Form M and form L are enantiotropic. Form M is more stable at high temperature while form L is more stable at low temperature. DSC: Form M melts at ~259° C. |
| Form N | probable hydrate form. DSC: 1st endo at 44° C. for dehydration, 2nd endo at 127° C. for solid-state transition, and 3rd endo at 256° C. for melt. |
| Form O | probable THF solvate |
| Form P | probable DMAc solvate |
| Form Q | obtained from DMSO/EtOAc (1:5) suspension; possibly mixed solvate |
| Form R | obtained from DMSO/MTBE (1:5) suspension; possibly mixed solvate |
| Form S | obtained from DMSO/toluene (1:5) suspension; possibly mixed solvate |
| Form T | probable IPAc solvate |
| Form U | probable AcOH solvate |
| Form V | probable NMP solvate |
| Form W | probable anisole solvate |
| Form X | probable CPME solvate |
| Form Y | probable MTBE solvate |
| Form Z | probable nBuOH solvate |
| Form AA | obtained from 97:3 Acetone:water suspension; possibly acetone/water solvate |
| Form AB | probable EtOAc solvate |
| Form AC | probable toluene solvate |

6.12 Preparation of Form A of Hydrobromide Salt of Compound 1

(S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1) free base (2 g) was charged to acetone (70 mL) at 25° C. and the solution was heated to 40° C. Compound 1 hydrobromide salt (0.1 g) was charged as seed. A hydrobromic acid solution was prepared by mixing 48 wt % hydrobromic acid (0.440 mL) and water (7.6 mL). The hydrobromic acid solution was charged to the acetone mixture over 9 hours maintaining 40° C. to crystallize the Compound 1 HBr Salt. The slurry was cooled to 20° C. The slurry was filtered and washed with three acetone washes (6 mL each). The wet solids were dried in a vacuum oven to give Compound 1 hydrobromide salt, a white to off-white solid (2 g, 88% yield). $^1$H NMR (500 MHz, DMSO-d6) δ ppm 1.93-2.06 (m, 1H), 2.39-2.48 (m, 1H), 2.55-2.66 (m, 1H), 2.93 (ddd, J=17.51, 13.62, 5.49 Hz, 1H), 3.14-3.29 (m, 3H), 3.40-3.49 (m, 2H), 3.73 (br d, J=12.05 Hz, 2H), 4.19-4.54 (m, 4H), 5.13 (dd, J=13.28, 5.19 Hz, 1H), 5.32 (s, 2H), 7.23 (t, J=8.77 Hz, 1H), 7.35 (dd, J=7.86, 5.11 Hz, 2H), 7.46-7.53 (m, 1H), 7.55-7.68 (m, 5H), 7.79 (dd, J=13.12, 1.68 Hz, 1H), 9.92 (s, 1H), 10.98 (s, 1H), melting point 283° C.

6.13 Polymorphism Screening of Hydrobromide Salt of Compound 1

Stress Polymorph Screening Using Form A as Starting Form:

50 to 60 mg of Form A of Compound 1 HBr salt was slurried in a solvent at room temperature or at 50° C. for several days, and the results are listed in the following table:

TABLE 22

Stress polymorph slurry screen - Form A of Compound 1 HBr as starting form

| Solvent | Temperature | Time | Experiment | XRPD Result |
|---|---|---|---|---|
| Ethyl Acetate | 50° C. | 10 days | Suspension | Form A$^a$ |
| Isopropanol | 50° C. | 10 days | Suspension | Form A |
| Acetone | Room | 10 days | Suspension | Form A |
| Dichloromethane | 4° C. | 10 days | Suspension | Form A |
| Acetonitrile | 50° C. | 10 days | Suspension | Form A |
| Tetrahydrofuran | Room | 10 days | Suspension | Form A |

TABLE 22-continued

Stress polymorph slurry screen - Form A of Compound 1 HBr as starting form

| Solvent | Temperature | Time | Experiment | XRPD Result |
|---|---|---|---|---|
| Water | 50° C. | 10 days | Suspension | Form A[a] |
| H₂O/Methanol (⅓ by volume) | Room | 10 days | Suspension | Form A |
| H₂O/Acetonitrile (⅓ by volume) | 4° C. | 10 days | Suspension | Form A |
| Ethanol | 50° C. | 10 days | Suspension | Form A[a] |
| MTBE | Room | 10 days | Suspension | Form A[a] |
| Anisole | 50° C. | 10 days | Suspension | Form A |
| Toluene | 50° C. | 10 days | Suspension | Form A |
| DMAc | Room | 10 days | Suspension | Form A |
| DMSO | Room | 10 days | Drop into water | Form A |
| 1,4-Dioxane | 50° C. | 2 days | Slurry | Form A |
| MeOH | 50° C. | 2 days | Slurry | Form A |
| DMF | 50° C. | 2 days | Slurry | Form A |
| NMP | 50° C. | 2 days | Slurry | Form A |

[a]with extra small peak at 18°. Additional studies confirmed the small peak is attributed to Compound 1 free base.

Slow Evaporation Using a Centrifuge Apparatus Overnight:

The results are listed in the following table:

TABLE 23

Slow evaporation

| Crystallization Solvent | Results |
|---|---|
| 1,4 Dioxane | no solids observed |
| DMAc | Form E as DMAc Solvate; turned to Form A upon drying |
| 1:2 MeCN:H₂O | Highly crystalline Form A |
| MeOH | Weakly crystalline Form A |
| DMF | Form E as DMF solvate - isomorphous of DMAc solvate; turned to Form A upon drying |
| DMSO | Only film |
| NMP | Form F as NMP solvate; 3 day ambient drying still maintained the same pattern |
| Anisole | Only film |

Amorphous Form:

three batches of amorphous Compound 1 HBr salt were prepared by lyophilization (Apparatus:DSD Labconco FreeZone 2.5 L −84° C.), and confirmed by XRPD. DSC of the material showed an amorphous glass transition temperature with onset ~162° C. (Inflection temperature at 165.9° C. with ΔCp=0.39 J/(g ° C.)). No new form was observed from the DSC temperature cycling experiment starting with amorphous material.

Polymorph Screening Using Amorphous HBr Salt as Starting Form:

About 50 mg amorphous Compound 1 HBr salt was added to vial with ~1.0 to 2.0 mL of solvent each to maintain as slurry. The mixture was slurried at room temperature for 2 hours, at 50° C. for 0.5 hour, at room temperature for 6 days, and then at 50° C. for 4 hours. The solids were isolated and analyzed by XRPD. The results are listed in the following table:

TABLE 24

Polymorph slurry screen using amorphous Compound 1 HBr as starting form

| Solvent | Experiment | XRPD Result |
|---|---|---|
| Ethyl Acetate | Suspension | Form A |
| Toluene | Suspension | Form G- likely hydrated toluene solvate |
| CHCl₃ | Suspension | Wet (Form I) is different from dry; dry phase as hydrate Form H - hydrate with trace CHCl₃ |
| Methanol | Suspension | Form A |
| Acetonitrile | Suspension | Form A |
| Tetrahydrofuran | Suspension | Form A |
| Water | Suspension | Form A |
| nitromethane | Suspension | Form A |
| 1,4-dioxane | Suspension | Form J as 1,4-dioxane solvate (wet); loss of crystallinity upon drying |
| MEK | Suspension | Form A |
| CPME | Suspension | Form A |
| Acetone/H₂O (96.2/3.8 v/v) | Suspension | Form A |
| DMSO:H₂O (2:9) | | Form A |

Study of Hydrate Form H and Anhydrous Form A:

A slurry experiment in water at room temperature overnight was conducted (20 mg Form H in 0.5 ml water). Anhydrous Form A was the final form observed by XRPD.

In another experiment, 25 mg amorphous HBr salt was seeded with 5 mg hydrate Form H in 1.0 mL water, and the mixture was slurried at 4° C. and 50° C., respectively. Anhydrous Form A was the final form observed by XRPD suggesting Form A is the most stable form in water under the conditions studied.

The following table summarizes the solid forms of a hydrobromide salt of Compound 1.

TABLE 25

Summary of solid forms of a hydrobromide salt of Compound 1

| Name | Description |
|---|---|
| Form A | The most stable form among identified forms; anhydrous with a melt onset at approximately 283° C. |
| Form B | isomorphic solvates with acetone, EtOAc, MEK, THF, THF/H₂O, toluene, water, 1,4-dioxane |
| Form C | probable anhydrous phase |
| Form D | obtained from MeOH; possibly a methanol solvate |
| Form E | obtained from DMAc and DMF; ambient drying overnight turned to Form A; isomorphic solvates |
| Form F | obtained from NMP; likely NMP solvate |
| Form G | obtained from toluene; likely a hydrated toluene solvate |
| Form H | obtained from de-solvation of Form I; likely a hydrate; converted to Form A when slurry in water |
| Form I | obtained from CHCl₃; likely a CHCl₃ solvate |
| Form J | obtained from 1,4-dioxane; likely a 1,4-dioxane solvate; turned to amorphous upon drying |

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A solid form of a free base of Compound 1:

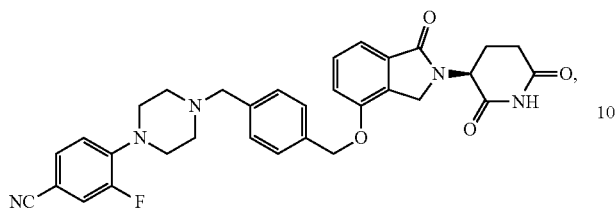

which is selected from the group consisting of Form A of a free base of Compound 1, characterized by an X-ray powder diffraction (XRPD) pattern comprising peaks at approximately 11.3, 14.1, and 17.4° 2θ;
Form B of a free base of Compound 1, characterized by an XRPD pattern comprising peaks at approximately 6.6, 16.3, and 17.1° 2θ;
Form C of a free base of Compound 1, characterized by an XRPD pattern comprising peaks at approximately 14.2, 15.9, and 21.5° 2θ;
Form D of a free base of Compound 1, characterized by an XRPD pattern comprising peaks at approximately 6.1, 11.1, and 18.5° 2θ;
Form E of a free base of Compound 1, characterized by an XRPD pattern comprising peaks at approximately 6.2, 14.3, and 18.8° 2θ;
Form F of a free base of Compound 1, characterized by an XRPD pattern comprising peaks at approximately 5.0, 14.3, and 26.3° 2θ;
Form G of a free base of Compound 1, characterized by an XRPD pattern comprising peaks at approximately 6.4, 19.1, and 19.6° 2θ;
Form H of a free base of Compound 1, characterized by an XRPD pattern comprising peaks at approximately 5.4, 7.5, and 10.7° 2θ;
Form I of a free base of Compound 1, characterized by an XRPD pattern comprising peaks at approximately 14.9, 15.6, and 21.3° 2θ;
Form J of a free base of Compound 1, characterized by an XRPD pattern comprising peaks at approximately 13.8, 15.2, and 22.0° 2θ;
Form L of a free base of Compound 1, characterized by an XRPD pattern comprising peaks at approximately 15.9, 17.9, and 26.2° 2θ;
Form M of a free base of Compound 1, characterized by an XRPD pattern comprising peaks at approximately 14.1, 17.0, and 18.4° 2θ;
Form N of a free base of Compound 1, characterized by an XRPD pattern comprising peaks at approximately 13.0, 25.0, and 25.7° 2θ;
Form O of a free base of Compound 1, characterized by an XRPD pattern comprising peaks at approximately 6.5, 16.5, and 20.6° 2θ;
Form P of a free base of Compound 1, characterized by an XRPD pattern comprising peaks at approximately 14.3, 16.3, and 21.0° 2θ;
Form Q of a free base of Compound 1, characterized by an XRPD pattern comprising peaks at approximately 5.7, 15.5, and 20.7° 2θ;
Form R of a free base of Compound 1, characterized by an XRPD pattern comprising peaks at approximately 14.9, 25.4, and 26.7° 2θ; and
Form S of a free base of Compound 1, characterized by an XRPD pattern comprising peaks at approximately 6.6, 16.5, and 20.8° 2θ.

2. A solid form of a salt of Compound 1:

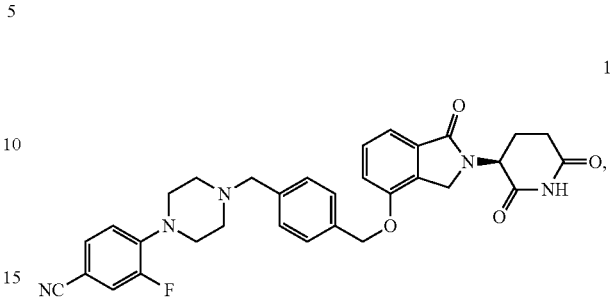

which is selected from the group consisting of Form A of a hydrochloride salt of Compound 1, characterized by an X-ray powder diffraction (XRPD) pattern comprising peaks at approximately 14.1, 16.6, and 26.0° 2θ;
Form B of a hydrochloride salt of Compound 1, characterized by an XRPD pattern comprising peaks at approximately 6.1, 13.4, and 24.6° 2θ;
Form C of a hydrochloride salt of Compound 1, characterized by an XRPD pattern comprising peaks at approximately 7.2, 8.2, and 15.0° 2θ;
Form D of a hydrochloride salt of Compound 1, characterized by an XRPD pattern comprising peaks at approximately 14.6, 25.1, and 25.6° 2θ;
Form E of a hydrochloride salt of Compound 1, characterized by an XRPD pattern comprising peaks at approximately 5.5, 19.4, and 25.7° 2θ;
Form F of a hydrochloride salt of Compound 1, characterized by an XRPD pattern comprising peaks at approximately 7.4, 9.6, and 24.9° 2θ;
Form G of a hydrochloride salt of Compound 1, characterized by an XRPD pattern comprising peaks at approximately 9.5, 13.9, and 25.1° 2θ;
Form H of a hydrochloride salt of Compound 1, characterized by an XRPD pattern comprising peaks at approximately 7.3, 16.3, and 26.7° 2θ;
Form I of a hydrochloride salt of Compound 1, characterized by an XRPD pattern comprising peaks at approximately 4.9, 16.1, and 21.5° 2θ;
Form L of a hydrochloride salt of Compound 1, characterized by an XRPD pattern comprising peaks at approximately 10.1, 19.1, and 24.6° 2θ;
Form M of a hydrochloride salt of Compound 1, characterized by an XRPD pattern comprising peaks at approximately 10.3, 19.3, and 24.6° 2θ;
Form N of a hydrochloride salt of Compound 1, characterized by an XRPD pattern comprising peaks at approximately 9.9, 15.4, and 18.3° 2θ;
Form O of a hydrochloride salt of Compound 1, characterized by an XRPD pattern comprising peaks at approximately 7.6, 16.9, and 18.1° 2θ;
Form P of a hydrochloride salt of Compound 1, characterized by an XRPD pattern comprising peaks at approximately 9.5, 16.6, and 18.9° 2θ;
Form Q of a hydrochloride salt of Compound 1, characterized by an XRPD pattern comprising peaks at approximately 7.6, 15.5, and 17.7° 2θ;
Form R of a hydrochloride salt of Compound 1, characterized by an XRPD pattern comprising peaks at approximately 17.7, 20.1, and 21.6° 2θ;

Form S of a hydrochloride salt of Compound 1, characterized by an XRPD pattern comprising peaks at approximately 16.6, 18.6, and 22.4° 2θ;
Form T of a hydrochloride salt of Compound 1, characterized by an XRPD pattern comprising peaks at approximately 7.7, 16.9, and 17.8° 2θ;
Form U of a hydrochloride salt of Compound 1, characterized by an XRPD pattern comprising peaks at approximately 9.1, 19.2, and 24.4° 2θ;
Form V of a hydrochloride salt of Compound 1, characterized by an XRPD pattern comprising peaks at approximately 7.2, 9.5, and 14.3° 2θ;
Form W of a hydrochloride salt of Compound 1, characterized by an XRPD pattern comprising peaks at approximately 9.6, 16.8, and 17.6° 2θ;
Form X of a hydrochloride salt of Compound 1, characterized by an XRPD pattern comprising peaks at approximately 9.5, 16.8, and 17.6° 2θ;
Form Y of a hydrochloride salt of Compound 1, characterized by an XRPD pattern comprising peaks at approximately 7.6, 16.7, and 18.2° 2θ;
Form Z of a hydrochloride salt of Compound 1, characterized by an XRPD pattern comprising peaks at approximately 17.3, 18.8, and 20.4° 2θ;
Form AA of a hydrochloride salt of Compound 1, characterized by an XRPD pattern comprising peaks at approximately 8.3, 15.5, and 18.2° 2θ;
Form AB of a hydrochloride salt of Compound 1, characterized by an XRPD pattern comprising peaks at approximately 7.7, 18.2, and 20.9° 2θ;
Form AC of a hydrochloride salt of Compound 1, characterized by an XRPD pattern comprising peaks at approximately 14.1, 18.2, and 25.8° 2θ;
Form A of a mesylate salt of Compound 1, characterized by an XRPD pattern comprising peaks at approximately 16.9, 17.7, and 22.7° 2θ;
Form B of a mesylate salt of Compound 1, characterized by an XRPD pattern comprising peaks at approximately 5.7, 9.1, and 26.1° 2θ;
Form A of a hydrobromide salt of Compound 1, characterized by an XRPD pattern comprising peaks at approximately 10.3, 19.3, and 24.0° 2θ;
Form B of a hydrobromide salt of Compound 1, characterized by an XRPD pattern comprising peaks at approximately 5.8, 13.9, and 25.3° 2θ;
Form C of a hydrobromide salt of Compound 1, characterized by an XRPD pattern comprising peaks at approximately 9.7, 10.1, and 12.1° 2θ;
Form D of a hydrobromide salt of Compound 1, characterized by an XRPD pattern comprising peaks at approximately 12.2, 12.4, and 24.5° 2θ;
Form E of a hydrobromide salt of Compound 1, characterized by an XRPD pattern comprising peaks at approximately 8.1, 13.5, and 24.4° 2θ;
Form F of a hydrobromide salt of Compound 1, characterized by an XRPD pattern comprising peaks at approximately 18.4, 23.6, and 24.5° 2θ;
Form G of a hydrobromide salt of Compound 1, characterized by an XRPD pattern comprising peaks at approximately 10.6, 18.1, and 25.1° 2θ;
Form H of a hydrobromide salt of Compound 1, characterized by an XRPD pattern comprising peaks at approximately 7.5, 15.1, and 18.0° 2θ;
Form I of a hydrobromide salt of Compound 1, characterized by an XRPD pattern comprising peaks at approximately 18.8, 21.4, and 25.4° 2θ;
Form J of a hydrobromide salt of Compound 1, characterized by an XRPD pattern comprising peaks at approximately 19.4, 25.2, and 25.9° 2θ;
Form A of a besylate salt of Compound 1, characterized by an XRPD pattern comprising peaks at approximately 13.2, 21.1, and 24.3° 2θ;
Form B of a besylate salt of Compound 1, characterized by an XRPD pattern comprising peaks at approximately 16.9, 17.7, and 21.9° 2θ;
Form A of a glycolate salt of Compound 1, characterized by an XRPD pattern comprising peaks at approximately 13.6, 17.6, and 22.2° 2θ; and
Form A of an L-malate salt of Compound 1, characterized by an XRPD pattern comprising peaks at approximately 8.1, 14.7, and 25.3° 2θ.

3. A pharmaceutical composition comprising a solid form of claim 1, and a pharmaceutically acceptable excipient or carrier.

4. A method of treating multiple myeloma comprising administering a therapeutically effective amount of a solid form of claim 1 to a patient having multiple myeloma.

5. A pharmaceutical composition comprising a solid form of claim 2, and a pharmaceutically acceptable excipient or carrier.

6. A method of treating multiple myeloma comprising administering a therapeutically effective amount of a solid form of claim 2 to a patient having multiple myeloma.

7. The solid form of claim 2, which is Form B of a besylate salt of Compound 1, characterized by an XRPD pattern comprising peaks at approximately 16.9, 17.7, and 21.9° 2θ.

8. The solid form of claim 7, wherein the XRPD pattern further comprises peaks at approximately 11.2, 17.6, and 23.0° 2θ.

9. The solid form of claim 8, wherein the XRPD pattern further comprises peaks at approximately 7.3 and 25.4° 2θ.

10. The solid form of claim 7, which is characterized by an XRPD pattern that matches the XRPD pattern presented in FIG. 85.

11. The solid form of claim 2, which is Form L of a hydrochloride salt of Compound 1, characterized by an XRPD pattern comprising peaks at approximately 10.1, 19.1, and 24.6° 2θ.

12. The solid form of claim 11, wherein the XRPD pattern further comprises peaks at approximately 8.4, 15.7, and 16.1° 2θ.

13. The solid form of claim 12, wherein the XRPD pattern further comprises peaks at approximately 19.4 and 26.9° 2θ.

14. The solid form of claim 11, which is characterized by an XRPD pattern that matches the XRPD pattern presented in FIG. 138.

15. The solid form of claim 2, which is Form M of a hydrochloride salt of Compound 1, characterized by an XRPD pattern comprising peaks at approximately 10.3, 19.3, and 24.6° 2θ.

16. The solid form of claim 15, wherein the XRPD pattern further comprises one or more peaks at approximately 4.2, 14.7, 15.1, and 16.9° 2θ.

17. The solid form of claim 16, wherein the XRPD pattern further comprises peaks at approximately 15.9 and 16.1° 2θ.

18. The solid form of claim 15, which is characterized by an XRPD pattern that matches the XRPD pattern presented in FIG. 142.

19. The solid form of claim 2, which is Form N of a hydrochloride salt of Compound 1, characterized by an XRPD pattern comprising peaks at approximately 9.9, 15.4, and 18.3° 2θ.

20. The solid form of claim 19, wherein the XRPD pattern further comprises peaks at approximately 17.2, 25.8, and 27.8° 2θ.

21. The solid form of claim 20, wherein the XRPD pattern further comprises peaks at approximately 17.8, 19.9, and 23.8° 2θ.

22. The solid form of claim 19, which is characterized by an XRPD pattern that matches the XRPD pattern presented in FIG. 144.

23. A solid form of a hydrobromide salt of Compound 1:

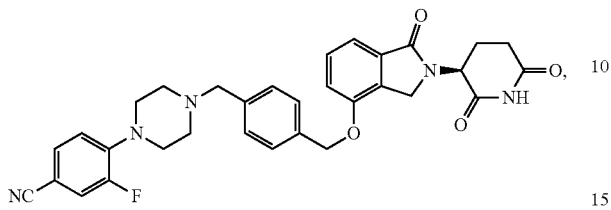

characterized by an X-ray powder diffraction (XRPD) pattern comprising peaks at approximately 10.3, 19.3, and 24.0° 2θ.

24. The solid form of claim 23, wherein the XRPD pattern further comprises peaks at approximately 17.1 and 20.7° 2θ.

25. The solid form of claim 24, wherein the XRPD pattern further comprises peaks at approximately 12.8 and 15.6° 2θ.

26. The solid form of claim 23, which is characterized by an XRPD pattern that matches the XRPD pattern presented in FIG. 76.

27. A pharmaceutical composition comprising a solid form of claim 23, and a pharmaceutically acceptable excipient or carrier.

28. A method of treating multiple myeloma comprising administering a therapeutically effective amount of a solid form of claim 23 to a patient having multiple myeloma.

* * * * *

UNITED STATES PATENT AND TRADEMARK OFFICE
CERTIFICATE OF CORRECTION

| | | |
|---|---|---|
| PATENT NO. | : 11,370,777 B2 | Page 1 of 1 |
| APPLICATION NO. | : 16/737739 | |
| DATED | : June 28, 2022 | |
| INVENTOR(S) | : Artman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this
Nineteenth Day of December, 2023

Katherine Kelly Vidal
*Director of the United States Patent and Trademark Office*